(12) United States Patent
Edmunds et al.

(10) Patent No.: US 6,534,445 B1
(45) Date of Patent: Mar. 18, 2003

(54) SUBSTITUTED PYRIDINE HERBICIDES

(75) Inventors: Andrew Edmunds, Basel (CH); Christoph Lüthy, Münchenstein (CH); Karl Seckinger, Riegel (DE); Alain De Mesmaeker, Kaenerkinden (CH); Walter Kunz, Oberwil (CH); Jürgen Schaetzer, Rheinfelden (DE)

(73) Assignee: Syngenta Participations AG (CH)

( * ) Notice: Subject to any disclaimer, the term of this patent is extended or adjusted under 35 U.S.C. 154(b) by 0 days.

(21) Appl. No.: 09/887,372

(22) Filed: Jun. 22, 2001

Related U.S. Application Data

(63) Continuation of application No. PCT/EP99/10326, filed on Dec. 22, 1999.

(30) Foreign Application Priority Data

Dec. 23, 1998 (CH) ................................................ 2547/98

(51) Int. Cl.⁷ ........................ C07D 213/50; A01N 43/40
(52) U.S. Cl. ..................... 504/130; 546/282.1; 546/340
(58) Field of Search .......................... 504/130; 546/340, 546/282.1

(56) References Cited

FOREIGN PATENT DOCUMENTS

| DE | 39 02 818 A1 | 8/1989 |
| EP | 0 245 230 A1 | 11/1987 |
| EP | 0 316 491 A1 | 5/1989 |
| EP | 0 353 187 A2 | 1/1990 |
| GB | 2 205 316 A | 12/1988 |
| WO | 92/22203 | 12/1992 |
| WO | 96/26200 | 8/1996 |
| WO | 97/34485 | 9/1997 |
| WO | WO 97/46530 | * 12/1997 |

OTHER PUBLICATIONS

E. Okada et al., "A simple and convenient synthetic method for α–trifluoromethylpyridines", Heterocycles, vol. 46, pp. 129–132 (1997).
T. Terasawa et al., "Novel heterocyclic synthons, synthesis and properties of thia—and oxacyclohexane–3,5–diones", J. Org. Chem., vol. 42, No. 7, pp. 1163–1169 (1977).
T. Mukaiyama et al., "A convenient method for the synthesis of carboxylic esters", Chemistry Letters, pp. 1045–1048 (1975).
C. Ferri, "Reaktionen der organischen Synthese", Georg Thieme Verlag, Stuttgart, pp. 460–461 (1978).
Helvetica Chimica Acta, vol. 71, pp. 596–601 (1988).

* cited by examiner

Primary Examiner—Zinna Northington Davis
(74) Attorney, Agent, or Firm—William A. Teoli, Jr.; Thomas Hamilton

(57) ABSTRACT

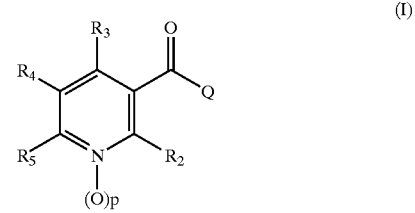

Compounds of formula (I), in which the substituents are as defined in claim 1 and the agrochemically tolerated salts M+ and all stereoisomers and tautomers of the compounds of formula (I) are suitable for use as herbicides.

14 Claims, No Drawings

SUBSTITUTED PYRIDINE HERBICIDES

This application is a continuation of International Application PCT/EP99/10326, filed Dec. 22, 1999, which is fully incorporated by reference herein.

The present invention relates to novel, herbicidally active pyridine ketones, to their preparation, to compositions comprising these compounds, and to their use for controlling weeds, especially in crops of useful plants, or for inhibiting plant growth.

Herbicidally active pyridine ketones are described, for example, in WO 97/46530. There have now been found novel pyridine ketones which have herbicidal and growth-inhibitory properties.

The present invention therefore relates to compounds of the formula I

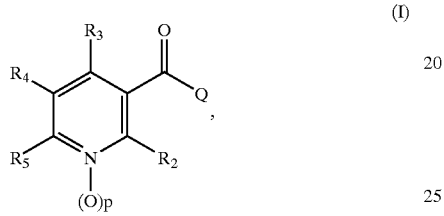

in which p is 0 or 1;

$R_5$ is $C_1$–$C_6$haloalkyl;

$R_2$ is hydrogen, $C_1$–$C_6$alkyl, $C_1$–$C_6$haloalkyl, $C_2$–$C_6$alkenyl, $C_2$–$C_6$haloalkenyl, vinyl which is substituted by $C_1$–$C_2$alkoxycarbonyl or phenyl, or is $C_2$–$C_6$alkynyl, $C_2$–$C_6$haloalkynyl, ethynyl which is substituted by trimethylsilyl, hydroxyl, $C_1$–$C_2$alkoxy, $C_1$–$C_2$alkoxycarbonyl or phenyl, or is $C_3$–$C_6$allenyl, $C_3$–$C_6$cycloalkyl, $C_3$–$C_6$cycloalkyl which is substituted by halogen, or is $C_1$–$C_6$alkoxy, $C_3$–$C_6$alkenyloxy, $C_3$–$C_6$alkynyloxy, $C_1$–$C_6$haloalkoxy, $C_3$–$C_6$haloalkenyloxy, cyano-$C_1$–$C_4$alkoxy, $C_1$–$C_4$alkoxy-$C_1$–$C_4$alkoxy, $C_1$–$C_4$alkylthio-$C_1$–$C_4$alkoxy, $C_1$–$C_4$alkylsulfinyl-$C_1$–$C_4$alkoxy, $C_1$–$C_4$alkylsulfonyl-$C_1$–$C_4$alkoxy, $C_1$–$C_4$alkoxycarbonyl-$C_1$–$C_4$alkoxy, $C_1$–$C_6$alkylthio, $C_1$–$C_6$alkylsulfinyl, $C_1$–$C_6$alkylsulfonyl, $C_1$–$C_6$haloalkylthio, $C_1$–$C_6$haloalkylsulfinyl, $C_1$–$C_6$haloalkylsulfonyl, $C_1$–$C_4$alkoxycarbonyl-$C_1$–$C_4$alkylthio, $C_1$–$C_4$alkoxycarbonyl-$C_1$–$C_4$alkylsulfinyl, $C_1$–$C_4$alkoxycarbonyl-$C_1$–$C_4$alkylsulfonyl, benzyl-$S(O)_{n1}$—, $C_1$–$C_6$alkylamino, $C_2$–$C_6$dialkylamino, $C_1$–$C_6$alkylaminosulfonyl, di-($C_1$–$C_6$alkylamino)sulfonyl, benzyloxy, benzyl, phenyl, phenoxy, phenylthio, phenylsulfinyl or phenylsulfonyl, it being possible for the phenyl-containing groups, in turn, to be substituted by $C_1$–$C_3$alkyl, $C_1$–$C_3$haloalkyl, $C_1$–$C_3$alkoxy, $C_1$–$C_3$haloalkoxy, halogen, cyano or nitro or $R_2$ is $OS(O)_{n2}$—$R_{21}$, $N(R_{23})$—$S(O)_{n3}$—$R_{22}$, cyano, carbamoyl, $C_1$–$C_4$alkoxycarbonyl, formyl, halogen, thiocyanato, amino, hydroxy-$C_1$–$C_4$alkyl, $C_1$–$C_4$alkoxy-$C_1$–$C_4$alkyl, $C_1$–$C_4$alkyl-$S(O)_{n4}$—$C_1$–$C_4$alkyl, cyano-$C_1$–$C_4$alkyl, $C_1$–$C_6$alkylcarbonyloxy-$C_1$–$C_4$alkyl, $C_1$–$C_4$alkoxycarbonyl-$C_1$–$C_4$alkyl, $C_1$–$C_4$alkoxycarbonyloxy-$C_1$–$C_4$alkyl, $C_1$–$C_4$thiocyanato-$C_1$–$C_4$alkyl, benzoyloxy-$C_1$–$C_4$alkyl, $C_2$–$C_6$oxiranyl, $C_1$–$C_4$alkylamino-$C_1$–$C_4$alkyl, di-($C_1$–$C_4$-alkyl)amino-$C_1$–$C_4$alkyl, $C_1$–$C_{12}$alkylthiocarbonyl-$C_1$–$C_4$alkyl or for formyl-$C_1$–$C_4$alkyl, or $R_2$ is a five- to ten-membered monocyclic or fused bicyclic ring system which can be aromatic or partially saturated and can contain 1 to 4 hetero atoms selected from the group consisting of nitrogen, oxygen and sulfur, the ring system being bonded to the pyridine ring via a $C_1$–$C_4$alkylene, —CH=CH—, —C≡C—, —CH$_2$O—, —CH$_2$N($C_1$–$C_4$alkyl)—, —CH$_2$SO—, or —CH$_2$SO$_2$ group and it not being possible for each ring system to contain more than 2 oxygen atoms and not more than 2 sulfur atoms, and it being possible for the ring system itself to be mono-, di- or trisubstituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_1$–$C_6$alkoxy, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_2$–$C_5$alkoxyalkylthio, $C_3$–$C_5$acetylalkylthio, $C_3$–$C_6$alkoxycarbonylalkylthio, $C_2$–$C_4$cyanoalkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylaminosulfonyl, di-($C_1$–$C_2$alkyl)aminosulfonyl, di-($C_1$–$C_4$alkyl)amino, halogen, cyano, nitro, phenyl and benzylthio, it being possible for phenyl and benzylthio, in turn, to be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or nitro, and substituents on the nitrogen in the heterocyclic ring being other than halogen;

$R_3$ is hydrogen, $C_1$–$C_6$alkyl, $C_1$–$C_6$haloalkyl, $C_2$–$C_6$alkenyl, $C_2$–$C_6$haloalkenyl, $C_2$–$C_6$alkynyl, $C_2$–$C_6$haloalkynyl, $C_3$–$C_6$cycloalkyl, $C_1$–$C_6$alkoxy, $C_1$–$C_6$haloalkoxy, $C_1$–$C_6$alkylthio, $C_1$–$C_6$alkylsulfinyl, $C_1$–$C_6$alkylsulfonyl, $C_1$–$C_6$haloalkylthio, $C_1$–$C_6$haloalkylsulfinyl, $C_1$–$C_6$haloalkylsulfonyl, $C_1$–$C_6$alkylamino, $C_2$–$C_6$dialkylamino, $C_1$–$C_6$alkylaminosulfonyl, $C_2$–$C_6$dialkylaminosulfonyl, phenyl, phenylthio, phenylsulfinyl, phenylsulfonyl or phenoxy, it being possible for phenyl, in turn, to be substituted by $C_1$–$C_3$alkyl, $C_1$–$C_3$haloalkyl, $C_1$–$C_3$alkoxy, $C_1$–$C_3$haloalkoxy, halogen, cyano or nitro, or $R_3$ is —N($R_{23}$)—$S(O)_n$—$R_{22}$, cyano, halogen, amino, $C_1$–$C_4$alkoxy-$C_1$–$C_4$alkyl or $C_1$–$C_4$alkyl-$S(O)_n$—$C_1$–$C_4$alkyl;

$R_4$ is hydrogen, $C_1$–$C_6$alkyl, hydroxyl, $C_1$–$C_6$alkoxy, $C_1$–$C_6$haloalkoxy, $C_3$–$C_6$alkenyloxy, $C_3$–$C_6$haloalkenyloxy, $C_3$–$C_6$alkynyloxy, $C_1$–$C_4$alkylcarbonyloxy, $C_1$–$C_4$alkylsulfonyloxy, tosyloxy, $C_1$–$C_4$alkylthio, $C_1$–$C_4$alkylsulfinyl, $C_1$–$C_4$alkylsulfonyl, $C_1$–$C_4$alkylamino, $C_1$–$C_4$dialkylamino, $C_1$–$C_4$alkoxycarbonyl, $C_1$–$C_4$haloalkyl, formyl, cyano, halogen, phenyl or phenoxy, it being possible for phenyl, in turn, to be substituted by $C_1$–$C_3$alkyl, $C_1$–$C_3$haloalkyl, $C_1$–$C_3$alkoxy, $C_1$–$C_3$haloalkoxy, halogen, cyano or nitro;

or $R_4$ is a five to ten-membered monocyclic or $R_3$-fused bicyclic ring system which can contain 1 to 4 hetero atoms selected from the group consisting of nitrogen, oxygen and sulfur, the ring system, unless fused, being bonded to the pyridine ring directly or via a $C_1$–$C_4$alkylene, —CH=CH—, —C≡C—, —CH$_2$O—, —CH$_2$N($C_1$–$C_4$alkyl)—, —CH$_2$S—, —CH$_2$SO—, or —CH$_2$SO$_2$— group and it not being possible for the ring system to contain more than 2 oxygen atoms and not more than two sulfur atoms, and it being possible for the ring system itself to be mono-, di- or trisubstituted by C$_1$–C$_6$alkyl, C$_1$–C$_6$haloalkyl, C$_2$–C$_6$alkenyl, C$_2$–C$_6$haloalkenyl, C$_2$–C$_6$alkynyl, C$_2$–C$_6$haloalkynyl, C$_1$–C$_6$alkoxy, C$_1$–C$_6$haloalkoxy, C$_3$–C$_6$alkenyloxy, C$_3$–C$_6$alkynyloxy, C$_1$–C$_6$alkylthio, C$_1$–C$_6$haloalkylthio, C$_3$–C$_6$alkenylthio, C$_3$–C$_6$haloalkenylthio, C$_3$–C$_6$alkynylthio, C$_1$–C$_4$alkoxy-C$_1$–C$_2$alkylthio, C$_1$–C$_4$alkylcarbonyl-C$_1$–C$_2$alkylthio, C$_1$–C$_4$alkoxycarbonyl-C$_1$–C$_2$alkylthio, cyano-C$_1$–C$_4$alkylthio, C$_1$–C$_6$alkylsulfinyl, C$_1$–C$_6$haloalkylsulfinyl, C$_1$–C$_6$alkylsulfonyl, C$_1$–C$_6$haloalkylsulfonyl, aminosulfonyl, C$_1$–C$_2$alkylaminosulfonyl, di-(C$_1$–C$_2$alkyl)aminosulfonyl, di-(C$_1$–C$_4$alkyl)amino, halogen, cyano, nitro, phenyl and benzylthio, it being possible for phenyl and benzylthio, in turn, to be substituted on the phenyl ring by C$_1$–C$_3$alkyl, C$_1$–C$_3$haloalkyl, C$_1$–C$_3$alkoxy, C$_1$–C$_3$haloalkoxy, halogen, cyano or nitro, and substituents on the nitrogen in the heterocyclic ring being other than halogen;

R$_{21}$ is C$_1$–C$_4$alkyl or C$_1$–C$_4$haloalkyl;

R$_{22}$ is C$_1$–C$_4$alkyl, C$_1$–C$_4$haloalkyl or di-(C$_1$–C$_4$alkyl) amino;

R$_{23}$, R$_{24}$, R$_{25}$ independently of one another are hydrogen or C$_1$–C$_4$alkyl;

n, n$_1$, n$_2$, n$_3$ and n$_4$ independently of one another are 0, 1 or 2;

Q is Q$_1$

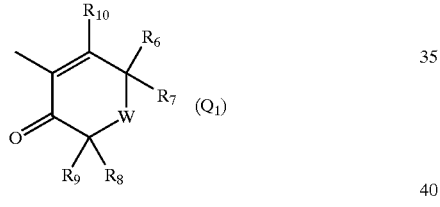

in which

R$_6$, R$_7$, R$_8$ and R$_9$ independently of one another are hydrogen, C$_1$–C$_6$alkyl, C$_1$–C$_6$haloalkyl, C$_2$–C$_6$alkenyl, C$_2$–C$_6$alkynyl, C$_1$–C$_6$alkoxycarbonyl, C$_1$–C$_6$alkylcarbonyl, C$_1$–C$_6$alkyl-S(O)$_{n17}$, C$_1$–C$_6$alkyl-NHS(O)$_2$, C$_1$–C$_6$alkylamino, di-(C$_1$–C$_6$alkyl)amino, hydroxyl, C$_1$–C$_6$alkoxy, C$_3$–C$_6$alkenyloxy, C$_3$–C$_6$alkynyloxy, hydroxy-C$_1$–C$_6$alkyl, C$_1$–C$_4$alkylsulfonyloxy-C$_1$–C$_6$alkyl, tosyloxy-C$_1$–C$_6$alkyl, C$_1$–C$_6$alkoxy-C$_1$–C$_6$alkyl, C$_1$–C$_6$alkyl-S(O)$_{n4}$—C$_1$–C$_6$alkyl, cyano-C$_1$–C$_6$alkyl, C$_1$–C$_6$alkoxy-C$_1$–C$_6$alkoxy, benzyloxy-C$_1$–C$_6$alkyl, C$_1$–C$_6$alkoxycarbonyl-C$_1$–C$_6$alkyl, C$_1$–C$_6$alkoxycarbonyloxy-C$_1$–C$_6$alkyl, thiocyanato-C$_1$–C$_6$alkyl, oxiranyl, C$_1$–C$_6$alkylamino-C$_1$–C$_6$alkyl, di(C$_1$–C$_6$alkyl)amino-C$_1$–C$_6$alkyl, formyl-C$_1$–C$_6$alkyl, C$_1$–C$_6$alkyloximo, halogen, cyano, nitro, phenyl or phenyl which is substituted by C$_1$–C$_4$alkyl, C$_1$–C$_4$haloalkyl, C$_1$–C$_4$alkoxy, C$_1$–C$_4$haloalkoxy, C$_1$–C$_4$alkylcarbonyl, C$_1$–C$_4$alkoxycarbonyl, amino, C$_1$–C$_4$alkylamino, di-C$_1$–C$_4$alkylamino, C$_1$–C$_4$alkyl-S(O)$_{n18}$, C$_1$–C$_4$alkyl-S(O)$_2$O, C$_1$–C$_4$haloalkyl-S(O)$_{n5}$, C$_1$–C$_4$haloalkyl-S(O)$_2$O, C$_1$–C$_4$alkyl-S(O)$_2$NH, C$_1$–C$_4$alkyl-S(O)$_{n19}$N(C$_1$–C$_4$alkyl)$_2$, halogen, nitro, COOH or cyano;

or adjacent R$_6$ and R$_7$ or R$_8$ and R$_9$ together are —(CH$_2$)$_m$—, C(O)O(CH$_2$)$_{n20}$— or —S(O)$_{n21}$(CH$_2$)$_{n22}$—;

n$_5$, n$_{17}$, n$_{18}$, n$_{19}$ and n$_{21}$ independently of one another are 0, 1 or 2;

n$_{20}$ is 2 or 3;

n$_{22}$ is 2, 3 or 4;

m is 2, 3, 4, 5, or 6;

W is oxygen, S(O)$_{n6}$, —CR$_{11}$R$_{12}$, —CR$_{63}$R$_{64}$CR$_{65}$R$_{66}$, —C(O)— or —NR$_{13}$;

R$_{63}$, R$_{64}$, R$_{65}$ and R$_{66}$ independently of one another are hydrogen or C$_1$–C$_6$alkyl, or R$_{65}$ together with R$_7$ or R$_9$ forms a direct bond;

n$_6$ is 0, 1 or 2;

R$_{11}$ is hydrogen, C$_1$–C$_4$alkyl, C$_1$–C$_4$haloalkyl, C$_1$–C$_4$alkoxy-C$_1$–C$_4$alkyl, C$_1$–C$_4$alkylthio-C$_1$–C$_4$alkyl, C$_1$–C$_4$alkylthio-C$_3$–C$_6$cycloalkyl, C$_1$–C$_4$alkycarbonyloxy-C$_1$–C$_4$alkyl, C$_1$–C$_4$alkysulfonyloxy-C$_1$–C$_4$alkyl, tosyloxy-C$_1$–C$_4$alkyl, di-(C$_1$–C$_3$alkoxyalkyl)methyl, di-(C$_1$–C$_3$alkthioalkyl)methyl, (C$_1$–C$_3$alkoxyalkyl)-(C$_1$–C$_3$alkthioalkyl)methyl, C$_3$–C$_5$oxacycloalkyl, C$_3$–C$_5$thiacycloalkyl, C$_3$–C$_4$dioxacycloalkyl, C$_3$–C$_4$dithiacycloalkyl, C$_3$–C$_4$oxathiacycloalkyl, formyl, C$_1$–C$_4$alkoxycarbonyl, carbamoyl, C$_1$–C$_4$alkylaminocarbonyl, di-(C$_1$–C$_4$alkyl) aminocarbonyl, phenylaminocarbonyl, benzylaminocarbonyl or phenyl which, in turn, can be substituted by C$_1$–C$_4$alkyl, C$_1$–C$_4$haloalkyl, C$_1$–C$_4$alkoxy, C$_1$–C$_4$haloalkoxy, C$_1$–C$_4$alkylcarbonyl, C$_1$–C$_4$alkoxycarbonyl, amino, C$_1$–C$_4$alkylamino, di-C$_1$–C$_4$alkylamino, C$_1$–C$_4$alkyl-S(O)$_{n21}$, C$_1$–C$_4$alkyl-S(O)$_2$O, C$_1$–C$_4$haloalkyl-S(O)$_{n7}$, C$_1$–C$_4$haloalkyl-S(O)$_2$O, C$_1$–C$_4$alkyl-S(O)$_2$NH, C$_1$–C$_4$alkyl-S(O)$_{n20}$N(C$_1$–C$_4$alkyl), halogen, nitro, COOH or cyano;

n$_7$, n$_{20}$ and n$_{21}$ independently of one another are 0, 1 or 2;

or R$_{12}$ together with R$_6$ or R$_9$ is a group —(CH$_2$)$_o$—;

o is 1, 2, 3, 4 or 5;

R$_{12}$ is hydrogen, C$_1$–C$_4$alkyl or C$_1$–C$_4$haloalkyl;

or R$_{12}$ together with R$_{11}$ is a group —(CH$_2$)$_{m1}$;

m$_1$ is 2, 3, 4, 5, or 6;

R$_{10}$ is hydroxyl, O$^-$M$^+$, halogen, cyano, SCN, OCN, C$_1$–C$_{12}$alkoxy, C$_1$–C$_4$alkoxycarbonyl-C$_1$–C$_4$alkoxy, C$_1$–C$_{12}$alkylthio, C$_1$–C$_{12}$alkylsulfinyl, C$_1$–C$_{12}$alkylsulfonyl, C$_1$–C$_{12}$haloalkylthio, C$_1$–C$_{12}$haloalkylsulfinyl, C$_1$–C$_{12}$haloalkylsulfonyl, C$_1$–C$_6$alkoxy-C$_1$–C$_6$alkylthio, C$_1$–C$_6$alkoxy-C$_1$–C$_6$alkylsulfinyl, C$_1$–C$_6$alkoxy-C$_1$–C$_6$alkylsulfonyl, C$_2$–C$_{12}$alkenylthio, C$_2$–C$_{12}$alkenylsulfinyl, C$_2$–C$_{12}$alkenylsulfonyl, C$_2$–C$_{12}$alkynylthio, C$_2$–C$_{12}$alkynylsulfinyl, C$_2$–C$_{12}$alkynylsulfonyl, C$_2$–C$_{12}$haloalkenylthio, C$_2$–C$_{12}$haloalkenylsulfinyl, C$_2$–C$_{12}$haloalkenylsulfonyl, C$_1$–C$_4$-alkoxycarbonyl-C$_1$–C$_4$alkylthio, C$_1$–C$_4$alkoxycarbonyl-C$_1$–C$_4$alkylsulfinyl, C$_1$–C$_4$alkoxycarbonyl-C$_1$–C$_4$alkylsulfonyl, (C$_1$–C$_4$alkoxy)$_2$P(O)O, C$_1$–C$_4$alkyl-(C$_1$–C$_4$alkoxy)P(O)O, H(C$_1$–C$_4$alkoxy)P(O)O, R$_{14}$R$_{15}$N, R$_{14}$R$_{15}$NNH, R$_{16}$R$_{17}$NC(O)O—, R$_{16}$R$_{17}$NC(O)NH—, C$_1$–C$_{12}$alkyl-S(O)$_2$NR$_{18}$, C$_1$–C$_4$haloalkyl-S(O)$_2$NR$_{19}$, C$_1$–C$_{12}$alkyl-S(O)$_2$O, C$_1$–C$_4$haloalkyl-S(O)$_2$O, C$_1$–C$_{18}$alkylcarbonyloxy, it being possible for the alkyl group to be substituted by halogen, C$_1$–C$_6$alkoxy, C$_1$–C$_6$alkylthio or cyano, or is C$_2$–C$_{18}$alkenylcarbonyloxy, $C_2$–$C_{18}$alkynylcarbonyloxy,
$C_3$–$C_6$cycloalkylcarbonyloxy,
$C_1$–$C_{12}$alkoxycarbonyloxy,
$C_1$–$C_{12}$alkylthiocarbonyloxy,
$C_1$–$C_{12}$alkylthiocarbamoyl, $C_1$–$C_6$alkyl-NH(CS)N($C_1$–$C_6$alkyl)-NH—, di-$C_1$–$C_6$alkyl-N(CS)N($C_1$–$C_6$alkyl)-NH—, benzyloxy, benzylthio, benzylsulfinyl, benzylsulfonyl, phenoxy, phenylthio, phenylsulfinyl, phenylsulfonyl, phenylsulfonylamino, phenylsulfonyloxy or benzoyloxy, it being possible for the phenyl groups, in turn, to be substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, $C_1$–$C_4$alkylamino, di-$C_1$–$C_4$alkylamino, $C_1$–$C_4$alkylthio, $C_1$–$C_4$alkylsulfinyl, $C_1$–$C_4$alkylsulfonyl, $C_1$–$C_4$alkyl-S(O)$_2$O, $C_1$–$C_4$haloalkylthio, $C_1$–$C_4$haloalkylsulfinyl, $C_1$–$C_4$haloalkylsulfonyl, $C_1$–$C_4$haloalkyl-S(O)$_2$O, $C_1$–$C_4$alkyl-S(O)$_2$NH, $C_1$–$C_4$alkyl-S(O)$_2$N($C_1$–$C_4$alkyl), halogen, nitro or cyano;
or $R_{10}$ is a group $Ar_1$-thio, $Ar_2$-sulfinyl, $Ar_3$-sulfonyl, —OCO-$Ar_4$ or NH-$Ar_5$ in which $Ar_1$, $Ar_3$, $Ar_4$ and $Ar_5$ independently of one another are a five- to ten-membered monocyclic or fused bicyclic ring system which can be aromatic or partially saturated and can contain 1 to 4 hetero atoms selected from the group consisting of nitrogen, oxygen and sulfur, and it being possible for each ring system to contain not more than 2 oxygen atoms and not more than two sulfur atoms, and it being possible for the ring system itself to be mono-, di- or trisubstituted by $C_1$–$C_6$alkyl, $C_1$–$C_6$haloalkyl, $C_1$–$C_6$alkenyl, $C_3$–$C_6$haloalkenyl, $C_3$–$C_6$alkynyl, $C_3$–$C_6$haloalkynyl, $C_1$–$C_6$alkoxy, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_2$–$C_5$alkoxyalkylthio, $C_3$–$C_5$acetylalkylthio, $C_3$–$C_6$alkoxycarbonylalkylthio, $C_2$–$C_4$-cyanoalkylthio, $C_1$–$C_6$alkylsulfinyl, $C_1$–$C_6$haloalkylsulfinyl, $C_1$–$C_6$alkylsulfonyl, $C_1$–$C_6$-haloalkylsulfonyl, aminosulfonyl, $C_1$–$C_2$alkylaminosulfonyl, di-($C_1$–$C_2$alkyl) aminosulfonyl, di-($C_1$–$C_4$alkyl)amino, halogen, cyano, nitro, phenyl and benzylthio, it being possible for phenyl and benzylthio, in turn, to be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or nitro, and where substituents on the nitrogen in the heterocyclic ring are other than halogen;
$R_{14}$, $R_{15}$, $R_{16}$, $R_{17}$ and $R_{18}$ independently of one another are hydrogen or $C_1$–$C_6$alkyl;
$n_8$, $n_9$, $n_{10}$, $n_{11}$, $n_{12}$, $n_{13}$ and $n_{14}$ independently of one another are 0, 1 or 2;
$R_{13}$ is hydrogen, $C_1$–$C_4$alkyl, $C_1$–$C_4$alkythio-$C_1$–$C_4$carbonyl, $G_1$–$C_4$alkylsulfinyl-$C_1$–$C_4$carbonyl, $C_1$–$C_4$alkylsulfonyl-$C_1$–$C_4$carbonyl, $C_1$–$C_4$alkoxycarbonyl, $C_1$–$C_4$alkylcarbonyl, phenylcarbonyl, or is phenyl which, in turn, can be substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, $C_1$–$C_4$alkylamino, di-$C_1$–$C_4$-alkylamino, $C_1$–$C_4$alkyl-S(O)$_{n15}$, $C_1$–$C_4$alkyl-S(O)$_2$O, $C_1$–$C_4$haloalkyl-S(O)$_{n16}$, $C_1$–$C_4$haloalkyl-S(O)$_2$O, $C_1$–$C_4$alkyl-S(O)$_2$NH, $C_1$–$C_4$alkyl-S(O)$_2$N($C_1$–$C_4$alkyl), halogen, nitro, or cyano; and $n_{15}$ and $n_{16}$ independently of one another are 0, 1 or 2;
and the agrochemically tolerated salts M$^+$ and all stereoisomers and tautomers of the compounds of the formula I.

The alkyl groups in the definitions of the substituents can be straight-chain or branched and are, for example, methyl, ethyl, n-propyl, iso-propyl, n-butyl, sec-butyl, iso-butyl, tert-butyl, pentyl, hexyl, heptyl, octyl, nonyl, decyl, undecyl and dodecyl and their branched isomers. Alkoxy, alkenyl and alkynyl radicals are derived from the abovementioned alkyl radicals. The alkenyl and alkynyl groups can be mono- or polyunsaturated.

An alkylene group for example, —(CH$_2$)$_m$—, —(CH$_2$)$_{m1}$— or —(CH$_2$)$_o$— can be substituted by one or more methyl group; preferably, such alkylene groups are in each case unsubstituted. The same also applies to the —C(O)O(CH$_2$)$_{n20}$— and —S(O)$_{n21}$(CH$_2$)$_{n22}$— group and to all $C_3$–$C_6$-cycloalkyl-, $C_3$–$C_5$oxacycloalkyl-, $C_3$–$C_5$thiacycloalkyl-, $C_3$–$C_4$dioxacycloalkyl-, $C_3$–$C_4$-dithiacycloalkyl-, $C_3$–$C_4$oxathiacycloalkyl-containing groups.

Halogen is, as a rule, fluorine, chlorine, bromine or iodine. This also applies analogously to halogen in conjunction with other meanings such as haloalkyl or halophenyl.

Haloalkyl groups with a chain length of 1 up to 6 carbon atoms are, for example, fluoromethyl, difluoromethyl, trifluoromethyl, chloromethyl, dichloromethyl, trichloromethyl, 2,2,2-trifluoroethyl, 1-fluoroethyl, 2-fluoroethyl, 2-chloroethyl, 2-fluoroprop-2-yl, pentafluoroethyl, 1,1-difluoro-2,2,2-trichloroethyl, 2,2,3,3-tetrafluoroethyl and 2,2,2-trichloroethyl, pentafluoroethyl, heptafluoro-n-propyl, perfluoro-n-hexyl; haloalkyl groups in the meanings $R_2$, $R_3$ and, in particular, $R_5$ are preferably trichloromethyl, fluoromethyl, dichlorofluoromethyl, difluorochloromethyl, difluoromethyl, trifluoromethyl, pentafluoroethyl or heptafluoro-n-propyl.

Suitable as haloalkyl are monohalogenated or polyhalogenated alkenyl groups, where halogen is fluorine, chlorine, bromine and iodine, and in particular fluorine and chlorine, for example 1-chlorovinyl, 2-chlorovinyl, 2,2-difluorovinyl, 2,2-difluoroprop-1-en-2-yl, 2,2-dichlorovinyl, 3-fluoroprop-1-enyl, chloroprop-1-en-1-yl, 3-bromoprop-1-en-1-yl, 2,3, 3-trifluoroprop-2-en-1-yl, 2,3,3-trichloroprop-2-en-1-yl and 4,4,4-trifluorobut-2-en-1-yl. Preferred amongst the monohalogenated, dihalogenated or trihalogenated $C_2$–$C_6$alkenyl groups are those which have a chain length of 2 to 5 carbon atoms.

Suitable as haloalkynyl are, for example, monohalogenated or polyhalogenated alkynyl groups, where halogen is bromine, iodine and, in particular, fluorine and chlorine, for example 3-fluoropropynyl, 3-chloropropynyl, 3-bromopropynyl, 3,3,3-trifluoropropynyl and 4,4,4-trifluorobut-2-yn-1-yl. Preferred amongst the monohalogenated or polyhalogenated alkynyl groups are those which have a chain length of 2 to 5 carbon atoms.

A monohalogenated or polyhalogenated $C_3$–$C_6$cycloalkyl group is, for example, the 2,2-dichlorocyclopropyl, 2,2-dibromocyclopropyl, 2,2,3,3-tetrafluorocyclobutyl or 2,2-difluoro-3,3-dichlorocyclobutyl group.

Alkoxy groups preferably have a chain length of 1 to 6 carbon atoms. Alkoxy is, for example, methoxy, ethoxy, propoxy, i-propoxy, n-butoxy, iso-butoxy, sec-butoxy and tert-butoxy and the pentyloxy and hexyloxy isomers; preferably methoxy and ethoxy. Alkylcarbonyl is preferably acetyl or propionyl. Alkoxycarbonyl is, for example, methoxycarbonyl, ethoxycarbonyl, propoxycarbonyl, isopropoxycarbonyl, n-butoxycarbonyl, iso-butoxycarbonyl, sec-butoxycarbonyl or tert-butoxycarbonyl; preferably methoxycarbonyl, ethoxycarbonyl or tert-butoxycarbonyl. Haloalkoxy groups preferably have a chain length of 1 to 6 carbon atoms.

Haloalkoxy is, for example, fluoromethoxy, difluoromethoxy, trifluoromethoxy, 2,2,2-trifluoro-ethoxy, 1,1,2,2-tetrafluoroethoxy, 1-fluoroethoxy, 2-fluoroethoxy, 2-chloroethoxy, 2,2-difluoroethoxy and 2,2,2-trichloroethoxy; preferably fluoromethoxy, difluoromethoxy, 2-chloroethoxy and trifluoromethoxy.

Alkylthio groups preferably have a chain length of 1 to 8 carbon atoms. Alkylthio is, for example, methylthio, ethylthio, propylthio, iso-propylthio, n-butylthio, iso-butylthio, sec-butylthio or tert-butylthio, preferably methylthio and ethylthio. Alkylsulfinyl is, for example, methylsulfinyl, ethylsulfinyl, propylsulfinyl, iso-propylsulfinyl, n-butylsulfinyl, iso-butylsulfinyl, sec-butylsulfinyl, tert-butylsulfinyl; preferably methylsulfinyl and ethylsulfinyl.

Alkylsulfonyl is, for example, methylsulfonyl, ethylsulfonyl, propylsulfonyl, iso-propylsulfonyl, n-butylsulfonyl, iso-butylsulfonyl, sec-butylsulfonyl or tert-butylsulfonyl; preferably methylsulfonyl or ethylsulfonyl.

Alkylamino is, for example, methylamino, ethylamino, n-propylamino, iso-propylamino or the butylamino isomers. Dialkylamino is, for example, dimethylamino, methylethylamino, diethylamino, n-propylmethylamino, di-butylamino and di-iso-propylamino. Preferred are alkylamino groups having a chain length of 1 to 4 carbon atoms. Alkoxyalkyl groups preferably have 1 to 6 carbon atoms. Alkoxyalkyl is, for example, methoxymethyl, methoxyethyl, ethoxymethyl, ethoxyethyl, n-propoxymethyl, n-propoxyethyl, iso-propoxymethyl or isopropoxyethyl. Alkylthioalkyl groups preferably have 1 to 6 carbon atoms. Alkylthioalkyl is, for example, methylthiomethyl, methylthioethyl, ethylthiomethyl, ethylthioethyl, n-propylthiomethyl, n-propylthioethyl, iso-propylthiomethyl, iso-propylthioethyl, butylthiomethyl, butylthioethyl or butylthiobutyl.

Phenyl, also as part of a substituent such as phenoxy, benzyl, benzyloxy, benzoyl, phenylthio, phenylalkyl, phenoxyalkyl or tosyl can be in monosubstituted or polysubstituted form. In this case, the substituents can be in any of the ortho, meta and/or para position(s).

Allenyl is, for example, $CH_2=C=CH_2$ $CH_2=CH—CH_2—CH=CH_2$, $CH_2=CH—CH_2—CH_2—CH=CH_2$ or $CH_2=CH—CH_2—CH=CH—CH_3$.

The invention also extends to the salts $M^+$ which the compounds of the formula 1, in particular those compounds of the formula I in which $R_{10}$ is $O^-M^+$, can form, preferably with amines, alkali metal bases, alkaline earth metal bases or quaternary ammonium bases The following must be emphasized as salt formers amongst the alkali metal bases and alkaline earth metal bases: the hydroxides of lithium, sodium, potassium, magnesium or calcium, in particular those of sodium or potassium. Examples of amines which are suitable for ammonium salt formation are not only ammonia, but also primary, secondary and tertiary $C_1-C_{18}$alkylamines, $C_1-C_4$hydroxyalkylamines and $C_2-C_4$alkoxyalkylamines, for example methylamine, ethylamine, n-propylamine, iso-propylamine, the four butylamine isomers, n-amylamine, iso-amylamine, hexylamine, heptylamine, octylamine, nonylamine, decylamine, pentadecylamine, hexadecylamine, heptadecylamine, octadecylamine, methylethylamine, methylisopropylamine, methylhexylamine, methyinonylamine, methyl- pentadecylamine, methyloctadecylamine, ethylbutylamine, ethylheptylamine, ethyloctylamine, hexylheptylamine, hexyloctylamine, dimethylamine, diethylamine, di-n-propylamine, di-iso-propylamine, di-n-butylamine, di-n-amylamine, di-iso-amylamine, dihexylamine, diheptylamine, dioctylamine, ethanolamine, n-propanolamine, iso-propanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, tri-iso-propylamine, tri-n-butylamine, tri-iso-butylamine, tri-sec-butylamine, tri-n-amylamine, methoxyethylamine and ethoxyethylamine; heterocyclic amines for example, pyridine, quinoline, iso-quinoline, morpholine, piperidine, pyrrolidine, indoline, quinuclidine and azepine; primary arylamines for example anilines, methoxyanilines, ethoxyanilines, o-, m-, p-toluidines, phenylenediamines, naphthylamines and o-, m- and p-chloroanilines; but in particular triethylamine, iso-propylamine and di-iso-propylamine. Examples of quaternary ammonium bases which are suitable for salt formation are, for example, $[N(R_a\ R_b\ R_c\ R_d)]^+OH^-$, where $R_a$, $R_b$, $R_c$ and $R_d$ independently of one another are $C_1-C_4$alkyl. Other suitable tetraalkylammonium bases with other anions can be obtained, for example, by anion exchange reactions. $M^+$ preferably represents an ammonium salt, in particular $NH_4^+$, or an alkali metal, in particular potassium or sodium.

The compounds of the formula I can occur in various tautomeric forms, for example, if $R_{10}$ is hydroxyl, in the preferred formulation I' and I'''

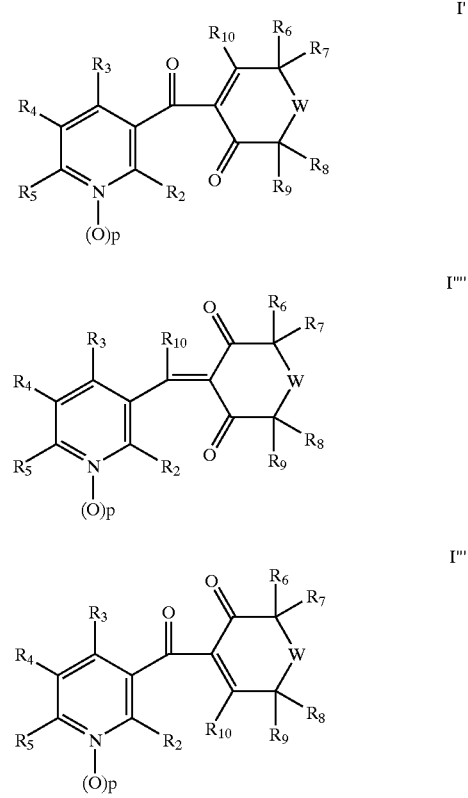

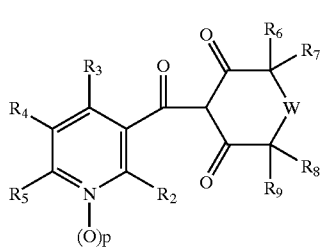

Preferred among the compounds of the formula I are those in which p is 0;

$R_5$ is $C_1$-$C_6$haloalkyl;

$R_2$ is hydrogen, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$-haloalkylsulfonyl, benzyl-S(O)$_{n1}$—, $C_1$-$C_6$alkylamino, $C_2$-$C_6$dialkylamino, $C_1$-$C_6$-alkylaminosulfonyl, $C_2$-$C_6$-dialkylaminosulfonyl, phenyl, phenoxy, phenylthio, phenylsulfinyl or phenylsulfonyl, it being possible for the phenyl group, in turn, to be substituted by $C_1$-$C_3$-alkyl, $C_1$-$C_3$haloalkyl, $C_1$-$C_3$alkoxy, $C_1$-$C_3$haloalkoxy, halogen, cyano or nitro, or is OS(O)$_{n2}$—R$_{21}$, N(R$_{23}$)—S(O)$_{n3}$—R$_{22}$, cyano, halogen, amino, $C_1$-$C_4$alkoxy-$C_1$-$C_4$alkyl, $C_1$-$C_4$alkyl-S(O)$_{n4}$—$C_1$-$C_4$alkyl, cyano-$C_1$-$C_4$alkyl or $C_1$-$C_4$alkoxy-$C_1$-$C_4$alkoxy;

$R_3$ is hydrogen, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_1$-$C_6$alkoxy, $C_1$-$C_6$haloalkoxy, $C_1$-$C_6$alkylithio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$-haloalkylsulfonyl, $C_1$-$C_6$alkylamino, $C_2$-$C_6$dialkylamino, $C_1$-$C_6$alkylaminosulfonyl, $C_2$-$C_6$-dialkylaminosulfonyl, phenyl, phenylthio, phenylsulfinyl, phenylsulfonyl or phenoxy, it being possible for phenyl, in turn, to be substituted by $C_1$-$C_3$alkyl, $C_1$-$C_3$haloalkyl, $C_1$-$C_3$alkoxy, $C_1$-$C_3$haloalkoxy, halogen, cyano or nitro, or is —N(R$_{23}$)—S(O)$_n$—R$_{22}$, cyano, halogen, amino, $C_1$-$C_4$alkoxy-$C_1$-$C_4$alkyl or $C_1$-$C_4$alkyl-S(O)$_n$—$C_1$-$C_4$alkyl;

$R_4$ is hydrogen, $C_1$-$C_6$alkyl, $C_1$-$C_4$alkoxy, $C_1$-$C_4$haloalkoxy, $C_1$-$C_4$alkylcarbonyloxy, alkylthio, $C_1$-$C_4$alkylsulfinyl, $C_1$-$C_4$alkylsulfonyl, $C_1$-$C_4$haloalkyl, formyl, cyano, halogen, phenyl or phenoxy, it being possible for phenyl, in turn, to be substituted by $C_1$-$C_3$alkyl, $C_1$-$C_3$haloalkyl, $C_1$-$C_3$alkoxy, $C_1$-$C_3$haloalkoxy, halogen, cyano or nitro;

or $R_4$ is a five- to ten-membered monocyclic or $R_3$-fused bicyclic ring system which can contain 1 to 4 hetero atoms selected from the group consisting of nitrogen, oxygen and sulfur, the ring system being bonded to the pyridine ring via a $C_1$-$C_4$alkylene group and it not being possible for the ring system to contain more than 2 oxygen atoms and not more than two sulfur atoms, and it being possible for the ring system itself to be mono-, di- or trisubstituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$alkynyloxy, $C_1$-$C_6$-Alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_4$-alkoxy-$C_1$-$C_2$alkylthio, $C_1$-$C_4$alkylcarbonyl-$C_1$-$C_2$alkylthio, $C_1$-$C_4$alkoxycarbonyl-$C_1$-$C_2$alkylthio, cyano-$C_1$-$C_4$alkylthio, $C_1$-$C_6$alkylsulfinyl, $C_1$-$C_6$haloalkylsulfinyl, $C_1$-$C_6$alkylsulfonyl, $C_1$-$C_6$-haloalkylsulfonyl, aminosulfonyl, $C_1$-$C_2$alkylaminosulfonyl, $C_2$-$C_4$dialkylaminosulfonyl, halogen, cyano, nitro, phenyl and benzylthio, it being possible for phenyl and benzylthio, in turn, to be substituted on the phenyl ring by $C_1$-$C_3$alkyl, $C_1$-$C_3$haloalkyl, $C_1$-$C_3$alkoxy, $C_1$-$C_3$-haloalkoxy, halogen, cyano or nitro, and where substituents on the nitrogen in the heterocyclic ring are other than halogen;

$R_{21}$ and $R_{22}$ independently of one another are $C_1$-$C_4$alkyl or $C_1$-$C_4$haloalkyl;

$R_{23}$, $R_{24}$ and $R_{25}$ independently of one another are hydrogen or $C_1$-$C_4$alkyl;

n, $n_1$, $n_2$, $n_3$ and $n_4$ independently of one another are 0, 1 or 2;

Q is $Q_1$

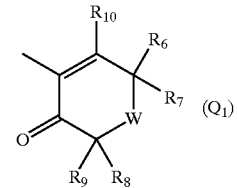

in which $R_6$, $R_7$, $R_8$ and $R_9$ independently of one another are hydrogen, $C_1$-$C_6$alkyl, $C_1$-$C_6$haloalkyl, $C_2$-$C_6$alkenyl, $C_2$-$C_6$alkynyl, $C_1$-$C_6$alkoxycarbonyl, $C_1$-$C_6$alkyl-S(O)$_{n17}$, $C_1$-$C_6$alkyl-NHS(O)$_2$, $C_1$-$C_6$alkylamino, di-($C_1$-$C_6$alkyl)amino, hydroxyl, $C_1$-$C_6$alkoxy, $C_3$-$C_6$alkenyloxy, $C_3$-$C_6$-alkynyloxy, hydroxy-$C_1$-$C_6$alkyl, $C_1$-$C_4$alkylsulfonyloxy-$C_1$-$C_6$alkyl, tosyloxy-$C_1$-$C_6$alkyl, halogen, cyano, nitro, phenyl or phenyl which is substituted by $C_1$-$C_4$alkyl, $C_1$-$C_4$haloalkyl, $C_1$-$C_4$alkoxy, $C_1$-$C_4$haloalkoxy, $C_1$-$C_4$alkylcarbonyl, $C_1$-$C_4$alkoxycarbonyl, amino, $C_1$-$C_4$-alkylamino, di-$C_1$-$C_4$alkylamino, $C_1$-$C_4$alkyl-S(O)$_{n18}$, $C_1$-$C_4$alkyl-S(O)$_2$O, $C_1$-$C_4$haloalkyl-S(O)$_{n5}$, $C_1$-$C_4$haloalkyl-S(O)$_2$O, $C_1$-$C_4$alkyl-S(O)$_2$NH, $C_1$-$C_4$alkyl-S(O)$_{n19}$N ($C_1$-$C_4$alkyl), halogen, nitro, COOH or cyano;

or adjacent $R_6$ and $R_7$ or $R_8$ and $R_9$ together are —(CH$_2$)$_m$—;

$n_5$ $n_{17}$, $n_{18}$ and $n_{19}$ independently of one another are 0, 1 or 2;

m is 2, 3, 4, 5, or 6;

W is oxygen, S(O)$_{n6}$, —CR$_{11}$, R$_{12}$—, —C(O)— or —NR$_{13}$—;

$n_6$ is 0, 1 or 2;

$R_{11}$ is hydrogen, $C_1$-$C_4$alkyl, $C_1$-$C_4$haloalkyl, $C_1$-$C_4$alkoxy-$C_1$-$C_4$alkyl, $C_1$-$C_4$alkylthio-$C_1$-$C_4$alkyl, $C_1$-$C_4$alkylcarbonyloxy-$C_1$-$C_4$alkyl, $C_1$-$C_4$alkylsulfonyloxy-$C_1$-$C_4$alkyl, tosyloxy-$C_1$-$C_4$alkyl, di-($C_1$-$C_3$alkoxyalkyl)methyl, di- ($C_1$–$C_3$alkylthioalkyl)methyl, ($C_1$–$C_3$alkoxyalkyl)-($C_1$–$C_3$alkylthioalkyl)methyl, $C_3$–$C_5$oxacycloalkyl, $C_3$–$C_5$thiacycloalkyl, $C_3$–$C_4$dioxacycloalkyl, $C_3$–$C_4$-dithiacycloalkyl, $C_3$–$C_4$oxathiacycloalkyl, formyl, $C_1$–$C_4$alkoxycarbonyl or phenyl which, in turn, can be substituted by $C_1$–$C_4$alkyl, $C_1$–$C_4$haloalkyl, $C_1$–$C_4$alkoxy, $C_1$–$C_4$haloalkoxy, $C_1$–$C_4$-alkylcarbonyl, $C_1$–$C_4$alkoxycarbonyl, amino, $C_1$–$C_4$alkylamino, di-$C_1$–$C_4$alkylamino, $C_1$–$C_4$alkyl-S(O)$_{n21}$, $C_1$–$C_4$alkyl-S(O)$_2$O, $C_1$–$C_4$haloalkyl-S(O)$_7$, $C_1$–$C_4$haloalkyl-S(O)$_2$O, $C_1$–$C_4$alkyl-S(O)$_2$NH, $C_1$–$C_4$alkyl-S(O)$_{n20}$N($C_1$–$C_4$alkyl), halogen, nitro, COOH or cyano;

$n_7$, $n_{20}$ and $n_{21}$ independently of one another are 0, 1 or 2;

or $R_{12}$ together with $R_9$ is a group —(CH$_2$)$_o$—;

o is 1, 2, 3, 4 or 5;

$R_{12}$ is hydrogen, $C_1$–$C_4$alkyl or $C_1$–$C_4$haloalkyl; or $R_{12}$ together with $R_{11}$ is a group —(CH$_2$)$_{m1}$;

$m_1$ is 2, 3, 4, 5, or 6;

$R_{10}$ is hydroxyl, O$^-$M$^+$, halogen, $C_1$–$C_{12}$alkoxy, $C_1$–$C_{12}$alkylcarbonyloxy, $C_2$–$C_4$-alkenylcarbonyloxy, $C_3$–$C_6$cycloalkylcarbonyloxy, $C_1$–$C_{12}$alkoxycarbonyloxy, $C_1$–$C_{12}$-alkylcarbonyloxy, $R_{23}R_{24}$N—C(O)O, $C_1$–$C_{12}$alkylS(O)$_{n8}$—, $C_1$–$C_4$haloalkyl-S(O)$_{n9}$—, $C_2$–$C_{12}$-alkenylS(O)$_{n10}$—, $C_2$–$C_{12}$haloalkenylS(O)$_{n11}$—, $C_2$–$C_{12}$alkynylS(O)$_{n12}$—; benzyloxy, phenoxy, phenylthio, phenylsulfinyl or phenylsulfonyl, where the phenyl group, in turn, can be substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, $C_1$–$C_4$alkylamino, di-$C_1$–$C_4$alkylamino, $C_1$–$C_4$alkyl-S(O)$_{n13}$, $C_1$–$C_4$alkyl-S(O)$_2$O, $C_1$–$C_4$haloalkyl-S(O)$_{n14}$, $C_1$–$C_4$haloalkyl-S(O)$_2$O, $C_1$–$C_4$alkyl-S(O)$_2$NH, $C_1$–$C_4$alkyl-S(O)$_2$N($C_1$–$C_4$alkyl), halogen, nitro or cyano, or is $C_1$–$C_4$alkyl-S(O)$_2$O, phenyl-S(O)$_2$O, phenyl-S(O)$_2$O, ($C_{1-4}$alkoxy)$_2$P(O)O, $C_1$–$C_4$alkyl($C_1$–$C_4$alkoxy)P(O)O, or H($C_1$–$C_4$alkoxy)P(O)O;

$n_8$, $n_9$, $n_{10}$, $n_{11}$, $n_{12}$, $n_{13}$ and no independently of one another are 0, 1 or 2;

$R_{13}$ is hydrogen, $C_1$–$C_4$alkyl, $C_1$–$C_4$alkoxycarbonyl or phenyl which, in turn, can be substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, $C_1$–$C_4$alkylamino, di-$C_1$–$C_4$alkylamino, $C_1$–$C_4$alkyl-S(O)$_{n15}$, $C_1$–$C_4$alkyl-S(O)$_2$O, $C_1$–$C_4$haloalkyl-S(O)$_{n16}$, $C_1$–$C_4$haloalkyl-S(O)$_2$O, $C_1$–$C_4$alkyl-S(O)$_2$NH, $C_1$–$C_4$alkyl-S(O)$_2$N($C_1$–$C_4$alkyl), halogen, nitro or cyano;

$n_{15}$ and $n_{16}$ independently of one another are 0, 1 or 2; and the agrochemically tolerated salts M$^+$ and all stereoisomers and tautomers of the compounds of the formula I.

In a preferred group of compounds of the formula I, $R_{10}$ is halogen, thiocyanato, $C_1$–$C_{12}$alkylthio, $C_1$–$C_{12}$alkylsulfinyl, $C_1$–$C_{12}$alkylsulfonyl, $C_1$–$C_{12}$haloalkylthio, $C_1$–$C_{12}$-haloalkylsulfinyl, $C_1$–$C_{12}$haloalkylsulfonyl, $C_1$–$C_{12}$alkenylthio, $C_2$–$C_{12}$alkenylsulfinyl, $C_2$–$C_{12}$-alkenylsulfonyl, $C_2$–$C_{12}$haloalkenylthio, $C_2$–$C_{12}$haloalkenylsulfinyl, $C_2$–$C_{12}$-haloalkenylsulfinyl, $C_2$–$C_{12}$alkynylthio, $C_2$–$C_{12}$alkynylsulfinyl, $C_2$–$C_{12}$alkynylsulfonyl, $C_1$–$C_4$alkoxycarbonyl-$C_1$–$C_2$alkylthio, $C_1$–$C_4$alkoxycarbonyl-$C_1$–$C_2$alkylsulfinyl, $C_1$–$C_4$alkoxycarbonyl-$C_1$–$C_2$alkylsulfonyl, $C_1$–$C_8$alkyl-S(O)$_2$NH, $C_1$–$C_8$haloalkyl-S(O)$_2$NH, $C_1$–$C_8$alkyl-S(O)$_2$O, $C_1$–$C_{18}$alkylcarbonyloxy, $C_2$–$C_{18}$alkenylcarbonyloxy, $C_3$–$C_6$cycloalkylcarbonyloxy, $C_1$–$C_{12}$alkoxycarbonyloxy, $C_1$–$C_{12}$-alkylthiocarbonyloxy, $R_{16}R_{17}$NC(O)O—, $R_{16}R_{17}$NC(S)O—, benzylthio, benzylsulfinyl, benzylsulfonyl, phenylthio, phenylsulfinyl, phenylsulfonyl, phenylsulfonyloxy or benzoyloxy, it being possible for the phenyl groups, in turn, to be substituted as indicated in claim 1; or is a group Ar$_1$-thio, Ar$_1$-sulfinyl, Ar$_1$-sulfonyl in which Ar$_1$ is a five- or six-membered monocyclic ring system which can be aromatic or partially saturated and can contain 1 to 2 hetero atoms selected from the group consisting of nitrogen, oxygen and sulfur and which, in turn, can be substituted as indicated in claim 1; or is thienylcarbonyloxy or furylcarbonyloxy, it being possible for these, in turn, to be substituted by methyl or halogen, or pyridylcarbonyloxy which, in turn, can be substituted as indicated in claim 1.

In preferred compounds of the formula I, furthermore, $R_{10}$ is hydroxyl or O$^-$M$^+$.

Other compounds of the formula I which must be emphasized are those in which W is oxygen, —CR$_{11}$R$_{12}$— or —C(O)—, where, in particular when W is —CR$_{11}$R$_{12}$—, a) $R_6$ is hydrogen, methyl, ethyl, cyano, methoxycarbonyl, ethoxycarbonyl, methylthio, methylsulfinyl, methylsulfonyl or methoxy; and $R_7$, $R_8$, $R_9$, $R_{11}$ and $R_{12}$ independently of one another are hydrogen, $C_1$–$C_4$alkyl, $C_1$–$C_3$haloalkyl, $C_2$–$C_3$alkenyl or $C_2$–$C_3$alkynyl, or b) adjacent $R_6$ and $R_7$ and/or $R_8$ and $R_9$ together are —(CH$_2$)$_m$—, —C(O)O(CH$_2$)$_2$- or S(O)$_{n21}$(CH$_2$)$_3$—; or c) $R_6$ is hydrogen, methyl, ethyl, methoxycarbonyl, ethoxycarbonyl, methylthio, methylsulfinyl, methylsulfonyl or methoxy and $R_{12}$ together with $R_9$ is —(CH$_2$)$_o$—.

Furthermore, preferred groups of compounds of the formula I are those in which

W is oxygen and $R_6$, $R_7$, $R_8$ and $R_9$ independently of one another are hydrogen or $C_1$–$C_3$alkyl; or W is —C(O)— and $R_6$, $R_7$, $R_8$ and $R_9$ independently of one another are $C_1$–$C_3$alkyl; or $R_2$ is hydrogen and $R_3$ is methyl; or $R_2$ is methyl, ethyl, n-propyl, i-propyl, vinyl, methoxymethyl, methoxycarbonyloxymethyl, ethoxycarbonyloxymethyl, acetoxymethyl, propionyloxymethyl, chloromethyl, bromomethyl, fluoromethyl, difluoromethyl, trifluoromethyl or cyanomethyl.

Other compounds of the formula I which must be emphasized are those in which $R_4$ is hydrogen or methyl or $R_5$ is trifluoromethyl, difluorochloromethyl, pentafluoroethyl, heptafluoropropyl or difluoromethyl.

In a further preferred group of compounds of the formula I, $R_3$ is hydrogen, $R_2$ is $C_1$–$C_4$alkyl, $C_1$–$C_3$haloalkyl, cyclopropyl, $C_2$–$C_3$alkenyl, $C_2$–$C_3$haloalkenyl, $C_2$–$C_3$alkynyl, allenyl, $C_1$–$C_2$-alkoxy-$C_1$–$C_2$alkyl, $C_1$–$C_2$alkylthio-$C_1$–$C_2$alkyl, cyano-$C_1$–$C_2$alkyl, $C_1$–$C_2$alkoxycarbonyl-$C_1$–$C_2$-alkyl, $C_1$–$C_4$alkylcarbonyloxy-$C_1$–$C_2$alkyl, $C_1$–$C_3$alkoxy, $C_1$–$C_3$haloalkoxy, allyloxy, propargyloxy, $C_1$–$C_3$alkylthio, $C_1$–$C_3$alkylsulfinyl or cyano.

The compounds of the formula I in which Q is a group Q$_1$ can be prepared using processes which are known per se, for example those described in EP-A-0 353 187 and EP-A-0 316 491, for example either by a) reacting a compound of the formula III

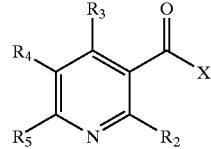

(III)

in which $R_2$, $R_3$, $R_4$ and $R_5$ have the meaning given under formula I and X is a leaving group, for example halogen or cyano, with a compound of the formula II

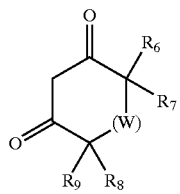

(II)

in which $R_6$, $R_7$, $R_8$, $R_9$ and W have the meaning given under formula I in the presence of a base and in an inert organic solvent to give the compound of the formula IV

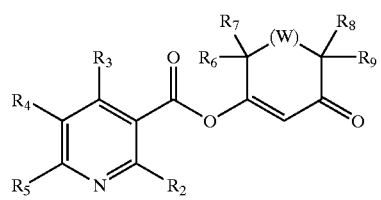

(IV)

and subsequently isomerizing the latter, for example in the presence of a base and a catalytic amount of dimethylaminopyridine (DMAP) or a cyanide source; or b) reacting a compound of the formula XVI

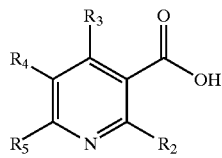

(XVI)

in which $R_2$, $R_3$, $R_4$ and $R_5$ have the meaning given under formula I with compounds of the formula II

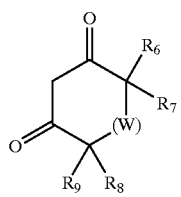

(II)

in which $R_6$, $R_7$, $R_8$, $R_9$ and W have the meaning given under formula I in an inert organic solvent in the presence of a base and a coupling agent to give the compound of the formula IV

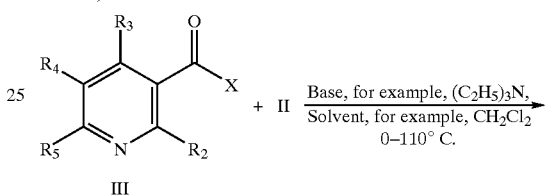

(IV)

and subsequently isomerizing the latter, for example as described under route a). The preparation of the compounds of the formula I is illustrated in greater detail in reaction scheme 1 below.

Reaction scheme 1

Route a):

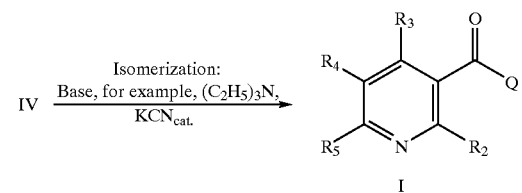

Route b):

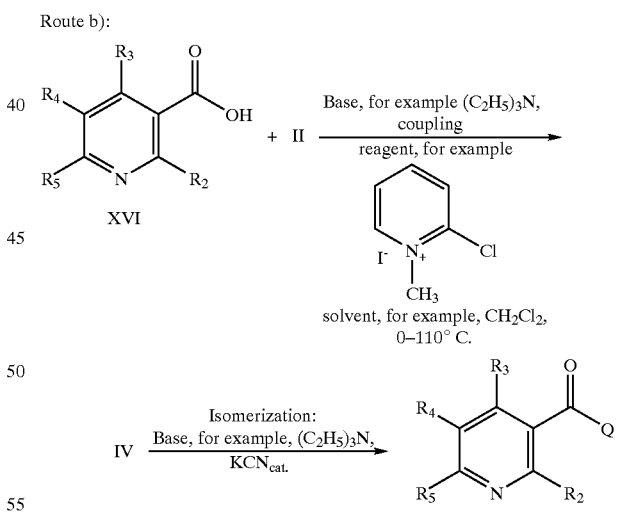

The compounds of the formula I with the group $Q_1$ in which $R_{10}$ is hydroxyl can preferably be prepared in accordance with this reaction scheme. The starting material for the preparation of the compounds of the formula I in which Q is the group $Q_1$ and $R_{10}$ is hydroxyl is, in accordance with reaction scheme 1, route a), the carboxylic acid derivatives of the formula III in which X is a leaving group for example halogen, for example iodine, bromine and, in particular chlorine N-oxyphthalimide or N,O-dimethylhydroxylamino or part of an activated ester, for example

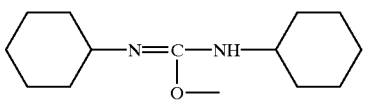

(formed from dicyclohexylcarbodiimide (DCC) and the corresponding carboxylic acid) or

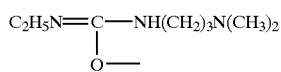

(formed from N-ethyl-N'-(3-dimethylaminopropyl) carbodiimide (EDC) and the corresponding carboxylic acid). These are reacted with the dione derivatives of the formula II in an inert organic solvent, for example a halogenated hydrocarbon, for example dichloromethane, a nitrile, for example acetonitrile, or an aromatic hydrocarbon, for example toluene, and in the presence of a base, for example an alkylamine, preferably triethylamine, an aromatic amine, for example pyridine or 4-dimethylaminopyridine (DMAP) to give the isomeric enol ethers of the formula IV. This esterification is successfully carried out at temperatures from 0° C. to 110° C.

The isomerization of the ester derivatives of the formula IV to give the dione derivatives of the formula I (in which $R_{10}$ is OH) can be carried out, for example, in analogy to EP-A-0 353 187 or EP-A-0 316 491 in the presence of a base, for example an alkylamine, for example triethylamine, a carbonate, for example potassium carbonate, and a catalytic amount of DMAP or a catalytic amount of a cyanide source, for example acetone cyanohydrin or potassium cyanide. Both reaction steps can be carried out in situ without isolation of the intermediates IV, in particular when using a cyanide compound of the formula III (X=cyano), or in the presence of a catalytic amount of acetone cyanohydrin or potassium cyanide.

In accordance with reaction scheme 1, route b), the desired diones of the formula I (in which $R_{10}$ is hydroxyl) can be obtained, for example, analogously to Chem. Lett. 1975, 1045 by esterifying the carboxylic acids of the formula XVI with the dione derivatives of the formula II in an inert solvent, for example a halogenated hydrocarbon, e.g. dichloromethane, a nitrite, e.g. acetonitrile or an aromatic hydrocarbon, e.g. toluene, in the presence of a base, for example an alkylamine, e.g. triethylamine, and a coupling agent, for example 2-chloro-1-methylpyridinium iodide. Depending on the solvent used, this esterification is successfully carried out at temperatures from 0° C. to 110° C. and first yields, as described under route a), the isomeric ester of the formula IV which can be isomerized as described under route a), for example in the presence of a base and a catalytic amount of DMAP, or a cyanide source, to give the desired dione derivatives of the formula I ($R_{10}$=hydroxyl).

The activated carboxylic acid derivatives of the formula III in reaction scheme I (route a) in which X is a leaving group, for example halogen, e.g. bromine, iodine or, in particular, chlorine, can be prepared by known standard methods, for example as described by C. Ferri "Reaktionen der organischen Synthese" ["Reactions in organic synthesis"], Georg Thieme Verlag, Stuttgart, 1978, page 460 et seq. This is shown in the reaction scheme 2 which follows.

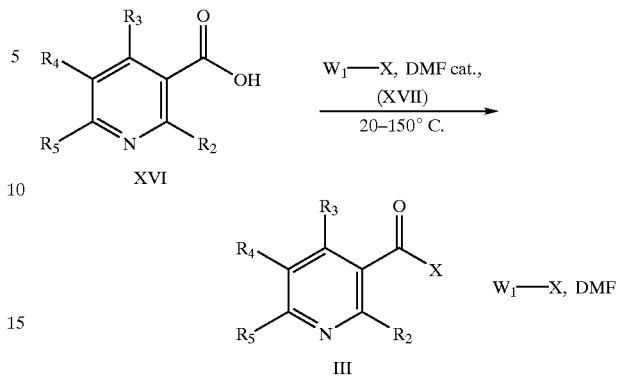

Reaction scheme 2

In accordance with reaction scheme 2, the compounds of the formula III in which X has the abovementioned meaning are prepared, for example, by using a halogenating agent, for example thionyl halides, e.g. thionyl chloride or thionyl bromide; phosphorus halides or phosphorus oxyhalides, e.g. phosphorus pentachloride or phosphorus oxychloride, or phosphorus pentabromide or phosphoryl bromide; or oxalyl halides, for example oxalyl chloride, or by employing a reagent for forming activated esters, for example N,N'-dicyclohexylcarbodiimide (DCC) or N-ethyl-N'-(3-dimethylaminopropyl)carbodiimide (EDC), of the formula XVII. Examples of meanings of X for the compound of the formula XVII as halogenating agent is a leaving group, for example halogen, e.g. fluorine, bromine or iodine and, in particular, chlorine, and $W_1$ is, for example, $PCl_2$, SOCl, SOBr or ClCOCO.

The reaction is preferably carried out in an inert organic solvent, for example in aliphatic, halogenated aliphatic, aromatic or halogenated aromatic hydrocarbons, e.g. n-hexane, benzene, toluene, xylenes, dichloromethane, 1,2-dichloroethane or chlorobenzene, at reaction temperatures in the range of −20° C. to the reflux temperature of the reaction mixture, preferably at 40–150° C., and in the presence of a catalytic amount of N,N-dimethylformamide. Such reactions are generally known, and various variations with regard to the leaving group X are described in the literature.

Compounds of the formula I in which $R_{10}$ is other than hydroxyl or halogen can be prepared by conversion methods which are generally known from the literature, for example by acylation or carbamoylation methods using appropriate acid chlorides in the presence of a suitable base, starting from compounds in which $R_{10}$ is hydroxyl, or can be prepared by nucleophilic substitution reactions on chlorides of the formula I in which $R_{10}$ is halogen, which can also be obtained by known methods by reaction with a chlorinating agent such as phosgene, thionyl chloride or oxalyl chloride. In this case, examples of compounds which are employed are suitably substituted amines, or, directly, hydroxylamines, or alkylsulfonamides, mercaptans, thiophenols, phenols, $Ar_5$—$NH_2$ or $Ar_1$—SH, in the presence of a base, for example 5-ethyl-2-methylpyridine, diisopropylethylamine, triethylamine, sodium bicarbonate, sodium acetate or potassium carbonate.

Compounds of the formula I in which $R_{10}$ contains thio groups can be oxidized in analogy to known standard methods, for example using peracids, e.g. metachloroperbenzoic acid (m-CPBA) or peracetic acid, to give the corresponding sulfones and sulfoxides of the formula I. The degree of oxidation on the sulfur atom (SO— or $SO_2$—) can be controlled by the amount of oxidant.

Also, the resulting derivatives of the formula I in which $R_{10}$ is other than hydroxyl can exist in various isomeric forms which, if appropriate, can be isolated in pure form. The invention therefore also extends to all of these stereoisomeric forms. Examples of these isomeric forms are the formulae I*, I and I* below in which Q is the group $Q_1$ (see also note and scheme on page 10 above).

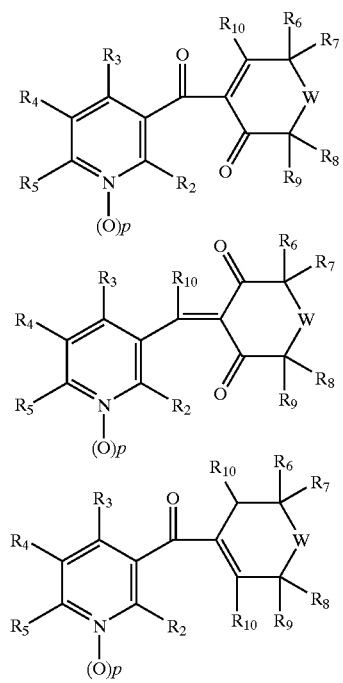

Furthermore, the skilled worker knows in which sequence certain reactions are expediently carried out to avoid any side reactions. Unless a directed synthesis for isolating pure isomers is carried out, the product may be obtained as a mixture of two or more isomers. The isomers can be resolved by methods known per se.

Compounds of the formula I in which n is 1, i.e. the corresponding N-oxides of the formula I, can be synthesized by reacting a compound of the formula I in which n is 0 with a suitable oxidant, for example with the $H_2O_2$-urea adduct in the presence of an acid anhydride, e.g. trifluoroacetic anhydride.

Compounds of the formula I in which R in the ortho-position relative to the pyridine nitrogen is 1-chloro-$C_1$–$C_2$alkyl, 1-hydroxy-$C_1$–$C_2$alkyl, 1-($C_1$–$C_6$alkyl-carbonyloxy)-$C_1$–$C_2$alkyl, 1-benzoyloxy-$C_1$–$C_2$alkyl, 1-($C_1$–$C_4$alkoxycarbonyloxy)-$C_1$–$C_2$alkyl, 1-($C_1$–$C_4$alkylthio)-$C_1$–$C_2$-alkyl, 1-($C_1$–$C_4$alkylsulfinyl)-$C_1$–$C_2$alkyl, 1-($C_1$–$C_4$alkylsulfonyl)-$C_1$–$C_2$alkyl, 1-thiocyanato-$C_1$–$C_2$alkyl, 1-cyano-$C_1$–$C_2$alkyl, can also be prepared by, for example, heating an N-oxide of the formula I under known reaction conditions, for example in the presence of tosyl chloride (see, for example, Parham, W. E.; Sloan, K. B.; Reddy, K. R.; Olson, P. E.; *J Org Chem* 1973, 38, 927) or in the presence of an acid anhydride (see, for example, Konno, K.; Hashimoto, K.; Shirahama, H.; Matsumoto, T.; *Heterocycles* 1986, 24, 2169) and, if appropriate, subsequently further reacting the product. These reaction sequences may be demonstrated with reference to the following example:

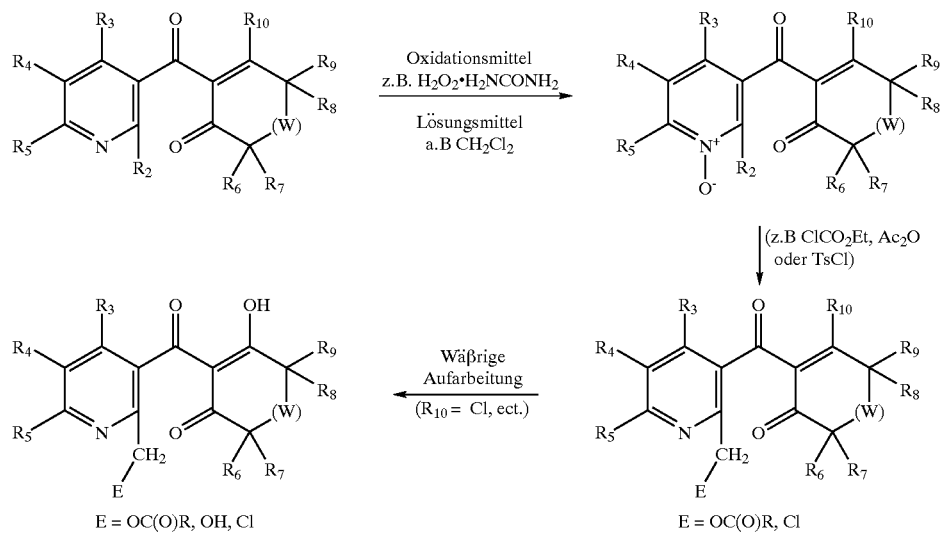

All other compounds from within the scope of the formula I can be readily prepared taking into consideration the chemical properties of the pyridyl or Q moiety.

The end products of the formula I can be isolated in the customary manner by concentration or by evaporating the solvent and purified by recrystallization or trituration of the solid residue in solvents in which they are not readily soluble, such as ethers, aromatic hydrocarbons or chlorinated hydrocarbons, by distillation or by means of column chromatography and a suitable eluent.

Compounds of the formula I in which R in the ortho-position relative to the pyridine nitrogen, in particular 1-bromo-$C_1$–$C_2$alkyl, 1-chloro-$C_1$–$C_2$alkyl, 1-fluoro-$C_1$–$C_2$alkyl, 1,1-dibromomethyl, 1,1dichloromethyl, formyl, 1-($C_1$–$C_4$alkylthio)-$C_1$–$C_2$alkyl, 1-($C_1$–$C_4$alkylsulfinyl)-$C_1$–$C_2$alkyl, 1-($C_1$–$C_4$alkylsulfonyl)-$C_1$–$C_2$alkyl, 1-thiocyanato-$C_1$–$C_2$alkyl or 1-cyano-$C_1$–$C_2$alkyl, can also be prepared, for example, by oxidizing a compound of the formula I in which $R_{10}$ is, in particular, chlorine, $C_1$–$C_4$alkoxycarbonyloxy or benzoylcarbonyloxy under known halogenation conditions, for example with N-bromosuccinimide or N-chlorosuccinimide in the presence of light and a free-radical initiator, for example benzoyl peroxide, to give the 1-bromo or 1-chloro, 1,1-dibromo or 1,1-dichloro compound, and subsequently refunctionalizing the latter to give the corresponding derivatives. Again, these reaction sequences may be demonstrated with reference to the example below.

is $C_1$–$C_6$alkyl with a suitable base, for example lithium diisopropylamide or n-butyllithium, at temperatures between −100 and −20° C. (preferably −70 and −50° C.) in an inert solvent (for example tetrahydrofuran) to give the corresponding dianion. The skilled worker knows how such carbanions can be converted by means of electrophilic substitution, for example with a chloroformic ester. This

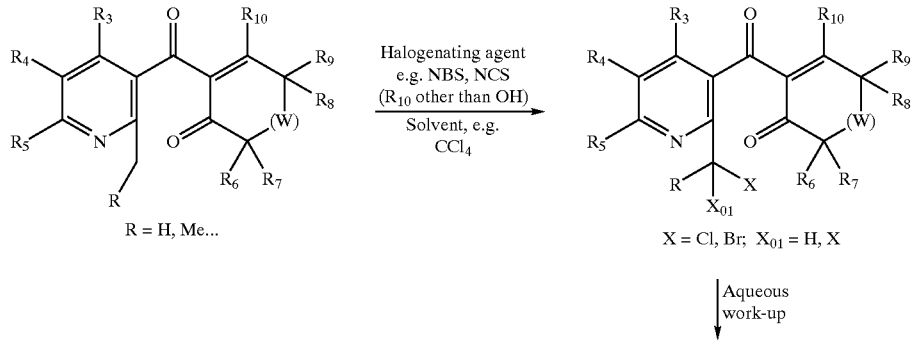

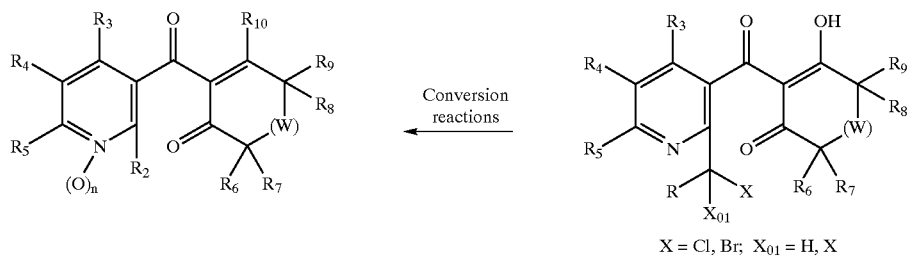

Compounds of the formula I can also be synthesized by reacting a compound of the formula I in which p is 0 and $R_2$ is $C_1$–$C_6$alkyl with a suitable base, for example lithium reaction sequence may be demonstrated with reference to the following example:

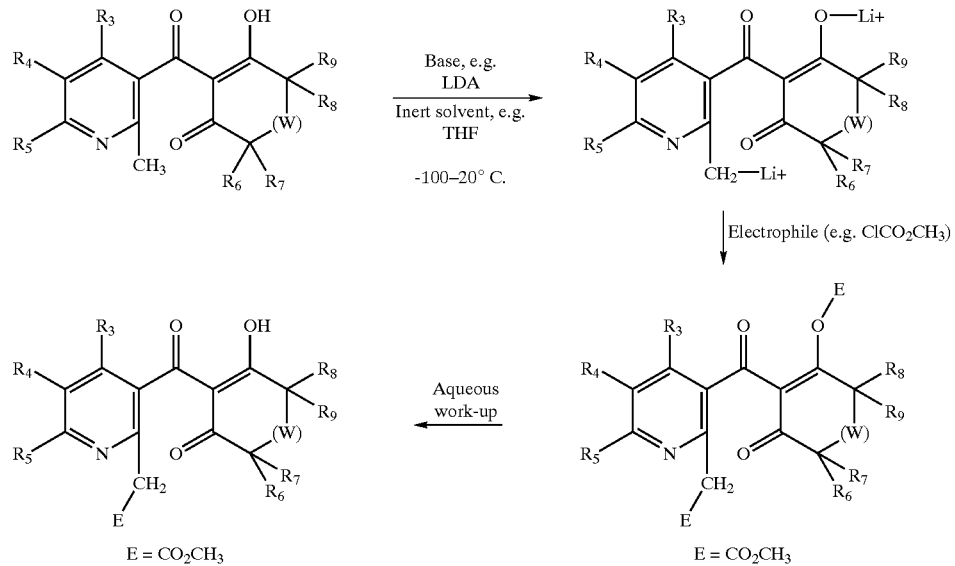

Other compounds from within the scope of the formula I can be prepared with suitable electrophiles taking into consideration the chemical properties of the pyridyl or Q moiety.

The compounds of the formula IIIa

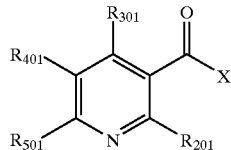

in which $R_{501}$ is $C_1$–$C_6$haloalkyl;

$R_{301}$ is hydrogen;

$R_{401}$ is hydrogen or $C_1$–$C_6$alkyl; and $R_{201}$ is $C_1$–$C_6$alkyl, $C_1$–$C_6$haloalkyl-$C_1$–$C_4$alkyl, $C_2$–$C_6$alkenyl, $C_2$–$C_6$haloalkenyl, or $C_1$–$C_2$-alkoxycarbonyl- or phenyl-substituted vinyl, $C_2$–$C_6$alkynyl or $C_2$–$C_6$haloalkynyl; or trimethylsilyl-, hydroxyl-, $G_1$–$C_2$alkoxy-, $C_1$–$C_2$alkoxycarbonyl- or phenyl-substituted ethynyl or $C_3$–$C_6$allenyl; or $C_3$–$C_6$cycloalkyl, halogen-substituted $C_3$–$C_6$cycloalkyl, $C_1$–$C_4$alkoxy-$C_1$–$C_4$-alkyl, $C_1$–$C_4$alkyl-$S(O)_{n4}$—$C_1$–$C_4$alkyl, cyano-$C_1$–$C_4$alkyl, $C_1$–$C_4$alkoxycarbonyl-$C_1$–$C_4$alkyl, $C_1$–$C_4$-thiocyanato, oxiranyl, $C_1$–$C_4$alkylamino-$C_1$–$C_4$alkyl, $C_1$–$C_4$dialkylamino-$C_1$–$C_4$alkyl, hydroxy-$C_1$–$C_4$alkyl, $C_1$–$C_{12}$alkylthiocarbonyl-$C_1$–$C_4$alkyl or formyl-$C_1$–$C_4$alkyl, or $R_{201}$ is a five- to ten-membered monocyclic or fused bicyclic ring system which can be aromatic or partially saturated and can contain 1 to 4 hetero atoms selected from the group consisting of nitrogen, oxygen and sulfur, the ring system being bonded to the pyridine ring via a $C_1$–$C_4$-alkylene, —CH=CH—, —C≡C—, —CH$_2$O—, —CH$_2$N ($C_1$–$C_4$alkyl)—, —CH$_2$S—, —CH$_2$SO— or —CH$_2$SO$_2$— group and it not being possible for each ring system to contain more than 2 oxygen atoms and more than two sulfur atoms, and it being possible for the ring system itself to be mono-, di- or trisubstituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_1$–$C_6$alkoxy, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$-alkynylthio, $C_2$–$C_5$alkoxyalkylthio, $C_3$–$C_5$acetylalkylthio, $C_3$–$C_6$alkoxycarbonylalkylthio, $C_2$–$C_4$-cyanoalkylthio, $C_1$–$C_6$alkylsulfinyl, $C_1$–$C_6$haloalkylsulfinyl, $C_1$–$C_6$alkylsulfonyl, $C_1$–$C_6$-haloalkylsulfonyl, aminosulfonyl, $C_1$–$C_2$alkylaminosulfonyl, di-($C_1$–$C_2$alkyl)aminosulfonyl, di-($C_1$–$C_4$alkyl)amino, halogen, cyano, nitro, phenyl and benzylthio, it being possible for phenyl and benzylthio, in turn, to be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or nitro, and where the substituents on the nitrogen in the heterocyclic ring are other than halogen; and X is halogen or cyano, are novel and were developed specifically for the preparation of the compounds of the formula I and are therefore a further subject of the present invention.

The compounds of the formula XVIa

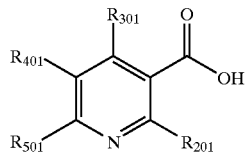

in which $R_{201}$, $R_{301}$, $R_{401}$ and $R_{501}$ have the abovementioned meaning, with the proviso that, if $R_{501}$ is trifluoromethyl and, simultaneously, $R_{301}$ and $R_{401}$ are hydrogen, then $R_{201}$ is other than $C_1$–$C_6$alkyl, are novel and therefore a further subject of the present invention.

The compounds of the formula $Q_1$ (or formula II) are known and can be prepared by met hods similar to those described, for example in J. Org. Chem. (1977), 42, 1163-9, Brit. UK Pat. Appl. GB 2205316, DE 3902818, GB 8706557, DE 4434987, WO 9213821 and Aust. J. Chem. (1976), 29(11), 2525–31, Chem. Commun. (1998), (16), 1691–1692.

The compounds of the formula XVI (or XVIa and XVIb) are synthesized by methods similar to known methods, for example as in Heterocycles, 46, 129 (1997) or Helvetica Chimica Acta 71, 596 (1988), and is characterized in that either a) a compound of the formula V

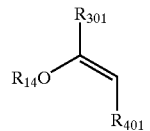

in which $R_{301}$ is hydrogen;

$R_{401}$ is hydrogen, $C_1$–$C_6$alkyl or phenyl, it being possible for phenyl, in turn, to be substituted by $C_1$–$C_3$alkyl, $C_1$–$C_3$haloalkyl, $C_1$–$C_3$alkoxy, $C_1$–$C_3$haloalkoxy, halogen, cyano or nitro;

or $R_{401}$ is a five- to ten-membered monocyclic or fused bicyclic ring system which can contain 1 to 4 hetero atoms selected from the group consisting of nitrogen, oxygen and sulfur and it not being possible for the ring system to contain more than 2 oxygen atoms and more than two sulfur atoms, and it being possible for the ring system itself to be mono, di- or trisubstituted by $C_1$–$C_6$alkyl, $C_1$–$C_6$haloalkyl, $C_2$–$C_6$alkenyl, $C_2$–$C_6$haloalkenyl, $C_2$–$C_6$alkynyl, $C_2$–$C_6$haloalkynyl, $C_1$–$C_6$alkoxy, $C_1$–$C_6$haloalkoxy, $C_3$–$C_6$alkenyloxy, $C_3$–$C_6$alkynyloxy, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_1$–$C_4$alkoxy-$C_1$,$C_2$alkylthio, $C_1$–$C_4$alkylcarbonyl-$C_1$–$C_2$alkylthio, $C_1$–$C_4$alkoxycarbonyl-$C_1$–$C_2$-alkylthio, cyano-$C_1$–$C_4$alkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylaminosulfonyl, di-($C_1$–$C_2$alkyl)aminosulfonyl, halogen, cyano, nitro, phenyl and benzylthio, it being possible for phenyl and benzylthio, in turn, to be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or nitro, and where substituents on the nitrogen in the heterocyclic ring are other than halogen; and
$R_{14}$ is $C_1$–$C_4$alkyl;
is acylated with a compound of the formula VI

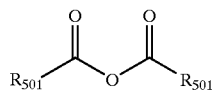
(VI)

in which $R_{501}$ is $C_1$–$C_6$haloalkyl to give the compound of the formula VII

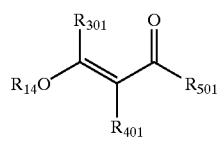
(VII)

in which $R_{301}$, $R_{401}$, $R_{501}$ and $R_{14}$ have the abovementioned meaning in the presence of a base, for example an aromatic amine, e.g. pyridine, and the alkoxy group is subsequently exchanged for the amino group with ammonia in an organic solvent, for example a halogenated hydrocarbon, e.g. dichloromethane, a nitrile, e.g. acetonitrile. The resulting compound of the formula VIII

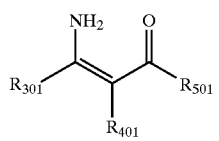
(VIII)

is subsequently subjected to a condensation reaction with a compound of the formula IX

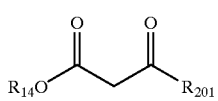
(IX)

in which $R_{201}$ is $C_1$–$C_6$alkyl, $C_1$–$C_6$haloalkyl-$C_1$–$C_4$alkyl, $C_2$–$C_6$alkenyl, $C_2$–$C_6$haloalkenyl, $C_2$–$C_6$-alkynyl, $C_2$–$C_6$haloalkynyl, $C_3$–$C_6$cycloalkyl, $C_1$–$C_4$alkoxy-$C_1$–$C_4$alkyl, $C_1$–$C_4$alkyl-S(O)$_{n4}$—$C_1$–$C_4$-alkyl, cyano-$C_1$–$C_4$alkyl, $C_1$–$C_4$alkoxycarbonyl-$C_1$–$C_4$alkyl, $C_1$–$C_4$alkoxycarbonyloxy-$C_1$–$C_4$alkyl, $C_1$–$C_4$thiocyanato-$C_1$–$C_4$alkyl, oxiranyl, $C_1$–$C_4$alkylamino-$C_1$–$C_4$alkyl, di-($C_1$–$C_4$alkyl)amino-$C_1$–$C_4$alkyl or formyl-$C_1$–$C_4$alkyl;
or $R_{201}$ is a group $Ar_6$—$C_1$–$C_4$alkyl in which $Ar_6$ is a five- to ten-membered monocyclic or fused bicyclic ring system which can be aromatic or partially saturated and can contain 1 to 4 hetero atoms selected from the group consisting of nitrogen, oxygen and sulfur, it not being possible for each ring system to contain more than 2 oxygen atoms and more than two sulfur atoms and it being possible for the ring system itself to be mono-, di- or trisubstituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$alkoxy, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$-alkynylthio, $C_2$–$C_5$alkoxyalkylthio, $C_3$–$C_5$acetylalkylthio, $C_3$–$C_6$alkoxycarbonylalkylthio, $C_2$–$C_4$-cyanoalkylthio, $C_1$–$C_6$alkylsulfinyl, $C_1$–$C_6$haloalkylsulfinyl, $C_1$–$C_6$alkylsulfonyl, $C_1$–$C_6$-haloalkylsulfonyl, aminosulfonyl, $C_1$–$C_2$alkylaminosulfonyl, di-($C_1$–$C_2$alkyl)aminosulfonyl, di-($C_1$–$C_4$alkyl)amino, halogen, cyano, nitro, phenyl and benzylthio, it being possible for phenyl and benzylthio, in turn, to be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or nitro, and where substituents on the nitrogen in the heterocyclic ring are other than halogen, and $R_{14}$ has the abovementioned meaning, and subsequently hydrolysing the resulting compound of the formula Xa

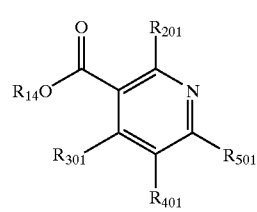
(Xa)

is subsequently hydrolysed to give the compound of the formula XVIa

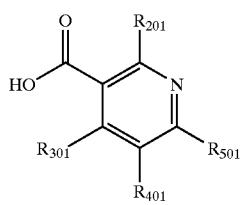
(XVIa)

in which $R_{201}$, $R_{301}$, $R_{401}$ and $R_{501}$ have the abovementioned meaning; or
b) a compound of the formula XI

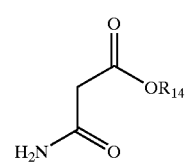
(XI)

in which $R_{14}$ has the abovementioned meaning is subjected to a condensation reaction with a compound of the formula XII

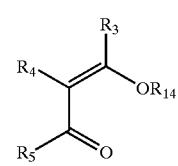
(XII)

and the resulting compound of the formula XIII

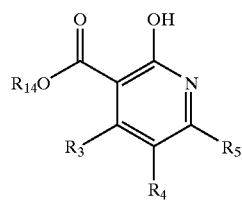

(XIII)

in which $R_3$, $R_4$ and $R_5$ have the abovementioned meaning and $R_{14}$ is $C_1$–$C_4$alkyl, is chlorinated to give the compound of the formula XIV

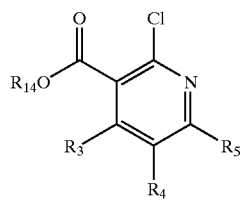

(XIV)

in which $R_3$, $R_4$, $R_5$ and $R_{14}$ have the abovementioned meaning (for example using $POCl_3$), and this compound is subsequently reacted with a nucleophile of the formula XV in which Z is SH, OH or amino and $R_{15}$ is $C_1$–$C_6$alkyl, $C_3$–$C_6$alkenyl, $C_3$–$C_6$haloalkenyl, $C_3$–$C_6$-alkynyl, $C_3$–$C_6$haloalkynyl, $C_1$–$C_6$alkylsulfonyl, $C_1$–$C_6$haloalkyl, phenyl or benzyl, it being possible for the phenyl group, in turn, to be substituted by $C_1$–$C_3$alkyl, $C_1$–$C_3$haloalkyl, $C_1$–$C_3$-alkoxy, $C_1$–$C_3$haloalkoxy, halogen, cyano or nitro, or is $C_1$–$C_4$alkoxy-$C_1$–$C_4$alkyl, $C_1$–$C_4$-alkylthio-$C_1$–$C_4$alkyl, $C_1$–$C_4$alkylsulfinyl-$C_1$–$C_4$alkyl, $C_1$–$C_4$alkylsulfonyl-$C_1$–$C_4$alkyl, $C_1$–$C_4$-alkylsulfonyl or di-($C_1$–$C_4$alkyl)aminosulfonyl, or $R_{15}$ is a five- to ten-membered monocyclic or fused bicyclic ring system which can be aromatic or partially saturated and can contain 1 to 4 hetero atoms selected from the group consisting of nitrogen, oxygen and sulfur, it not being possible for each ring system to contain more than 2 oxygen atoms and more than two sulfur atoms and it being possible for the ring system itself to be mono-, di- or trisubstituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_1$–$C_6$alkoxy, $C_1$–$C_6$-haloalkoxy, $C_3$–$C_6$alkenyloxy, $C_3$–$C_6$alkynyloxy, mercapto, $C_1$–$C_6$alkylthio, $C_1$–$C_6$-haloalkylthio, $C_3$–$C_6$alkenylthio, $C_3$–$C_6$haloalkenylthio, $C_3$–$C_6$alkynylthio, $C_2$–$C_5$alkoxyalkylthio, $C_3$–$C_5$acetylalkylthio, $C_3$–$C_6$alkoxy-carbonylalkylthio, $C_2$–$C_4$cyanoalkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylaminosulfonyl, di-($C_1$–$C_2$alkyl)aminosulfonyl, $(CH_2)_nR_7$, $NR_8R_9$, halogen, cyano, nitro, phenyl and benzylthio, it being possible for phenyl and benzylthio, in turn, to be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or nitro, and substituents on the nitrogen in the heterocyclic ring being other than halogen, in the presence of a base to give compounds of the formula Xb

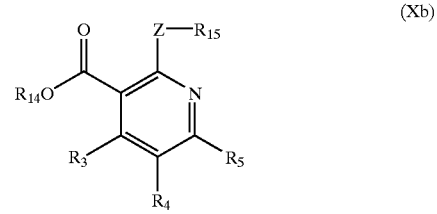

(Xb)

in which $R_{14}$, $R_{15}$, $R_3$, $R_4$, $R_5$ and Z have the abovementioned meanings and the resulting compound is subsequently hydrolysed to give the compound of the formula XVIb

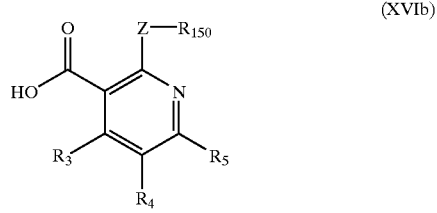

(XVIb)

in which $R_{15}$, $R_3$, $R_4$, $R_5$ and Z have the abovementioned meaning.

Compounds in which Z-$R_{15}$ and Z are oxygen and $R_{15}$ is $C_1$–$C_6$alkyl, $C_3$–$C_6$alkenyl, $C_3$–$C_6$-alkynyl, $C_1$–$C_6$haloalkyl, $C_3$–$C_6$haloalkenyl, cyano-$C_1$–$C_4$alkyl, $C_1$–$C_4$alkoxy-$C_1$–$C_4$alkyl, $C_1$–$C_4$alkylthio-$C_1$–$C_4$alkyl or $C_1$–$C_4$alkoxycarbonyl-$C_1$–$C_4$alkyl can also be reacted starting from XIII by direct alkylation with the corresponding alkylating agent L-$R_{15}$ XVa in which L is a leaving group such as chlorine, bromine, iodine, mesyloxy or tosyloxy.

Compounds of the formula XVIb in which Z-$R_{15}$ is fluorine are prepared by reacting a compound of the formula XIV with potassium fluoride and, if appropriate, a catalytic amount of 18-crown-6 in the presence of a polar aprotic solvent, for example acetonitrile, dimethylformamide or sulfolane. Compounds of the formula XVIc in which Z-$R_{15}$ is hydrogen are prepared by reducing the chlorine group in formula XIV, for example with hydrogen in the presence of a suitable metal catalyst or with ammonium formate, in a suitable solvent. The preparation of the compounds of the formula XVI or XVIa, XVIb and XVIc are illustrated in greater detail in reaction schemes 3 and 4 which follow.

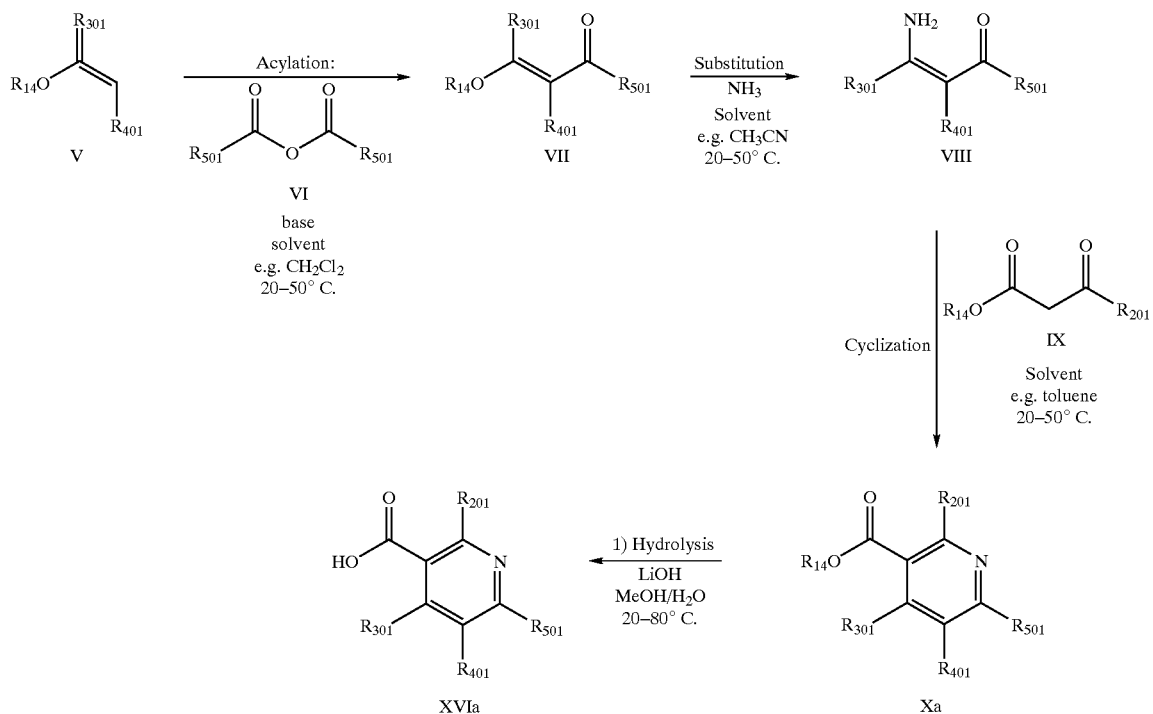
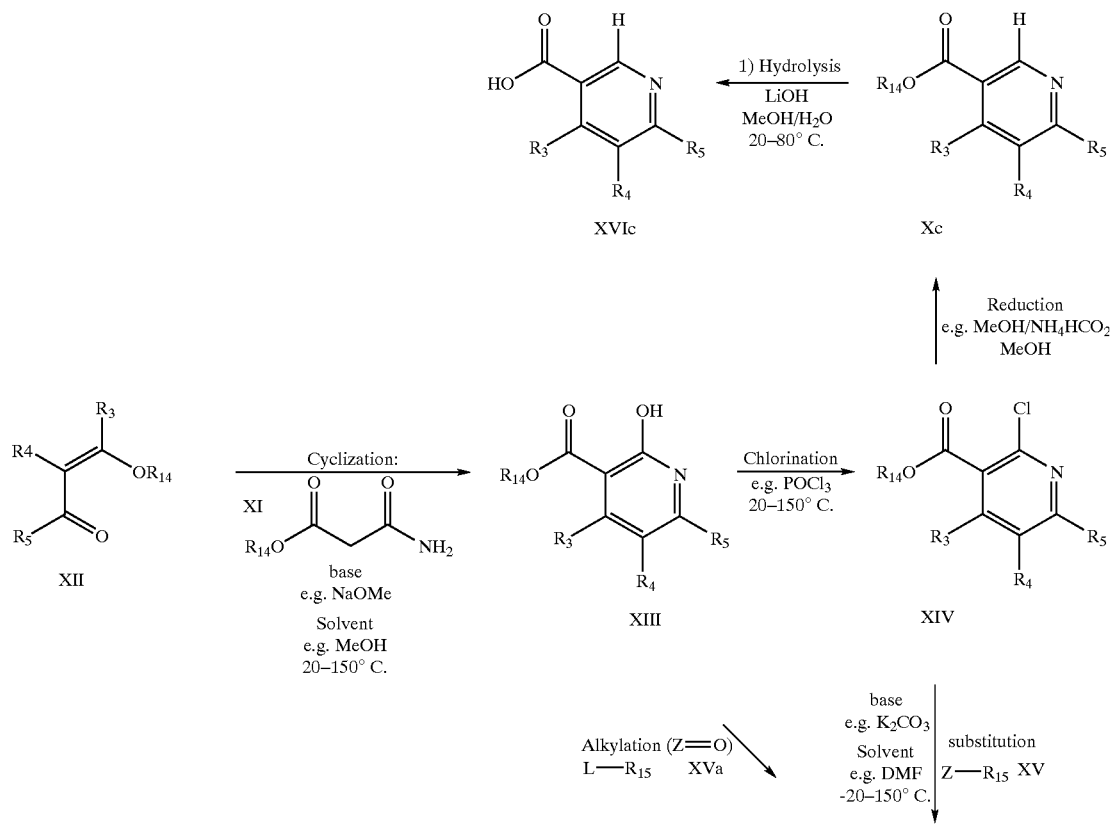

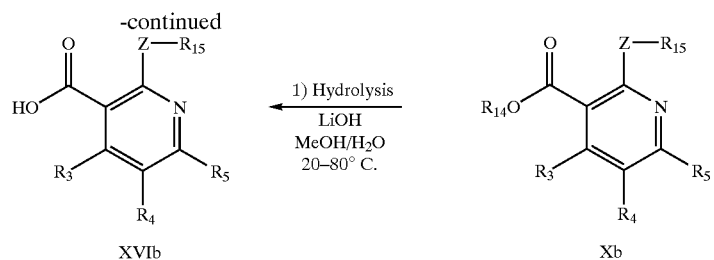

Compounds of the formula XVId in which $R_2$ is bromomethyl, cyanomethyl, thiocyanatomethyl, $C_2$–$C_6$alkenyl, $C_2$–$C_6$haloalkenyl, a $C_1$–$C_2$alkoxycarbonyl- or phenyl-substituted vinyl, $C_2$–$C_6$alkynyl, $C_2$–$C_6$haloalkynyl, a trimethylsilyl-, hydroxyl-, $C_1$–$C_2$alkoxy-, $C_1$–$C_2$alkoxycarbonyl- or phenyl-substituted ethynyl, $C_3$–$C_6$allenyl, $C_3$–$C_6$cycloalkyl or mono or poly-halogenated $C_3$–$C_6$cycloalkyl can be prepared, for example, in accordance with generally known conversion methods which are shown in reaction scheme 4a.

Reaction scheme 4a

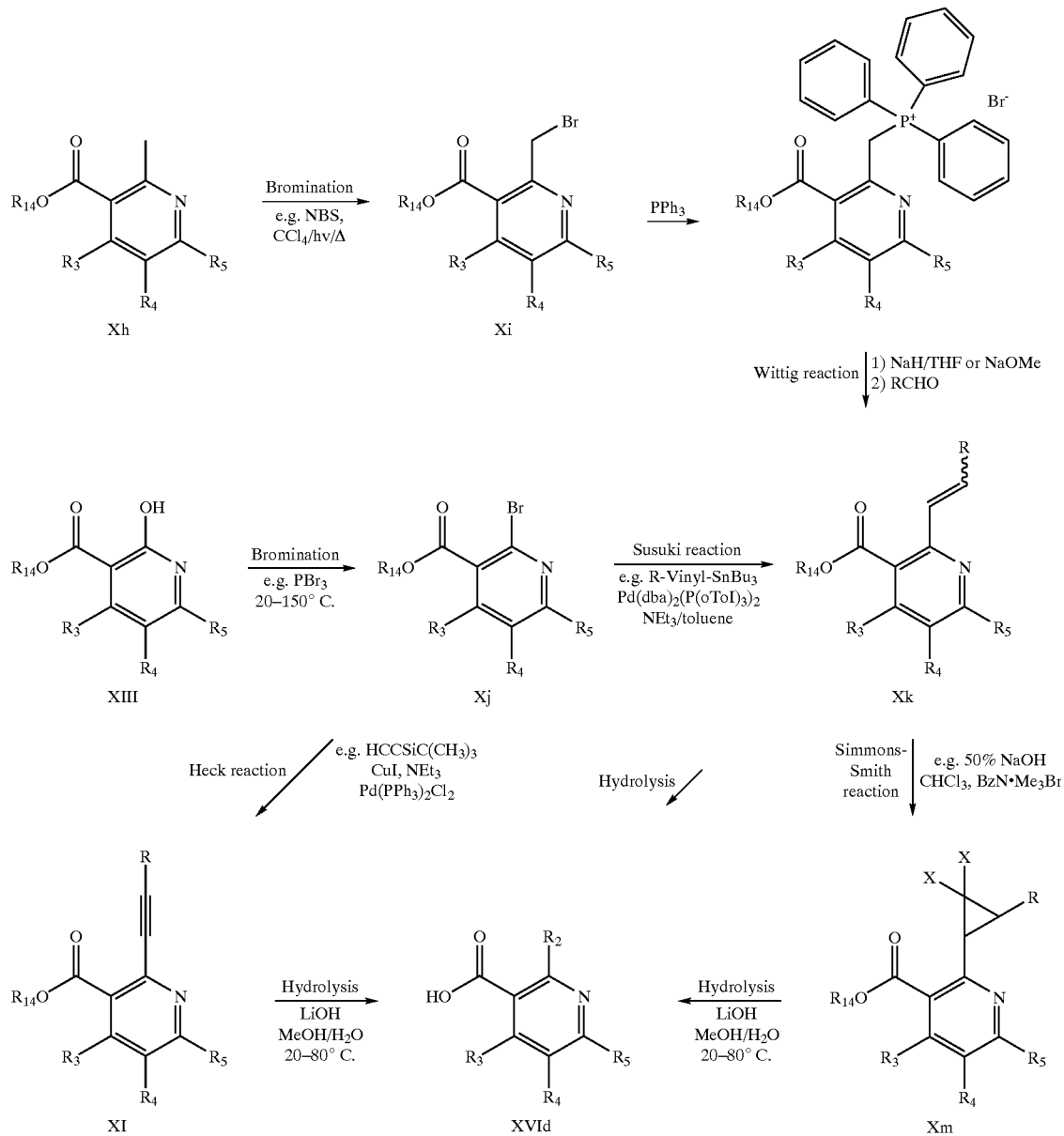

Intermediates of the formula XVIa in which $R_{501}$ is $CF_2Cl$ are prepared as described in scheme 3 or by reacting a compound of the formula Xa in which $R_{501}$ is trichloromethyl with hydrofluoric acid in a pressurized vessel at temperatures between 0 and 220° C. (preferably 60–200° C.).

Compounds of the formula XVIa in which $R_{501}$ is $CHF_2$ can be prepared as in scheme 3 or by heating a compound of the formula Xa in which $R_{301}$, $R_{401}$, $R_{14}$ and $R_{201}$ have the abovementioned meaning and $R_{501}$ is $CF_2Cl$ in an inert solvent, for example toluene or benzene, at temperatures between 25 and 120° C. (preferably 80–120° C.) with tributyltin hydride or 1,1,1,3,3,3-hexamethyl-2-(trimethylsilyl)trisilane in the presence of a catalytic amount of azo-isobutyronitrile and subsequently hydrolysing the resulting compound to give the compound of the formula XVIa in which $R_{501}$ is $CHF_2$.

Compounds of the formula XVIa in which $R_{201}$, $R_{301}$, $R_{401}$ and $R_{501}$ have the abovementioned meaning can also be prepared by reacting a compound of the formula Xc in which $R_{14}$, $R_{301}$, $R_{401}$ and $R_{501}$ have the abovementioned meaning and $R_{201}$ is $CH_2Cl$ by nucleophilic substitution, for example with an alkali metal iodide in an inert solvent, to give the corresponding iodides, or by means of gaseous hydrobromic acid in lower carboxylic acids such as glacial acetic acid to give the corresponding bromine derivatives (for example in accordance with US-3974166) or by means of alkali metal fluoride in a dipolar solvent such as sulfolane to give the corresponding fluorine derivatives, or, to prepare an alkoxy radical Xd, by reacting a halogen derivative Xc with an alcohol or phenol in the presence of a base such as sodium hydride or an alkaline earth metal oxide or alkaline earth metal carbonate or directly with an alkali metal alkoxide in an inert solvent such as dimethylformamide or in an excess of the alcohol ROH which corresponds to the group to be introduced at temperatures between −5 and 160° C., or, in order to prepare a corresponding aromatic or aliphatic thioether Xe, by reacting, analogously to what has been said above, either the halide Xc with an aliphatic or aromatic thiol in the presence of a base such as sodium hydride or with an alkali metal salt of a thiol in an inert solvent at −10–150° C., or, in order to prepare corresponding sulfinyl or sulfonyl derivatives Xe, by carrying out the reaction with an oxidant such as m-chloroperbenzoic acid or sodium periodate or sodium perborate, with the temperature control known in the art, depending on the degree of oxidation (for example −30° C.–+50° C. for n=1) or −20° C.–+100° C. for n=2) in an inert solvent such as dichloromethane to give Xf, or, in order to prepare cyanomethylene derivatives of the formula Xg, by reacting a halide of the formula Xc with an alkali metal cyanide or tetraalkylammonium cyanide or copper cyanide in an inert solvent such as dichloromethane, tetrahydrofuran or dimethylformamide at temperatures between 0° C. and 220° C.

The preparation of the compounds of the formula XVIa ($R_{501}=CF_2Cl$) and of the intermediates of the formulae Xc, Xd, Xe, Xf, and Xg are illustrated in greater detail in the reaction schemes 5, 6 and 7 which follow.

Reaction scheme 5

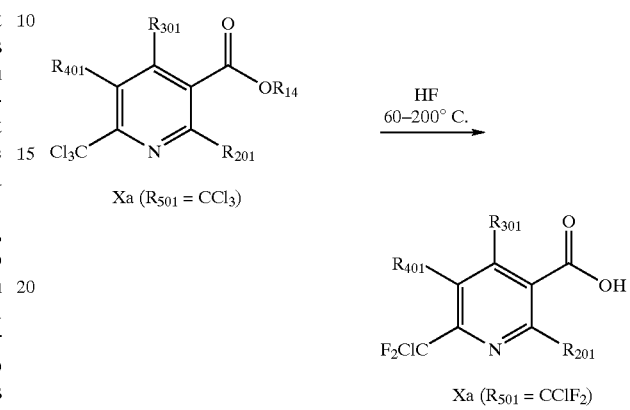

Reaction scheme 6

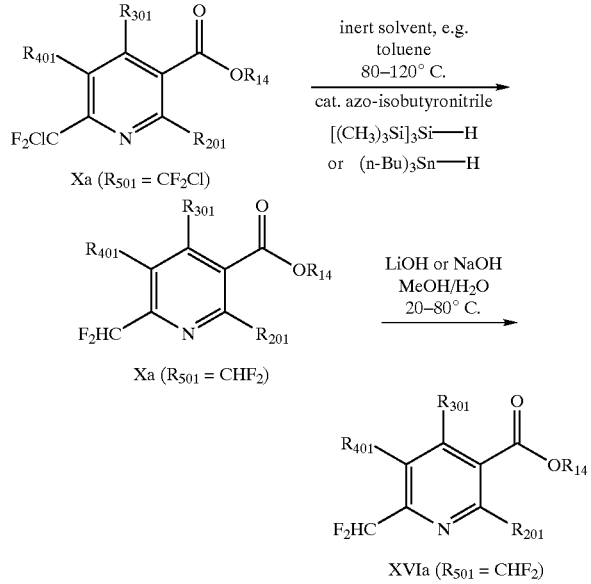

Reaction scheme 7

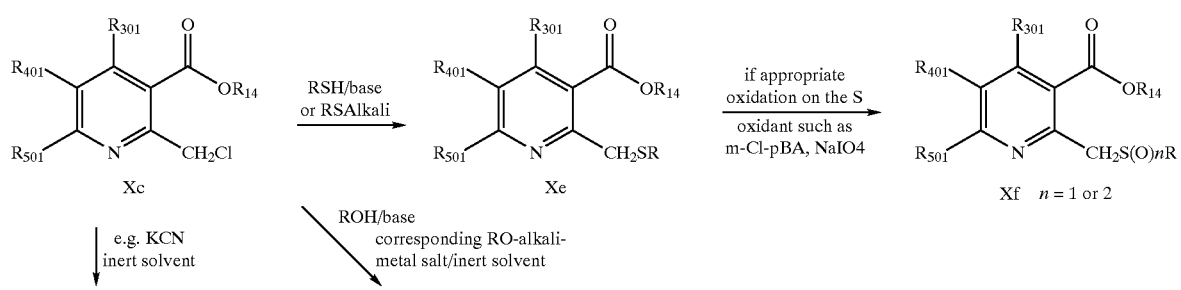

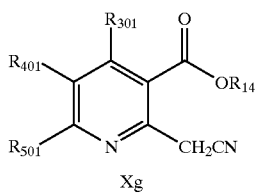
Xg

-continued

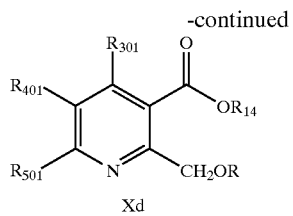
Xd

To prepare all other compounds of the formula X and XVI which are functionalized in accordance with the definition of $R_{201}$ (Z—$R_{15}$) to $R_{501}$, a multiplicity of known standard methods are suitable, for example alkylation, halogenation, acylation, amidation, oximation, oxidation and reduction, the choice of the preparation methods which are suitable depending on the properties (reactivities) of the substituents in the intermediates.

The reactions to give compounds of the formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitrites such as acetonitrile or propionitrile, amides such as N,N-dimethylformamide, diethylformamide or N-methylpyrrolidinone. The reaction temperatures are advantageously between −20° C. and +120° C. In general, the reactions are slightly exothermic and, as a rule, they can be carried out at room temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo-[5.4.0]undec-7-ene However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate, may also be used as bases. The compounds of the formula I can be isolated in the customary manner by concentrating and/or by evaporating the solvent and purified by recrystallization or trituration of the solid residue in solvents in which they are not readily soluble, such as ethers, aromatic hydrocarbons or chlorinated hydrocarbons.

All application methods which are conventionally used in agriculture, for example pre-emergence application, post-emergence application and seed treatment, as well as various methods and techniques, for example the controlled release of active ingredients, are suitable for the use according to the invention of the compounds of the formula I or of compositions comprising them. To this end, the active ingredient in solution is applied to mineral carriers for granules or to polymerized granules (urea/formaldehyde) and dried. If appropriate, an additional coating can be applied (coated granules), which allows the active ingredient to be released in a controlled manner over a specific period of time.

The compounds of the formula I can be employed as herbicides as such, i.e. as obtained from synthesis. However, they are preferably processed in the customary manner together with the auxiliaries conventionally used in the art of formulation, for example to give emulsifiable concentrates, directly sprayable or dilutable solutions, dilute emulsions, wettable powders, soluble powders, dusts, granules or microcapsules. Such formulations are described, for example, in WO 97/34485 on pages 9 to 13. The application methods such as spraying, atomizing, dusting, wetting, scattering or pouring, as well as the type of composition, are chosen to suit the intended aims and the prevailing circumstances.

The formulations, i.e. the compositions, preparations or products which comprise the active ingredient of the formula I or at least one active ingredient of the formula I and, as a rule, one or more solid or liquid formulation auxiliaries are prepared in the known manner, for example by intimately mixing and/or grinding the active ingredients together with the formulation auxiliaries, for example solvents or solid carriers. Furthermore, surface-active compounds (surfactants) may additionally be used when preparing the formulations. Examples of solvents and solid carriers are indicated for example in WO 97/34485 on page 6.

Suitable surface-active compounds are, depending on the nature of the active ingredient of the formula I to be formulated, non-ionic, cationic and/or anionic surfactants and surfactant mixtures which have good emulsifying, dispersing and wetting properties.

Examples of suitable anionic, non-ionic and cationic surfactants are enumerated, for example, in WO 97/34485 on pages 7 and 8.

The surfactants conventionally used in the art of formulation which are described, inter alia, in "McCutcheon's Detergents and Emulsifiers Annual" MC Publishing Corp., Ridgewood N.J., 1981, Stache, H., "Tensid-Taschenbuch" ["Surfactants Guide"], Carl Hanser Verlag, Munich/Vienna, 1981, and M. and J. Ash, "Encyclopedia of Surfactants", Vol I–III, Chemical Publishing Co., New York, 1980-81, are furthermore also suitable for preparing the herbicidal compositions according to the invention.

As a rule, the herbicidal formulations comprise 0.1 to 99% by weight, in particular 0.1 to 95% by weight, of herbicide, 1 to 99.9% by weight, in particular 5 to 99.8% by weight, of a solid or liquid formulation auxiliary and 0 to 25% by weight, in particular 0.1 to 25% by weight, of a surfactant. While concentrated compositions are more preferred as commercially available goods, the end consumer uses, as a rule, dilute compositions. The compositions can also comprise further additives such as stabilizers, for example epoxidized or non-epoxidized vegetable oils (epoxidized coconut oil, rapeseed oil or soya oil), antifoams, e.g. silicone oil, preservatives, viscosity regulators, binders, tackifiers and fertilizers or other active ingredients.

As a rule, the active ingredients of the formula I are applied to the plant or its environment at rates of 0.001 to 4 kg/ha, in particular 0.005 to 2 kg/ha. The dosage required for the desired action can be determined by experiments. It depends on the type of the action, the developmental stage of the crop plant and of the weed, and on the application (location, timing, method) and can, owing to these parameters, vary within wide limits.

The compounds of the formula I are distinguished by herbicidal and growth-inhibitory properties which allow them to be employed in crops of useful plants, in particular in cereals, cotton, soya, sugar beet, sugar cane, plantation crops, rapeseed, maize and rice and for the non-selective control of weeds. Crops are also to be understood as including those which have been rendered tolerant to herbicides or classes of herbicides by means of conventional plant breeding or by genetic engineering methods. The weeds to be controlled may be both mono- and dicotyledonous weeds such as Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola and Veronica.

The examples which follow illustrate the invention in greater detail without limiting it.

PREPARATION EXAMPLES

Example H1

Preparation of 3-Hydroxy-4,4-dimethyl-2-(2-methyl-6-trifluoromethylpyridine-3-carbonyl) cyclohex-2-enone (Compound A2-B24)

6.68 g (0.0305 mol) of methyl 2-methyl-6-trifluoromethylnicotinate (prepared as described in Heterocycles, 46, 129 (1997)) are dissolved in 250 ml of methanol/water (3:1 mixture), and 1.92 g (0.046 mol) of lithium hydroxide hydrate are added portionwise at a temperature of 22° C. After 4 hours at 22° C., the reaction mixture is poured onto ethyl acetate and 2 N hydrochloric acid, and the organic phase is washed three times with water, dried with sodium sulfate and evaporated, and the residue is triturated with a small amount of hexane. After filtration, 5.69 g (90% of theory) of 2-methyl-6-trifluoromethylnicotinic acid of melting point 147–149° C. are obtained.

The resulting 2-methyl-6-trifluoromethylnicotinic acid (1.026 g, 0.005 mol) is dissolved in 20 ml of oxalyl chloride. Three drops of dimethylformamide are added and the mixture is refluxed for 1 hour. The mixture is then concentrated on a rotary evaporator and the residue (2-methyl-6-trifluoromethylnicotinoyl chloride) is taken up in 100 ml of methylene chloride. At a temperature of 0° C., 1.6 ml (0.0115 mol) of triethylamine and 0.7 g (0.005 mol) of 4,4-dimethylcyclohexane-1,3-dione are added. After 2 hours at a temperature of 22° C., the solvent is removed on a vacuum rotary evaporator, the residue which remains is dissolved in 55 ml of acetonitrile, and 0.15 ml (0.0016 mol) of acetone cyanohydrin and 0.79 ml (0.0057 mol) of triethylamine are added in order to subject the intermediate to a rearrangement reaction. After the reaction solution has been stirred for 4 hours at room temperature, it is evaporated. The syrup which remains is chromatographed on silica gel. Elution with a mixture of toluene, ethyl alcohol, dioxane, triethylamine and water (100:40:20:20:5 parts by volume) gives a pale yellow viscous oil (Rf 0.39 on the abovementioned mixture as mobile phase), which is dissolved in dichloromethane and washed in succession with 75 ml of 5% hydrochloric acid and 75 ml of water. Evaporation to dryness of the organic solution which has been dried with $Na_2SO_4$ yields 1.05 g (63%) of pure 3-hydroxy-4,4-dimethyl-2-(2-methyl-6-trifluoromethylpyridine-3-carbonyl)cyclohex-2-enone in the form of white crystals of melting point 75–77° C.

$^1$H NMR ($d_6$-DMSO, δ in ppm): 1.342, s, 6H: 2.088, t, J 9 Hz, 2H: 2.685, s, 3H: 2.982, t, J 9 Hz, 2H:8.030, d, J 8.1 Hz, 1H: 8.094, d, (J, 8.1 Hz), 1H.

Example H2

Preparation of 5-Methyl-5-trifluoromethylcyclohexane-1,3-dione (Compound H-B1066)

0.64 g of sodium were introduced into 40 ml of ethanol, and 3.23 ml of methyl acetoacetate and 4.9 g of isopropyl 4,4,4-trifluoro-3-methylbut-2-enoate were introduced, and the mixture was heated at the boil for 18 hours. After the mixture has been partitioned between dilute hydrochloric acid and ethyl acetate, the mixture is evaporated. The remaining unpurified methyl 2-methyl-4,6dioxo-2-trifluoromethylcyclohexanecarboxylate is hydrolysed in a mixture of methanol and water at boiling point in the presence of 9.1 g of sodium hydroxide.

The mixture is subsequently acidified with hydrochloric acid and extracted with fresh ethyl acetate. After recrystallization (ethyl acetate), pure 5-methyl-5-trifluoromethylcyclohexane-1,3-dione of melting point 150–152° C. is obtained.

Example H3

Preparation of Methyl 2-Hydroxy-1-methoxy-5-methyl-4-oxocyclohex-2-enecarboxylate (Example H-B1069)

A 30% solution of 35.8 g of sodium methoxide is introduced into 65 ml of dimethyl sulfoxide and, within 20 minutes, treated with a mixture of 16.7 g of 3-methyl-3-butene-2-one and 32.4 g of dimethyl methoxymalonate at a temperature of 30–35° C. The mixture is stirred for 1 hour at a temperature of 35° C., and is then acidified with hydrochloric acid and extracted repeatedly with dichloromethane. The organic phases are washed with water, dried and concentrated. Crystallization from hot ethyl acetate and hexane gives pure methyl 2-hydroxy-1-methoxy-5-methyl-4-oxocyclohex-2-enecarboxylate of melting point 117–117.5° C.

Example H4

Preparation of Methyl 2-Hydroxy-1-methoxy-5-methyl-3-(2-methyl-6-trifluoromethylpyridine-3-carbonyl)-4-oxocyclohex-2-enecarboxylate (Compound A2-B1069)

2.23 g of fresh 2-methyl-6-trifluoromethylnicotinoyl chloride are added to a mixture of 2.14 g of methyl 2-hydroxy-1-methoxy-5-methyl-4-oxocyclohex-2-enecarboxylate and 2.02 g of triethylamine in 30 ml of acetonitrile. After approximately 30 minutes, 0.065 g of potassium cyanide is added and the mixture is stirred for 18 hours. At pH 2, the mixture is subsequently partitioned between water and ethyl acetate, dried over magnesium sulfate and evaporated. Filtration on silica gel (mobile phase ethyl acetate/methanoltriethylamine 85:10:5) gives the pure methyl 2-hydroxy-1-methoxy-methyl-3-(2-methyl-6-trifluoromethylpyridine-3-carbonyl)-4-oxocyclohex-2-enecarboxylate as a viscous oil.

Example H5

Preparation of 3-Hydroxy-4-methoxy-6-methyl-2-(2-methyl-6-trifluoromethyl-pyridine-3-carbonyl) cyclohex-2-enone (Compound A2-B1070)

1.4 g of methyl 2-hydroxy-1-methoxy-5-methyl-3-(2-methyl-6-trifluoromethylpyridine-3-carbonyl)-4- oxocyclohex-2-enecarboxylate in dioxane/water (5:3) are treated with 0.586 g of potassium hydroxide and the mixture is stirred for 3 hours. The mixture is then acidified (pH 3) and extracted with fresh ethyl acetate. The crude product is purified by chromatography analogously to Example H4. 3-Hydroxy-4-methoxy-6-methyl-2-(2-methyl-6-trifluoromethyl-pyridine-3-carbonyl)cyclohex-2-enone is obtained as a viscous oil (according to $^1$H-NMR as a mixture of 3 tautomeric forms).

Example H6

5-Chloro-2,2,6,6-tetramethyl-4-(2-methyl-6-trifluoromethylpyridine-3-carbonyl)-cyclohex-4-ene-1,3-dione (Compound A2-B1105) and 6-[Chloro-(2-methyl-6-trifluoromethyl-pyridin-3-yl)methylene]-2,2,4,4-tetramethylcyclohexane-1,3,5-trione 7.0 g (55 mmol) of oxalyl chloride are introduced into 18.5 g (50 mmol) of 5-hydroxy-2,2,6,6-tetramethyl-4-2-methyl-6-trifluoromethylpyridine-3-carbonyl)cyclohex-4-ene-1,3-dione (compound A2-B354), dissolved in 50 ml of dichloromethane; 5 drops of dimethylformamide are added, and the mixture is slowly heated up to boiling point. After approximately 30 minutes, after the evolution of gas has ceased, the mixture is evaporated and the product is crystallized by adding n-hexane. The main product obtained is pure 5-chloro-2,2,6,6-tetramethyl-4-(2-methyl-6-trifluoromethylpyridine-3-carbonyl)cyclohex-4-ene-1,3-dione, m.p. 119.5–120° C. Further HPLC-separation of the mother liquor using 5–10% ethyl acetate in hexane gives the isomer 6[chloro-(2-methyl-6-trifluoromethylpyridine-3-yl) methylene]-2,2,4,4-tetramethylcyclohexane-1,3,5-trione, m.p. 92.5–93° C.

Example H7

5-Chloro-2,2,6,6-tetramethyl-4-(2-methyl-1-oxy-6-trifluoromethylpyridine-3-carbonyl)cyclohex-4-ene-1,3-dione (Compound A1210-B1105)

1.94 g (5 mmol) of 5-chloro-2,2,6,6-tetramethyl-4-(2-methyl-6-trifluoromethylpyridine-3-carbonyl)cyclohex-4-ene-1,3-dione are treated in 20 ml of dichloroethane at a temperature of −10° C. with 0.94 g (10 mmol) of hydrogen peroxide/urea adduct and 1.89 g (9 mmol) of trifluoroacetic anhydride. The reaction mixture is warmed to room temperature, with stirring, and held for a further 4 hours at this temperature. The mixture is then partitioned between ethyl acetate and water of pH 5, washed with sodium chloride solution and evaporated. The residue which is filtered through silica gel is pure 5-chloro-2,2,6,6-tetramethyl-4-(2-methyl-1-oxy-6-trifluoromethylpyridine-3-carbonyl)cyclohex-4-ene-1,3-dione of melting point 145.5–146° C.

Example H8

4-(2-Bromomethyl-6-trifluoromethylpyridine-3-carbonyl)-5-chloro-2,2,6,6-tetramethylcyclohex-4-ene-1,3-dione (Compound A1029-B1105)

0.39 g (1 mmol) of 5-chloro-2,2,6,6-tetramethyl-4-(2-methyl-6-trifluoromethylpyridine-3-carbonyl)cyclohex-4-ene-1,3-dione and 0.20 g (1.1 mmol) of N-bromsuccinimide are refluxed in the presence of a catalytic amount of dibenzoyl peroxide in 10 ml of carbon tetrachloride. After the reaction has subsided, the resulting succinimide is removed by filtration and the crude product is purified by column chromatography (mobile phase: ethyl acetatelhexane 1:4). This gives pure 4-(2-bromomethyl-6-trifluoromethylpyridine-3-carbonyl)-5-chloro-2,2,6,6-tetramethylcyclohex-4-ene-1,3-dione of melting point 94.5–95° C.

Example H9

2-(2-Acetoxymethyl-6-trifluoromethylpyridine-3-carbonyl)-4,4,6,6-tetramethyl-3,5-dioxocyclohex-1-enyl Acetate (Compound A1099-B1107)

0.4 g (1 mmol) of 5-chloro-2,2,6,6-tetramethyl-4-(2-methyl-1-oxy-6-trifluoromethylpyridine-3-carbonyl) cyclohex-4-ene-1,3-dione (Example H7) is refluxed for 25 minutes in the presence of 3 ml of acetic anhydride. The mixture is then concentrated and partitioned between ethyl acetate and sodium bicarbonate solution at pH 6.5. The crude product, separated on silica gel (mobile phase: ethyl acetate/hexane 1:4) yields the pure 2-(2-acetoxymethyl-6-trifluormethylpyridine-3-carbonyl)-4,4,6,6-tetramethyl-3,5-dioxocyclohex-1-enyl acetate as an oil; $^1$H-NMR (CDCl$_3$): 7.98 d, CH, 7.72 d, CH, 5.62 s, CH$_2$, 2.22 and 2.20 2×OAc, 1.58, s, 2×CH$_3$, 1.44 ppm, s, 2×CH$_3$.

Example H10

5-Hydroxy-2-methyl-4-(2-methyl-6-trifluoromethylpyridine-3-carbonyl)bicyclo[4.1.0] hept-4-en-3-one (Compound A2-D109) and 3-hydroxy-7-methyl-2-(2-methyl-6-trifluoromethylpyridine-3-carbonyl)cyclohepta-2,6-dienone (Compound A2-F5)

0.82 g (2 mmol) of ethyl trans-5-hydroxy-2-methyl-4-(2-methyl-6-trifluoromethylpyridine-3-carbonyl)-3-oxobicyclo [4.1.0]hept-4-en-2-carboxylate (Compound A2-D111)is stirred in a 2:1 mixture of dioxane/water together with 0.254 g (4.5 mmol) of potassium hydroxide at room temperature until all of the starting material is reacted. Then, ethyl acetate is added, the mixture is acidified to pH 3 using 4 N HCl, and the 2-phase mixture is then heated for approx. 1 hour at a temperature of 40° C. The aqueous phase which is saturated with sodium chloride is then separated off. The ethyl acetate extract is evaporated to dryness and the product is chromatographed on silica gel (mobile phase ethyl acetate/hexane 1:2). The 1st fraction which is isolated is 3-hydroxy-7-methyl-2-(2-methyl-6-trifluoromethylpyridine-3-carbonyl)cyclohepta-2,6-dienone as pure tautomer mixture, $^1$H-NMR (CDCl$_3$): 17.72 and 17.08, 2s, OH, 7.6–7.45, 2 arom. H, 6.68 and 6.62, 2t, CH, 2.84, m, 2.63, m, 2.52, m, 4H, 2.62 and 2.54, 2s, CH$_3$, 2.03 and 1.77 ppm, 2s, CH$_3$. Subsequent elution with 100% ethyl acetate gives, as the 2nd fraction, the isomer and tautomer mixture of 5-hydroxy-2-methyl-4-(2-methyl-6-trifluoromethylpyridine-3-carbonyl)bicyclo[4.1.0]hept-4-en-3-one, $^1$H-NMR (CDCl$_3$): i.a. 17.62 and 17.48, 2s, OH, 7.6–7.45, 2 arom. H, 2.54, m, 2.48, 2s CH$_3$, 1.22 and 1.14, 2d, CH$_3$, 1.00 to 0.05 ppm, 2H.

Example H11

5-Hydroxy-2-methanesulfinyl-2-methyl-4-(2-methyl-6-trifluoromethylpyridine-3-carbonyl)bicyclo [4.1.0]hept-4-en-3-one (Compound A2-D114)

0.87 g (2.3 mmol) of 5-hydroxy-2-methyl-2-methylsulfanyl-4-(2-methyl-6-trifluoromethylpyridine-3-carbonyl)bicyclo[4.1.0]hept-4-en-3-one (Compound A2-D113), dissolved in 8 ml of methanol, is warmed for 3 hours at a temperature of 50° C. in the presence of 0.56 g of sodium periodate. The mixture is then partitioned between ethyl acetate an d sodium chloride solution, concentrated, and the crude product is purified by chromatography (mobile phase: ethyl acetate/m ethanol 19:1). Pure 5-hydroxy-2-methanesulfinyl-2-methyl-4-(2-methyl-6-trifluoromethylpyridine-3-carbonyl)bicyclo[4.1.0]hept-4-en-3-one is obtained as tautomer and isomer mixture of melting point 159.5–160° C.

Example H12

2-Prop-2-ynyloxy-6-trifluoromethylnicotinic Acid (Compound A1025)

47 g (0.2 mol) of 2-oxo-6-trifluoromethyl-1,2-dihydropyridine-3-carboxylic acid, 20 ml (0.25 mol) of propargyl bromide and 43 g (0.31 mol) of potassium carbonate are heated to a temperature of 75° C. in a mixture of 40 ml of dimethylformamide and 80 ml of acetonitrile in the presence of a catalytic amount of 18-crown-6 ether. After 5 hours, the mixture is partitioned between ethyl acetate and saturated sodium chloride solution. The crude product is filtered through a silica gel column using 15% ethyl acetate in hexane. The main component, which is obtained in the form of an oil, is the pure ethyl 2-prop-2-ynyloxy-6-trifluoromethylnicotinate; $^1$H-NMR (CDCl$_3$): 8.31, d, CH, 7.38, d, CH, 5.13, d, CH$_2$, 4.41, q, CH$_2$, 2.48, t, CCH, 1.41 ppm, t, CH$_3$. 36.3 g (0.13 mol) of this product is stirred over a period of 16 hours with a solution of 11.5 g (0.17 mol) of potassium hydroxide in 50 ml of water and 50 ml of dioxane. After acidification and extraction with ethyl acetate, crystalline 2-prop-2-ynyloxy-6-trifluoromethylnicotinic acid is obtained; $^1$H-NMR (CDCl$_3$): 10.0, b, OH, 8.53, d, CH, 7.44, d, CH, 5.22, d, CH$_2$, 2.54 ppm, t, CCH.

Example H13

2-Methylthio-6-trifluoromethylnicotinic Acid (Compound A15)

9.4 g (40 mmol) of 2-oxo-6-trifluoromethyl-1,2-dihydropyridine-3-carboxylic acid are introduced into a 1-molar solution of 21.7 g of phosphorus tribromide (80 mmol) in dichloromethane at a temperature of 35° C. Then, the solvent is distilled off and the reaction mixture is heated slowly to boiling point, approx. 175° C. After 18 hours, the mixture is cooled to 0° C., diluted with dichloromethane and stirred with ice-water of pH 1.8. The organic phase is then washed with cold sodium carbonate solution and with 15% sodium chloride solution, dried over magnesium sulfate and concentrated. The residue is ethyl 2-bromo-6-trifluoromethylnicotinate in the form of an oil; $^1$H-NMR (CDCl$_3$): 8.20, d, CH, 7.72 d, CH, 4.46, q, CH$_2$, 1.42 ppm, t, CH$_3$ of melting point 164–166° C.

1.0 g (3.4 mmol) of this product, dissolved in a small amount of acetonitrile, is heated for 45 minutes to a temperature of 70° C. together with 0.26 g of sodium methanethiolate (3.4 mmol) in the presence of a catalytic amount of 1 5-crown-5 ether. The solution, which is cooled to room temperature, is then treated with 0.22 g (5.5 mmol) of sodium hydroxide and 5 ml of water, and stirring is continued for 3 hours. The neutral components are subsequently removed with a small amount of diethyl ether, and the aqueous phase is brought to pH 2.5 and extracted twice using ethyl acetate. This gives 2-methylthio-6-trifluoromethylnicotinic acid as crystalline product; $^1$H-NMR (CDCl$_3$): 8.46, d, CH, 7.43, d, CH, 2.58 ppm, s, SCH$_3$.

Example H14

2-Methanesulfonylamino-6-trifluoromethylnicotinic Acid (Compound A1203)

0.52 g of methanesulfonamide is introduced into a tetrahydrofuran suspension of 0.24 g of 55% sodium hydride in oil. After the evolution of hydrogen has ceased, 1.5 g (5 mmol) of ethyl 2-bromo-6-trifluoromethylnicotinate, 0.3 g (5.2 mmol) of potassium fluoride and a catalytic amount of crown ether and 5 ml of N-methylpyrrolidone are added and the mixture is heated at the boil for 18 hours. The reaction mixture is then partitioned between ethyl acetate and water and freed from organic neutral constituents. The aqueous phase is brought to pH 2.9, extracted 3 times with fresh ethyl acetate, dried and concentrated. A crystalline product, ethyl 2-methanesulfonylamino-6-trifluoromethylnicotinate, is obtained from ether/hexane; $^1$H-NMR (CDCl$_3$): 10.48, s, NH, 8.49, d, CH, 7.38, d, CH, 4.45, q, CH$_2$, 3.51, s, SO$_2$CH$_3$, 1.42 ppm, t, CH$_3$.

0.43 g (1.4 mmol) of the above product is hydrolysed at room temperature using a 1:1 solution of 0.22 g (3.9 mmol) of potassium hydroxide in dioxane/water. After the solution, which has been acidified to pH 2.5, has been extracted with ethyl acetate, 2-methanesulfonylamino-6-trifluoromethylnicotinic acid is obtained as crystallisate; $^1$H-NMR (d$_6$-DMSO): 8.62, d, CH, 7.72, d, CH, 3.52 ppm, s, SO$_2$CH$_3$.

Example H15

(3-Methoxycarbonyl-6-trifluoromethylpyridin-2-ylmethyl)triphenylphosphonium bromide 50 g (0.23 mol) of methyl 2-methyl-6-trifluoromethylnicotinate and 49 g (0.28 mol) of N-bromosuccinimide are heated for 90 minutes at 50° C. in 500 ml of carbon tetrachloride in the presence of a catalytic amount of α,α-azaisobutyronitrile with illumination by a 150 watt lamp. Precipitated succinimide is filtered off, and the product methyl 2-bromomethyl-6-trifluoromethylnicotinate is then isolated as main component by means of column chromatography (mobile phase ethyl acetate/hexane 1:15), $^1$H-NMR (CDCl$_3$): 4.01, s, 3H; 5.03, s, 2H; 7.72, d (J 8.2 Hz), 1H; 8.43 ppm, d, (J 8.2 Hz), 1H. 25.6 g (35 mmol) of the above product are taken up in toluene and treated with 10.6 g (40 mmol) of triphenylphosphine. After the mixture has been heated for 2 hours at boiling point, pure (3-methoxycarbonyl-6-trifluoromethylpyridine-2-ylmethyl)triphenylphosphonium bromide of melting point 215–217° C. crystallizes out upon cooling.

Example H16

2-Vinyl-6-trifluoromethylnicotinic Acid (Compound A21) and 2-(2,2-Dichloro-cycloproyl)-6-trifluoromethylnicotinic Acid (Compound A1092)

5.7 g (10 mmol) of (3-methoxycarbonyl-6-trifluoromethylpyridine-2-ylmethyl)triphenyl-phosphonium bromide are dissolved at room temperature in a 2-phase system of 25 ml of chloroform and 2.1 g (20 mmol) of sodium carbonate and reacted, in 10 ml of water, with a 35% aqueous solution of 1.7 g (20 mmol) of formaldehyde. After 1.5 hours, the organic phase is separated off and filtered through silica gel. Methyl 2-vinyl-6-trifluoromethylnicotinate is obtained as an oil, $^1$H-NMR (CDCl$_3$): 8.31, d, CH, 7.10, dd, CH, 7.09, d, CH, 6.68, dd, CH, 5.68, dd, CH, 3.97 ppm, s, OCH$_3$.

0.97 g (4.1 mmol) of this product is again taken up in chloroform and reacted with 6 ml of 50% sodium hydroxide solution with vigorous stirring in the presence of 90 mg of benzyltrimethylammonium bromide. After 20 hours, the organic phase is separated off, concentrated and purified by HPLC (mobile phase: ethyl acetate/hexane 1:4). This gives pure methyl 2-(2,2-dichlorocyclopropyl)-6-trifluoromethylnicotinate, $^1$H-NMR (CDCl$_3$): 8.50, d, CH, 7.70, d, CH, 4.08, s, OCH$_3$, 3.68, dd, CH, 2.64, dd, CH, 2.05 ppm, dd, CH.

Hydrolysis of the above esters gives, accordingly, the 2-vinyl-6-trifluoromethylnicotinic acid, $^1$H-NMR (CDCl$_3$): 8.40, d, CH, 7.22, dd, CH, 7.09, d, CH, 6.68, dd, CH, 5.58 ppm, dd, CH, and 2-(2,2-dichlorocyclopropyl)-6-trifluoromethylnicotinic acid, $^1$H-NMR (CDCl$_3$): 8.64, d, CH, 7.23, d, CH, 3.78, dd, CH, 2,67, dd, CH, 2,08 ppm, dd, CH.

Example H17

2-Propa-1,2-dienyl-6-trifluoromethylnicotinic Acid (A1096) and 2-(3-Chloro-propenyl)-6-trifluoromethylnicotinic Acid (Compound A1095)

6.7 g (11 mmol) of ((3-methoxycarbonyl-6-trifluoromethylpyridin-2-yl)methyl)triphenyl-phosphonium bromide are reacted with 2 ml of 45% aqueous chloroacetaldehyde solution (14 mmol) and 1.5 g (14 mmol) of sodium carbonate with vigorous stirring in a 2-phase system of 20 ml of chloroform and 7 ml of water. After 2 hours, the organic solution is separated off and washed with half-saturated sodium chloride solution. The product is separated on silica gel (mobile phase ethyl acetatelhexane 1:4). As the 1 st fraction, methyl 2-propa-1,2-dienyl-6-trifluoromethylnicotinate, $^1$H-NMR (CDCl$_3$): 7.62, m, CH, 7.55, d, CH, 7.32, d, CH, 7.04, d, CH, 7.02, m, CH, 3.98 ppm, s, OCH$_3$, is isolated, and methyl 2-(3-chloropropenyl)-6-trifluoromethylnicotinate, $^1$H-NMR (CDCl$_3$): 8.85, d, CH, 7.65, dd, 7.58, d, CH, CH, 7.28, dd, CH, 4.32, d, CH$_2$Cl, 3.98 ppm, s, OCH$_3$ is isolated as the 2nd fraction.

Hydrolysis of the above esters gives 2-propa-1,2-dienyl-6-trifluoromethylnicotinic acid, m.p. 194–196° C., and 2-(3-chloropropenyl)-6-trifluoromethylnicotinic acid, m.p. 137–138° C.

Example H18

2-Chloro-4-methyl-6-trifluoromethylnicotinic Acid (Compound A1205)

In a pressurized vessel, 7.5 g (0.03 mol) of ((3-ethoxycarbonyl)-4-methyl-6-trifluoromethyl)-pyrid-2-one is heated for 3 hours at a temperature of 170° C. in the presence of 5.8 ml of phenyl dichlorophosphate. When cold, the reaction solution is filtered directly over a short silica gel column (mobile phase: ethyl acetate/hexane 1:9), and the 2-chloro-4-methyl-6-trifluoromethylpyridin-3-ylethyl ester is obtained as oily product. The latter is hydrolysed in the presence of aqueous potassium hydroxide solution in dioxane at a temperature of 40° C. After acidification to pH 2.7, extraction with ethyl acetate gives 2-chloro-4-methyl-6-trifluoromethylnicotinic acid as crystalline product: $^1$H NMR (CDCl$_3$): 9.55, b, OH, 7.55, s, 1H; 3.80, s, CH$_3$, 2.56 ppm, s, CH$_3$.

Example H19

4-Methyl-6-trifluoromethylnicotinic Acid (Compound A531)

To a suspension of 0.55 g of 10% Pd/C in 20 ml of methanol there are added 3.0 g (16.8 mmol) of the 2-chloro-4-methyl-6-trifluoromethylpyridin-3-ylethyl ester and, in 2 portions, a total of 5 g of ammonium formate, and the mixture is stirred for 24 hours at room temperature. The reaction mixture is then filtered through Celite and partitioned between ethyl acetate and sodium chloride solution. Chromatographic purification (mobile phase 1:9) gives the 4-methyl-6-trifluoromethylpyridin-3-ylethyl ester in the form of an oil: hydrolysis in accordance with the above processes gives 4-methyl-6-trifluoromethylnicotinic acid: $^1$H NMR (CDCl$_3$): 9.32, s, 1H, 7.62, s, 1H, 2.79 ppm, s, CH$_3$.

Example H20

5-Methyl-5-methylsulfanylbicyclo[4.1.0]heptane-2, 4-dione (Compound H-D113)

A 1-molar solution of 16.7 g (0.1 mol) of lithium bistrimethylsilylamide in tetrahydrofuran is added at a temperature of 0° C. to a solution of 13.4 g (0.1 mol) of methyl 2-methylmercaptopropionate in 30 ml of tetrahydrofuran. After the mixture has been stirred for 1 hour, 11.8 g (0.1 mol) of 5-chloropent-3-en-2-one are added dropwise in the course of 20 minutes in such a way that the temperature can be maintained at 0° C. After the mixture has been stirred for a further 30 minutes, ice-water is added, and the mixture is acidified with hydrochloric acid and extracted with diethyl acetate. The crude product is chromatographed with ethyl acetate/hexane 15/85. This gives methyl 2-(2-acetylcyclopropyl)-2-methylsulfanylpropionate, $^1$H-NMR (CDCl$_3$): 3.74, s, OCH$_3$, 2.19 and 2.14, 2s, SCH$_3$, 2.12, and 2.00, 2s, CH$_3$, 2.2–1.9, 1H, 1.3, s, CH$_3$, 1.3 to 1.0 ppm, 2H, as a 3:7 isomer mixture.

2.45 g (11 mmol) of the above product, which is enriched in the more polar isomer, is heated with 4.5 g (25 mmol) of 30% sodium ethoxide solution in a mixture of toluene/dimethylformamide 19:1 for 90 minutes at 115° C. The mixture is then taken up in ethyl acetate and washed with dilute hydrochloric acid at pH 3. The residue which has been isolated is purified on silica gel (mobile phase ethyl acetate/hexane 1:2). This gives the isomer I of 5-methyl-5-methylsulfanylbicyclo[4.1.0]heptane-2,4-dione, $^1$H-NMR (CDCl$_3$): 3.48, d, CH, 3.00 d, CH, 2.21, m, CH, 1.94, m, CH, 1.86, s, CH$_3$, 1.57, s, CH$_3$, 1.44, m, CH, 1.04 ppm, m, CH.

The isomer II of 5-methyl-5-methylsulfanylbicyclo[4.1.0]heptane-2,4-dione, $^1$H-NMR (CDCl$_3$): 3.78, d, CH, 3.14 d, CH, 2.22, m, CH, 1.93, m, CH, 2.08, s, CH$_3$, 1.58, s, CH$_3$, 1.6–1.4 ppm, 2H, is obtained from the product which is enriched in apolar isomers.

Example H21

4-Methylcyclohept-4-ene-1,3-dione (Compound H-F5)

1.0 g (5.4 mmol) of the 5-methyl-5-methylsulfanylbicyclo [4.1.0]heptane-2,4-dione isomers II is hydrogenated for 90 minutes under atmospheric pressure in 15 ml of methanol in the presence of 5 g Raney nickel. The mixture is concentrated and purified over silica gel (mobile phase ethyl acetatelhexane 1:1), and 4-methylcyclohept-4-ene-1,3-dione, $^1$H-NMR (CDCl$_3$): 6.84, m, CH, 3.94, s, CH$_2$, 2.77, m, CH$_2$, 2,59, m, CH$_2$, 1.88 ppm, s, CH$_3$, is obtained as an oil.

Example H22

2-Oxaspiro[4.5]decane-1,6,8-trione (Compound H-E16)

A suspension of sodium hydride (55% in oil, 27.5 mmol) in 70 ml of anhydrous tetrahydroturan is cooled to a temperature of −20° C., and a solution of 2-acylbutyrolactone (2.69 ml, 25 mmol) in 5 ml of tetrahydrofuran is subsequently added dropwise. After the reaction mixture has been stirred for 1 hour at this temperature, it is treated dropwise with a solution of methyl acrylate (4.5 ml, 50 mmol) in tetrahydrofuran at a temperature of −20° C. The reaction mixture is subsequently allowed to warm to room temperature and is stirred for 8 hours. The mixture is then poured into ice-water and acidified with 2 N hydrochloric acid to pH 1. After extraction with ethyl acetate, drying over sodium sulfate and concentration in vacuo, the product is purified by flash chromatography (eluent: ethyl acetate/acetic acid 1:1). This gives 2-oxaspiro[4.5]decane-1,6,8-trione in the form of a white powder of melting point 145–148° C.

Example H23

Spiro[2.5]octane-4,6-dione (Compound H-C1)

3.4 g of sodium hydride (55% suspension in oil, 78.0 mmol) were introduced into 1 l of tert-butanol and the mixture was stirred for a few minutes at room temperature. Then, 2-acylbutyrolactone (100 g, 0.78 mol) is added and the reaction mixture is treated with methyl acrylate (67.2 g, 0.78 mmol) over a period of 3.5 hours at a temperature of approx. 30° C. The reaction mixture is taken up in diethyl ether and washed in succession with 75 ml of saturated $NaH_2PO_4$ solution, water and saturated sodium chloride solution, dried over sodium sulfate and concentrated. This gives 162 g of methyl 3-(3-acetyl-2-oxotetrahydrofuran-3-yl)propionate as colourless oil, which can be reacted further without purification.

2.0 g (9.3 mmol) of the above product and 2.1 g of sodium iodide (14.0 mmol) are dissolved in 10 ml of 1,3-dimethyl-2-imidazolidinone and the solution is heated for 3 hours at 210° C. After cooling, the reaction mixture is poured into dilute aqueous saturated $NaH_2PO_4$ solution and extracted with diethyl ether, dried over sodium sulfate and concentrated. This gives methyl 3-(1-acetylcyclopropyl)propionate as a colourless oil.

74.5 g of methyl 3-(1-acetylcyclopropyl)propionate (0.32 mol) are dissolved in 1 l of tetrahydrofuran and the solution is treated portionwise with 14.3 g of sodium hydride (55% suspension in oil, 0.32 mol) at room temperature. After 1 hour, the reaction mixture is diluted with 200 ml of dimethylformamide and warmed to 70° C. After 8 hours, tetrahydrofuran is removed in vacuo, and the residue is poured into 2 N hydrochloric acid and extracted with diethyl ether. The organic phase is dried over sodium sulfate and concentrated, and column chromatography over silica gel (methylene chloride:ethanol 9:1 as eluent) gives spiro[2.5] octane-4,6-dione in the form of white crystals of melting point 116–118° C.

Example H24

2-(4,6-Dimethoxypyrimidin-2-ylsulfanylmethyl)-6-trifluoromethylnicotinic Acid (Compound A1088)

2.0 g (7.89 mmol) of methyl 2-chloromethyl-6-trifluoromethylnicotinate (prepared analogously to Heterocycles, 46, 129 (1997) by heating methyl 4-chloro-3-oxobutyrate and 4-amino-1,1,1-trifluorobut-3-en-2-one in toluene in the presence of trifluoroacetic acid) are introduced into 30 ml of acetonitrile and 1.63 g (11.83 mmol) of $K_2CO_3$ and reacted with 1.49 g (8.67 mmol) of 4,6-dimethoxypyrimidin-2-thiol at room temperature. After 4 hours, the mixture is poured into ethyl acetate/water, the ethyl acetate phase is removed, and the aqueous phase is reextracted with ethyl acetate. The combined ethyl acetate phases are dried over sodium sulfate, concentrated and purified by recrystallization from ethyl acetate/hexane. This gives methyl 2-(4,6-dimethoxypyrimidin-2-ylsulfanylmethyl)-6-trifluoromethylnicotinate in the form of white crystals of melting point 123–124° C.

Hydrolysis of the above esters (analogously to Example H1) gives, accordingly, 2-(4,6-dimethoxypyrimidin-2-ylsulfanylmethyl)-6-trifluoromethynicotinic acid in the form of white crystals of melting point 157–158° C. $^1$H-NMR (CDCl$_3$): 3.96, s, 6H; 3.99, s, 3H; 5.03, s, 2H; 5.72, s, 1H; 7.66, d (J, 8.1 Hz), 1H; 8.40 ppm, d (J, 8.1 Hz), 1H.

Example H25

2-Cyanomethyl-6-trifluoromethylnicotinic Acid (Compound A1103)

2.0 g (7.89 mmol) of methyl 2-chloromethyl-6-trifluoromethylnicotinate and 565 mg (8.67 mmol) of potassium cyanide are reacted in 20 ml of acetonitrile/water mixture (1:1) in the presence of 270 mg of tetrabutylammonium hydrogen sulfate. After the reaction has ended, the mixture is poured into water and extracted with ethyl acetate. After the ethyl acetate phase has been dried over sodium sulfate and concentrated, the crude product is purified by means of HPLC (ethyl acetate: hexane as eluent). This gives 610 mg (32% of theory) of methyl 2-cyanomethyl-6-trifluoromethylnicotinate in the form of an oil. $^1$H-NMR (CDCl$_3$): 3.96, s, 3H; 4.38, s, 2H; 7.72, d (J, 8.1 Hz), 1H; 8.48 ppm, d (J, 8.1 Hz), 1H.

Hydrolysis analogous to the methods already mentioned above yields 2-cyanomethyl-6-trifluoromethylnicotinic acid in the form of yellow crystals of melting point 152–153° C. $^1$H-NMR (CDCl$_3$): 4.18, s, 2H; 7.72, d (J, 8.1 Hz), 1H; 8.52 ppm, d (J, 8.1 Hz), 1H.

Example H26

3-(6-Difluoromethyl-2-methyloyridine-3-carbonyl)-2-hydroxy-1-methyl-4-oxocyclohex-2-enecarboxylate (Compound A124-B34)

200 mg (0.516 mmol) of methyl 3-[6-(chlorodifluoromethyl)-2-methylpyridine-3-carbonyl]-2-hydroxy-1-methyl-4-oxocyclohex-2-enecarboxylate (compound A94-B34) is heated for 3 hours at a temperature of 120° C. in 8 ml of toluene in the presence of 0.18 ml (0.62 mmol) tris(trimethylsilyl)silane. The viscous residue which remains is chromatographed on silica gel. The pale yellow viscous oil which is obtained by eluting with a mixture of toluene, ethyl alcohol, dioxane, triethylamine and water (100:40:20:20:5 by volume) is dissolved in dichloromethane and washed in succession with aqueous hydrochloric acid and water. Evaporation of the organic solution which has been dried with $Na_2SO_4$ yields 140 mg (73%) of pure methyl 3-(6-difluoromethyl-2-methylpyridine-3-carbonyl)-2-hydroxy-1-methyl-4-oxocyclohex-2-enecarboxylate in the form of a pale yellow oil. $^1$H-NMR (CDCl$_3$): 1.28, s, 3H; 1.79–1.97, m, 1H; 2.39–2.46, m, 1H; 2.43, s, 3H; 2.69, dt (J, 19.2 and 4.8 Hz), 1H; 2.82–2.92, m, 1H; 3.67, s, 3H; 6.55, t, (J, 55.5 Hz), 1H; 7.43, d (J, 7.8 Hz), 1H; 7.49, d (J, 7.8 Hz), 1H; 17.20 ppm, br s, 1H.

Example H27

3-Hydroxy-2-(2-methyl-1-oxy-6-trifluoromethylpyridine-3-carbonyl)cyclohex-2-enone (Compound A1210-B1)

16.1 g (0.054 mol) of 3-hydroxy-2-(2-methyl-6-trifluoromethylpyridine-3-carbonyl)cyclohex-2-enone (Example A2-B1) and 10.2 g (0.11 mol) of urea/hydrogen peroxide complex are dissolved in 150 ml of methylene chloride, and 22.1 ml (0.162 mol) of trifluoroacetic anhydride are subsequently added dropwise at a temperature of 25° C. After the reaction mixture has been stirred for 14 hours at a temperature of 25° C., it is poured into ethyl acetate and water, and the organic phase is washed twice with water, dried with sodium sulfate and concentrated. The residue is chromatographed on silica gel (eluent: ethyl acetate/methanol 9/1). This gives 2.4 g (14%) of the desired product in the form of white crystals (m.p. 117–119° C). $^1$H-NMR ($d_6$-DMSO): 1.98, m, 2H; 2.30, s, 3H; 2.60, t (J, 7.25 Hz), 4H: 7.32, d(J, 9.8 Hz), 1H; 7.92 ppm, d (J, 9.8 Hz), 1H.

Example H28

2-(2-Methyl-6-trifluoromethylpyridine-3-carbonyl)-3-phenylsulfanylcylohex-2-enone (Compound A2-B1102)

4.0 g (0.0134 mol) of 3-hydroxy-2-(2-methyl-6-trifluoromethylpyridine-3-carbonyl)cyclohex-2-enone (compound A2-B1) are suspended in 25 ml of oxalyl chloride, and 0.1 ml of dimethylformamide is subsequently added dropwise. After the vigorous evolution of gas has ceased, the mixture is held for 1.5 hours at a bath temperature of 45° C. and subsequently concentrated, and the residue (3-chloro-2-(2-methyl-6-trifluoromethylpyridine-3-carbonyl)-cyclohex-2-enone) is dissolved in 60 ml of methylene chloride. Triethylamine (3.7 ml, 0.0268 mol), dimethylaminopyridine (160 mg, 1.34 mmol) and 1.5 ml (0.0147 mol) of thiophenol are added at a temperature of 0–5° C. After 20 hours at a temperature of 22° C., the reaction mixture is concentrated and purified on silica gel (hexane/ethyl acetate 5:1). Trituration in hexane gives pure 2-(2-methyl-6-trifluoromethylpyridine-3-carbonyl)-3-phenylsulfanylcyclohex-2-enone in the form of white crystals of melting point 124–125° C. $^1$H-NMR (CDCl$_3$): 1.99, m, 2H; 2.41, m 4H; 2.80, s, 3H; 2.60: 7.40–7.60, m, 6H; 7.80 ppm, d(J, 8.2 Hz), 1H.

Example H29

3-Benzenesulfonyl-2-(2-methyl-6-trifluoromethylpyridine-3-carbonyl)cyclohex-2-enone (Compound A2-B1104)

0.8 g (0.00204 mol) of the 2-(2-methyl-6-trifluoromethylpyridine-3-carbonyl)-3-phenylsulfanylcyclohex-2-enone obtained above is dissolved in 30 ml of methylene chloride, and 1.39 ml of peracetic acid (39% in acetic acid, 0.00816 mol) are subsequently added dropwise at a temperature of 25° C. After 4 hours at 25° C., the reaction mixture is poured into ethyl acetate and water, the organic phase is washed with water, dried with sodium sulfate and concentrated, and the residue is triturated with a small amount of hexane and ethyl acetate. Filtration gives 0.72 g (84% of theory) of 3-benzenesulfonyl-2-(2-methyl-6-trifluoromethyl-pyridine-3-carbonyl)cyclohex-2-enone in the form of white crystals of melting point 165–167° C. $^1$H-NMR (CDCl$_3$): 2.30, m, 2H; 2.55, t (J, 7 Hz), 2H; 2.71, m, 2H; 3.05, s, 3H;: 7.40–7.80, m, 4H; 7.80–8.05 ppm, m, 3H.

Example H30

6-Difluoromethyl-2-methylnicotinic Acid (Compound A124)

6.1 g (0.026 mol) of methyl 6-(chlorodifluoromethyl)-2-methylnicotinate (prepared analogously to Heterocycles, 46, 129 (1997) by heating methyl 3-oxobutyrate and 4-amino-1-chloro-1,1-difluorobut-3-en-2-one in toluene in the presence of trifluoroacetic acid) is heated at a temperature of 120° C. in the presence of 430 mg (0.26 mol) of tris (trimethylsilyl)silane in 150 ml of toluene. After 1.5 hours, the reaction mixture is concentrated and purified on silica gel (hexane/ethyl acetate 13:1). This gives 3.8 g (73% of theory) of methyl 6-difluoromethyl-2-methylnicotinate as colourless oil.

Hydrolysis of the above esters (analogously to Example H1) gives, accordingly, 6-difluoromethyl-2-methylnicotinic acid in the form of white crystals of melting point 135–136° C. $^1$H-NMR (CDCl$_3$): 2.68, s, 3H; 6.583, t (J, 55.2 Hz), 1H;: 7.54, d (J, 8.1 Hz), 1H; 7.54 ppm, d (J, 8.1 Hz), 1H.

Example H31

6-(Chlorodifluoromethyl)-2-methylnicotinic Acid (Compound A-94)

5.0 g (18.62 mmol) of methyl 2-methyl-6-trichloromethylnicotinate (prepared analogously to Heterocycles, 46, 129 (1997)) are cooled to a temperature of −40° C. in a pressurized container, and 35 g (1.75 mol) of distilled hydrofluoric acid are subsequently passed in at this temperature. The mixture is heated for 10 hours at 200° C. (pressure approx. 55 bar). After cooling, the pressure is released using a gas-washing system, HF is removed by suction, and the reaction mixture is poured into ethyl acetate/ice. The ethyl acetate phase is separated off, and the aqueous phase is reextracted using ethyl acetate. The combined ethyl acetate phases are washed with water, dried over sodium sulfate and concentrated, and the residue is triturated with a small amount of hexane and ethyl acetate. Filtration gives 2.2 g (53% of theory) of 6-chlorodifluoromethyl-2-methylnicotinic acid as pale green crystals of melting point 134–135° C.

$^1$H-NMR (CDCl$_3$): 2.987, s, 3H; 7.64, d (J, 8.1 Hz), 1H; 8.513 ppm, d (J, 8.1 Hz), 1H.

Example H32

2-[2-(4,6-Dimethoxypyrimidine-2-sulfonylmethyl)-6-trifluoromethylpyridine-3-carbonyl]-3-hydroxycyclohex-2-enone (Compound A1090-B1)

100 mg of 2-[2-(4,6-dimethoxypyrimidin-2-ylsulfanylmethyl)-6-trifluoromethylpyridine-3-carbonyl]-3-hydroxycyclohex-2-enone (compound A1088-B1) are dissolved in methylene chloride, and 0.3 ml of peracetic acid (39% in acetic acid) is subsequently added dropwise at a temperature of 25° C. After 15 hours at 25° C., the reaction mixture is poured into ethyl acetate and water, and the organic phase is washed with water, dried with sodium sulfate and concentrated. This gives 95 mg of 2-[2-(4,6-dimethoxypyrimidine-2-sulfonylmethyl)-6-trifluoromethylpyridine-3-carbonyl]-3-hydroxycyclohex-2-enone in the form of a resin. $^1$H-NMR (CDCl$_3$): 3.79, s, 6H; 3.91, s, 3H; 4.99, s, 2H; 6.09, s, 1H; 7.52, d (J, 9 Hz), 1H; 7.68 ppm, d (J, 9 Hz), 1H.

In the tables which follow, Ph is the phenyl group and CC an ethyne group.

TABLE 1

Compounds of the formula XVId:

(XVId)

| Comp. No. | $R_2$ | $R_3$ | $R_4$ | $R_5$ | p |
|---|---|---|---|---|---|
| A1 | H | H | H | $CF_3$ | 0 |
| A2 | $CH_3$ | H | H | $CF_3$ | 0 |
| A3 | $CH_3CH_2$ | H | H | $CF_3$ | 0 |
| A4 | $(CH_3)_2CH$ | H | H | $CF_3$ | 0 |
| A5 | $(CH_3)_3C$ | H | H | $CF_3$ | 0 |
| A6 | cyclopropyl | H | H | $CF_3$ | 0 |
| A7 | $CH_3(CH_2)_2$ | H | H | $CF_3$ | 0 |
| A8 | $CH_3OCH_2$ | H | H | $CF_3$ | 0 |
| A9 | $CH_3O(CH_2)_2$ | H | H | $CF_3$ | 0 |
| A10 | Ph | H | H | $CF_3$ | 0 |
| A11 | PhO | H | H | $CF_3$ | 0 |
| A12 | PhS | H | H | $CF_3$ | 0 |
| A13 | PhSO | H | H | $CF_3$ | 0 |
| A14 | $PhSO_2$ | H | H | $CF_3$ | 0 |
| A15 | $CH_3S$ | H | H | $CF_3$ | 0 |
| A16 | $CH_3SO$ | H | H | $CF_3$ | 0 |
| A17 | $CF_3$ | H | H | $CF_3$ | 0 |
| A18 | $F_2CH$ | H | H | $CF_3$ | 0 |
| A19 | HCC | H | H | $CF_3$ | 0 |
| A20 | $CH_3CC$ | H | H | $CF_3$ | 0 |
| A21 | $CH_2=CH$ | H | H | $CF_3$ | 0 |
| A22 | $CH_2=CHCH_2$ | H | H | $CF_3$ | 0 |
| A23 | $CH_3SO_2N(CH_3)$ | H | H | $CF_3$ | 0 |
| A24 | $(CH_3)_2N$ | H | H | $CF_3$ | 0 |
| A25 | $(CH_3)_2NSO_2$ | H | H | $CF_3$ | 0 |
| A26 | $ClCH_2$ | H | H | $CF_3$ | 0 |
| A27 | $CH_3SCH_2$ | H | H | $CF_3$ | 0 |
| A28 | $CH_3SOCH_2$ | H | H | $CF_3$ | 0 |
| A29 | $CH_3SO_2CH_2$ | H | H | $CF_3$ | 0 |
| A30 | [1.2.4]-triazol-1-ylmethyl | H | H | $CF_3$ | 0 |
| A31 | $CH_3$ | $CF_3$ | H | $CH_3$ | 0 |
| A32 | $CH_3$ | $CH_3$ | H | $CF_3$ | 0 |
| A33 | H | H | H | $CF_3CF_2$ | 0 |
| A34 | $CH_3$ | H | H | $CF_3CF_2$ | 0 |
| A35 | $CH_3CH_2$ | H | H | $CF_3CF_2$ | 0 |
| A36 | cyclopropyl | H | H | $CF_3CF_2$ | 0 |
| A37 | $(CH_3)_3C$ | H | H | $CF_3CF_2$ | 0 |
| A38 | $(CH_3)_2CH$ | H | H | $CF_3CF_2$ | 0 |
| A39 | $CH_3(CH_2)_2$ | H | H | $CF_3CF_2$ | 0 |
| A40 | $CH_3OCH_2$ | H | H | $CF_3CF_2$ | 0 |
| A41 | $CH_3O(CH_2)_2$ | H | H | $CF_3CF_2$ | 0 |
| A42 | Ph | H | H | $CF_3CF_2$ | 0 |
| A43 | PhO | H | H | $CF_3CF_2$ | 0 |
| A44 | PhS | H | H | $CF_3CF_2$ | 0 |
| A45 | PhSO | H | H | $CF_3CF_2$ | 0 |
| A46 | $PhSO_2$ | H | H | $CF_3CF_2$ | 0 |
| A47 | $CH_3S$ | H | H | $CF_3CF_2$ | 0 |
| A48 | $CH_3SO$ | H | H | $CF_3CF_2$ | 0 |
| A49 | $CF_3$ | H | H | $CF_3CF_2$ | 0 |
| A50 | $F_2CH$ | H | H | $CF_3CF_2$ | 0 |
| A51 | HCC | H | H | $CF_3CF_2$ | 0 |
| A52 | $CH_3CC$ | H | H | $CF_3CF_2$ | 0 |
| A53 | $CH_2=CH$ | H | H | $CF_3CF_2$ | 0 |
| A54 | $CH_2=CHCH_2$ | H | H | $CF_3CF_2$ | 0 |
| A55 | $CH_3SO_2N(CH_3)$ | H | H | $CF_3CF_2$ | 0 |
| A56 | $(CH_3)_2N$ | H | H | $CF_3CF_2$ | 0 |
| A57 | $(CH_3)_2NSO_2$ | H | H | $CF_3CF_2$ | 0 |
| A58 | $ClCH_2$ | H | H | $CF_3CF_2$ | 0 |
| A59 | $CH_3SCH_2$ | H | H | $CF_3CF_2$ | 0 |
| A60 | $CH_3SOCH_2$ | H | H | $CF_3CF_2$ | 0 |
| A61 | $CH_3SO_2CH_2$ | H | H | $CF_3CF_2$ | 0 |
| A62 | [1.2.4]-triazol-1-ylmethyl | H | H | $CF_3CF_2$ | 0 |
| A63 | H | H | H | $CF_3CF_2CF_2$ | 0 |
| A64 | $CH_3$ | H | H | $CF_3CF_2CF_2$ | 0 |

TABLE 1-continued

Compounds of the formula XVId:

(XVId)

| Comp. No. | R$_2$ | R$_3$ | R$_4$ | R$_5$ | p |
|---|---|---|---|---|---|
| A65 | CH$_3$CH$_2$ | H | H | CF$_3$CF$_2$CF$_2$ | 0 |
| A66 | cyclopropyl | H | H | CF$_3$CF$_2$CF$_2$ | 0 |
| A67 | (CH$_3$)$_3$C | H | H | CF$_3$CF$_2$CF$_2$ | 0 |
| A68 | (CH$_3$)$_2$CH | H | H | CF$_3$CF$_2$CF$_2$ | 0 |
| A69 | CH$_3$(CH$_2$)$_2$ | H | H | CF$_3$CF$_2$CF$_2$ | 0 |
| A70 | CH$_3$OCH$_2$ | H | H | CF$_3$CF$_2$CF$_2$ | 0 |
| A71 | CH$_3$O(CH$_2$)$_2$ | H | H | CF$_3$CF$_2$CF$_2$ | 0 |
| A72 | Ph | H | H | CF$_3$CF$_2$CF$_2$ | 0 |
| A73 | PhO | H | H | CF$_3$CF$_2$CF$_2$ | 0 |
| A74 | PhS | H | H | CF$_3$CF$_2$CF$_2$ | 0 |
| A75 | PhSO | H | H | CF$_3$CF$_2$CF$_2$ | 0 |
| A76 | PhSO$_2$ | H | H | CF$_3$CF$_2$CF$_2$ | 0 |
| A77 | CH$_3$S | H | H | CF$_3$CF$_2$CF$_2$ | 0 |
| A78 | CH$_3$SO | H | H | CF$_3$CF$_2$CF$_2$ | 0 |
| A79 | CF$_3$ | H | H | CF$_3$CF$_2$CF$_2$ | 0 |
| A80 | F$_2$CH | H | H | CF$_3$CF$_2$CF$_2$ | 0 |
| A81 | HCC | H | H | CF$_3$CF$_2$CF$_2$ | 0 |
| A82 | CH$_3$CC | H | H | CF$_3$CF$_2$CF$_2$ | 0 |
| A83 | CH$_2$=CH | H | H | CF$_3$CF$_2$CF$_2$ | 0 |
| A84 | CH$_2$=CHCH$_2$ | H | H | CF$_3$CF$_2$CF$_2$ | 0 |
| A85 | CH$_3$SO$_2$N(CH$_3$) | H | H | CF$_3$CF$_2$CF$_2$ | 0 |
| A86 | (CH$_3$)$_2$N | H | H | CF$_3$CF$_2$CF$_2$ | 0 |
| A87 | (CH$_3$)$_2$NSO$_2$ | H | H | CF$_3$CF$_2$CF$_2$ | 0 |
| A88 | ClCH$_2$ | H | H | CF$_3$CF$_2$CF$_2$ | 0 |
| A89 | CH$_3$SCH$_2$ | H | H | CF$_3$CF$_2$CF$_2$ | 0 |
| A90 | CH$_3$SOCH$_2$ | H | H | CF$_3$CF$_2$CF$_2$ | 0 |
| A91 | CH$_3$SO$_2$CH$_2$ | H | H | CF$_3$CF$_2$CF$_2$ | 0 |
| A92 | [1.2.4]-triazol-1-ylmethyl | H | H | CF$_3$CF$_2$CF$_2$ | 0 |
| A93 | H | H | H | CF$_2$Cl | 0 |
| A94 | CH$_3$ | H | H | CF$_2$Cl | 0 |
| A95 | CH$_3$CH$_2$ | H | H | CF$_2$Cl | 0 |
| A96 | cyclopropyl | H | H | CF$_2$Cl | 0 |
| A97 | (CH$_3$)$_3$C | H | H | CF$_2$Cl | 0 |
| A98 | (CH$_3$)$_2$CH | H | H | CF$_2$Cl | 0 |
| A99 | CH$_3$(CH$_2$)$_2$ | H | H | CF$_2$Cl | 0 |
| A100 | CH$_3$OCH$_2$ | H | H | CF$_2$Cl | 0 |
| A101 | CH$_3$O(CH$_2$)$_2$ | H | H | CF$_2$Cl | 0 |
| A102 | Ph | H | H | CF$_2$Cl | 0 |
| A103 | PhO | H | H | CF$_2$Cl | 0 |
| A104 | PhS | H | H | CF$_2$Cl | 0 |
| A105 | PhSO | H | H | CF$_2$Cl | 0 |
| A106 | PhSO$_2$ | H | H | CF$_2$Cl | 0 |
| A107 | CH$_3$S | H | H | CF$_2$Cl | 0 |
| A108 | CH$_3$SO | H | H | CF$_2$Cl | 0 |
| A109 | CF$_3$ | H | H | CF$_2$Cl | 0 |
| A110 | F$_2$CH | H | H | CF$_2$Cl | 0 |
| A111 | HCC | H | H | CF$_2$Cl | 0 |
| A112 | CH$_3$CC | H | H | CF$_2$Cl | 0 |
| A113 | CH$_2$=CH | H | H | CF$_2$Cl | 0 |
| A114 | CH$_2$=CHCH$_2$ | H | H | CF$_2$Cl | 0 |
| A115 | CH$_3$SO$_2$N(CH$_3$) | H | H | CF$_2$Cl | 0 |
| A116 | (CH$_3$)$_2$N | H | H | CF$_2$Cl | 0 |
| A117 | (CH$_3$)$_2$NSO$_2$ | H | H | CF$_2$Cl | 0 |
| A118 | ClCH$_2$ | H | H | CF$_2$Cl | 0 |
| A119 | CH$_3$SCH$_2$ | H | H | CF$_2$Cl | 0 |
| A120 | CH$_3$SOCH$_2$ | H | H | CF$_2$Cl | 0 |
| A121 | CH$_3$SO$_2$CH$_2$ | H | H | CF$_2$Cl | 0 |
| A122 | [1.2.4]-triazol-1-ylmethyl | H | H | CF$_2$Cl | 0 |
| A123 | H | H | H | CHF$_2$ | 0 |
| A124 | CH$_3$ | H | H | CHF$_2$ | 0 |
| A125 | CH$_3$CH$_2$ | H | H | CHF$_2$ | 0 |
| A126 | cyclopropyl | H | H | CHF$_2$ | 0 |
| A127 | (CH$_3$)$_3$C | H | H | CHF$_2$ | 0 |
| A128 | (CH$_3$)$_2$CH | H | H | CHF$_2$ | 0 |

TABLE 1-continued

Compounds of the formula XVId:

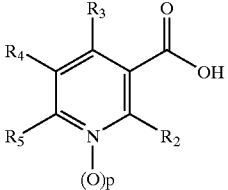

(XVId)

| Comp. No. | $R_2$ | $R_3$ | $R_4$ | $R_5$ | p |
|---|---|---|---|---|---|
| A129 | $CH_3(CH_2)_2$ | H | H | $CHF_2$ | 0 |
| A130 | $CH_3OCH_2$ | H | H | $CHF_2$ | 0 |
| A131 | $CH_3O(CH_2)_2$ | H | H | $CHF_2$ | 0 |
| A132 | Ph | H | H | $CHF_2$ | 0 |
| A133 | PhO | H | H | $CHF_2$ | 0 |
| A134 | PhS | H | H | $CHF_2$ | 0 |
| A135 | PhSO | H | H | $CHF_2$ | 0 |
| A136 | $PhSO_2$ | H | H | $CHF_2$ | 0 |
| A137 | $CH_3S$ | H | H | $CHF_2$ | 0 |
| A138 | $CH_3SO$ | H | H | $CHF_2$ | 0 |
| A139 | $CF_3$ | H | H | $CHF_2$ | 0 |
| A140 | $F_2CH$ | H | H | $CHF_2$ | 0 |
| A141 | HCC | H | H | $CHF_2$ | 0 |
| A142 | $CH_3CC$ | H | H | $CHF_2$ | 0 |
| A143 | $CH_2$=CH | H | H | $CHF_2$ | 0 |
| A144 | $CH_2$=$CHCH_2$ | H | H | $CHF_2$ | 0 |
| A145 | $CH_3SO_2N(CH_3)$ | H | H | $CHF_2$ | 0 |
| A146 | $(CH_3)_2N$ | H | H | $CHF_2$ | 0 |
| A147 | $(CH_3)_2NSO_2$ | H | H | $CHF_2$ | 0 |
| A148 | $ClCH_2$ | H | H | $CHF_2$ | 0 |
| A149 | $CH_3SCH_2$ | H | H | $CHF_2$ | 0 |
| A150 | $CH_3SOCH_2$ | H | H | $CHF_2$ | 0 |
| A151 | $CH_3SO_2CH_2$ | H | H | $CHF_2$ | 0 |
| A152 | [1.2.4]-triazol-1-ylmethyl | H | H | $CHF_2$ | 0 |
| A153 | H | H | H | $CCl_3$ | 0 |
| A154 | $CH_3$ | H | H | $CCl_3$ | 0 |
| A155 | $CH_3CH_2$ | H | H | $CCl_3$ | 0 |
| A156 | cyclopropyl | H | H | $CCl_3$ | 0 |
| A157 | $(CH_3)_3C$ | H | H | $CCl_3$ | 0 |
| A158 | $(CH_3)_2CH$ | H | H | $CCl_3$ | 0 |
| A159 | $CH_3(CH_2)_2$ | H | H | $CCl_3$ | 0 |
| A160 | $CH_3OCH_2$ | H | H | $CCl_3$ | 0 |
| A161 | $CH_3O(CH_2)_2$ | H | H | $CCl_3$ | 0 |
| A162 | Ph | H | H | $CCl_3$ | 0 |
| A163 | PhO | H | H | $CCl_3$ | 0 |
| A164 | PhS | H | H | $CCl_3$ | 0 |
| A165 | PhSO | H | H | $CCl_3$ | 0 |
| A166 | $PhSO_2$ | H | H | $CCl_3$ | 0 |
| A167 | $CH_3S$ | H | H | $CCl_3$ | 0 |
| A168 | $CH_3SO$ | H | H | $CCl_3$ | 0 |
| A169 | $CF_3$ | H | H | $CCl_3$ | 0 |
| A170 | $F_2CH$ | H | H | $CCl_3$ | 0 |
| A171 | HCC | H | H | $CCl_3$ | 0 |
| A172 | $CH_3CC$ | H | H | $CCl_3$ | 0 |
| A173 | $CH_2$=CH | H | H | $CCl_3$ | 0 |
| A174 | $CH_2$=$CHCH_2$ | H | H | $CCl_3$ | 0 |
| A175 | $CH_3SO_2N(CH_3)$ | H | H | $CCl_3$ | 0 |
| A176 | $(CH_3)_2N$ | H | H | $CCl_3$ | 0 |
| A177 | $(CH_3)_2NSO_2$ | H | H | $CCl_3$ | 0 |
| A178 | $ClCH_2$ | H | H | $CCl_3$ | 0 |
| A179 | $CH_3SCH_2$ | H | H | $CCl_3$ | 0 |
| A180 | $CH_3SOCH_2$ | H | H | $CCl_3$ | 0 |
| A181 | $CH_3SO_2CH_2$ | H | H | $CCl_3$ | 0 |
| A182 | [1.2.4]-triazol-1-ylmethyl | H | H | $CCl_3$ | 0 |
| A183 | H | H | $CH_3$ | $CF_3$ | 0 |
| A184 | $CH_3$ | H | $CH_3$ | $CF_3$ | 0 |
| A185 | $CH_3CH_2$ | H | $CH_3$ | $CF_3$ | 0 |
| A186 | cyclopropyl | H | $CH_3$ | $CF_3$ | 0 |
| A187 | $(CH_3)_3C$ | H | $CH_3$ | $CF_3$ | 0 |
| A188 | $(CH_3)_2CH$ | H | $CH_3$ | $CF_3$ | 0 |
| A189 | $CH_3(CH_2)_2$ | H | $CH_3$ | $CF_3$ | 0 |
| A190 | $CH_3OCH_2$ | H | $CH_3$ | $CF_3$ | 0 |
| A191 | $CH_3O(CH_2)_2$ | H | $CH_3$ | $CF_3$ | 0 |
| A192 | Ph | H | $CH_3$ | $CF_3$ | 0 |

TABLE 1-continued

Compounds of the formula XVId:

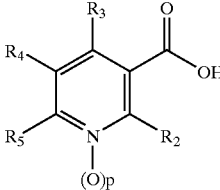

(XVId)

| Comp. No. | R$_2$ | R$_3$ | R$_4$ | R$_5$ | p |
|---|---|---|---|---|---|
| A193 | PhO | H | CH$_3$ | CF$_3$ | 0 |
| A194 | PhS | H | CH$_3$ | CF$_3$ | 0 |
| A195 | PhSO | H | CH$_3$ | CF$_3$ | 0 |
| A196 | PhSO$_2$ | H | CH$_3$ | CF$_3$ | 0 |
| A197 | CH$_3$S | H | CH$_3$ | CF$_3$ | 0 |
| A198 | CH$_3$SO | H | CH$_3$ | CF$_3$ | 0 |
| A199 | CF$_3$ | H | CH$_3$ | CF$_3$ | 0 |
| A200 | F$_2$CH | H | CH$_3$ | CF$_3$ | 0 |
| A201 | HCC | H | CH$_3$ | CF$_3$ | 0 |
| A202 | CH$_3$CC | H | CH$_3$ | CF$_3$ | 0 |
| A203 | CH$_2$=CH | H | CH$_3$ | CF$_3$ | 0 |
| A204 | CH$_2$=CHCH$_2$ | H | CH$_3$ | CF$_3$ | 0 |
| A205 | CH$_3$SO$_2$N(CH$_3$) | H | CH$_3$ | CF$_3$ | 0 |
| A206 | (CH$_3$)$_2$N | H | CH$_3$ | CF$_3$ | 0 |
| A207 | (CH$_3$)$_2$NSO$_2$ | H | CH$_3$ | CF$_3$ | 0 |
| A208 | ClCH$_2$ | H | CH$_3$ | CF$_3$ | 0 |
| A209 | CH$_3$SCH$_2$ | H | CH$_3$ | CF$_3$ | 0 |
| A210 | CH$_3$SOCH$_2$ | H | CH$_3$ | CF$_3$ | 0 |
| A211 | CH$_3$SO$_2$CH$_2$ | H | CH$_3$ | CF$_3$ | 0 |
| A212 | H | H | CH$_3$ | CF$_3$CF$_2$ | 0 |
| A213 | CH$_3$ | H | CH$_3$ | CF$_3$CF$_2$ | 0 |
| A214 | CH$_3$CH$_2$ | H | CH$_3$ | CF$_3$CF$_2$ | 0 |
| A215 | cyclopropyl | H | CH$_3$ | CF$_3$CF$_2$ | 0 |
| A216 | (CH$_3$)$_3$C | H | CH$_3$ | CF$_3$CF$_2$ | 0 |
| A217 | (CH$_3$)$_2$CH | H | CH$_3$ | CF$_3$CF$_2$ | 0 |
| A218 | CH$_3$(CH$_2$)$_2$ | H | CH$_3$ | CF$_3$CF$_2$ | 0 |
| A219 | CH$_3$OCH$_2$ | H | CH$_3$ | CF$_3$CF$_2$ | 0 |
| A220 | CH$_3$O(CH$_2$)$_2$ | H | CH$_3$ | CF$_3$CF$_2$ | 0 |
| A221 | Ph | H | CH$_3$ | CF$_3$CF$_2$ | 0 |
| A222 | PhO | H | CH$_3$ | CF$_3$CF$_2$ | 0 |
| A223 | PhS | H | CH$_3$ | CF$_3$CF$_2$ | 0 |
| A224 | PhSO | H | CH$_3$ | CF$_3$CF$_2$ | 0 |
| A225 | PhSO$_2$ | H | CH$_3$ | CF$_3$CF$_2$ | 0 |
| A226 | CH$_3$S | H | CH$_3$ | CF$_3$CF$_2$ | 0 |
| A227 | CH$_3$SO | H | CH$_3$ | CF$_3$CF$_2$ | 0 |
| A228 | CF$_3$ | H | CH$_3$ | CF$_3$CF$_2$ | 0 |
| A229 | F$_2$CH | H | CH$_3$ | CF$_3$CF$_2$ | 0 |
| A230 | HCC | H | CH$_3$ | CF$_3$CF$_2$ | 0 |
| A231 | CH$_3$CC | H | CH$_3$ | CF$_3$CF$_2$ | 0 |
| A232 | CH$_2$=CH | H | CH$_3$ | CF$_3$CF$_2$ | 0 |
| A233 | CH$_2$=CHCH$_2$ | H | CH$_3$ | CF$_3$CF$_2$ | 0 |
| A234 | CH$_3$SO$_2$N(CH$_3$) | H | CH$_3$ | CF$_3$CF$_2$ | 0 |
| A235 | (CH$_3$)$_2$N | H | CH$_3$ | CF$_3$CF$_2$ | 0 |
| A236 | (CH$_3$)$_2$NSO$_2$ | H | CH$_3$ | CF$_3$CF$_2$ | 0 |
| A237 | ClCH$_2$ | H | CH$_3$ | CF$_3$CF$_2$ | 0 |
| A238 | CH$_3$SCH$_2$ | H | CH$_3$ | CF$_3$CF$_2$ | 0 |
| A239 | CH$_3$SOCH$_2$ | H | CH$_3$ | CF$_3$CF$_2$ | 0 |
| A240 | CH$_3$SO$_2$CH$_2$ | H | CH$_3$ | CF$_3$CF$_2$ | 0 |
| A241 | H | H | CH$_3$ | CF$_3$CF$_2$CF$_2$ | 0 |
| A242 | CH$_3$ | H | CH$_3$ | CF$_3$CF$_2$CF$_2$ | 0 |
| A243 | CH$_3$CH$_2$ | H | CH$_3$ | CF$_3$CF$_2$CF$_2$ | 0 |
| A244 | cyclopropyl | H | CH$_3$ | CF$_3$CF$_2$CF$_2$ | 0 |
| A245 | (CH$_3$)$_3$C | H | CH$_3$ | CF$_3$CF$_2$CF$_2$ | 0 |
| A246 | (CH$_3$)$_2$CH | H | CH$_3$ | CF$_3$CF$_2$CF$_2$ | 0 |
| A247 | CH$_3$(CH$_2$)$_2$ | H | CH$_3$ | CF$_3$CF$_2$CF$_2$ | 0 |
| A248 | CH$_3$OCH$_2$ | H | CH$_3$ | CF$_3$CF$_2$CF$_2$ | 0 |
| A249 | CH$_3$O(CH$_2$)$_2$ | H | CH$_3$ | CF$_3$CF$_2$CF$_2$ | 0 |
| A250 | Ph | H | CH$_3$ | CF$_3$CF$_2$CF$_2$ | 0 |
| A251 | PhO | H | CH$_3$ | CF$_3$CF$_2$CF$_2$ | 0 |
| A252 | PhS | H | CH$_3$ | CF$_3$CF$_2$CF$_2$ | 0 |
| A253 | PhSO | H | CH$_3$ | CF$_3$CF$_2$CF$_2$ | 0 |
| A254 | PhSO$_2$ | H | CH$_3$ | CF$_3$CF$_2$CF$_2$ | 0 |
| A255 | CH$_3$S | H | CH$_3$ | CF$_3$CF$_2$CF$_2$ | 0 |
| A256 | CH$_3$SO | H | CH$_3$ | CF$_3$CF$_2$CF$_2$ | 0 |

TABLE 1-continued

Compounds of the formula XVId:

(XVId)

| Comp. No. | R$_2$ | R$_3$ | R$_4$ | R$_5$ | p |
|---|---|---|---|---|---|
| A257 | CF$_3$ | H | CH$_3$ | CF$_3$CF$_2$CF$_2$ | 0 |
| A258 | F$_2$CH | H | CH$_3$ | CF$_3$CF$_2$CF$_2$ | 0 |
| A259 | HCC | H | CH$_3$ | CF$_3$CF$_2$CF$_2$ | 0 |
| A260 | CH$_3$CC | H | CH$_3$ | CF$_3$CF$_2$CF$_2$ | 0 |
| A261 | CH$_2$=CH | H | CH$_3$ | CF$_3$CF$_2$CF$_2$ | 0 |
| A262 | CH$_2$=CHCH$_2$ | H | CH$_3$ | CF$_3$CF$_2$CF$_2$ | 0 |
| A263 | CH$_3$SO$_2$N(CH$_3$) | H | CH$_3$ | CF$_3$CF$_2$CF$_2$ | 0 |
| A264 | (CH$_3$)$_2$N | H | CH$_3$ | CF$_3$CF$_2$CF$_2$ | 0 |
| A265 | (CH$_3$)$_2$NSO$_2$ | H | CH$_3$ | CF$_3$CF$_2$CF$_2$ | 0 |
| A266 | ClCH$_2$ | H | CH$_3$ | CF$_3$CF$_2$CF$_2$ | 0 |
| A267 | CH$_3$SCH$_2$ | H | CH$_3$ | CF$_3$CF$_2$CF$_2$ | 0 |
| A268 | CH$_3$SOCH$_2$ | H | CH$_3$ | CF$_3$CF$_2$CF$_2$ | 0 |
| A269 | CH$_3$SO$_2$CH$_2$ | H | CH$_3$ | CF$_3$CF$_2$CF$_2$ | 0 |
| A270 | H | H | CH$_3$ | CF$_2$Cl | 0 |
| A271 | CH$_3$ | H | CH$_3$ | CF$_2$Cl | 0 |
| A272 | CH$_3$CH$_2$ | H | CH$_3$ | CF$_2$Cl | 0 |
| A273 | cyclopropyl | H | CH$_3$ | CF$_2$Cl | 0 |
| A274 | (CH$_3$)$_3$C | H | CH$_3$ | CF$_2$Cl | 0 |
| A275 | (CH$_3$)$_2$CH | H | CH$_3$ | CF$_2$Cl | 0 |
| A276 | CH$_3$(CH$_2$)$_2$ | H | CH$_3$ | CF$_2$Cl | 0 |
| A277 | CH$_3$OCH$_2$ | H | CH$_3$ | CF$_2$Cl | 0 |
| A278 | CH$_3$O(CH$_2$)$_2$ | H | CH$_3$ | CF$_2$Cl | 0 |
| A279 | Ph | H | CH$_3$ | CF$_2$Cl | 0 |
| A280 | PhO | H | CH$_3$ | CF$_2$Cl | 0 |
| A281 | PhS | H | CH$_3$ | CF$_2$Cl | 0 |
| A282 | PhSO | H | CH$_3$ | CF$_2$Cl | 0 |
| A283 | PhSO$_2$ | H | CH$_3$ | CF$_2$Cl | 0 |
| A284 | CH$_3$S | H | CH$_3$ | CF$_2$Cl | 0 |
| A285 | CH$_3$SO | H | CH$_3$ | CF$_2$Cl | 0 |
| A286 | CF$_3$ | H | CH$_3$ | CF$_2$Cl | 0 |
| A287 | F$_2$CH | H | CH$_3$ | CF$_2$Cl | 0 |
| A288 | HCC | H | CH$_3$ | CF$_2$Cl | 0 |
| A289 | CH$_3$CC | H | CH$_3$ | CF$_2$Cl | 0 |
| A290 | CH$_2$=CH | H | CH$_3$ | CF$_2$Cl | 0 |
| A291 | CH$_2$=CHCH$_2$ | H | CH$_3$ | CF$_2$Cl | 0 |
| A292 | CH$_3$SO$_2$N(CH$_3$) | H | CH$_3$ | CF$_2$Cl | 0 |
| A293 | (CH$_3$)$_2$N | H | CH$_3$ | CF$_2$Cl | 0 |
| A294 | (CH$_3$)$_2$NSO$_2$ | H | CH$_3$ | CF$_2$Cl | 0 |
| A295 | ClCH$_2$ | H | CH$_3$ | CF$_2$Cl | 0 |
| A296 | CH$_3$SCH$_2$ | H | CH$_3$ | CF$_2$Cl | 0 |
| A297 | CH$_3$SOCH$_2$ | H | CH$_3$ | CF$_2$Cl | 0 |
| A298 | CH$_3$SO$_2$CH$_2$ | H | CH$_3$ | CF$_2$Cl | 0 |
| A299 | H | H | CH$_3$ | CHF$_2$ | 0 |
| A300 | CH$_3$ | H | CH$_3$ | CHF$_2$ | 0 |
| A301 | CH$_3$CH$_2$ | H | CH$_3$ | CHF$_2$ | 0 |
| A302 | cyclopropyl | H | CH$_3$ | CHF$_2$ | 0 |
| A303 | (CH$_3$)$_3$C | H | CH$_3$ | CHF$_2$ | 0 |
| A304 | (CH$_3$)$_2$CH | H | CH$_3$ | CHF$_2$ | 0 |
| A305 | CH$_3$(CH$_2$)$_2$ | H | CH$_3$ | CHF$_2$ | 0 |
| A306 | CH$_3$OCH$_2$ | H | CH$_3$ | CHF$_2$ | 0 |
| A307 | CH$_3$O(CH$_2$)$_2$ | H | CH$_3$ | CHF$_2$ | 0 |
| A308 | Ph | H | CH$_3$ | CHF$_2$ | 0 |
| A309 | PhO | H | CH$_3$ | CHF$_2$ | 0 |
| A310 | PhS | H | CH$_3$ | CHF$_2$ | 0 |
| A311 | PhSO | H | CH$_3$ | CHF$_2$ | 0 |
| A312 | PhSO$_2$ | H | CH$_3$ | CHF$_2$ | 0 |
| A313 | CH$_3$S | H | CH$_3$ | CHF$_2$ | 0 |
| A314 | CH$_3$SO | H | CH$_3$ | CHF$_2$ | 0 |
| A315 | CF$_3$ | H | CH$_3$ | CHF$_2$ | 0 |
| A316 | F$_2$CH | H | CH$_3$ | CHF$_2$ | 0 |
| A317 | HCC | H | CH$_3$ | CHF$_2$ | 0 |
| A318 | CH$_3$CC | H | CH$_3$ | CHF$_2$ | 0 |
| A319 | CH$_2$=CH | H | CH$_3$ | CHF$_2$ | 0 |
| A320 | CH$_2$=CHCH$_2$ | H | CH$_3$ | CHF$_2$ | 0 |

TABLE 1-continued

Compounds of the formula XVId:

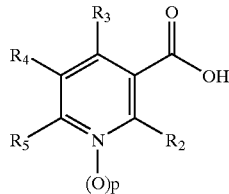

(XVId)

| Comp. No. | $R_2$ | $R_3$ | $R_4$ | $R_5$ | p |
|---|---|---|---|---|---|
| A321 | $CH_3SO_2N(CH_3)$ | H | $CH_3$ | $CHF_2$ | 0 |
| A322 | $(CH_3)_2N$ | H | $CH_3$ | $CHF_2$ | 0 |
| A323 | $(CH_3)_2NSO_2$ | H | $CH_3$ | $CHF_2$ | 0 |
| A324 | $ClCH_2$ | H | $CH_3$ | $CHF_2$ | 0 |
| A325 | $CH_3SCH_2$ | H | $CH_3$ | $CHF_2$ | 0 |
| A326 | $CH_3SOCH_2$ | H | $CH_3$ | $CHF_2$ | 0 |
| A327 | $CH_3SO_2CH_2$ | H | $CH_3$ | $CHF_2$ | 0 |
| A328 | H | H | $CH_3$ | $CCl_3$ | 0 |
| A329 | $CH_3$ | H | $CH_3$ | $CCl_3$ | 0 |
| A330 | $CH_3CH_2$ | H | $CH_3$ | $CCl_3$ | 0 |
| A331 | cyclopropyl | H | $CH_3$ | $CCl_3$ | 0 |
| A332 | $(CH_3)_3C$ | H | $CH_3$ | $CCl_3$ | 0 |
| A333 | $(CH_3)_2CH$ | H | $CH_3$ | $CCl_3$ | 0 |
| A334 | $CH_3(CH_2)_2$ | H | $CH_3$ | $CCl_3$ | 0 |
| A335 | $CH_3OCH_2$ | H | $CH_3$ | $CCl_3$ | 0 |
| A336 | $CH_3O(CH_2)_2$ | H | $CH_3$ | $CCl_3$ | 0 |
| A337 | Ph | H | $CH_3$ | $CCl_3$ | 0 |
| A338 | PhO | H | $CH_3$ | $CCl_3$ | 0 |
| A339 | PhS | H | $CH_3$ | $CCl_3$ | 0 |
| A340 | PhSO | H | $CH_3$ | $CCl_3$ | 0 |
| A341 | $PhSO_2$ | H | $CH_3$ | $CCl_3$ | 0 |
| A342 | $CH_3S$ | H | $CH_3$ | $CCl_3$ | 0 |
| A343 | $CH_3SO$ | H | $CH_3$ | $CCl_3$ | 0 |
| A344 | $CF_3$ | H | $CH_3$ | $CCl_3$ | 0 |
| A345 | $F_2CH$ | H | $CH_3$ | $CCl_3$ | 0 |
| A346 | HCC | H | $CH_3$ | $CCl_3$ | 0 |
| A347 | $CH_3CC$ | H | $CH_3$ | $CCl_3$ | 0 |
| A348 | $CH_2=CH$ | H | $CH_3$ | $CCl_3$ | 0 |
| A349 | $CH_2=CHCH_2$ | H | $CH_3$ | $CCl_3$ | 0 |
| A350 | $CH_3SO_2N(CH_3)$ | H | $CH_3$ | $CCl_3$ | 0 |
| A351 | $(CH_3)_2N$ | H | $CH_3$ | $CCl_3$ | 0 |
| A352 | $(CH_3)_2NSO_2$ | H | $CH_3$ | $CCl_3$ | 0 |
| A353 | $ClCH_2$ | H | $CH_3$ | $CCl_3$ | 0 |
| A354 | $CH_3SCH_2$ | H | $CH_3$ | $CCl_3$ | 0 |
| A355 | $CH_3SOCH_2$ | H | $CH_3$ | $CCl_3$ | 0 |
| A356 | $CH_3SO_2CH_2$ | H | $CH_3$ | $CCl_3$ | 0 |
| A357 | H | H | Ph | $CF_3$ | 0 |
| A358 | $CH_3$ | H | Ph | $CF_3$ | 0 |
| A359 | $CH_3CH_2$ | H | Ph | $CF_3$ | 0 |
| A360 | cyclopropyl | H | Ph | $CF_3$ | 0 |
| A361 | $(CH_3)_3C$ | H | Ph | $CF_3$ | 0 |
| A362 | $(CH_3)_2CH$ | H | Ph | $CF_3$ | 0 |
| A363 | $CH_3(CH_2)_2$ | H | Ph | $CF_3$ | 0 |
| A364 | $CH_3OCH_2$ | H | Ph | $CF_3$ | 0 |
| A365 | $CH_3O(CH_2)_2$ | H | Ph | $CF_3$ | 0 |
| A366 | Ph | H | Ph | $CF_3$ | 0 |
| A367 | PhO | H | Ph | $CF_3$ | 0 |
| A368 | PhS | H | Ph | $CF_3$ | 0 |
| A369 | PhSO | H | Ph | $CF_3$ | 0 |
| A370 | $PhSO_2$ | H | Ph | $CF_3$ | 0 |
| A371 | $CH_3S$ | H | Ph | $CF_3$ | 0 |
| A372 | $CH_3SO$ | H | Ph | $CF_3$ | 0 |
| A373 | $CF_3$ | H | Ph | $CF_3$ | 0 |
| A374 | $F_2CH$ | H | Ph | $CF_3$ | 0 |
| A375 | HCC | H | Ph | $CF_3$ | 0 |
| A376 | $CH_3CC$ | H | Ph | $CF_3$ | 0 |
| A377 | $CH_2=CH$ | H | Ph | $CF_3$ | 0 |
| A378 | $CH_2=CHCH_2$ | H | Ph | $CF_3$ | 0 |
| A379 | $CH_3SO_2N(CH_3)$ | H | Ph | $CF_3$ | 0 |
| A380 | $(CH_3)_2N$ | H | Ph | $CF_3$ | 0 |
| A381 | $(CH_3)_2NSO_2$ | H | Ph | $CF_3$ | 0 |
| A382 | $ClCH_2$ | H | Ph | $CF_3$ | 0 |
| A383 | $CH_3SCH_2$ | H | Ph | $CF_3$ | 0 |
| A384 | $CH_3SOCH_2$ | H | Ph | $CF_3$ | 0 |

TABLE 1-continued

Compounds of the formula XVId:

(XVId)

| Comp. No. | R$_2$ | R$_3$ | R$_4$ | R$_5$ | p |
|---|---|---|---|---|---|
| A385 | CH$_3$SO$_2$CH$_2$ | H | Ph | CF$_3$ | 0 |
| A386 | H | H | Ph | CF$_3$CF$_2$ | 0 |
| A387 | CH$_3$ | H | Ph | CF$_3$CF$_2$ | 0 |
| A388 | CH$_3$CH$_2$ | H | Ph | CF$_3$CF$_2$ | 0 |
| A389 | cyclopropyl | H | Ph | CF$_3$CF$_2$ | 0 |
| A390 | (CH$_3$)$_3$C | H | Ph | CF$_3$CF$_2$ | 0 |
| A391 | (CH$_3$)$_2$CH | H | Ph | CF$_3$CF$_2$ | 0 |
| A392 | CH$_3$(CH$_2$)$_2$ | H | Ph | CF$_3$CF$_2$ | 0 |
| A393 | CH$_3$OCH$_2$ | H | Ph | CF$_3$CF$_2$ | 0 |
| A394 | CH$_3$O(CH$_2$)$_2$ | H | Ph | CF$_3$CF$_2$ | 0 |
| A395 | Ph | H | Ph | CF$_3$CF$_2$ | 0 |
| A396 | PhO | H | Ph | CF$_3$CF$_2$ | 0 |
| A397 | PhS | H | Ph | CF$_3$CF$_2$ | 0 |
| A398 | PhSO | H | Ph | CF$_3$CF$_2$ | 0 |
| A399 | PhSO$_2$ | H | Ph | CF$_3$CF$_2$ | 0 |
| A400 | CH$_3$S | H | Ph | CF$_3$CF$_2$ | 0 |
| A401 | CH$_3$SO | H | Ph | CF$_3$CF$_2$ | 0 |
| A402 | CF$_3$ | H | Ph | CF$_3$CF$_2$ | 0 |
| A403 | F$_2$CH | H | Ph | CF$_3$CF$_2$ | 0 |
| A404 | HCC | H | Ph | CF$_3$CF$_2$ | 0 |
| A405 | CH$_3$CC | H | Ph | CF$_3$CF$_2$ | 0 |
| A406 | CH$_2$=CH | H | Ph | CF$_3$CF$_2$ | 0 |
| A407 | CH$_2$=CHCH$_2$ | H | Ph | CF$_3$CF$_2$ | 0 |
| A408 | CH$_3$SO$_2$N(CH$_3$) | H | Ph | CF$_3$CF$_2$ | 0 |
| A409 | (CH$_3$)$_2$N | H | Ph | CF$_3$CF$_2$ | 0 |
| A410 | (CH$_3$)$_2$NSO$_2$ | H | Ph | CF$_3$CF$_2$ | 0 |
| A411 | ClCH$_2$ | H | Ph | CF$_3$CF$_2$ | 0 |
| A412 | CH$_3$SCH$_2$ | H | Ph | CF$_3$CF$_2$ | 0 |
| A413 | CH$_3$SOCH$_2$ | H | Ph | CF$_3$CF$_2$ | 0 |
| A414 | CH$_3$SO$_2$CH$_2$ | H | Ph | CF$_3$CF$_2$ | 0 |
| A415 | H | H | Ph | CF$_3$CF$_2$CF$_2$ | 0 |
| A416 | CH$_3$ | H | Ph | CF$_3$CF$_2$CF$_2$ | 0 |
| A417 | CH$_3$CH$_2$ | H | Ph | CF$_3$CF$_2$CF$_2$ | 0 |
| A418 | cyclopropyl | H | Ph | CF$_3$CF$_2$CF$_2$ | 0 |
| A419 | (CH$_3$)$_3$C | H | Ph | CF$_3$CF$_2$CF$_2$ | 0 |
| A420 | (CH$_3$)$_2$CH | H | Ph | CF$_3$CF$_2$CF$_2$ | 0 |
| A421 | CH$_3$(CH$_2$)$_2$ | H | Ph | CF$_3$CF$_2$CF$_2$ | 0 |
| A422 | CH$_3$OCH$_2$ | H | Ph | CF$_3$CF$_2$CF$_2$ | 0 |
| A423 | CH$_3$O(CH$_2$)$_2$ | H | Ph | CF$_3$CF$_2$CF$_2$ | 0 |
| A424 | Ph | H | Ph | CF$_3$CF$_2$CF$_2$ | 0 |
| A425 | PhO | H | Ph | CF$_3$CF$_2$CF$_2$ | 0 |
| A426 | PhS | H | Ph | CF$_3$CF$_2$CF$_2$ | 0 |
| A427 | PhSO | H | Ph | CF$_3$CF$_2$CF$_2$ | 0 |
| A428 | PhSO$_2$ | H | Ph | CF$_3$CF$_2$CF$_2$ | 0 |
| A429 | CH$_3$S | H | Ph | CF$_3$CF$_2$CF$_2$ | 0 |
| A430 | CH$_3$SO | H | Ph | CF$_3$CF$_2$CF$_2$ | 0 |
| A431 | CF$_3$ | H | Ph | CF$_3$CF$_2$CF$_2$ | 0 |
| A432 | F$_2$CH | H | Ph | CF$_3$CF$_2$CF$_2$ | 0 |
| A433 | HCC | H | Ph | CF$_3$CF$_2$CF$_2$ | 0 |
| A434 | CH$_3$CC | H | Ph | CF$_3$CF$_2$CF$_2$ | 0 |
| A435 | CH$_2$=CH | H | Ph | CF$_3$CF$_2$CF$_2$ | 0 |
| A436 | CH$_2$=CHCH$_2$ | H | Ph | CF$_3$CF$_2$CF$_2$ | 0 |
| A437 | CH$_3$SO$_2$N(CH$_3$) | H | Ph | CF$_3$CF$_2$CF$_2$ | 0 |
| A438 | (CH$_3$)$_2$N | H | Ph | CF$_3$CF$_2$CF$_2$ | 0 |
| A439 | (CH$_3$)$_2$NSO$_2$ | H | Ph | CF$_3$CF$_2$CF$_2$ | 0 |
| A440 | ClCH$_2$ | H | Ph | CF$_3$CF$_2$CF$_2$ | 0 |
| A441 | CH$_3$SCH$_2$ | H | Ph | CF$_3$CF$_2$CF$_2$ | 0 |
| A442 | CH$_3$SOCH$_2$ | H | Ph | CF$_3$CF$_2$CF$_2$ | 0 |
| A443 | CH$_3$SO$_2$CH$_2$ | H | Ph | CF$_3$CF$_2$CF$_2$ | 0 |
| A444 | H | H | Ph | CF$_2$Cl | 0 |
| A445 | CH$_3$ | H | Ph | CF$_2$Cl | 0 |
| A446 | CH$_3$CH$_2$ | H | Ph | CF$_2$Cl | 0 |
| A447 | cyclopropyl | H | Ph | CF$_2$Cl | 0 |
| A448 | (CH$_3$)$_3$C | H | Ph | CF$_2$Cl | 0 |

TABLE 1-continued

Compounds of the formula XVId:

(XVId)

| Comp. No. | R$_2$ | R$_3$ | R$_4$ | R$_5$ | p |
|---|---|---|---|---|---|
| A449 | (CH$_3$)$_2$CH | H | Ph | CF$_2$Cl | 0 |
| A450 | CH$_3$(CH$_2$)$_2$ | H | Ph | CF$_2$Cl | 0 |
| A451 | CH$_3$OCH$_2$ | H | Ph | CF$_2$Cl | 0 |
| A452 | CH$_3$O(CH$_2$)$_2$ | H | Ph | CF$_2$Cl | 0 |
| A453 | Ph | H | Ph | CF$_2$Cl | 0 |
| A454 | PhO | H | Ph | CF$_2$Cl | 0 |
| A455 | PhS | H | Ph | CF$_2$Cl | 0 |
| A456 | PhSO | H | Ph | CF$_2$Cl | 0 |
| A457 | PhSO$_2$ | H | Ph | CF$_2$Cl | 0 |
| A458 | CH$_3$S | H | Ph | CF$_2$Cl | 0 |
| A459 | CH$_3$SO | H | Ph | CF$_2$Cl | 0 |
| A460 | CF$_3$ | H | Ph | CF$_2$Cl | 0 |
| A461 | F$_2$CH | H | Ph | CF$_2$Cl | 0 |
| A462 | HCC | H | Ph | CF$_2$Cl | 0 |
| A463 | CH$_3$CC | H | Ph | CF$_2$Cl | 0 |
| A464 | CH$_2$=CH | H | Ph | CF$_2$Cl | 0 |
| A465 | CH$_2$=CHCH$_2$ | H | Ph | CF$_2$Cl | 0 |
| A466 | CH$_3$SO$_2$N(CH$_3$) | H | Ph | CF$_2$Cl | 0 |
| A467 | (CH$_3$)$_2$N | H | Ph | CF$_2$Cl | 0 |
| A468 | (CH$_3$)$_2$NSO$_2$ | H | Ph | CF$_2$Cl | 0 |
| A469 | ClCH$_2$ | H | Ph | CF$_2$Cl | 0 |
| A470 | CH$_3$SCH$_2$ | H | Ph | CF$_2$Cl | 0 |
| A471 | CH$_3$SOCH$_2$ | H | Ph | CF$_2$Cl | 0 |
| A472 | CH$_3$SO$_2$CH$_2$ | H | Ph | CF$_2$Cl | 0 |
| A473 | H | H | Ph | CHF$_2$ | 0 |
| A474 | CH$_3$ | H | Ph | CHF$_2$ | 0 |
| A475 | CH$_3$CH$_2$ | H | Ph | CHF$_2$ | 0 |
| A476 | cyclopropyl | H | Ph | CHF$_2$ | 0 |
| A477 | (CH$_3$)$_3$C | H | Ph | CHF$_2$ | 0 |
| A478 | (CH$_3$)$_2$CH | H | Ph | CHF$_2$ | 0 |
| A479 | CH$_3$(CH$_2$)$_2$ | H | Ph | CHF$_2$ | 0 |
| A480 | CH$_3$OCH$_2$ | H | Ph | CHF$_2$ | 0 |
| A481 | CH$_3$O(CH$_2$)$_2$ | H | Ph | CHF$_2$ | 0 |
| A482 | Ph | H | Ph | CHF$_2$ | 0 |
| A483 | PhO | H | Ph | CHF$_2$ | 0 |
| A484 | PhS | H | Ph | CHF$_2$ | 0 |
| A485 | PhSO | H | Ph | CHF$_2$ | 0 |
| A486 | PhSO$_2$ | H | Ph | CHF$_2$ | 0 |
| A487 | CH$_3$S | H | Ph | CHF$_2$ | 0 |
| A488 | CH$_3$SO | H | Ph | CHF$_2$ | 0 |
| A489 | CF$_3$ | H | Ph | CHF$_2$ | 0 |
| A490 | F$_2$CH | H | Ph | CHF$_2$ | 0 |
| A491 | HCC | H | Ph | CHF$_2$ | 0 |
| A492 | CH$_3$CC | H | Ph | CHF$_2$ | 0 |
| A493 | CH$_2$=CH | H | Ph | CHF$_2$ | 0 |
| A494 | CH$_2$=CHCH$_2$ | H | Ph | CHF$_2$ | 0 |
| A495 | CH$_3$SO$_2$N(CH$_3$) | H | Ph | CHF$_2$ | 0 |
| A496 | (CH$_3$)$_2$N | H | Ph | CHF$_2$ | 0 |
| A497 | (CH$_3$)$_2$NSO$_2$ | H | Ph | CHF$_2$ | 0 |
| A498 | ClCH$_2$ | H | Ph | CHF$_2$ | 0 |
| A499 | CH$_3$SCH$_2$ | H | Ph | CHF$_2$ | 0 |
| A500 | CH$_3$SOCH$_2$ | H | Ph | CHF$_2$ | 0 |
| A501 | CH$_3$SO$_2$CH$_2$ | H | Ph | CHF$_2$ | 0 |
| A502 | H | H | Ph | CCl$_3$ | 0 |
| A503 | CH$_3$ | H | Ph | CCl$_3$ | 0 |
| A504 | CH$_3$CH$_2$ | H | Ph | CCl$_3$ | 0 |
| A505 | cyclopropyl | H | Ph | CCl$_3$ | 0 |
| A506 | (CH$_3$)$_3$C | H | Ph | CCl$_3$ | 0 |
| A507 | (CH$_3$)$_2$CH | H | Ph | CCl$_3$ | 0 |
| A508 | CH$_3$(CH$_2$)$_2$ | H | Ph | CCl$_3$ | 0 |
| A509 | CH$_3$OCH$_2$ | H | Ph | CCl$_3$ | 0 |
| A510 | CH$_3$O(CH$_2$)$_2$ | H | Ph | CCl$_3$ | 0 |
| A511 | Ph | H | Ph | CCl$_3$ | 0 |
| A512 | PhO | H | Ph | CCl$_3$ | 0 |

TABLE 1-continued

Compounds of the formula XVId:

(XVId)

| Comp. No. | R₂ | R₃ | R₄ | R₅ | p |
|---|---|---|---|---|---|
| A513 | PhS | H | Ph | CCl₃ | 0 |
| A514 | PhSO | H | Ph | CCl₃ | 0 |
| A515 | PhSO₂ | H | Ph | CCl₃ | 0 |
| A516 | CH₃S | H | Ph | CCl₃ | 0 |
| A517 | CH₃SO | H | Ph | CCl₃ | 0 |
| A518 | CF₃ | H | Ph | CCl₃ | 0 |
| A519 | F₂CH | H | Ph | CCl₃ | 0 |
| A520 | HCC | H | Ph | CCl₃ | 0 |
| A521 | CH₃CC | H | Ph | CCl₃ | 0 |
| A522 | CH₂=CH | H | Ph | CCl₃ | 0 |
| A523 | CH₂=CHCH₂ | H | Ph | CCl₃ | 0 |
| A524 | CH₃SO₂N(CH₃) | H | Ph | CCl₃ | 0 |
| A525 | (CH₃)₂N | H | Ph | CCl₃ | 0 |
| A526 | (CH₃)₂NSO₂ | H | Ph | CCl₃ | 0 |
| A527 | ClCH₂ | H | Ph | CCl₃ | 0 |
| A528 | CH₃SCH₂ | H | Ph | CCl₃ | 0 |
| A529 | CH₃SOCH₂ | H | Ph | CCl₃ | 0 |
| A530 | CH₃SO₂CH₂ | H | Ph | CCl₃ | 0 |
| A531 | H | CH₃ | H | CF₃ | 0 |
| A532 | H | CH₃CH₂ | H | CF₃ | 0 |
| A533 | H | cyclopropyl | H | CF₃ | 0 |
| A534 | H | (CH₃)₃CH | H | CF₃ | 0 |
| A535 | H | (CH₃)₂CH | H | CF₃ | 0 |
| A536 | H | CH₃(CH₂)₂ | H | CF₃ | 0 |
| A537 | H | CH₃OCH₂ | H | CF₃ | 0 |
| A538 | H | CH₃O(CH₂)₂ | H | CF₃ | 0 |
| A539 | H | Ph | H | CF₃ | 0 |
| A540 | H | PhO | H | CF₃ | 0 |
| A541 | H | PhS | H | CF₃ | 0 |
| A542 | H | PhSO | H | CF₃ | 0 |
| A543 | H | PhSO₂ | H | CF₃ | 0 |
| A544 | H | CH₃S | H | CF₃ | 0 |
| A545 | H | CH₃SO | H | CF₃ | 0 |
| A546 | H | CF₃ | H | CF₃ | 0 |
| A547 | H | F₂CH | H | CF₃ | 0 |
| A548 | H | HCC | H | CF₃ | 0 |
| A549 | H | CH₃CC | H | CF₃ | 0 |
| A550 | H | CH₂=CH | H | CF₃ | 0 |
| A551 | H | CH₂=CHCH₂ | H | CF₃ | 0 |
| A552 | H | CH₃SO₂N(CH₃) | H | CF₃ | 0 |
| A553 | H | (CH₃)₂N | H | CF₃ | 0 |
| A554 | H | (CH₃)₂NSO₂ | H | CF₃ | 0 |
| A555 | H | CH₃SCH₂ | H | CF₃ | 0 |
| A556 | H | CH₃SOCH₂ | H | CF₃ | 0 |
| A557 | H | CH₃SO₂CH₂ | H | CF₃ | 0 |
| A558 | H | CH₃ | H | CF₃CF₂ | 0 |
| A559 | H | CH₃CH₂ | H | CF₃CF₂ | 0 |
| A560 | H | cyclopropyl | H | CF₃CF₂ | 0 |
| A561 | H | (CH₃)₃C | H | CF₃CF₂ | 0 |
| A562 | H | (CH₃)₂CH | H | CF₃CF₂ | 0 |
| A563 | H | CH₃(CH₂)₂ | H | CF₃CF₂ | 0 |
| A564 | H | CH₃OCH₂ | H | CF₃CF₂ | 0 |
| A565 | H | CH₃O(CH₂)₂ | H | CF₃CF₂ | 0 |
| A566 | H | Ph | H | CF₃CF₂ | 0 |
| A567 | H | PhO | H | CF₃CF₂ | 0 |
| A568 | H | PhS | H | CF₃CF₂ | 0 |
| A569 | H | PhSO | H | CF₃CF₂ | 0 |
| A570 | H | PhSO₂ | H | CF₃CF₂ | 0 |
| A571 | H | CH₃S | H | CF₃CF₂ | 0 |
| A572 | H | CH₃SO | H | CF₃CF₂ | 0 |
| A573 | H | CF₃ | H | CF₃CF₂ | 0 |
| A574 | H | F₂CH | H | CF₃CF₂ | 0 |
| A575 | H | HCC | H | CF₃CF₂ | 0 |
| A576 | H | CH₃CC | H | CF₃CF₂ | 0 |

TABLE 1-continued

Compounds of the formula XVId:

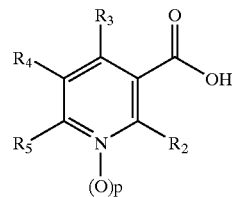

(XVId)

| Comp. No. | $R_2$ | $R_3$ | $R_4$ | $R_5$ | p |
|---|---|---|---|---|---|
| A577 | H | $CH_2=CH$ | H | $CF_3CF_2$ | 0 |
| A578 | H | $CH_2=CHCH_2$ | H | $CF_3CF_2$ | 0 |
| A579 | H | $CH_3SO_2N(CH_3)$ | H | $CF_3CF_2$ | 0 |
| A580 | H | $(CH_3)_2N$ | H | $CF_3CF_2$ | 0 |
| A581 | H | $(CH_3)_2NSO_2$ | H | $CF_3CF_2$ | 0 |
| A582 | H | $CH_3SCH_2$ | H | $CF_3CF_2$ | 0 |
| A583 | H | $CH_3SOCH_2$ | H | $CF_3CF_2$ | 0 |
| A584 | H | $CH_3SO_2CH_2$ | H | $CF_3CF_2$ | 0 |
| A585 | H | $CH_3$ | H | $CF_3CF_2CF_2$ | 0 |
| A586 | H | $CH_3CH_2$ | H | $CF_3CF_2CF_2$ | 0 |
| A587 | H | cyclopropyl | H | $CF_3CF_2CF_2$ | 0 |
| A588 | H | $(CH_3)_3C$ | H | $CF_3CF_2CF_2$ | 0 |
| A589 | H | $(CH_3)_2CH$ | H | $CF_3CF_2CF_2$ | 0 |
| A590 | H | $CH_3(CH_2)_2$ | H | $CF_3CF_2CF_2$ | 0 |
| A591 | H | $CH_3OCH_2$ | H | $CF_3CF_2CF_2$ | 0 |
| A592 | H | $CH_3O(CH_2)_2$ | H | $CF_3CF_2CF_2$ | 0 |
| A593 | H | Ph | H | $CF_3CF_2CF_2$ | 0 |
| A594 | H | PhO | H | $CF_3CF_2CF_2$ | 0 |
| A595 | H | PhS | H | $CF_3CF_2CF_2$ | 0 |
| A596 | H | PhSO | H | $CF_3CF_2CF_2$ | 0 |
| A597 | H | $PhSO_2$ | H | $CF_3CF_2CF_2$ | 0 |
| A598 | H | $CH_3S$ | H | $CF_3CF_2CF_2$ | 0 |
| A599 | H | $CH_3SO$ | H | $CF_3CF_2CF_2$ | 0 |
| A600 | H | $CF_3$ | H | $CF_3CF_2CF_2$ | 0 |
| A601 | H | $F_2CH$ | H | $CF_3CF_2CF_2$ | 0 |
| A602 | H | HCC | H | $CF_3CF_2CF_2$ | 0 |
| A603 | H | $CH_3CC$ | H | $CF_3CF_2CF_2$ | 0 |
| A604 | H | $CH_2=CH$ | H | $CF_3CF_2CF_2$ | 0 |
| A605 | H | $CH_2=CHCH_2$ | H | $CF_3CF_2CF_2$ | 0 |
| A606 | H | $CH_3SO_2N(CH_3)$ | H | $CF_3CF_2CF_2$ | 0 |
| A607 | H | $(CH_3)_2N$ | H | $CF_3CF_2CF_2$ | 0 |
| A608 | H | $(CH_3)_2NSO_2$ | H | $CF_3CF_2CF_2$ | 0 |
| A609 | H | $CH_3SCH_2$ | H | $CF_3CF_2CF_2$ | 0 |
| A610 | H | $CH_3SOCH_2$ | H | $CF_3CF_2CF_2$ | 0 |
| A611 | H | $CH_3SO_2CH_2$ | H | $CF_3CF_2CF_2$ | 0 |
| A612 | H | $CH_3$ | H | $CF_2Cl$ | 0 |
| A613 | H | $CH_3CH_2$ | H | $CF_2Cl$ | 0 |
| A614 | H | cyclopropyl | H | $CF_2Cl$ | 0 |
| A615 | H | $(CH_3)_3C$ | H | $CF_2Cl$ | 0 |
| A616 | H | $(CH_3)_2CH$ | H | $CF_2Cl$ | 0 |
| A617 | H | $CH_3(CH_2)_2$ | H | $CF_2Cl$ | 0 |
| A618 | H | $CH_3OCH_2$ | H | $CF_2Cl$ | 0 |
| A619 | H | $CH_3O(CH_2)_2$ | H | $CF_2Cl$ | 0 |
| A620 | H | Ph | H | $CF_2Cl$ | 0 |
| A621 | H | PhO | H | $CF_2Cl$ | 0 |
| A622 | H | PhS | H | $CF_2Cl$ | 0 |
| A623 | H | PhSO | H | $CF_2Cl$ | 0 |
| A624 | H | $PhSO_2$ | H | $CF_2Cl$ | 0 |
| A625 | H | $CH_3S$ | H | $CF_2Cl$ | 0 |
| A626 | H | $CH_3SO$ | H | $CF_2Cl$ | 0 |
| A627 | H | $CF_3$ | H | $CF_2Cl$ | 0 |
| A628 | H | $F_2CH$ | H | $CF_2Cl$ | 0 |
| A629 | H | HCC | H | $CF_2Cl$ | 0 |
| A630 | H | $CH_3CC$ | H | $CF_2Cl$ | 0 |
| A631 | H | $CH_2=CH$ | H | $CF_2Cl$ | 0 |
| A632 | H | $CH_2=CHCH_2$ | H | $CF_2Cl$ | 0 |
| A633 | H | $CH_3SO_2N(CH_3)$ | H | $CF_2Cl$ | 0 |
| A634 | H | $(CH_3)_2N$ | H | $CF_2Cl$ | 0 |
| A635 | H | $(CH_3)_2NSO_2$ | H | $CF_2Cl$ | 0 |
| A636 | H | $CH_3SCH_2$ | H | $CF_2Cl$ | 0 |
| A637 | H | $CH_3SOCH_2$ | H | $CF_2Cl$ | 0 |
| A638 | H | $CH_3SO_2CH_2$ | H | $CF_2Cl$ | 0 |
| A639 | H | $CH_3$ | H | $CHF_2$ | 0 |
| A640 | H | $CH_3CH_2$ | H | $CHF_2$ | 0 |

TABLE 1-continued

Compounds of the formula XVId:

$$\text{(XVId)}$$

| Comp. No. | $R_2$ | $R_3$ | $R_4$ | $R_5$ | p |
|---|---|---|---|---|---|
| A641 | H | cyclopropyl | H | $CHF_2$ | 0 |
| A642 | H | $(CH_3)_3C$ | H | $CHF_2$ | 0 |
| A643 | H | $(CH_3)_2CH$ | H | $CHF_2$ | 0 |
| A644 | H | $CH_3(CH_2)_2$ | H | $CHF_2$ | 0 |
| A645 | H | $CH_3OCH_2$ | H | $CHF_2$ | 0 |
| A646 | H | $CH_3O(CH_2)_2$ | H | $CHF_2$ | 0 |
| A647 | H | Ph | H | $CHF_2$ | 0 |
| A648 | H | PhO | H | $CHF_2$ | 0 |
| A649 | H | PhS | H | $CHF_2$ | 0 |
| A650 | H | PhSO | H | $CHF_2$ | 0 |
| A651 | H | $PhSO_2$ | H | $CHF_2$ | 0 |
| A652 | H | $CH_3S$ | H | $CHF_2$ | 0 |
| A653 | H | $CH_3SO$ | H | $CHF_2$ | 0 |
| A654 | H | $CF_3$ | H | $CHF_2$ | 0 |
| A655 | H | $F_2CH$ | H | $CHF_2$ | 0 |
| A656 | H | HCC | H | $CHF_2$ | 0 |
| A657 | H | $CH_3CC$ | H | $CHF_2$ | 0 |
| A658 | H | $CH_2$=CH | H | $CHF_2$ | 0 |
| A659 | H | $CH_2$=$CHCH_2$ | H | $CHF_2$ | 0 |
| A660 | H | $CH_3SO_2N(CH_3)$ | H | $CHF_2$ | 0 |
| A661 | H | $(CH_3)_2N$ | H | $CHF_2$ | 0 |
| A662 | H | $(CH_3)_2NSO_2$ | H | $CHF_2$ | 0 |
| A663 | H | $CH_3SCH_2$ | H | $CHF_2$ | 0 |
| A664 | H | $CH_3SOCH_2$ | H | $CHF_2$ | 0 |
| A665 | H | $CH_3SO_2CH_2$ | H | $CHF_2$ | 0 |
| A666 | H | $CH_3$ | H | $CCl_3$ | 0 |
| A667 | H | $CH_3CH_2$ | H | $CCl_3$ | 0 |
| A668 | H | cyclopropyl | H | $CCl_3$ | 0 |
| A669 | H | $(CH_3)_3C$ | H | $CCl_3$ | 0 |
| A670 | H | $(CH_3)_2CH$ | H | $CCl_3$ | 0 |
| A671 | H | $CH_3(CH_2)_2$ | H | $CCl_3$ | 0 |
| A672 | H | $CH_3OCH_2$ | H | $CCl_3$ | 0 |
| A673 | H | $CH_3O(CH_2)_2$ | H | $CCl_3$ | 0 |
| A674 | H | Ph | H | $CCl_3$ | 0 |
| A675 | H | PhO | H | $CCl_3$ | 0 |
| A676 | H | PhS | H | $CCl_3$ | 0 |
| A677 | H | PhSO | H | $CCl_3$ | 0 |
| A678 | H | $PhSO_2$ | H | $CCl_3$ | 0 |
| A679 | H | $CH_3S$ | H | $CCl_3$ | 0 |
| A680 | H | $CH_3SO$ | H | $CCl_3$ | 0 |
| A681 | H | $CF_3$ | H | $CCl_3$ | 0 |
| A682 | H | $F_2CH$ | H | $CCl_3$ | 0 |
| A683 | H | HCC | H | $CCl_3$ | 0 |
| A684 | H | $CH_3CC$ | H | $CCl_3$ | 0 |
| A685 | H | $CH_2$=CH | H | $CCl_3$ | 0 |
| A686 | H | $CH_2$=$CHCH_2$ | H | $CCl_3$ | 0 |
| A687 | H | $CH_3SO_2N(CH_3)$ | H | $CCl_3$ | 0 |
| A688 | H | $(CH_3)_2N$ | H | $CCl_3$ | 0 |
| A689 | H | $(CH_3)_2NSO_2$ | H | $CCl_3$ | 0 |
| A690 | H | $CH_3SCH_2$ | H | $CCl_3$ | 0 |
| A691 | H | $CH_3SOCH_2$ | H | $CCl_3$ | 0 |
| A692 | H | $CH_3SO_2CH_2$ | H | $CCl_3$ | 0 |
| A693 | H | $CH_3$ | $CH_3$ | $CF_3$ | 0 |
| A694 | H | $CH_3CH_2$ | $CH_3$ | $CF_3$ | 0 |
| A695 | H | cyclopropyl | $CH_3$ | $CF_3$ | 0 |
| A696 | H | $(CH_3)_3C$ | $CH_3$ | $CF_3$ | 0 |
| A697 | H | $(CH_3)_2CH$ | $CH_3$ | $CF_3$ | 0 |
| A698 | H | $CH_3(CH_2)_2$ | $CH_3$ | $CF_3$ | 0 |
| A699 | H | $CH_3OCH_2$ | $CH_3$ | $CF_3$ | 0 |
| A700 | H | $CH_3O(CH_2)_2$ | $CH_3$ | $CF_3$ | 0 |
| A701 | H | Ph | $CH_3$ | $CF_3$ | 0 |
| A702 | H | PhO | $CH_3$ | $CF_3$ | 0 |
| A703 | H | PhS | $CH_3$ | $CF_3$ | 0 |
| A704 | H | PhSO | $CH_3$ | $CF_3$ | 0 |

TABLE 1-continued

Compounds of the formula XVId:

(XVId)

| Comp. No. | R$_2$ | R$_3$ | R$_4$ | R$_5$ | p |
|---|---|---|---|---|---|
| A705 | H | PhSO$_2$ | CH$_3$ | CF$_3$ | 0 |
| A706 | H | CH$_3$S | CH$_3$ | CF$_3$ | 0 |
| A707 | H | CH$_3$SO | CH$_3$ | CF$_3$ | 0 |
| A708 | H | CF$_3$ | CH$_3$ | CF$_3$ | 0 |
| A709 | H | F$_2$CH | CH$_3$ | CF$_3$ | 0 |
| A710 | H | HCC | CH$_3$ | CF$_3$ | 0 |
| A711 | H | CH$_3$CC | CH$_3$ | CF$_3$ | 0 |
| A712 | H | CH$_2$=CH | CH$_3$ | CF$_3$ | 0 |
| A713 | H | CH$_2$=CHCH$_2$ | CH$_3$ | CF$_3$ | 0 |
| A714 | H | CH$_3$SO$_2$N(CH$_3$) | CH$_3$ | CF$_3$ | 0 |
| A715 | H | (CH$_3$)$_2$N | CH$_3$ | CF$_3$ | 0 |
| A716 | H | (CH$_3$)$_2$NSO$_2$ | CH$_3$ | CF$_3$ | 0 |
| A717 | H | CH$_3$SCH$_2$ | CH$_3$ | CF$_3$ | 0 |
| A718 | H | CH$_3$SOCH$_2$ | CH$_3$ | CF$_3$ | 0 |
| A719 | H | CH$_3$SO$_2$CH$_2$ | CH$_3$ | CF$_3$ | 0 |
| A720 | H | CH$_3$ | CH$_3$ | CF$_3$CF$_2$ | 0 |
| A721 | H | CH$_3$CH$_2$ | CH$_3$ | CF$_3$CF$_2$ | 0 |
| A722 | H | cyclopropyl | CH$_3$ | CF$_3$CF$_2$ | 0 |
| A723 | H | (CH$_3$)$_3$C | CH$_3$ | CF$_3$CF$_2$ | 0 |
| A724 | H | (CH$_3$)$_2$CH | CH$_3$ | CF$_3$CF$_2$ | 0 |
| A725 | H | CH$_3$(CH$_2$)$_2$ | CH$_3$ | CF$_3$CF$_2$ | 0 |
| A726 | H | CH$_3$OCH$_2$ | CH$_3$ | CF$_3$CF$_2$ | 0 |
| A727 | H | CH$_3$O(CH$_2$)$_2$ | CH$_3$ | CF$_3$CF$_2$ | 0 |
| A728 | H | Ph | CH$_3$ | CF$_3$CF$_2$ | 0 |
| A729 | H | PhO | CH$_3$ | CF$_3$CF$_2$ | 0 |
| A730 | H | PhS | CH$_3$ | CF$_3$CF$_2$ | 0 |
| A731 | H | PhSO | CH$_3$ | CF$_3$CF$_2$ | 0 |
| A732 | H | PhSO$_2$ | CH$_3$ | CF$_3$CF$_2$ | 0 |
| A733 | H | CH$_3$S | CH$_3$ | CF$_3$CF$_2$ | 0 |
| A734 | H | CH$_3$SO | CH$_3$ | CF$_3$CF$_2$ | 0 |
| A735 | H | CF$_3$ | CH$_3$ | CF$_3$CF$_2$ | 0 |
| A736 | H | F$_2$CH | CH$_3$ | CF$_3$CF$_2$ | 0 |
| A737 | H | HCC | CH$_3$ | CF$_3$CF$_2$ | 0 |
| A738 | H | CH$_3$CC | CH$_3$ | CF$_3$CF$_2$ | 0 |
| A739 | H | CH$_2$=CH | CH$_3$ | CF$_3$CF$_2$ | 0 |
| A740 | H | CH$_2$=CHCH$_2$ | CH$_3$ | CF$_3$CF$_2$ | 0 |
| A741 | H | CH$_3$SO$_2$N(CH$_3$) | CH$_3$ | CF$_3$CF$_2$ | 0 |
| A742 | H | (CH$_3$)$_2$N | CH$_3$ | CF$_3$CF$_2$ | 0 |
| A743 | H | (CH$_3$)$_2$NSO$_2$ | CH$_3$ | CF$_3$CF$_2$ | 0 |
| A744 | H | CH$_3$SCH$_2$ | CH$_3$ | CF$_3$CF$_2$ | 0 |
| A745 | H | CH$_3$SOCH$_2$ | CH$_3$ | CF$_3$CF$_2$ | 0 |
| A746 | H | CH$_3$SO$_2$CH$_2$ | CH$_3$ | CF$_3$CF$_2$ | 0 |
| A747 | H | CH$_3$ | CH$_3$ | CF$_3$CF$_2$CF$_2$ | 0 |
| A748 | H | CH$_3$CH$_2$ | CH$_3$ | CF$_3$CF$_2$CF$_2$ | 0 |
| A749 | H | cyclopropyl | CH$_3$ | CF$_3$CF$_2$CF$_2$ | 0 |
| A750 | H | (CH$_3$)$_3$C | CH$_3$ | CF$_3$CF$_2$CF$_2$ | 0 |
| A751 | H | (CH$_3$)$_2$CH | CH$_3$ | CF$_3$CF$_2$CF$_2$ | 0 |
| A752 | H | CH$_3$(CH$_2$)$_2$ | CH$_3$ | CF$_3$CF$_2$CF$_2$ | 0 |
| A753 | H | CH$_3$OCH$_2$ | CH$_3$ | CF$_3$CF$_2$CF$_2$ | 0 |
| A754 | H | CH$_3$O(CH$_2$)$_2$ | CH$_3$ | CF$_3$CF$_2$CF$_2$ | 0 |
| A755 | H | Ph | CH$_3$ | CF$_3$CF$_2$CF$_2$ | 0 |
| A756 | H | PhO | CH$_3$ | CF$_3$CF$_2$CF$_2$ | 0 |
| A757 | H | PhS | CH$_3$ | CF$_3$CF$_2$CF$_2$ | 0 |
| A758 | H | PhSO | CH$_3$ | CF$_3$CF$_2$CF$_2$ | 0 |
| A759 | H | PhSO$_2$ | CH$_3$ | CF$_3$CF$_2$CF$_2$ | 0 |
| A760 | H | CH$_3$S | CH$_3$ | CF$_3$CF$_2$CF$_2$ | 0 |
| A761 | H | CH$_3$SO | CH$_3$ | CF$_3$CF$_2$CF$_2$ | 0 |
| A762 | H | CF$_3$ | CH$_3$ | CF$_3$CF$_2$CF$_2$ | 0 |
| A763 | H | F$_2$CH | CH$_3$ | CF$_3$CF$_2$CF$_2$ | 0 |
| A764 | H | HCC | CH$_3$ | CF$_3$CF$_2$CF$_2$ | 0 |
| A765 | H | CH$_3$CC | CH$_3$ | CF$_3$CF$_2$CF$_2$ | 0 |
| A766 | H | CH$_2$=CH | CH$_3$ | CF$_3$CF$_2$CF$_2$ | 0 |
| A767 | H | CH$_2$=CHCH$_2$ | CH$_3$ | CF$_3$CF$_2$CF$_2$ | 0 |
| A768 | H | CH$_3$SO$_2$N(CH$_3$) | CH$_3$ | CF$_3$CF$_2$CF$_2$ | 0 |

TABLE 1-continued

Compounds of the formula XVId:

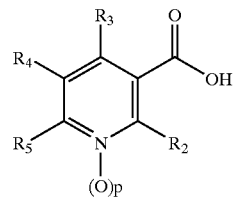

(XVId)

| Comp. No. | $R_2$ | $R_3$ | $R_4$ | $R_5$ | p |
|---|---|---|---|---|---|
| A769 | H | $(CH_3)_2N$ | $CH_3$ | $CF_3CF_2CF_2$ | 0 |
| A770 | H | $(CH_3)_2NSO_2$ | $CH_3$ | $CF_3CF_2CF_2$ | 0 |
| A771 | H | $CH_3SCH_2$ | $CH_3$ | $CF_3CF_2CF_2$ | 0 |
| A772 | H | $CH_3SOCH_2$ | $CH_3$ | $CF_3CF_2CF_2$ | 0 |
| A773 | H | $CH_3SO_2CH_2$ | $CH_3$ | $CF_3CF_2CF_2$ | 0 |
| A774 | H | $CH_3$ | $CH_3$ | $CF_2Cl$ | 0 |
| A775 | H | $CH_3CH_2$ | $CH_3$ | $CF_2Cl$ | 0 |
| A776 | H | cyclopropyl | $CH_3$ | $CF_2Cl$ | 0 |
| A777 | H | $(CH_3)_3C$ | $CH_3$ | $CF_2Cl$ | 0 |
| A778 | H | $(CH_3)_2CH$ | $CH_3$ | $CF_2Cl$ | 0 |
| A779 | H | $CH_3(CH_2)_2$ | $CH_3$ | $CF_2Cl$ | 0 |
| A780 | H | $CH_3OCH_2$ | $CH_3$ | $CF_2Cl$ | 0 |
| A781 | H | $CH_3O(CH_2)_2$ | $CH_3$ | $CF_2Cl$ | 0 |
| A782 | H | Ph | $CH_3$ | $CF_2Cl$ | 0 |
| A783 | H | PhO | $CH_3$ | $CF_2Cl$ | 0 |
| A784 | H | PhS | $CH_3$ | $CF_2Cl$ | 0 |
| A785 | H | PhSO | $CH_3$ | $CF_2Cl$ | 0 |
| A786 | H | $PhSO_2$ | $CH_3$ | $CF_2Cl$ | 0 |
| A787 | H | $CH_3S$ | $CH_3$ | $CF_2Cl$ | 0 |
| A788 | H | $CH_3SO$ | $CH_3$ | $CF_2Cl$ | 0 |
| A789 | H | $CF_3$ | $CH_3$ | $CF_2Cl$ | 0 |
| A790 | H | $F_2CH$ | $CH_3$ | $CF_2Cl$ | 0 |
| A791 | H | HCC | $CH_3$ | $CF_2Cl$ | 0 |
| A792 | H | $CH_3CC$ | $CH_3$ | $CF_2Cl$ | 0 |
| A793 | H | $CH_2=CH$ | $CH_3$ | $CF_2Cl$ | 0 |
| A794 | H | $CH_2=CHCH_2$ | $CH_3$ | $CF_2Cl$ | 0 |
| A795 | H | $CH_3SO_2N(CH_3)$ | $CH_3$ | $CF_2Cl$ | 0 |
| A796 | H | $(CH_3)_2N$ | $CH_3$ | $CF_2Cl$ | 0 |
| A797 | H | $(CH_3)_2NSO_2$ | $CH_3$ | $CF_2Cl$ | 0 |
| A798 | H | $CH_3SCH_2$ | $CH_3$ | $CF_2Cl$ | 0 |
| A799 | H | $CH_3SOCH_2$ | $CH_3$ | $CF_2Cl$ | 0 |
| A800 | H | $CH_3SO_2CH_2$ | $CH_3$ | $CF_2Cl$ | 0 |
| A801 | H | $CH_3$ | $CH_3$ | $CHF_2$ | 0 |
| A802 | H | $CH_3CH_2$ | $CH_3$ | $CHF_2$ | 0 |
| A803 | H | cyclopropyl | $CH_3$ | $CHF_2$ | 0 |
| A804 | H | $(CH_3)_3C$ | $CH_3$ | $CHF_2$ | 0 |
| A805 | H | $(CH_3)_2CH$ | $CH_3$ | $CHF_2$ | 0 |
| A806 | H | $CH_3(CH_2)_2$ | $CH_3$ | $CHF_2$ | 0 |
| A807 | H | $CH_3OCH_2$ | $CH_3$ | $CHF_2$ | 0 |
| A808 | H | $CH_3O(CH_2)_2$ | $CH_3$ | $CHF_2$ | 0 |
| A809 | H | Ph | $CH_3$ | $CHF_2$ | 0 |
| A810 | H | PhO | $CH_3$ | $CHF_2$ | 0 |
| A811 | H | PhS | $CH_3$ | $CHF_2$ | 0 |
| A812 | H | PhSO | $CH_3$ | $CHF_2$ | 0 |
| A813 | H | $PhSO_2$ | $CH_3$ | $CHF_2$ | 0 |
| A814 | H | $CH_3S$ | $CH_3$ | $CHF_2$ | 0 |
| A815 | H | $CH_3SO$ | $CH_3$ | $CHF_2$ | 0 |
| A816 | H | $CF_3$ | $CH_3$ | $CHF_2$ | 0 |
| A817 | H | $F_2CH$ | $CH_3$ | $CHF_2$ | 0 |
| A818 | H | HCC | $CH_3$ | $CHF_2$ | 0 |
| A819 | H | $CH_3CC$ | $CH_3$ | $CHF_2$ | 0 |
| A820 | H | $CH_2=CH$ | $CH_3$ | $CHF_2$ | 0 |
| A821 | H | $CH_2=CHCH_2$ | $CH_3$ | $CHF_2$ | 0 |
| A822 | H | $CH_3SO_2N(CH_3)$ | $CH_3$ | $CHF_2$ | 0 |
| A823 | H | $(CH_3)_2N$ | $CH_3$ | $CHF_2$ | 0 |
| A824 | H | $(CH_3)_2NSO_2$ | $CH_3$ | $CHF_2$ | 0 |
| A825 | H | $CH_3SCH_2$ | $CH_3$ | $CHF_2$ | 0 |
| A826 | H | $CH_3SOCH_2$ | $CH_3$ | $CHF_2$ | 0 |
| A827 | H | $CH_3SO_2CH_2$ | $CH_3$ | $CHF_2$ | 0 |
| A828 | H | $CH_3$ | $CH_3$ | $CCl_3$ | 0 |
| A829 | H | $CH_3CH_2$ | $CH_3$ | $CCl_3$ | 0 |
| A830 | H | cyclopropyl | $CH_3$ | $CCl_3$ | 0 |
| A831 | H | $(CH_3)_3C$ | $CH_3$ | $CCl_3$ | 0 |
| A832 | H | $(CH_3)_2CH$ | $CH_3$ | $CCl_3$ | 0 |

TABLE 1-continued

Compounds of the formula XVId:

$$\text{(XVId)}$$

| Comp. No. | $R_2$ | $R_3$ | $R_4$ | $R_5$ | p |
|---|---|---|---|---|---|
| A833 | H | $CH_3(CH_2)_2$ | $CH_3$ | $CCl_3$ | 0 |
| A834 | H | $CH_3OCH_2$ | $CH_3$ | $CCl_3$ | 0 |
| A835 | H | $CH_3O(CH_2)_2$ | $CH_3$ | $CCl_3$ | 0 |
| A836 | H | Ph | $CH_3$ | $CCl_3$ | 0 |
| A837 | H | PhO | $CH_3$ | $CCl_3$ | 0 |
| A838 | H | PhS | $CH_3$ | $CCl_3$ | 0 |
| A839 | H | PhSO | $CH_3$ | $CCl_3$ | 0 |
| A840 | H | $PhSO_2$ | $CH_3$ | $CCl_3$ | 0 |
| A841 | H | $CH_3S$ | $CH_3$ | $CCl_3$ | 0 |
| A842 | H | $CH_3SO$ | $CH_3$ | $CCl_3$ | 0 |
| A843 | H | $CF_3$ | $CH_3$ | $CCl_3$ | 0 |
| A844 | H | $F_2CH$ | $CH_3$ | $CCl_3$ | 0 |
| A845 | H | HCC | $CH_3$ | $CCl_3$ | 0 |
| A846 | H | $CH_3CC$ | $CH_3$ | $CCl_3$ | 0 |
| A847 | H | $CH_2\!=\!CH$ | $CH_3$ | $CCl_3$ | 0 |
| A848 | H | $CH_2\!=\!CHCH_2$ | $CH_3$ | $CCl_3$ | 0 |
| A849 | H | $CH_3SO_2N(CH_3)$ | $CH_3$ | $CCl_3$ | 0 |
| A850 | H | $(CH_3)_2N$ | $CH_3$ | $CCl_3$ | 0 |
| A851 | H | $(CH_3)_2NSO_2$ | $CH_3$ | $CCl_3$ | 0 |
| A852 | H | $CH_3SCH_2$ | $CH_3$ | $CCl_3$ | 0 |
| A853 | H | $CH_3SOCH_2$ | $CH_3$ | $CCl_3$ | 0 |
| A854 | H | $CH_3SO_2CH_2$ | $CH_3$ | $CCl_3$ | 0 |
| A855 | H | $CH_3$ | Ph | $CF_3$ | 0 |
| A856 | H | $CH_3CH_2$ | Ph | $CF_3$ | 0 |
| A857 | H | $(CH_3)_2CH$ | Ph | $CF_3$ | 0 |
| A858 | H | $(CH_3)_2CH$ | Ph | $CF_3$ | 0 |
| A859 | H | cyclopropyl | Ph | $CF_3$ | 0 |
| A860 | H | $CH_3(CH_2)_2$ | Ph | $CF_3$ | 0 |
| A861 | H | $CH_3OCH_2$ | Ph | $CF_3$ | 0 |
| A862 | H | $CH_3O(CH_2)_2$ | Ph | $CF_3$ | 0 |
| A863 | H | Ph | Ph | $CF_3$ | 0 |
| A864 | H | PhO | Ph | $CF_3$ | 0 |
| A865 | H | PhS | Ph | $CF_3$ | 0 |
| A866 | H | PhSO | Ph | $CF_3$ | 0 |
| A867 | H | $PhSO_2$ | Ph | $CF_3$ | 0 |
| A868 | H | $CH_3S$ | Ph | $CF_3$ | 0 |
| A869 | H | $CH_3SO$ | Ph | $CF_3$ | 0 |
| A870 | H | $CF_3$ | Ph | $CF_3$ | 0 |
| A871 | H | $F_2CH$ | Ph | $CF_3$ | 0 |
| A872 | H | HCC | Ph | $CF_3$ | 0 |
| A873 | H | $CH_3CC$ | Ph | $CF_3$ | 0 |
| A874 | H | $CH_2\!=\!CH$ | Ph | $CF_3$ | 0 |
| A875 | H | $CH_2\!=\!CHCH_2$ | Ph | $CF_3$ | 0 |
| A876 | H | $CH_3SO_2N(CH_3)$ | Ph | $CF_3$ | 0 |
| A877 | H | $(CH_3)_2N$ | Ph | $CF_3$ | 0 |
| A878 | H | $(CH_3)_2NSO_2$ | Ph | $CF_3$ | 0 |
| A879 | H | $CH_3SCH_2$ | Ph | $CF_3$ | 0 |
| A880 | H | $CH_3SOCH_2$ | Ph | $CF_3$ | 0 |
| A881 | H | $CH_3SO_2CH_2$ | Ph | $CF_3$ | 0 |
| A882 | H | $CH_3$ | Ph | $CF_3CF_2$ | 0 |
| A883 | H | $CH_3CH_2$ | Ph | $CF_3CF_2$ | 0 |
| A884 | H | cyclopropyl | Ph | $CF_3CF_2$ | 0 |
| A885 | H | $(CH_3)_3C$ | Ph | $CF_3CF_2$ | 0 |
| A886 | H | $(CH_3)_2CH$ | Ph | $CF_3CF_2$ | 0 |
| A887 | H | $CH_3(CH_2)_2$ | Ph | $CF_3CF_2$ | 0 |
| A888 | H | $CH_3OCH_2$ | Ph | $CF_3CF_2$ | 0 |
| A889 | H | $CH_3O(CH_2)_2$ | Ph | $CF_3CF_2$ | 0 |
| A890 | H | Ph | Ph | $CF_3CF_2$ | 0 |
| A891 | H | PhO | Ph | $CF_3CF_2$ | 0 |
| A892 | H | PhS | Ph | $CF_3CF_2$ | 0 |
| A893 | H | PhSO | Ph | $CF_3CF_2$ | 0 |
| A894 | H | $PhSO_2$ | Ph | $CF_3CF_2$ | 0 |
| A895 | H | $CH_3S$ | Ph | $CF_3CF_2$ | 0 |
| A896 | H | $CH_3SO$ | Ph | $CF_3CF_2$ | 0 |

TABLE 1-continued

Compounds of the formula XVId:

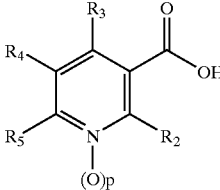

(XVId)

| Comp. No. | $R_2$ | $R_3$ | $R_4$ | $R_5$ | p |
|---|---|---|---|---|---|
| A897 | H | $CF_3$ | Ph | $CF_3CF_2$ | 0 |
| A898 | H | $F_2CH$ | Ph | $CF_3CF_2$ | 0 |
| A899 | H | HCC | Ph | $CF_3CF_2$ | 0 |
| A900 | H | $CH_3CC$ | Ph | $CF_3CF_2$ | 0 |
| A901 | H | $CH_2=CH$ | Ph | $CF_3CF_2$ | 0 |
| A902 | H | $CH_2=CHCH_2$ | Ph | $CF_3CF_2$ | 0 |
| A903 | H | $CH_3SO_2N(CH_3)$ | Ph | $CF_3CF_2$ | 0 |
| A904 | H | $(CH_3)_2N$ | Ph | $CF_3CF_2$ | 0 |
| A905 | H | $(CH_3)_2NSO_2$ | Ph | $CF_3CF_2$ | 0 |
| A906 | H | $CH_3SCH_2$ | Ph | $CF_3CF_2$ | 0 |
| A907 | H | $CH_3SOCH_2$ | Ph | $CF_3CF_2$ | 0 |
| A908 | H | $CH_3SO_2CH_2$ | Ph | $CF_3CF_2$ | 0 |
| A909 | H | $CH_3$ | Ph | $CF_3CF_2CF_2$ | 0 |
| A910 | H | $CH_3CH_2$ | Ph | $CF_3CF_2CF_2$ | 0 |
| A911 | H | cyclopropyl | Ph | $CF_3CF_2CF_2$ | 0 |
| A912 | H | $(CH_3)_3C$ | Ph | $CF_3CF_2CF_2$ | 0 |
| A913 | H | $(CH_3)_2CH$ | Ph | $CF_3CF_2CF_2$ | 0 |
| A914 | H | $CH_3(CH_2)_2$ | Ph | $CF_3CF_2CF_2$ | 0 |
| A915 | H | $CH_3OCH_2$ | Ph | $CF_3CF_2CF_2$ | 0 |
| A916 | H | $CH_3O(CH_2)_2$ | Ph | $CF_3CF_2CF_2$ | 0 |
| A917 | H | Ph | Ph | $CF_3CF_2CF_2$ | 0 |
| A918 | H | PhO | Ph | $CF_3CF_2CF_2$ | 0 |
| A919 | H | PhS | Ph | $CF_3CF_2CF_2$ | 0 |
| A920 | H | PhSO | Ph | $CF_3CF_2CF_2$ | 0 |
| A921 | H | $PhSO_2$ | Ph | $CF_3CF_2CF_2$ | 0 |
| A922 | H | $CH_3S$ | Ph | $CF_3CF_2CF_2$ | 0 |
| A923 | H | $CH_3SO$ | Ph | $CF_3CF_2CF_2$ | 0 |
| A924 | H | $CF_3$ | Ph | $CF_3CF_2CF_2$ | 0 |
| A925 | H | $F_2CH$ | Ph | $CF_3CF_2CF_2$ | 0 |
| A926 | H | HCC | Ph | $CF_3CF_2CF_2$ | 0 |
| A927 | H | $CH_3CC$ | Ph | $CF_3CF_2CF_2$ | 0 |
| A928 | H | $CH_2=CH$ | Ph | $CF_3CF_2CF_2$ | 0 |
| A929 | H | $CH_2=CHCH_2$ | Ph | $CF_3CF_2CF_2$ | 0 |
| A930 | H | $CH_3SO_2N(CH_3)$ | Ph | $CF_3CF_2CF_2$ | 0 |
| A931 | H | $(CH_3)_2N$ | Ph | $CF_3CF_2CF_2$ | 0 |
| A932 | H | $(CH_3)_2NSO_2$ | Ph | $CF_3CF_2CF_2$ | 0 |
| A933 | H | $CH_3SCH_2$ | Ph | $CF_3CF_2CF_2$ | 0 |
| A934 | H | $CH_3SOCH_2$ | Ph | $CF_3CF_2CF_2$ | 0 |
| A935 | H | $CH_3SO_2CH_2$ | Ph | $CF_3CF_2CF_2$ | 0 |
| A936 | H | $CH_3$ | Ph | $CF_2Cl$ | 0 |
| A937 | H | $CH_3CH_2$ | Ph | $CF_2Cl$ | 0 |
| A938 | H | cyclopropyl | Ph | $CF_2Cl$ | 0 |
| A939 | H | $(CH_3)_3C$ | Ph | $CF_2Cl$ | 0 |
| A940 | H | $(CH_3)_2CH$ | Ph | $CF_2Cl$ | 0 |
| A941 | H | $CH_3(CH_2)_2$ | Ph | $CF_2Cl$ | 0 |
| A942 | H | $CH_3OCH_2$ | Ph | $CF_2Cl$ | 0 |
| A943 | H | $CH_3O(CH_2)_2$ | Ph | $CF_2Cl$ | 0 |
| A944 | H | Ph | Ph | $CF_2Cl$ | 0 |
| A945 | H | PhO | Ph | $CF_2Cl$ | 0 |
| A946 | H | PhS | Ph | $CF_2Cl$ | 0 |
| A947 | H | PhSO | Ph | $CF_2Cl$ | 0 |
| A948 | H | $PhSO_2$ | Ph | $CF_2Cl$ | 0 |
| A949 | H | $CH_3S$ | Ph | $CF_2Cl$ | 0 |
| A950 | H | $CH_3SO$ | Ph | $CF_2Cl$ | 0 |
| A951 | H | $CF_3$ | Ph | $CF_2Cl$ | 0 |
| A952 | H | $F_2CH$ | Ph | $CF_2Cl$ | 0 |
| A953 | H | HCC | Ph | $CF_2Cl$ | 0 |
| A954 | H | $CH_3CC$ | Ph | $CF_2Cl$ | 0 |
| A955 | H | $CH_2=CH$ | Ph | $CF_2Cl$ | 0 |
| A956 | H | $CH_2=CHCH_2$ | Ph | $CF_2Cl$ | 0 |
| A957 | H | $CH_3SO_2N(CH_3)$ | Ph | $CF_2Cl$ | 0 |
| A958 | H | $(CH_3)_2N$ | Ph | $CF_2Cl$ | 0 |
| A959 | H | $(CH_3)_2NSO_2$ | Ph | $CF_2Cl$ | 0 |
| A960 | H | $CH_3SCH_2$ | Ph | $CF_2Cl$ | 0 |

TABLE 1-continued

Compounds of the formula XVId:

(XVId)

| Comp. No. | $R_2$ | $R_3$ | $R_4$ | $R_5$ | p |
|---|---|---|---|---|---|
| A961 | H | $CH_3SOCH_2$ | Ph | $CF_2Cl$ | 0 |
| A962 | H | $CH_3SO_2CH_2$ | Ph | $CF_2Cl$ | 0 |
| A963 | H | $CH_3$ | Ph | $CHF_2$ | 0 |
| A964 | H | $CH_3CH_2$ | Ph | $CHF_2$ | 0 |
| A965 | H | cyclopropyl | Ph | $CHF_2$ | 0 |
| A966 | H | $(CH_3)_3C$ | Ph | $CHF_2$ | 0 |
| A967 | H | $(CH_3)_2CH$ | Ph | $CHF_2$ | 0 |
| A968 | H | $CH_3(CH_2)_2$ | Ph | $CHF_2$ | 0 |
| A969 | H | $CH_3OCH_2$ | Ph | $CHF_2$ | 0 |
| A970 | H | $CH_3O(CH_2)_2$ | Ph | $CHF_2$ | 0 |
| A971 | H | Ph | Ph | $CHF_2$ | 0 |
| A972 | H | PhO | Ph | $CHF_2$ | 0 |
| A973 | H | PhS | Ph | $CHF_2$ | 0 |
| A974 | H | PhSO | Ph | $CHF_2$ | 0 |
| A975 | H | $PhSO_2$ | Ph | $CHF_2$ | 0 |
| A976 | H | $CH_3S$ | Ph | $CHF_2$ | 0 |
| A977 | H | $CH_3SO$ | Ph | $CHF_2$ | 0 |
| A978 | H | $CF_3$ | Ph | $CHF_2$ | 0 |
| A979 | H | $F_2CH$ | Ph | $CHF_2$ | 0 |
| A980 | H | HCC | Ph | $CHF_2$ | 0 |
| A981 | H | $CH_3CC$ | Ph | $CHF_2$ | 0 |
| A982 | H | $CH_2=CH$ | Ph | $CHF_2$ | 0 |
| A983 | H | $CH_2=CHCH_2$ | Ph | $CHF_2$ | 0 |
| A984 | H | $CH_3SO_2N(CH_3)$ | Ph | $CHF_2$ | 0 |
| A985 | H | $(CH_3)_2N$ | Ph | $CHF_2$ | 0 |
| A986 | H | $(CH_3)_2NSO_2$ | Ph | $CHF_2$ | 0 |
| A987 | H | $CH_3SCH_2$ | Ph | $CHF_2$ | 0 |
| A988 | H | $CH_3SOCH_2$ | Ph | $CHF_2$ | 0 |
| A989 | H | $CH_3SO_2CH_2$ | Ph | $CHF_2$ | 0 |
| A990 | H | $CH_3$ | Ph | $CCl_3$ | 0 |
| A991 | H | $CH_3CH_2$ | Ph | $CCl_3$ | 0 |
| A992 | H | cyclopropyl | Ph | $CCl_3$ | 0 |
| A993 | H | $(CH_3)_3C$ | Ph | $CCl_3$ | 0 |
| A994 | H | $(CH_3)_2CH$ | Ph | $CCl_3$ | 0 |
| A995 | H | $CH_3(CH_2)_2$ | Ph | $CCl_3$ | 0 |
| A996 | H | $CH_3OCH_2$ | Ph | $CCl_3$ | 0 |
| A997 | H | $CH_3O(CH_2)_2$ | Ph | $CCl_3$ | 0 |
| A998 | H | Ph | Ph | $CCl_3$ | 0 |
| A999 | H | PhO | Ph | $CCl_3$ | 0 |
| A1000 | H | PhS | Ph | $CCl_3$ | 0 |
| A1001 | H | PhSO | Ph | $CCl_3$ | 0 |
| A1002 | H | $PhSO_2$ | Ph | $CCl_3$ | 0 |
| A1003 | H | $CH_3S$ | Ph | $CCl_3$ | 0 |
| A1004 | H | $CH_3SO$ | Ph | $CCl_3$ | 0 |
| A1005 | H | $CF_3$ | Ph | $CCl_3$ | 0 |
| A1006 | H | $F_2CH$ | Ph | $CCl_3$ | 0 |
| A1007 | H | HCC | Ph | $CCl_3$ | 0 |
| A1008 | H | $CH_3CC$ | Ph | $CCl_3$ | 0 |
| A1009 | H | $CH_2=CH$ | Ph | $CCl_3$ | 0 |
| A1010 | H | $CH_2=CHCH_2$ | Ph | $CCl_3$ | 0 |
| A1011 | H | $CH_3SO_2N(CH_3)$ | Ph | $CCl_3$ | 0 |
| A1012 | H | $(CH_3)_2N$ | Ph | $CCl_3$ | 0 |
| A1013 | H | $(CH_3)_2NSO_2$ | Ph | $CCl_3$ | 0 |
| A1014 | H | $CH_3SCH_2$ | Ph | $CCl_3$ | 0 |
| A1015 | H | $CH_3SOCH_2$ | Ph | $CCl_3$ | 0 |
| A1016 | H | $CH_3SO_2CH_2$ | Ph | $CCl_3$ | 0 |
| A1017 | F | H | H | $CF_3$ | 0 |
| A1018 | Cl | H | H | $CF_3$ | 0 |
| A1019 | Br | H | H | $CF_3$ | 0 |
| A1020 | NC | H | H | $CF_3$ | 0 |
| A1021 | $CH_3SO_2O$ | H | H | $CF_3$ | 0 |
| A1022 | $CH_3O$ | H | H | $CF_3$ | 0 |
| A1023 | $CH_3CH_2O$ | H | H | $CF_3$ | 0 |
| A1024 | $CH_2CH=CH_2O$ | H | H | $CF_3$ | 0 |

TABLE 1-continued

Compounds of the formula XVId:

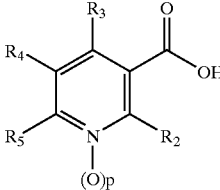

(XVId)

| Comp. No. | $R_2$ | $R_3$ | $R_4$ | $R_5$ | p |
|---|---|---|---|---|---|
| A1025 | HCCCH$_2$O | H | H | CF$_3$ | 0 |
| A1026 | PhCH$_2$S | H | H | CF$_3$ | 0 |
| A1027 | PhCH$_2$SO$_2$ | H | H | CF$_3$ | 0 |
| A1028 | ClCH$_2$CH$_2$ | H | H | CF$_3$ | 0 |
| A1029 | BrCH$_2$ | H | H | CF$_3$ | 0 |
| A1030 | FCH$_2$ | H | H | CF$_3$ | 0 |
| A1031 | CHF$_2$CH$_2$ | H | H | CF$_3$ | 0 |
| A1032 | CF$_3$CH$_2$ | H | H | CF$_3$ | 0 |
| A1033 | [1,3]-imidazol-1-ylmethyl | H | H | CF$_3$ | 0 |
| A1034 | CHCl$_2$CH$_2$ | H | H | CF$_3$ | 0 |
| A1035 | ClCH=CH | H | H | CF$_3$ | 0 |
| A1036 | Cl$_2$C=CH | H | H | CF$_3$ | 0 |
| A1037 | CF$_3$CH=CH | H | H | CF$_3$ | 0 |
| A1038 | ClCC | H | H | CF$_3$ | 0 |
| A1039 | PhCH$_2$ | H | H | CF$_3$ | 0 |
| A1040 | CH$_3$CH$_2$ | CH$_3$ | H | CF$_3$ | 0 |
| A1041 | CH$_3$ | OH | H | CF$_3$ | 0 |
| A1042 | CH$_3$ | F | H | CF$_3$ | 0 |
| A1043 | CH$_3$ | Cl | H | CF$_3$ | 0 |
| A1044 | F | CH$_3$ | H | CF$_3$ | 0 |
| A1045 | Cl | CH$_3$ | H | CF$_3$ | 0 |
| A1046 | H | F | H | CF$_3$ | 0 |
| A1047 | H | Cl | H | CF$_3$ | 0 |
| A1048 | H | Br | H | CF$_3$ | 0 |
| A1049 | H | OH | H | CF$_3$ | 0 |
| A1050 | H | OCH$_3$ | H | CF$_3$ | 0 |
| A1051 | H | OCHF$_2$ | H | CF$_3$ | 0 |
| A1052 | H | OSO$_2$CH$_3$ | H | CF$_3$ | 0 |
| A1053 | H | OSO$_2$CF$_3$ | H | CF$_3$ | 0 |
| A1054 | H | ClCH$_2$ | H | CF$_3$ | 0 |
| A1055 | H | BrCH$_2$ | H | CF$_3$ | 0 |
| A1056 | H | FCH$_2$ | H | CF$_3$ | 0 |
| A1057 | H | CHF$_2$CH$_2$ | H | CF$_3$ | 0 |
| A1058 | H | CF$_3$CH$_2$ | H | CF$_3$ | 0 |
| A1059 | H | triazolylmethyl | H | CF$_3$ | 0 |
| A1060 | H | CHCl$_2$CH$_2$ | H | CF$_3$ | 0 |
| A1061 | H | ClCH=CH | H | CF$_3$ | 0 |
| A1062 | H | Cl$_2$C=CH | H | CF$_3$ | 0 |
| A1063 | H | CF$_3$CH=CH | H | CF$_3$ | 0 |
| A1064 | H | ClCC | H | CF$_3$ | 0 |
| A1065 | H | CH$_3$C(O) | H | CF$_3$ | 0 |
| A1066 | H | Ph | H | CF$_3$ | 0 |
| A1067 | H | SO$_2$CH$_3$ | H | CF$_3$ | 0 |
| A1068 | H | SO$_2$CF$_3$ | H | CF$_3$ | 0 |
| A1069 | H | NC | H | CF$_3$ | 0 |
| A1070 | H | NO$_2$ | H | CF$_3$ | 0 |
| A1071 | CH$_3$ | H | F | CF$_3$ | 0 |
| A1072 | CH$_3$ | H | Cl | CF$_3$ | 0 |
| A1073 | CH$_3$ | H | Br | CF$_3$ | 0 |
| A1074 | CH$_3$ | H | NC | CF$_3$ | 0 |
| A1075 | CH$_3$ | H | CH$_3$O | CF$_3$ | 0 |
| A1076 | CH$_3$ | H | CH$_3$S | CF$_3$ | 0 |
| A1077 | CH$_3$ | H | CH$_3$SO | CF$_3$ | 0 |
| A1078 | CH$_3$ | H | CH$_2$SO$_2$ | CF$_3$ | 0 |
| A1079 | CH$_3$CH$_2$OCH$_2$ | H | H | CF$_3$ | 0 |
| A1080 | PhOCH$_2$ | H | H | CF$_3$ | 0 |
| A1081 | 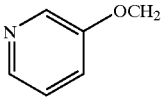 | H | H | CF$_3$ | 0 |
| A1082 | (CH$_3$)$_2$CH$_2$OCH$_2$ | H | H | CF$_3$ | 0 |

TABLE 1-continued

Compounds of the formula XVId:

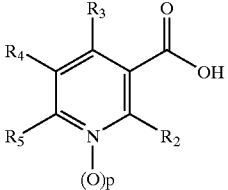

(XVId)

| Comp. No. | R₂ | R₃ | R₄ | R₅ | p |
|---|---|---|---|---|---|
| A1083 | BrCH₂CH₂ | H | H | CF₃ | 0 |
| A1084 | FCH₂CH₂ | H | H | CF₃ | 0 |
| A1085 | 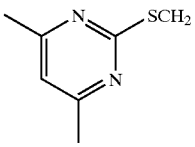 | H | H | CF₃ | 0 |
| A1086 | 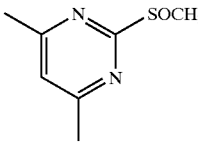 | H | H | CF₃ | 0 |
| A1087 | 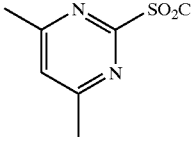 | H | H | CF₃ | 0 |
| A1088 | 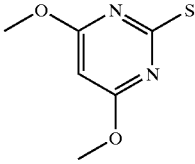 | H | H | CF₃ | 0 |
| A1089 | 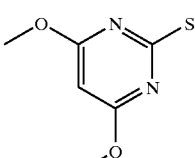 | H | H | CF₃ | 0 |
| A1090 | 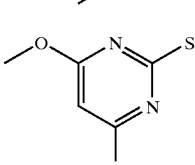 | H | H | CF₃ | 0 |
| A1091 | cyclopropyl-CH₂ | H | H | CF₃ | 0 |
| A1092 | 2,2-dichlorocycloprop-1-yl | H | H | CF₃ | 0 |
| A1093 | CH₃OC(O)CH=CH | H | H | CF₃ | 0 |
| A1094 | CH₃CH₂OC(O)CH=CH | H | H | CF₃ | 0 |
| A1095 | ClCH₂CH=CH | H | H | CF₃ | 0 |
| A1096 | CH=C=CH | H | H | CF₃ | 0 |
| A1097 | (CH₃)₂NCH₂ | H | H | CF₃ | 0 |
| A1098 | HOCH₂ | H | H | CF₃ | 0 |
| A1099 | CH₃C(O)OCH₂ | H | H | CF₃ | 0 |
| A1100 | PhC(O)OCH₂ | H | H | CF₃ | 0 |
| A1101 | PhCH₂CH₂ | H | H | CF₃ | 0 |
| A1102 | CH₃OC(O)CH₂ | H | H | CF₃ | 0 |

TABLE 1-continued

Compounds of the formula XVId:

(XVId)

| Comp. No. | R$_2$ | R$_3$ | R$_4$ | R$_5$ | p |
|---|---|---|---|---|---|
| A1103 | NCCH$_2$ | H | H | CF$_3$ | 0 |
| A1104 | CH$_3$(CH$_2$)$_7$SCH$_2$ | H | H | CF$_3$ | 0 |
| A1105 | CH$_3$(CH$_2$)$_7$SOCH$_2$ | H | H | CF$_3$ | 0 |
| A1106 | CH$_3$(CH$_2$)$_7$SO$_2$CH$_2$ | H | H | CF$_3$ | 0 |
| A1107 | PhC≡C– | H | H | CF$_3$ | 0 |
| A1108 | ClCH$_2$CC | H | H | CF$_3$ | 0 |
| A1109 | CHF$_2$CH$_2$CH$_2$ | H | H | CF$_3$ | 0 |
| A1110 | CHCl$_2$CH$_2$CH$_2$ | H | H | CF$_3$ | 0 |
| A1111 | CF$_3$SO$_2$O | H | H | CF$_3$ | 0 |
| A1112 | (pyridin-2-yl)C≡C– | H | H | CF$_3$ | 0 |
| A1113 | (pyridin-3-yl)C≡C– | H | H | CF$_3$ | 0 |
| A1114 | (pyridin-4-yl)C≡C– | H | H | CF$_3$ | 0 |
| A1115 | (pyridin-2-yl)CH$_2$ | H | H | CF$_3$ | 0 |
| A1116 | (pyridin-3-yl)CH$_2$ | H | H | CF$_3$ | 0 |
| A1117 | (pyridin-4-yl)CH$_2$ | H | H | CF$_3$ | 0 |
| A1118 | CH$_3$ON=CHCH$_2$ | H | H | CF$_3$ | 0 |
| A1119 | O=CHCH$_2$ | H | H | CF$_3$ | 0 |
| A1120 | CH$_3$CH$_2$OCH$_2$ | H | H | CF$_2$Cl | 0 |
| A1121 | PhOCH$_2$ | H | H | CF$_2$Cl | 0 |

TABLE 1-continued
Compounds of the formula XVId:
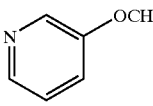
(XVId)
| Comp. No. | R₂ | R₃ | R₄ | R₅ | p |
|---|---|---|---|---|---|
| A1122 | 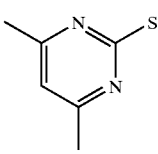 | H | H | CF₂Cl | 0 |
| A1123 | (CH₃)₂CH₂OCH₂ | H | H | CF₂Cl | 0 |
| A1124 | BrCH₂ | H | H | CF₂Cl | 0 |
| A1125 | FCH₂ | H | H | CF₂Cl | 0 |
| A1126 | 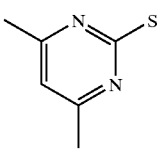 | H | H | CF₂Cl | 0 |
| A1127 | 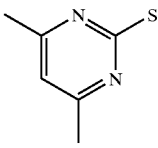 | H | H | CF₂Cl | 0 |
| A1128 | 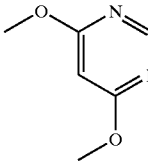 | H | H | CF₂Cl | 0 |
| A1129 | 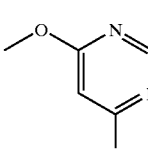 | H | H | CF₂Cl | 0 |
| A1130 | 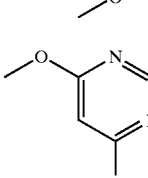 | H | H | CF₂Cl | 0 |
| A1131 |  | H | H | CF₂Cl | 0 |
| A1132 | cyclopropyl-CH₂ | H | H | CF₂Cl | 0 |
| A1133 | 2,2-dichlorocycloprop-1-yl | H | H | CF₂Cl | 0 |
| A1134 | CH₃OC(O)CH=CH | H | H | CF₂Cl | 0 |
| A1135 | CH₃CH₂OC(O)CH=CH | H | H | CF₂Cl | 0 |
| A1136 | ClCH₂CH=CH | H | H | CF₂Cl | 0 |

TABLE 1-continued

Compounds of the formula XVId:

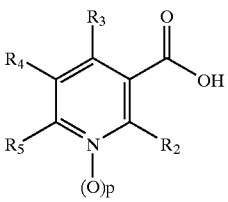

(XVId)

| Comp. No. | R₂ | R₃ | R₄ | R₅ | p |
|---|---|---|---|---|---|
| A1137 | CH=C=CH | H | H | CF₂Cl | 0 |
| A1138 | (CH₃)₂NCH₂ | H | H | CF₂Cl | 0 |
| A1139 | HOCH₂ | H | H | CF₂Cl | 0 |
| A1140 | CH₃C(O)OCH₂ | H | H | CF₂Cl | 0 |
| A1141 | PhC(O)OCH₂ | H | H | CF₂Cl | 0 |
| A1142 | PhCH₂ | H | H | CF₂Cl | 0 |
| A1143 | CH₃OC(O)CH₂ | H | H | CF₂Cl | 0 |
| A1144 | NCCH₂ | H | H | CF₂Cl | 0 |
| A1145 | CH₃(CH₂)₇SCH₂ | H | H | CF₂Cl | 0 |
| A1146 | CH₃(CH₂)₇SOCH₂ | H | H | CF₂Cl | 0 |
| A1147 | CH₃(CH₂)₇SO₂CH₂ | H | H | CF₂Cl | 0 |
| A1148 | 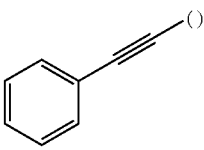 | H | H | CF₂Cl | 0 |
| A1149 | ClCH₂CC | H | H | CF₂Cl | 0 |
| A1150 | Br | H | H | CF₂Cl | 0 |
| A1151 | Cl | H | H | CF₂Cl | 0 |
| A1152 | CF₃SO₂O | H | H | CF₂Cl | 0 |
| A1153 | 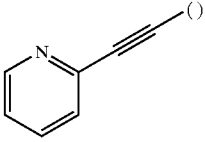 | H | H | CF₂Cl | 0 |
| A1154 | 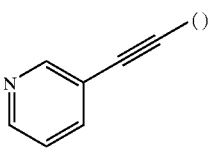 | H | H | CF₂Cl | 0 |
| A1155 | 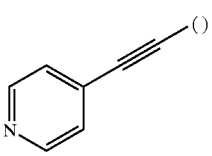 | H | H | CF₂Cl | 0 |
| A1156 | 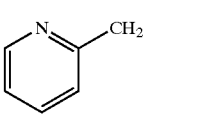 | H | H | CF₂Cl | 0 |
| A1157 | 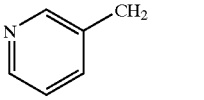 | H | H | CF₂Cl | 0 |

TABLE 1-continued
Compounds of the formula XVId:
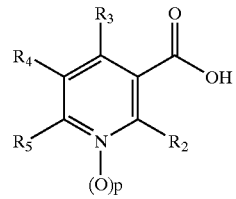
(XVId)
| Comp. No. | R₂ | R₃ | R₄ | R₅ | p |
|---|---|---|---|---|---|
| A1158 | 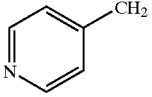 | H | H | $CF_2Cl$ | 0 |
| A1159 | $CH_3ON=CHCH_2$ | H | H | $CF_2Cl$ | 0 |
| A1160 | $O=CHCH_2$ | H | H | $CF_2Cl$ | 0 |
| A1161 | $CH_3CH_2OCH_2$ | H | H | $CF_2H$ | 0 |
| A1162 | $PhOCH_2$ | H | H | $CF_2H$ | 0 |
| A1163 | 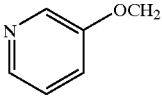 | H | H | $CF_2H$ | 0 |
| A1164 | $(CH_3)_2CH_2OCH_2$ | H | H | $CF_2H$ | 0 |
| A1165 | $BrCH_2$ | H | H | $CF_2H$ | 0 |
| A1166 | $FCH_2$ | H | H | $CF_2H$ | 0 |
| A1167 | 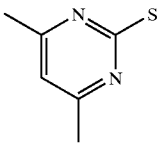 | H | H | $CF_2H$ | 0 |
| A1168 | 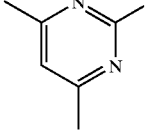 | H | H | $CF_2H$ | 0 |
| A1169 | 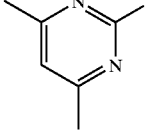 | H | H | $CF_2H$ | 0 |
| A1170 | 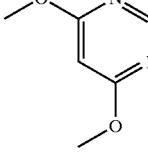 | H | H | $CF_2H$ | 0 |
| A1171 | 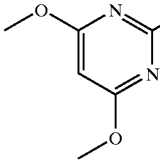 | H | H | $CF_2H$ | 0 |

TABLE 1-continued

Compounds of the formula XVId:

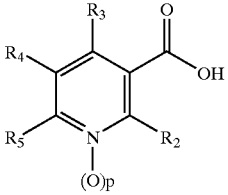

(XVId)

| Comp. No. | R₂ | R₃ | R₄ | R₅ | p |
|---|---|---|---|---|---|
| A1172 | 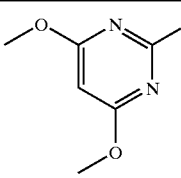 | H | H | CF₂H | 0 |
| A1173 | cyclopropyl-CH₂ | H | H | CF₂H | 0 |
| A1174 | 2,2-dichlorocycloprop-1-yl | H | H | CF₂H | 0 |
| A1175 | CH₃OC(O)CH=CH | H | H | CF₂H | 0 |
| A1176 | CH₃CH₂OC(O)CH=CH | H | H | CF₂H | 0 |
| A1177 | ClCH₂CH=CH | H | H | CF₂H | 0 |
| A1178 | CH=C=CH | H | H | CF₂H | 0 |
| A1179 | (CH₃)₂NCH₂ | H | H | CF₂H | 0 |
| A1180 | HOCH₂ | H | H | CF₂H | 0 |
| A1181 | CH₃C(O)OCH₂ | H | H | CF₂H | 0 |
| A1182 | PhC(O)OCH₂ | H | H | CF₂H | 0 |
| A1183 | PhCH₂ | H | H | CF₂H | 0 |
| A1184 | CH₃OC(O)CH₂ | H | H | CF₂H | 0 |
| A1185 | NCCH₂ | H | H | CF₂H | 0 |
| A1186 | CH₃(CH₂)₇SCH₂ | H | H | CF₂H | 0 |
| A1187 | CH₃(CH₂)₇SOCH₂ | H | H | CF₂H | 0 |
| A1188 | CH₃(CH₂)₇SO₂CH₂ | H | H | CF₂H | 0 |
| A1189 | 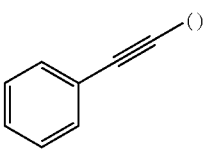 | H | H | CF₂H | 0 |
| A1190 | ClCH₂CC | H | H | CF₂H | 0 |
| A1191 | Br | H | H | CF₂H | 0 |
| A1192 | Cl | H | H | CF₂H | 0 |
| A1193 | CF₃SO₂O | H | H | CF₂H | 0 |
| A1194 | 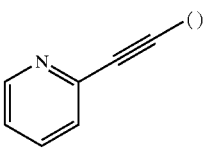 | H | H | CF₂H | 0 |
| A1195 | 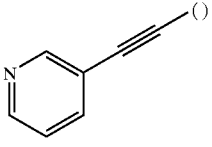 | H | H | CF₂H | 0 |
| A1196 | 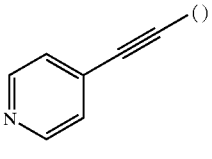 | H | H | CF₂H | 0 |

TABLE 1-continued

Compounds of the formula XVId:

(XVId)

| Comp. No. | R$_2$ | R$_3$ | R$_4$ | R$_5$ | p |
|---|---|---|---|---|---|
| A1197 | pyridin-2-yl-CH$_2$ | H | H | CF$_2$H | 0 |
| A1198 | pyridin-3-yl-CH$_2$ | H | H | CF$_2$H | 0 |
| A1199 | pyridin-4-yl-CH$_2$ | H | H | CF$_2$H | 0 |
| A1200 | CH$_3$ON=CHCH$_2$ | H | H | CF$_2$H | 0 |
| A1201 | O=CHCH$_2$ | H | H | CF$_2$H | 0 |
| A1202 | CH$_3$CH=CH | H | H | CF$_3$ | 0 |
| A1203 | CH$_3$SO$_2$NH | H | H | CF$_3$ | 0 |
| A1204 | CH$_3$CH$_2$CH$_2$O | H | CH$_3$ | CF$_3$ | 0 |
| A1205 | Cl | CH$_3$ | H | CF$_3$ | 0 |
| A1206 | F$_2$CHO | H | H | CF$_3$ | 0 |
| A1207 | CH$_3$CH$_2$C(O)OCH$_2$ | H | H | CF$_3$ | 0 |
| A1208 | CH$_3$CH$_2$OC(O)OCH$_2$ | H | H | CF$_3$ | 0 |
| A1209 | CH$_3$OCH$_2$OCH$_2$ | H | H | CF$_3$ | 0 |
| A1210 | CH$_3$ | H | H | CF$_3$ | 1 |
| A1211 | CH$_3$CH$_2$ | H | H | CF$_3$ | 1 |
| A1212 | cyclopropyl | H | H | CF$_3$ | 1 |
| A1213 | CH$_3$(CH$_2$)$_2$ | H | H | CF$_3$ | 1 |
| A1214 | CH$_3$OCH$_2$ | H | H | CF$_3$ | 1 |
| A1215 | CF$_3$ | H | H | CF$_3$ | 1 |
| A1216 | F$_2$CH | H | H | CF$_3$ | 1 |
| A1217 | ClCH$_2$ | H | H | CF$_3$ | 1 |
| A1218 | CH$_3$SO$_2$CH$_2$ | H | H | CF$_3$ | 1 |
| A1219 | CH$_3$ | CF$_3$ | H | CH$_3$ | 1 |
| A1220 | CH$_3$CH$_2$OCH$_2$ | H | H | CF$_3$ | 1 |
| A1221 | PhOCH$_2$ | H | H | CF$_3$ | 1 |
| A1222 | (CH$_3$)$_2$CH$_2$OCH$_2$ | H | H | CF$_3$ | 1 |
| A1223 | BrCH$_2$ | H | H | CF$_3$ | 1 |
| A1224 | FCH$_2$ | H | H | CF$_3$ | 1 |
| A1225 | 4,6-dimethylpyrimidin-2-yl-SO$_2$CH$_2$ | H | H | CF$_3$ | 1 |
| A1226 | 4,6-dimethoxypyrimidin-2-yl-SO$_2$CH$_2$ | H | H | CF$_3$ | 1 |
| A1227 | cyclopropyl-CH$_2$ | H | H | CF$_3$ | 1 |
| A1228 | 2,2-dichlorocycloprop-1-yl | H | H | CF$_3$ | 1 |
| A1229 | (CH$_3$)$_2$NCH$_2$ | H | H | CF$_3$ | 1 |
| A1230 | HOCH$_2$ | H | H | CF$_3$ | 1 |

TABLE 1-continued

Compounds of the formula XVId:

(XVId)

| Comp. No. | R₂ | R₃ | R₄ | R₅ | p |
|---|---|---|---|---|---|
| A1231 | CH₃C(O)OCH₂ | H | H | CF₃ | 1 |
| A1232 | PhC(O)OCH₂ | H | H | CF₃ | 1 |
| A1233 | PhCH₂ | H | H | CF₃ | 1 |
| A1234 | CH₃OC(O)CH₂ | H | H | CF₃ | 1 |
| A1235 | NCCH₂ | H | H | CF₃ | 1 |
| A1236 | CH₃(CH₂)₇SO₂CH₂ | H | H | CF₃ | 1 |
| A1237 | Br | H | H | CF₃ | 1 |
| A1238 | Cl | H | H | CF₃ | 1 |
| A1239 | O=CHCH₂ | H | H | CF₃ | 1 |
| A1240 | CH₃ | H | H | CF₂Cl | 1 |
| A1241 | CH₃CH₂ | H | H | CF₂Cl | 1 |
| A1242 | cyclopropyl | H | H | CF₂Cl | 1 |
| A1243 | CH₃(CH₂)₂ | H | H | CF₂Cl | 1 |
| A1244 | CH₃OCH₂ | H | H | CF₂Cl | 1 |
| A1245 | CF₃ | H | H | CF₂Cl | 1 |
| A1246 | F₂CH | H | H | CF₂Cl | 1 |
| A1247 | ClCH₂ | H | H | CF₂Cl | 1 |
| A1248 | CH₃SO₂CH₂ | H | H | CF₂Cl | 1 |
| A1249 | CH₃ | CF₃ | H | CF₂Cl | 1 |
| A1250 | CH₃CH₂OCH₂ | H | H | CF₂Cl | 1 |
| A1251 | PhOCH₂ | H | H | CF₂Cl | 1 |
| A1252 | (CH₃)₂CH₂OCH₂ | H | H | CF₂Cl | 1 |
| A1253 | BrCH₂ | H | H | CF₂Cl | 1 |
| A1254 | FCH₂ | H | H | CF₂Cl | 1 |
| A1255 | 4,6-dimethylpyrimidin-2-yl-SO₂CH₂ | H | H | CF₂Cl | 1 |
| A1256 | 4,6-dimethoxypyrimidin-2-yl-SO₂CH₂ | H | H | CF₂Cl | 1 |
| A1257 | cyclopropyl-CH₂ | H | H | CF₂Cl | 1 |
| A1258 | 2,2-dichlorocycloprop-1-yl | H | H | CF₂Cl | 1 |
| A1259 | (CH₃)₂NCH₂ | H | H | CF₂Cl | 1 |
| A1260 | HOCH₂ | H | H | CF₂Cl | 1 |
| A1261 | CH₃C(O)OCH₂ | H | H | CF₂Cl | 1 |
| A1262 | PhC(O)OCH₂ | H | H | CF₂Cl | 1 |
| A1263 | PhCH₂ | H | H | CF₂Cl | 1 |
| A1264 | CH₃OC(O)CH₂ | H | H | CF₂Cl | 1 |
| A1265 | NCCH₂ | H | H | CF₂Cl | 1 |
| A1266 | CH₃(CH₂)₇SO₂CH₂ | H | H | CF₂Cl | 1 |
| A1267 | Br | H | H | CF₂Cl | 1 |
| A1268 | Cl | H | H | CF₂Cl | 1 |
| A1269 | O=CHCH₂ | H | H | CF₂Cl | 1 |
| A1270 | CH₃ | H | H | CF₂H | 1 |
| A1271 | CH₃CH₂ | H | H | CF₂H | 1 |
| A1272 | cyclopropyl | H | H | CF₂H | 1 |
| A1273 | CH₃(CH₂)₂ | H | H | CF₂H | 1 |
| A1274 | CH₃OCH₂ | H | H | CF₂H | 1 |
| A1275 | CF₃ | H | H | CF₂H | 1 |
| A1276 | F₂CH | H | H | CF₂H | 1 |
| A1277 | ClCH₂ | H | H | CF₂H | 1 |
| A1278 | CH₃SO₂CH₂ | H | H | CF₂H | 1 |
| A1279 | CH₃ | CF₃ | H | CF₂H | 1 |

TABLE 1-continued

Compounds of the formula XVId:

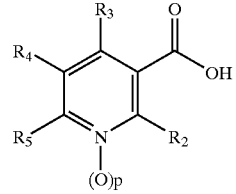

(XVId)

| Comp. No. | R₂ | R₃ | R₄ | R₅ | p |
|---|---|---|---|---|---|
| A1280 | CH₃CH₂OCH₂ | H | H | CF₂H | 1 |
| A1281 | PhOCH₂ | H | H | CF₂H | 1 |
| A1282 | (CH₃)₂CH₂OCH₂ | H | H | CF₂H | 1 |
| A1283 | BrCH₂ | H | H | CF₂H | 1 |
| A1284 | FCH₂ | H | H | CF₂H | 1 |
| A1285 | 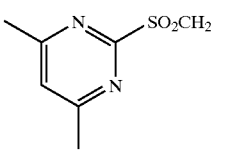 | H | H | CF₂H | 1 |
| A1286 | 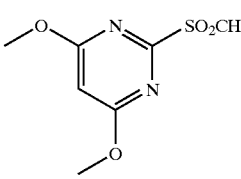 | H | H | CF₂H | 1 |
| A1287 | cyclopropyl-CH₂ | H | H | CF₂H | 1 |
| A1288 | 2,2-dichlorocycloprop-1-yl | H | H | CF₂H | 1 |
| A1289 | (CH₃)₂NCH₂ | H | H | CF₂H | 1 |
| A1290 | HOCH₂ | H | H | CF₂H | 1 |
| A1291 | CH₃C(O)OCH₂ | H | H | CF₂H | 1 |
| A1292 | PhC(O)OCH₂ | H | H | CF₂H | 1 |
| A1293 | PhCH₂ | H | H | CF₂H | 1 |
| A1294 | CH₃OC(O)CH₂ | H | H | CF₂H | 1 |
| A1295 | NCCH₂ | H | H | CF₂H | 1 |
| A1296 | CH₃(CH₂)₇SO₂CH₂ | H | H | CF₂H | 1 |
| A1297 | Br | H | H | CF₂H | 1 |
| A1298 | Cl | H | H | CF₂H | 1 |
| A1299 | O=CHCH₂ | H | H | CF₂H | 1 |
| A1300 | CH₃ | H | H | CF₃CF₂ | 1 |
| A1301 | HO | H | Ph | CF₃ | 0 |
| A1302 | CH₃ | H | CH₂=CH | CF₃ | 0 |
| A1303 | CH₃ | H | CH₃CH₂O | CF₃ | 0 |
| A1304 | HO | CH₃ | H | CF₃ | 0 |
| A1305 | HO | H | H | CF₃ | 0 |
| A1306 | (CH₃CH₂)₂N(O)CO | H | H | CF₃ | 0 |
| A1307 | CH₃ | H | Tosyl-O | CF₃ | 0 |
| A1308 | CH₃ | H | CH₃CC | CF₃ | 0 |
| A1309 | CH₃ | H | HCC | CF₃ | 0 |
| A1310 | CH₃ | H | ClCH₂CC | CF₃ | 0 |
| A1311 | CH₃ | H | PhCH₂O | CF₃ | 0 |
| A1312 | CH₃ | H | CF₃SO₂O | CF₃ | 0 |
| A1313 | CH₃ | H | (CH₃)₂N | CF₃ | 0 |
| A1314 | CH₃ | H | CH₃C(O)O | CF₃ | 0 |
| A1315 | CH₃ | H | CH₃CH₂C(O)O | CF₃ | 0 |
| A1316 | CH₃ | H | PhC(O)O | CF₃ | 0 |
| A1317 | CH₃ | H | 3-Pyridyl | CF₃ | 0 |
| A1318 | CH₃OCH₂OCH₂ | H | H | CF₂Cl | 0 |
| A1319 | CH₃OCH₂OCH₂ | H | H | CF₂H | 0 |
| A1320 | CH₃OCH₂OCH₂ | H | H | CF₂CF₃ | 0 |

TABLE 1-continued

Compounds of the formula XVId:

(XVId)

| Comp. No. | R$_2$ | R$_3$ | R$_4$ | R$_5$ | p |
|---|---|---|---|---|---|
| A1321 | CH$_3$OCH$_2$OCH$_2$ | H | H | CF$_3$ | 1 |
| A1322 | CH$_3$O | H | CH$_3$ | CF$_3$ | 0 |

In Table 2 which follows, Q is C$_1$

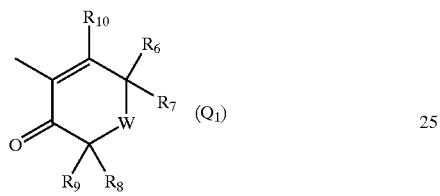

(Q$_1$)

and Q$_1$ the radicals B which follow:

TABLE 2

Radicals B:

| Radical | R$_6$ | R$_7$ | R$_8$ | R$_9$ | R$_{10}$ | W |
|---|---|---|---|---|---|---|
| B1 | H | H | H | H | OH | CH$_2$ |
| B2 | CH$_3$ | H | H | H | OH | CH$_2$ |
| B3 | CH$_3$CH$_2$ | H | H | H | OH | CH$_2$ |
| B4 | CH$_3$CH$_2$CH$_2$ | H | H | H | OH | CH$_2$ |
| B5 | (CH$_3$)$_2$CH | H | H | H | OH | CH$_2$ |
| B6 | (CH$_3$)$_3$C | H | H | H | OH | CH$_2$ |
| B7 | CH$_3$S | H | H | H | OH | CH$_2$ |
| B8 | CH$_3$SO | H | H | H | OH | CH$_2$ |
| B9 | CH$_3$SO$_2$ | H | H | H | OH | CH$_2$ |
| B10 | Ph | H | H | H | OH | CH$_2$ |
| B11 | CH$_3$O | H | H | H | OH | CH$_2$ |
| B12 | CH$_3$OC(O) | H | H | H | OH | CH$_2$ |
| B13 | CH$_3$CH$_2$OC(O) | H | H | H | OH | CH$_2$ |
| B14 | CH$_2$=CHCH$_2$ | H | H | H | OH | CH$_2$ |
| B15 | HCCCH$_2$ | H | H | H | OH | CH$_2$ |
| B16 | CF$_3$ | H | H | H | OH | CH$_2$ |
| B17 | (CH$_3$)$_2$NSO$_2$ | H | H | H | OH | CH$_2$ |
| B18 | (CH$_3$)$_2$N | H | H | H | OH | CH$_2$ |
| B19 | PhO | H | H | H | OH | CH$_2$ |
| B20 | PhS | H | H | H | OH | CH$_2$ |
| B21 | PhSO | H | H | H | OH | CH$_2$ |
| B22 | PhSO$_2$ | H | H | H | OH | CH$_2$ |
| B23 | CN | H | H | H | OH | CH$_2$ |
| B24 | CH$_3$ | CH$_3$ | H | H | OH | CH$_2$ |
| B25 | CH$_3$CH$_2$ | CH$_3$ | H | H | OH | CH$_2$ |
| B26 | CH$_3$CH$_2$CH$_2$ | CH$_3$ | H | H | OH | CH$_2$ |
| B27 | (CH$_3$)$_2$CH | CH$_3$ | H | H | OH | CH$_2$ |
| B28 | (CH$_3$)$_3$C | CH$_3$ | H | H | OH | CH$_2$ |
| B29 | CH$_3$S | CH$_3$ | H | H | OH | CH$_2$ |
| B30 | CH$_3$SO | CH$_3$ | H | H | OH | CH$_2$ |
| B31 | CH$_3$SO$_2$ | CH$_3$ | H | H | OH | CH$_2$ |
| B32 | Ph | CH$_3$ | H | H | OH | CH$_2$ |
| B33 | CH$_3$O | CH$_3$ | H | H | OH | CH$_2$ |
| B34 | CH$_3$OC(O) | CH$_3$ | H | H | OH | CH$_2$ |
| B35 | CH$_3$CH$_2$OC(O) | CH$_3$ | H | H | OH | CH$_2$ |
| B36 | CH$_2$=CHCH$_2$ | CH$_3$ | H | H | OH | CH$_2$ |
| B37 | HCCCH$_2$ | CH$_3$ | H | H | OH | CH$_2$ |

TABLE 2-continued

Radicals B:

| Radical | $R_6$ | $R_7$ | $R_8$ | $R_9$ | $R_{10}$ | W |
|---|---|---|---|---|---|---|
| B38 | $CF_3$ | $CH_3$ | H | H | OH | $CH_2$ |
| B39 | $(CH_3)_2NSO_2$ | $CH_3$ | H | H | OH | $CH_2$ |
| B40 | $(CH_3)_2N$ | $CH_3$ | H | H | OH | $CH_2$ |
| B41 | PhO | $CH_3$ | H | H | OH | $CH_2$ |
| B42 | PhS | $CH_3$ | H | H | OH | $CH_2$ |
| B43 | PhSO | $CH_3$ | H | H | OH | $CH_2$ |
| B44 | $PhSO_2$ | $CH_3$ | H | H | OH | $CH_2$ |
| B45 | CN | $CH_3$ | H | H | OH | $CH_2$ |
| B46 | $CH_3$ | H | $CH_3$ | H | OH | $CH_2$ |
| B47 | $CH_3CH_2$ | H | $CH_3$ | H | OH | $CH_2$ |
| B48 | $CH_3CH_2CH_2$ | H | $CH_3$ | H | OH | $CH_2$ |
| B49 | $(CH_3)_2CH$ | H | $CH_3$ | H | OH | $CH_2$ |
| B50 | $(CH_3)_3C$ | H | $CH_3$ | H | OH | $CH_2$ |
| B51 | $CH_3S$ | H | $CH_3$ | H | OH | $CH_2$ |
| B52 | $CH_3SO$ | H | $CH_3$ | H | OH | $CH_2$ |
| B53 | $CH_3SO_2$ | H | $CH_3$ | H | OH | $CH_2$ |
| B54 | Ph | H | $CH_3$ | H | OH | $CH_2$ |
| B55 | $CH_3O$ | H | $CH_3$ | H | OH | $CH_2$ |
| B56 | $CH_3OC(O)$ | H | $CH_3$ | H | OH | $CH_2$ |
| B57 | $CH_3CH_2OC(O)$ | H | $CH_3$ | H | OH | $CH_2$ |
| B58 | $CH_2=CHCH_2$ | H | $CH_3$ | H | OH | $CH_2$ |
| B59 | $HCCCH_2$ | H | $CH_3$ | H | OH | $CH_2$ |
| B60 | $CF_3$ | H | $CH_3$ | H | OH | $CH_2$ |
| B61 | $(CH_3)_2NSO_2$ | H | $CH_3$ | H | OH | $CH_2$ |
| B62 | $(CH_3)_2N$ | H | $CH_3$ | H | OH | $CH_2$ |
| B63 | PhO | H | $CH_3$ | H | OH | $CH_2$ |
| B64 | PhS | H | $CH_3$ | H | OH | $CH_2$ |
| B65 | PhSO | H | $CH_3$ | H | OH | $CH_2$ |
| B66 | $PhSO_2$ | H | $CH_3$ | H | OH | $CH_2$ |
| B67 | CN | H | $CH_3$ | H | OH | $CH_2$ |
| B68 | $CH_3$ | $CH_3$ | $CH_3$ | H | OH | $CH_2$ |
| B69 | $CH_3CH_2$ | $CH_3$ | $CH_3$ | H | OH | $CH_2$ |
| B70 | $CH_3CH_2CH_2$ | $CH_3$ | $CH_3$ | H | OH | $CH_2$ |
| B71 | $(CH_3)_2CH$ | $CH_3$ | $CH_3$ | H | OH | $CH_2$ |
| B72 | $(CH_3)_3C$ | $CH_3$ | $CH_3$ | H | OH | $CH_2$ |
| B73 | $CH_3S$ | $CH_3$ | $CH_3$ | H | OH | $CH_2$ |
| B74 | $CH_3SO$ | $CH_3$ | $CH_3$ | H | OH | $CH_2$ |
| B75 | $CH_3SO_2$ | $CH_3$ | $CH_3$ | H | OH | $CH_2$ |
| B76 | Ph | $CH_3$ | $CH_3$ | H | OH | $CH_2$ |
| B77 | $CH_3O$ | $CH_3$ | $CH_3$ | H | OH | $CH_2$ |
| B78 | $CH_3OC(O)$ | $CH_3$ | $CH_3$ | H | OH | $CH_2$ |
| B79 | $CH_3CH_2OC(O)$ | $CH_3$ | $CH_3$ | H | OH | $CH_2$ |
| B80 | $CH_2=CHCH_2$ | $CH_3$ | $CH_3$ | H | OH | $CH_2$ |
| B81 | $HCCCH_2$ | $CH_3$ | $CH_3$ | H | OH | $CH_2$ |
| B82 | $CF_3$ | $CH_3$ | $CH_3$ | H | OH | $CH_2$ |
| B83 | $(CH_3)_2NSO_2$ | $CH_3$ | $CH_3$ | H | OH | $CH_2$ |
| B84 | $(CH_3)_2N$ | $CH_3$ | $CH_3$ | H | OH | $CH_2$ |
| B85 | PhO | $CH_3$ | $CH_3$ | H | OH | $CH_2$ |
| B86 | PhS | $CH_3$ | $CH_3$ | H | OH | $CH_2$ |
| B87 | PhSO | $CH_3$ | $CH_3$ | H | OH | $CH_2$ |
| B88 | $PhSO_2$ | $CH_3$ | $CH_3$ | H | OH | $CH_2$ |
| B89 | CN | $CH_3$ | $CH_3$ | H | OH | $CH_2$ |
| B90 | $CH_3$ | $CH_3$ | $CH_3$ | $CH_3$ | OH | $CH_2$ |
| B91 | $CH_3CH_2$ | $CH_3$ | $CH_3$ | $CH_3$ | OH | $CH_2$ |
| B92 | $CH_3CH_2CH_2$ | $CH_3$ | $CH_3$ | $CH_3$ | OH | $CH_2$ |
| B93 | $(CH_3)_2CH$ | $CH_3$ | $CH_3$ | $CH_3$ | OH | $CH_2$ |
| B94 | $(CH_3)_3C$ | $CH_3$ | $CH_3$ | $CH_3$ | OH | $CH_2$ |
| B95 | $CH_3S$ | $CH_3$ | $CH_3$ | $CH_3$ | OH | $CH_2$ |
| B96 | $CH_3SO$ | $CH_3$ | $CH_3$ | $CH_3$ | OH | $CH_2$ |
| B97 | $CH_3SO_2$ | $CH_3$ | $CH_3$ | $CH_3$ | OH | $CH_2$ |
| B98 | Ph | $CH_3$ | $CH_3$ | $CH_3$ | OH | $CH_2$ |
| B99 | $CH_3O$ | $CH_3$ | $CH_3$ | $CH_3$ | OH | $CH_2$ |
| B100 | $CH_3OC(O)$ | $CH_3$ | $CH_3$ | $CH_3$ | OH | $CH_2$ |
| B101 | $CH_3CH_2OC(O)$ | $CH_3$ | $CH_3$ | $CH_3$ | OH | $CH_2$ |
| B102 | $CH_2=CHCH_2$ | $CH_3$ | $CH_3$ | $CH_3$ | OH | $CH_2$ |
| B103 | $HCCCH_2$ | $CH_3$ | $CH_3$ | $CH_3$ | OH | $CH_2$ |
| B104 | $CF_3$ | $CH_3$ | $CH_3$ | $CH_3$ | OH | $CH_2$ |
| B105 | $(CH_3)_2NSO_2$ | $CH_3$ | $CH_3$ | $CH_3$ | OH | $CH_2$ |
| B106 | $(CH_3)_2N$ | $CH_3$ | $CH_3$ | $CH_3$ | OH | $CH_2$ |
| B107 | PhO | $CH_3$ | $CH_3$ | $CH_3$ | OH | $CH_2$ |
| B108 | PhS | $CH_3$ | $CH_3$ | $CH_3$ | OH | $CH_2$ |
| B109 | PhSO | $CH_3$ | $CH_3$ | $CH_3$ | OH | $CH_2$ |
| B110 | $PhSO_2$ | $CH_3$ | $CH_3$ | $CH_3$ | OH | $CH_2$ |
| B111 | CN | $CH_3$ | $CH_3$ | $CH_3$ | OH | $CH_2$ |
| B112 | $CH_3CH_2$ | $CH_3CH_2$ | H | H | OH | $CH_2$ |

TABLE 2-continued

Radicals B:

| Radical | $R_6$ | $R_7$ | $R_8$ | $R_9$ | $R_{10}$ | W |
|---|---|---|---|---|---|---|
| B113 | $CH_3CH_2CH_2$ | $CH_3CH_2$ | H | H | OH | $CH_2$ |
| B114 | $(CH_3)_2CH$ | $CH_3CH_2$ | H | H | OH | $CH_2$ |
| B115 | $(CH_3)_3C$ | $CH_3CH_2$ | H | H | OH | $CH_2$ |
| B116 | $CH_3S$ | $CH_3CH_2$ | H | H | OH | $CH_2$ |
| B117 | $CH_3SO$ | $CH_3CH_2$ | H | H | OH | $CH_2$ |
| B118 | $CH_3SO_2$ | $CH_3CH_2$ | H | H | OH | $CH_2$ |
| B119 | Ph | $CH_3CH_2$ | H | H | OH | $CH_2$ |
| B120 | $CH_3O$ | $CH_3CH_2$ | H | H | OH | $CH_2$ |
| B121 | $CH_3OC(O)$ | $CH_3CH_2$ | H | H | OH | $CH_2$ |
| B122 | $CH_3CH_2OC(O)$ | $CH_3CH_2$ | H | H | OH | $CH_2$ |
| B123 | $CH_2{=}CHCH_2$ | $CH_3CH_2$ | H | H | OH | $CH_2$ |
| B124 | $HCCCH_2$ | $CH_3CH_2$ | H | H | OH | $CH_2$ |
| B125 | $CF_3$ | $CH_3CH_2$ | H | H | OH | $CH_2$ |
| B126 | $(CH_3)_2NSO_2$ | $CH_3CH_2$ | H | H | OH | $CH_2$ |
| B127 | $(CH_3)_2N$ | $CH_3CH_2$ | H | H | OH | $CH_2$ |
| B128 | PhO | $CH_3CH_2$ | H | H | OH | $CH_2$ |
| B129 | PhS | $CH_3CH_2$ | H | H | OH | $CH_2$ |
| B130 | PhSO | $CH_3CH_2$ | H | H | OH | $CH_2$ |
| B131 | $PhSO_2$ | $CH_3CH_2$ | H | H | OH | $CH_2$ |
| B132 | CN | $CH_3CH_2$ | H | H | OH | $CH_2$ |
| B133 | H | H | H | H | OH | $CHCH_3$ |
| B134 | $CH_3$ | H | H | H | OH | $CHCH_3$ |
| B135 | $CH_3CH_2$ | H | H | H | OH | $CHCH_3$ |
| B136 | $CH_3CH_2CH_2$ | H | H | H | OH | $CHCH_3$ |
| B137 | $(CH_3)_2CH$ | H | H | H | OH | $CHCH_3$ |
| B138 | $(CH_3)_3C$ | H | H | H | OH | $CHCH_3$ |
| B139 | $CH_3S$ | H | H | H | OH | $CHCH_3$ |
| B140 | $CH_3SO$ | H | H | H | OH | $CHCH_3$ |
| B141 | $CH_3SO_2$ | H | H | H | OH | $CHCH_3$ |
| B142 | Ph | H | H | H | OH | $CHCH_3$ |
| B143 | $CH_3O$ | H | H | H | OH | $CHCH_3$ |
| B144 | $CH_3OC(O)$ | H | H | H | OH | $CHCH_3$ |
| B145 | $CH_3CH_2OC(O)$ | H | H | H | OH | $CHCH_3$ |
| B146 | $CH_2{=}CHCH_2$ | H | H | H | OH | $CHCH_3$ |
| B147 | $HCCCH_2$ | H | H | H | OH | $CHCH_3$ |
| B148 | $CF_3$ | H | H | H | OH | $CHCH_3$ |
| B149 | $(CH_3)_2NSO_2$ | H | H | H | OH | $CHCH_3$ |
| B150 | $(CH_3)_2N$ | H | H | H | OH | $CHCH_3$ |
| B151 | PhO | H | H | H | OH | $CHCH_3$ |
| B152 | PhS | H | H | H | OH | $CHCH_3$ |
| B153 | PhSO | H | H | H | OH | $CHCH_3$ |
| B154 | $PhSO_2$ | H | H | H | OH | $CHCH_3$ |
| B155 | CN | H | H | H | OH | $CHCH_3$ |
| B156 | $CH_3$ | $CH_3$ | H | H | OH | $CHCH_3$ |
| B157 | $CH_3CH_2$ | $CH_3$ | H | H | OH | $CHCH_3$ |
| B158 | $CH_3CH_2CH_2$ | $CH_3$ | H | H | OH | $CHCH_3$ |
| B159 | $(CH_3)_2CH$ | $CH_3$ | H | H | OH | $CHCH_3$ |
| B160 | $(CH_3)_3C$ | $CH_3$ | H | H | OH | $CHCH_3$ |
| B161 | $CH_3S$ | $CH_3$ | H | H | OH | $CHCH_3$ |
| B162 | $CH_3SO$ | $CH_3$ | H | H | OH | $CHCH_3$ |
| B163 | $CH_3SO_2$ | $CH_3$ | H | H | OH | $CHCH_3$ |
| B164 | Ph | $CH_3$ | H | H | OH | $CHCH_3$ |
| B165 | $CH_3O$ | $CH_3$ | H | H | OH | $CHCH_3$ |
| B166 | $CH_3OC(O)$ | $CH_3$ | H | H | OH | $CHCH_3$ |
| B167 | $CH_3CH_2OC(O)$ | $CH_3$ | H | H | OH | $CHCH_3$ |
| B168 | $CH_2{=}CHCH_2$ | $CH_3$ | H | H | OH | $CHCH_3$ |
| B169 | $HCCCH_2$ | $CH_3$ | H | H | OH | $CHCH_3$ |
| B170 | $CF_3$ | $CH_3$ | H | H | OH | $CHCH_3$ |
| B171 | $(CH_3)_2NSO_2$ | $CH_3$ | H | H | OH | $CHCH_3$ |
| B172 | $(CH_3)_2N$ | $CH_3$ | H | H | OH | $CHCH_3$ |
| B173 | PhO | $CH_3$ | H | H | OH | $CHCH_3$ |
| B174 | PhS | $CH_3$ | H | H | OH | $CHCH_3$ |
| B175 | PhSO | $CH_3$ | H | H | OH | $CHCH_3$ |
| B176 | $PhSO_2$ | $CH_3$ | H | H | OH | $CHCH_3$ |
| B177 | CN | $CH_3$ | H | H | OH | $CHCH_3$ |
| B178 | $CH_3$ | H | $CH_3$ | H | OH | $CHCH_3$ |
| B179 | $CH_3CH_2$ | H | $CH_3$ | H | OH | $CHCH_3$ |
| B180 | $CH_3CH_2CH_2$ | H | $CH_3$ | H | OH | $OHCH_3$ |
| B181 | $(CH_3)_2CH$ | H | $CH_3$ | H | OH | $CHCH_3$ |
| B182 | $(CH_3)_3C$ | H | $CH_3$ | H | OH | $CHCH_3$ |
| B183 | $CH_3S$ | H | $CH_3$ | H | OH | $CHCH_3$ |
| B184 | $CH_3SO$ | H | $CH_3$ | H | OH | $CHCH_3$ |
| B185 | $CH_3SO_2$ | H | $CH_3$ | H | OH | $CHCH_3$ |
| B186 | Ph | H | $CH_3$ | H | OH | $CHCH_3$ |
| B187 | $CH_3O$ | H | $CH_3$ | H | OH | $CHCH_3$ |

TABLE 2-continued

Radicals B:

| Radical | $R_6$ | $R_7$ | $R_8$ | $R_9$ | $R_{10}$ | W |
|---|---|---|---|---|---|---|
| B188 | $CH_3OC(O)$ | H | $CH_3$ | H | OH | $CHCH_3$ |
| B189 | $CH_3CH_2OC(O)$ | H | $CH_3$ | H | OH | $CHCH_3$ |
| B190 | $CH_2=CHCH_2$ | H | $CH_3$ | H | OH | $CHCH_3$ |
| B191 | $HCCCH_2$ | H | $CH_3$ | H | OH | $CHCH_3$ |
| B192 | $CF_3$ | H | $CH_3$ | H | OH | $CHCH_3$ |
| B193 | $(CH_3)_2NSO_2$ | H | $CH_3$ | H | OH | $CHCH_3$ |
| B194 | $(CH_3)_2N$ | H | $CH_3$ | H | OH | $CHCH_3$ |
| B195 | PhO | H | $CH_3$ | H | OH | $CHCH_3$ |
| B196 | PhS | H | $CH_3$ | H | OH | $CHCH_3$ |
| B197 | PhSO | H | $CH_3$ | H | OH | $CHCH_3$ |
| B198 | $PhSO_2$ | H | $CH_3$ | H | OH | $CHCH_3$ |
| B199 | CN | H | $CH_3$ | H | OH | $CHCH_3$ |
| B200 | $CH_3$ | $CH_3$ | $CH_3$ | H | OH | $CHCH_3$ |
| B201 | $CH_3CH_2$ | $CH_3$ | $CH_3$ | H | OH | $CHCH_3$ |
| B202 | $CH_3CH_2CH_2$ | $CH_3$ | $CH_3$ | H | OH | $CHCH_3$ |
| B203 | $(CH_3)_2CH$ | $CH_3$ | $CH_3$ | H | OH | $CHCH_3$ |
| B204 | $(CH_3)_3C$ | $CH_3$ | $CH_3$ | H | OH | $CHCH_3$ |
| B205 | $CH_3S$ | $CH_3$ | $CH_3$ | H | OH | $CHCH_3$ |
| B206 | $CH_3SO$ | $CH_3$ | $CH_3$ | H | OH | $CHCH_3$ |
| B207 | $CH_3SO_2$ | $CH_3$ | $CH_3$ | H | OH | $CHCH_3$ |
| B208 | Ph | $CH_3$ | $CH_3$ | H | OH | $CHCH_3$ |
| B209 | $CH_3O$ | $CH_3$ | $CH_3$ | H | OH | $CHCH_3$ |
| B210 | $CH_3OC(O)$ | $CH_3$ | $CH_3$ | H | OH | $CHCH_3$ |
| B211 | $CH_3CH_2OC(O)$ | $CH_3$ | $CH_3$ | H | OH | $CHCH_3$ |
| B212 | $CH_2=CHCH_2$ | $CH_3$ | $CH_3$ | H | OH | $CHCH_3$ |
| B213 | $HCCCH_2$ | $CH_3$ | $CH_3$ | H | OH | $CHCH_3$ |
| B214 | $CF_3$ | $CH_3$ | $CH_3$ | H | OH | $CHCH_3$ |
| B215 | $(CH_3)_2NSO_2$ | $CH_3$ | $CH_3$ | H | OH | $CHCH_3$ |
| B216 | $(CH_3)_2N$ | $CH_3$ | $CH_3$ | H | OH | $CHCH_3$ |
| B217 | PhO | $CH_3$ | $CH_3$ | H | OH | $CHCH_3$ |
| B218 | PhS | $CH_3$ | $CH_3$ | H | OH | $CHCH_3$ |
| B219 | PhSO | $CH_3$ | $CH_3$ | H | OH | $CHCH_3$ |
| B220 | $PhSO_2$ | $CH_3$ | $CH_3$ | H | OH | $CHCH_3$ |
| B221 | CN | $CH_3$ | $CH_3$ | H | OH | $CHCH_3$ |
| B222 | $CH_3$ | $CH_3$ | $CH_3$ | $CH_3$ | OH | $CHCH_3$ |
| B223 | $CH_3CH_2$ | $CH_3$ | $CH_3$ | $CH_3$ | OH | $CHCH_3$ |
| B224 | $CH_3CH_2CH_2$ | $CH_3$ | $CH_3$ | $CH_3$ | OH | $CHCH_3$ |
| B225 | $(CH_3)_2CH$ | $CH_3$ | $CH_3$ | $CH_3$ | OH | $CHCH_3$ |
| B226 | $(CH_3)_3C$ | $CH_3$ | $CH_3$ | $CH_3$ | OH | $CHCH_3$ |
| B227 | $CH_3S$ | $CH_3$ | $CH_3$ | $CH_3$ | OH | $CHCH_3$ |
| B228 | $CH_3SO$ | $CH_3$ | $CH_3$ | $CH_3$ | OH | $CHCH_3$ |
| B229 | $CH_3SO_2$ | $CH_3$ | $CH_3$ | $CH_3$ | OH | $CHCH_3$ |
| B230 | Ph | $CH_3$ | $CH_3$ | $CH_3$ | OH | $CHCH_3$ |
| B231 | $CH_3O$ | $CH_3$ | $CH_3$ | $CH_3$ | OH | $CHCH_3$ |
| B232 | $CH_3OC(O)$ | $CH_3$ | $CH_3$ | $CH_3$ | OH | $CHCH_3$ |
| B233 | $CH_3CH_2OC(O)$ | $CH_3$ | $CH_3$ | $CH_3$ | OH | $CHCH_3$ |
| B234 | $CH_2=CHCH_2$ | $CH_3$ | $CH_3$ | $CH_3$ | OH | $CHCH_3$ |
| B235 | $HCCCH_2$ | $CH_3$ | $CH_3$ | $CH_3$ | OH | $CHCH_3$ |
| B236 | $CF_3$ | $CH_3$ | $CH_3$ | $CH_3$ | OH | $CHCH_3$ |
| B237 | $(CH_3)_2NSO_2$ | $CH_3$ | $CH_3$ | $CH_3$ | OH | $CHCH_3$ |
| B238 | $(CH_3)_2N$ | $CH_3$ | $CH_3$ | $CH_3$ | OH | $CHCH_3$ |
| B239 | PhO | $CH_3$ | $CH_3$ | $CH_3$ | OH | $CHCH_3$ |
| B240 | PhS | $CH_3$ | $CH_3$ | $OH_3$ | OH | $CHCH_3$ |
| B241 | PhSO | $CH_3$ | $CH_3$ | $CH_3$ | OH | $CHCH_3$ |
| B242 | $PhSO_2$ | $CH_3$ | $CH_3$ | $CH_3$ | OH | $CHCH_3$ |
| B243 | CN | $CH_3$ | $CH_3$ | $CH_3$ | OH | $CHCH_3$ |
| B244 | $CH_3CH_2$ | $CH_3CH_2$ | H | H | OH | $CHCH_3$ |
| B245 | $CH_3CH_2CH_2$ | $CH_3CH_2$ | H | H | OH | $CHCH_3$ |
| B246 | $(CH_3)_2CH$ | $CH_3CH_2$ | H | H | OH | $CHCH_3$ |
| B247 | $(CH_3)_3C$ | $CH_3CH_2$ | H | H | OH | $CHCH_3$ |
| B248 | $CH_3S$ | $CH_3CH_2$ | H | H | OH | $CHCH_3$ |
| B249 | $CH_3SO$ | $CH_3CH_2$ | H | H | OH | $CHCH_3$ |
| B250 | $CH_3SO_2$ | $CH_3CH_2$ | H | H | OH | $CHCH_3$ |
| B251 | Ph | $CH_3CH_2$ | H | H | OH | $CHCH_3$ |
| B252 | $CH_3O$ | $CH_3CH_2$ | H | H | OH | $CHCH_3$ |
| B253 | $CH_3OC(O)$ | $CH_3CH_2$ | H | H | OH | $CHCH_3$ |
| B254 | $CH_3CH_2OC(O)$ | $CH_3CH_2$ | H | H | OH | $CHCH_3$ |
| B255 | $CH_2=CHCH_2$ | $CH_3CH_2$ | H | H | OH | $CHCH_3$ |
| B256 | $HCCCH_2$ | $CH_3CH_2$ | H | H | OH | $CHCH_3$ |
| B257 | $CF_3$ | $CH_3CH_2$ | H | H | OH | $CHCH_3$ |
| B258 | $(CH_3)_2NSO_2$ | $CH_3CH_2$ | H | H | OH | $CHCH_3$ |
| B259 | $(CH_3)_2N$ | $CH_3CH_2$ | H | H | OH | $CHCH_3$ |
| B260 | PhO | $CH_3CH_2$ | H | H | OH | $CHCH_3$ |
| B261 | PhS | $CH_3CH_2$ | H | H | OH | $CHCH_3$ |
| B262 | PhSO | $CH_3CH_2$ | H | H | OH | $CHCH_3$ |

TABLE 2-continued

Radicals B:

| Radical | $R_6$ | $R_7$ | $R_8$ | $R_9$ | $R_{10}$ | W |
|---|---|---|---|---|---|---|
| B263 | $PhSO_2$ | $CH_3CH_2$ | H | H | OH | $CHCH_3$ |
| B264 | CN | $CH_3CH_2$ | H | H | OH | $CHCH_3$ |
| B265 | H | H | H | H | OH | C=O |
| B266 | $CH_3$ | H | H | H | OH | C=O |
| B267 | $CH_3CH_2$ | H | H | H | OH | C=O |
| B268 | $CH_3CH_2CH_2$ | H | H | H | OH | C=O |
| B269 | $(CH_3)_2CH$ | H | H | H | OH | C=O |
| B270 | $(CH_3)_3C$ | H | H | H | OH | C=O |
| B271 | $CH_3S$ | H | H | H | OH | C=O |
| B272 | $CH_3SO$ | H | H | H | OH | C=O |
| B273 | $CH_3SO_2$ | H | H | H | OH | C=O |
| B274 | Ph | H | H | H | OH | C=O |
| B275 | $CH_3O$ | H | H | H | OH | C=O |
| B276 | $CH_3OC(O)$ | H | H | H | OH | C=O |
| B277 | $CH_3CH_2OC(O)$ | H | H | H | OH | C=O |
| B278 | $CH_2=CHCH_2$ | H | H | H | OH | C=O |
| B279 | $HCCCH_2$ | H | H | H | OH | C=O |
| B280 | $CF_3$ | H | H | H | OH | C=O |
| B281 | $(CH_3)_2NSO_2$ | H | H | H | OH | C=O |
| B282 | $(CH_3)_2N$ | H | H | H | OH | C=O |
| B283 | PhO | H | H | H | OH | C=O |
| B284 | PhS | H | H | H | OH | C=O |
| B285 | PhSO | H | H | H | OH | C=O |
| B286 | $PhSO_2$ | H | H | H | OH | C=O |
| B287 | CN | H | H | H | OH | C=O |
| B288 | $CH_3$ | $CH_3$ | H | H | OH | C=O |
| B289 | $CH_3CH_2$ | $CH_3$ | H | H | OH | C=O |
| B290 | $CH_3CH_2CH_2$ | $CH_3$ | H | H | OH | C=O |
| B291 | $(CH_3)_2CH$ | $CH_3$ | H | H | OH | C=O |
| B292 | $(CH_3)_3C$ | $CH_3$ | H | H | OH | C=O |
| B293 | $CH_3S$ | $CH_3$ | H | H | OH | C=O |
| B294 | $CH_3SO$ | $CH_3$ | H | H | OH | C=O |
| B295 | $CH_3SO_2$ | $CH_3$ | H | H | OH | C=O |
| B296 | Ph | $CH_3$ | H | H | OH | C=O |
| B297 | $CH_3O$ | $CH_3$ | H | H | OH | C=O |
| B298 | $CH_3OC(O)$ | $CH_3$ | H | H | OH | C=O |
| B299 | $CH_3CH_2OC(O)$ | $CH_3$ | H | H | OH | C=O |
| B300 | $CH_2=CHCH_2$ | $CH_3$ | H | H | OH | C=O |
| B301 | $HCCCH_2$ | $CH_3$ | H | H | OH | C=O |
| B302 | $CF_3$ | $CH_3$ | H | H | OH | C=O |
| B303 | $(CH_3)_2NSO_2$ | $CH_3$ | H | H | OH | C=O |
| B304 | $(CH_3)_2N$ | $CH_3$ | H | H | OH | C=O |
| B305 | PhO | $CH_3$ | H | H | OH | C=O |
| B306 | PhS | $CH_3$ | H | H | OH | C=O |
| B307 | PhSO | $CH_3$ | H | H | OH | C=O |
| B308 | $PhSO_2$ | $CH_3$ | H | H | OH | C=O |
| B309 | CN | $CH_3$ | H | H | OH | C=O |
| B310 | $CH_3$ | H | $CH_3$ | H | OH | C=O |
| B311 | $CH_3CH_2$ | H | $CH_3$ | H | OH | C=O |
| B312 | $CH_3CH_2CH_2$ | H | $CH_3$ | H | OH | C=O |
| B313 | $(CH_3)_2CH$ | H | $CH_3$ | H | OH | C=O |
| B314 | $(CH_3)_3C$ | H | $CH_3$ | H | OH | C=O |
| B315 | $CH_3S$ | H | $CH_3$ | H | OH | C=O |
| B316 | $CH_3SO$ | H | $CH_3$ | H | OH | C=O |
| B317 | $CH_3SO_2$ | H | $CH_3$ | H | OH | C=O |
| B318 | Ph | H | $CH_3$ | H | OH | C=O |
| B319 | $CH_3O$ | H | $CH_3$ | H | OH | C=O |
| B320 | $CH_3OC(O)$ | H | $CH_3$ | H | OH | C=O |
| B321 | $CH_3CH_2OC(O)$ | H | $CH_3$ | H | OH | C=O |
| B322 | $CH_2=CHCH_2$ | H | $CH_3$ | H | OH | C=O |
| B323 | $HCCCH_2$ | H | $CH_3$ | H | OH | C=O |
| B324 | $CF_3$ | H | $CH_3$ | H | OH | C=O |
| B325 | $(CH_3)_2NSO_2$ | H | $CH_3$ | H | OH | C=O |
| B326 | $(CH_3)_2N$ | H | $CH_3$ | H | OH | C=O |
| B327 | PhO | H | $CH_3$ | H | OH | C=O |
| B328 | PhS | H | $CH_3$ | H | OH | C=O |
| B329 | PhSO | H | $CH_3$ | H | OH | C=O |
| B330 | $PhSO_2$ | H | $CH_3$ | H | OH | C=O |
| B331 | CN | H | $CH_3$ | H | OH | C=O |
| B332 | $CH_3$ | $CH_3$ | $CH_3$ | H | OH | C=O |
| B333 | $CH_3CH_2$ | $CH_3$ | $CH_3$ | H | OH | C=O |
| B334 | $CH_3CH_2CH_2$ | $CH_3$ | $CH_3$ | H | OH | C=O |
| B335 | $(CH_3)_2CH$ | $CH_3$ | $CH_3$ | H | OH | C=O |
| B336 | $(CH_3)_3C$ | $CH_3$ | $CH_3$ | H | OH | C=O |
| B337 | $CH_3S$ | $CH_3$ | $CH_3$ | H | OH | C=O |

TABLE 2-continued

Radicals B:

| Radical | R$_6$ | R$_7$ | R$_8$ | R$_9$ | R$_{10}$ | W |
|---|---|---|---|---|---|---|
| B338 | CH$_3$SO | CH$_3$ | CH$_3$ | H | OH | C=O |
| B339 | CH$_3$SO$_2$ | CH$_3$ | CH$_3$ | H | OH | C=O |
| B340 | Ph | CH$_3$ | CH$_3$ | H | OH | C=O |
| B341 | CH$_3$O | CH$_3$ | CH$_3$ | H | OH | C=O |
| B342 | CH$_3$OC(O) | CH$_3$ | CH$_3$ | H | OH | C=O |
| B343 | CH$_3$CH$_2$OC(O) | CH$_3$ | CH$_3$ | H | OH | C=O |
| B344 | CH$_2$=CHCH$_2$ | CH$_3$ | CH$_3$ | H | OH | C=O |
| B345 | HCCCH$_2$ | CH$_3$ | CH$_3$ | H | OH | C=O |
| B346 | CF$_3$ | CH$_3$ | CH$_3$ | H | OH | C=O |
| B347 | (CH$_3$)$_2$NSO$_2$ | CH$_3$ | CH$_3$ | H | OH | C=O |
| B348 | (CH$_3$)$_2$N | CH$_3$ | CH$_3$ | H | OH | C=O |
| B349 | PhO | CH$_3$ | CH$_3$ | H | OH | C=O |
| B350 | PhS | CH$_3$ | CH$_3$ | H | OH | C=O |
| B351 | PhSO | CH$_3$ | CH$_3$ | H | OH | C=O |
| B352 | PhSO$_2$ | CH$_3$ | CH$_3$ | H | OH | C=O |
| B353 | CN | CH$_3$ | CH$_3$ | H | OH | C=O |
| B354 | CH$_3$ | CH$_3$ | CH$_3$ | CH$_3$ | OH | C=O |
| B355 | CH$_3$CH$_2$ | CH$_3$ | CH$_3$ | CH$_3$ | OH | C=O |
| B356 | CH$_3$CH$_2$CH$_2$ | CH$_3$ | CH$_3$ | CH$_3$ | OH | C=O |
| B357 | (CH$_3$)$_2$CH | CH$_3$ | CH$_3$ | CH$_3$ | OH | C=O |
| B358 | (CH$_3$)$_3$C | CH$_3$ | CH$_3$ | CH$_3$ | OH | C=O |
| B359 | CH$_3$S | CH$_3$ | CH$_3$ | CH$_3$ | OH | C=O |
| B360 | CH$_3$SO | CH$_3$ | CH$_3$ | CH$_3$ | OH | C=O |
| B361 | CH$_3$SO$_2$ | CH$_3$ | CH$_3$ | CH$_3$ | OH | C=O |
| B362 | Ph | CH$_3$ | CH$_3$ | CH$_3$ | OH | C=O |
| B363 | CH$_3$O | CH$_3$ | CH$_3$ | CH$_3$ | OH | C=O |
| B364 | CH$_3$OC(O) | CH$_3$ | CH$_3$ | CH$_3$ | OH | C=O |
| B365 | CH$_3$CH$_2$OC(O) | CH$_3$ | CH$_3$ | CH$_3$ | OH | C=O |
| B366 | CH$_2$=CHCH$_2$ | CH$_3$ | CH$_3$ | CH$_3$ | OH | C=O |
| B367 | HCCCH$_2$ | CH$_3$ | CH$_3$ | CH$_3$ | OH | C=O |
| B368 | CF$_3$ | CH$_3$ | CH$_3$ | CH$_3$ | OH | C=O |
| B369 | (CH$_3$)$_2$NSO$_2$ | CH$_3$ | CH$_3$ | CH$_3$ | OH | C=O |
| B370 | (CH$_3$)$_2$N | CH$_3$ | CH$_3$ | CH$_3$ | OH | C=O |
| B371 | PhO | CH$_3$ | CH$_3$ | CH$_3$ | OH | C=O |
| B372 | PhS | CH$_3$ | CH$_3$ | CH$_3$ | OH | C=O |
| B373 | PhSO | CH$_3$ | CH$_3$ | CH$_3$ | OH | C=O |
| B374 | PhSO$_2$ | CH$_3$ | CH$_3$ | CH$_3$ | OH | C=O |
| B375 | CN | CH$_3$ | CH$_3$ | CH$_3$ | OH | C=O |
| B376 | CH$_3$CH$_2$ | CH$_3$CH$_2$ | H | H | OH | C=O |
| B377 | CH$_3$CH$_2$CH$_2$ | CH$_3$CH$_2$ | H | H | OH | C=O |
| B378 | (CH$_3$)$_2$CH | CH$_3$CH$_2$ | H | H | OH | C=O |
| B379 | (CH$_3$)$_3$C | CH$_3$CH$_2$ | H | H | OH | C=O |
| B380 | CH$_3$S | CH$_3$CH$_2$ | H | H | OH | C=O |
| B381 | CH$_3$SO | CH$_3$CH$_2$ | H | H | OH | C=O |
| B382 | CH$_3$SO$_2$ | CH$_3$CH$_2$ | H | H | OH | C=O |
| B383 | Ph | CH$_3$CH$_2$ | H | H | OH | C=O |
| B384 | CH$_3$O | CH$_3$CH$_2$ | H | H | OH | C=O |
| B385 | CH$_3$OC(O) | CH$_3$CH$_2$ | H | H | OH | C=O |
| B386 | CH$_3$CH$_2$OC(O) | CH$_3$CH$_2$ | H | H | OH | C=O |
| B387 | CH$_2$=CHCH$_2$ | CH$_3$CH$_2$ | H | H | OH | C=O |
| B388 | HCCCH$_2$ | CH$_3$CH$_2$ | H | H | CH | C=O |
| B389 | CF$_3$ | CH$_3$CH$_2$ | H | H | OH | C=O |
| B390 | (CH$_3$)$_2$NSO$_2$ | CH$_3$CH$_2$ | H | H | OH | C=O |
| B391 | (CH$_3$)$_2$N | CH$_3$CH$_2$ | H | H | OH | C=O |
| B392 | PhO | CH$_3$CH$_2$ | H | H | OH | C=O |
| B393 | PhS | CH$_3$CH$_2$ | H | H | OH | C=O |
| B394 | PhSO | CH$_3$CH$_2$ | H | H | OH | C=O |
| B395 | PhSO$_2$ | CH$_3$CH$_2$ | H | H | OH | C=O |
| B396 | CN | CH$_3$CH$_2$ | H | H | OH | C=O |
| B397 | H | H | H | H | OH | N—CH$_3$ |
| B398 | CH$_3$ | H | H | H | OH | N—CH$_3$ |
| B399 | CH$_3$CH$_2$ | H | H | H | OH | N—CH$_3$ |
| B400 | CH$_3$CH$_2$CH$_2$ | H | H | H | OH | N—CH$_3$ |
| B401 | (CH$_3$)$_2$CH | H | H | H | OH | N—CH$_3$ |
| B402 | (CH$_3$)$_3$C | H | H | H | OH | N—CH$_3$ |
| B403 | CH$_3$S | H | H | H | OH | N—CH$_3$ |
| B404 | CH$_3$SO | H | H | H | OH | N—CH$_3$ |
| B405 | CH$_3$SO$_2$ | H | H | H | OH | N—CH$_3$ |
| B406 | Ph | H | H | H | OH | N—CH$_3$ |
| B407 | CH$_3$O | H | H | H | OH | N—CH$_3$ |
| B408 | CH$_3$OC(O) | H | H | H | OH | N—CH$_3$ |
| B409 | CH$_3$CH$_2$OC(O) | H | H | H | OH | N—CH$_3$ |
| B410 | CH$_2$=CHCH$_2$ | H | H | H | OH | N—CH$_3$ |
| B411 | HCCCH$_2$ | H | H | H | OH | N—CH$_3$ |
| B412 | CF$_3$ | H | H | H | OH | N—CH$_3$ |

TABLE 2-continued

Radicals B:

| Radical | $R_6$ | $R_7$ | $R_8$ | $R_9$ | $R_{10}$ | W |
|---|---|---|---|---|---|---|
| B413 | $(CH_3)_2NSO_2$ | H | H | H | OH | N—$CH_3$ |
| B414 | $(CH_3)_2N$ | H | H | H | OH | N—$CH_3$ |
| B415 | PhO | H | H | H | OH | N—$CH_3$ |
| B416 | PhS | H | H | H | OH | N—$CH_3$ |
| B417 | PhSO | H | H | H | OH | N—$CH_3$ |
| B418 | $PhSO_2$ | H | H | H | OH | N—$CH_3$ |
| B419 | CN | H | H | H | OH | N—$CH_3$ |
| B420 | $CH_3$ | $CH_3$ | H | H | OH | N—$CH_3$ |
| B421 | $CH_3CH_2$ | $CH_3$ | H | H | OH | N—$CH_3$ |
| B422 | $CH_3CH_2CH_2$ | $CH_3$ | H | H | OH | N—$CH_3$ |
| B423 | $(CH_3)_2CH$ | $CH_3$ | H | H | OH | N—$CH_3$ |
| B424 | $(CH_3)_3C$ | $CH_3$ | H | H | OH | N—$CH_3$ |
| B425 | $CH_3S$ | $CH_3$ | H | H | OH | N—$CH_3$ |
| B426 | $CH_3SO$ | $CH_3$ | H | H | OH | N—$CH_3$ |
| B427 | $CH_3SO_2$ | $CH_3$ | H | H | OH | N—$CH_3$ |
| B428 | Ph | $CH_3$ | H | H | OH | N—$CH_3$ |
| B429 | $CH_3O$ | $CH_3$ | H | H | OH | N—$CH_3$ |
| B430 | $CH_3OC(O)$ | $CH_3$ | H | H | OH | N—$CH_3$ |
| B431 | $CH_3CH_2OC(O)$ | $CH_3$ | H | H | OH | N—$CH_3$ |
| B432 | $CH_2$=$CHCH_2$ | $CH_3$ | H | H | OH | N—$CH_3$ |
| B433 | $HCCCH_2$ | $CH_3$ | H | H | OH | N—$CH_3$ |
| B434 | $CF_3$ | $CH_3$ | H | H | OH | N—$CH_3$ |
| B435 | $(CH_3)_2NSO_2$ | $CH_3$ | H | H | OH | N—$CH_3$ |
| B436 | $(CH_3)_2N$ | $CH_3$ | H | H | OH | N—$CH_3$ |
| B437 | PhO | $CH_3$ | H | H | OH | N—$CH_3$ |
| B438 | PhS | $CH_3$ | H | H | OH | N—$CH_3$ |
| B439 | PhSO | $CH_3$ | H | H | OH | N—$CH_3$ |
| B440 | $PhSO_2$ | $CH_3$ | H | H | OH | N—$CH_3$ |
| B441 | CN | $CH_3$ | H | H | OH | N—$CH_3$ |
| B442 | $CH_3$ | H | $CH_3$ | H | OH | N—$CH_3$ |
| B443 | $CH_3CH_2$ | H | $CH_3$ | H | OH | N—$CH_3$ |
| B444 | $CH_3CH_2CH_2$ | H | $CH_3$ | H | OH | N—$CH_3$ |
| B445 | $(CH_3)_2CH$ | H | $CH_3$ | H | OH | N—$CH_3$ |
| B446 | $(CH_3)_3C$ | H | $CH_3$ | H | OH | N—$CH_3$ |
| B447 | $CH_3S$ | H | $CH_3$ | H | OH | N—$CH_3$ |
| B448 | $CH_3SO$ | H | $CH_3$ | H | OH | N—$CH_3$ |
| B449 | $CH_3SO_2$ | H | $CH_3$ | H | OH | N—$CH_3$ |
| B450 | Ph | H | $CH_3$ | H | OH | N—$CH_3$ |
| B451 | $CH_3O$ | H | $CH_3$ | H | OH | N—$CH_3$ |
| B452 | $CH_3OC(O)$ | H | $CH_3$ | H | OH | N—$CH_3$ |
| B453 | $CH_3CH_2OC(O)$ | H | $CH_3$ | H | OH | N—$CH_3$ |
| B454 | $CH_2$=$CHCH_2$ | H | $CH_3$ | H | OH | N—$CH_3$ |
| B455 | $HCCCH_2$ | H | $CH_3$ | H | OH | N—$CH_3$ |
| B456 | $CF_3$ | H | $CH_3$ | H | OH | N—$CH_3$ |
| B457 | $(CH_3)_2NSO_2$ | H | $CH_3$ | H | OH | N—$CH_3$ |
| B458 | $(CH_3)_2N$ | H | $CH_3$ | H | OH | N—$CH_3$ |
| B459 | PhO | H | $CH_3$ | H | OH | N—$CH_3$ |
| B460 | PhS | H | $CH_3$ | H | OH | N—$CH_3$ |
| B461 | PhSO | H | $CH_3$ | H | OH | N—$CH_3$ |
| B462 | $PhSO_2$ | H | $CH_3$ | H | OH | N—$CH_3$ |
| B463 | CN | H | $CH_3$ | H | OH | N—$CH_3$ |
| B464 | $CH_3$ | $CH_3$ | $CH_3$ | H | OH | N—$CH_3$ |
| B465 | $CH_3CH_2$ | $CH_3$ | $CH_3$ | H | OH | N—$CH_3$ |
| B466 | $CH_3CH_2CH_2$ | $CH_3$ | $CH_3$ | H | OH | N—$CH_3$ |
| B467 | $(CH_3)_2CH$ | $CH_3$ | $CH_3$ | H | OH | N—$CH_3$ |
| B468 | $(CH_3)_3C$ | $CH_3$ | $CH_3$ | H | OH | N—$CH_3$ |
| B469 | $CH_3S$ | $CH_3$ | $CH_3$ | H | OH | N—$CH_3$ |
| B470 | $CH_3SO$ | $CH_3$ | $CH_3$ | H | OH | N—$CH_3$ |
| B471 | $CH_3SO_2$ | $CH_3$ | $CH_3$ | H | OH | N—$CH_3$ |
| B472 | Ph | $CH_3$ | $CH_3$ | H | OH | N—$CH_3$ |
| B473 | $CH_3O$ | $CH_3$ | $CH_3$ | H | OH | N—$CH_3$ |
| B474 | $CH_3OC(O)$ | $CH_3$ | $CH_3$ | H | OH | N—$CH_3$ |
| B475 | $CH_3CH_2OC(O)$ | $CH_3$ | $CH_3$ | H | OH | N—$CH_3$ |
| B476 | $CH_2$=$CHCH_2$ | $CH_3$ | $CH_3$ | H | OH | N—$CH_3$ |
| B477 | $HCCCH_2$ | $CH_3$ | $CH_3$ | H | OH | N—$CH_3$ |
| B478 | $CF_3$ | $CH_3$ | $CH_3$ | H | OH | N—$CH_3$ |
| B479 | $(CH_3)_2NSO_2$ | $CH_3$ | $CH_3$ | H | OH | N—$CH_3$ |
| B480 | $(CH_3)_2N$ | $CH_3$ | $CH_3$ | H | OH | N—$CH_3$ |
| B481 | PhO | $CH_3$ | $CH_3$ | H | OH | N—$CH_3$ |
| B482 | PhS | $CH_3$ | $CH_3$ | H | OH | N—$CH_3$ |
| B483 | PhSO | $CH_3$ | $CH_3$ | H | OH | N—$CH_3$ |
| B484 | $PhSO_2$ | $CH_3$ | $CH_3$ | H | OH | N—$CH_3$ |
| B485 | CN | $CH_3$ | $CH_3$ | H | OH | N—$CH_3$ |
| B486 | $CH_3$ | $CH_3$ | $CH_3$ | $CH_3$ | OH | N—$CH_3$ |
| B487 | $CH_3CH_2$ | $CH_3$ | $CH_3$ | $CH_3$ | OH | N—$CH_3$ |

TABLE 2-continued

Radicals B:

| Radical | $R_6$ | $R_7$ | $R_8$ | $R_9$ | $R_{10}$ | W |
|---|---|---|---|---|---|---|
| B488 | $CH_3CH_2CH_2$ | $CH_3$ | $CH_3$ | $CH_3$ | OH | N—$CH_3$ |
| B489 | $(CH_3)_2CH$ | $CH_3$ | $CH_3$ | $CH_3$ | OH | N—$CH_3$ |
| B490 | $(CH_3)_3C$ | $CH_3$ | $CH_3$ | $CH_3$ | OH | N—$CH_3$ |
| B491 | $CH_3S$ | $CH_3$ | $CH_3$ | $CH_3$ | OH | N—$CH_3$ |
| B492 | $CH_3SO$ | $CH_3$ | $CH_3$ | $CH_3$ | OH | N—$CH_3$ |
| B493 | $CH_3SO_2$ | $CH_3$ | $CH_3$ | $CH_3$ | OH | N—$CH_3$ |
| B494 | Ph | $CH_3$ | $CH_3$ | $CH_3$ | OH | N—$CH_3$ |
| B495 | $CH_3O$ | $CH_3$ | $CH_3$ | $CH_3$ | OH | N—$CH_3$ |
| B496 | $CH_3OC(O)$ | $CH_3$ | $CH_3$ | $CH_3$ | OH | N—$CH_3$ |
| B497 | $CH_3CH_2OC(O)$ | $CH_3$ | $CH_3$ | $CH_3$ | OH | N—$CH_3$ |
| B498 | $CH_2$=$CHCH_2$ | $CH_3$ | $CH_3$ | $CH_3$ | OH | N—$CH_3$ |
| B499 | $HCCCH_2$ | $CH_3$ | $CH_3$ | $CH_3$ | OH | N—$CH_3$ |
| B500 | $CF_3$ | $CH_3$ | $CH_3$ | $CH_3$ | OH | N—$CH_3$ |
| B501 | $(CH_3)_2NSO_2$ | $CH_3$ | $CH_3$ | $CH_3$ | OH | N—$CH_3$ |
| B502 | $(CH_3)_2N$ | $CH_3$ | $CH_3$ | $CH_3$ | OH | N—$CH_3$ |
| B503 | PhO | $CH_3$ | $CH_3$ | $CH_3$ | OH | N—$CH_3$ |
| B504 | PhS | $CH_3$ | $CH_3$ | $CH_3$ | OH | N—$CH_3$ |
| B505 | PhSO | $CH_3$ | $CH_3$ | $CH_3$ | OH | N—$CH_3$ |
| B506 | $PhSO_2$ | $CH_3$ | $CH_3$ | $CH_3$ | OH | N—$CH_3$ |
| B507 | CN | $CH_3$ | $CH_3$ | $CH_3$ | OH | N—$CH_3$ |
| B508 | $CH_3CH_2$ | $CH_3CH_2$ | H | H | OH | N—$CH_3$ |
| B509 | $CH_3CH_2CH_2$ | $CH_3CH_2$ | H | H | OH | N—$CH_3$ |
| B510 | $(CH_3)_2CH$ | $CH_3CH_2$ | H | H | OH | N—$CH_3$ |
| B511 | $(CH_3)_3C$ | $CH_3CH_2$ | H | H | OH | N—$CH_3$ |
| B512 | $CH_3S$ | $CH_3CH_2$ | H | H | OH | N—$CH_3$ |
| B513 | $CH_3SO$ | $CH_3CH_2$ | H | H | OH | N—$CH_3$ |
| B514 | $CH_3SO_2$ | $CH_3CH_2$ | H | H | OH | N—$CH_3$ |
| B515 | Ph | $CH_3CH_2$ | H | H | OH | N—$CH_3$ |
| B516 | $CH_3O$ | $CH_3CH_2$ | H | H | OH | N—$CH_3$ |
| B517 | $CH_3OC(O)$ | $CH_3CH_2$ | H | H | OH | N—$CH_3$ |
| B518 | $CH_3CH_2OC(O)$ | $CH_3CH_2$ | H | H | OH | N—$CH_3$ |
| B519 | $CH_2$=$CHCH_2$ | $CH_3CH_2$ | H | H | OH | N—$CH_3$ |
| B520 | $HCCCH_2$ | $CH_3CH_2$ | H | H | OH | N—$CH_3$ |
| B521 | $CF_3$ | $CH_3CH_2$ | H | H | OH | N—$CH_3$ |
| B522 | $(CH_3)_2NSO_2$ | $CH_3CH_2$ | H | H | OH | N—$CH_3$ |
| B523 | $(CH_3)_2N$ | $CH_3CH_2$ | H | H | OH | N—$CH_3$ |
| B524 | PhO | $CH_3CH_2$ | H | H | OH | N—$CH_3$ |
| B525 | PhS | $CH_3CH_2$ | H | H | OH | N—$CH_3$ |
| B526 | PhSO | $CH_3CH_2$ | H | H | OH | N—$CH_3$ |
| B527 | $PhSO_2$ | $CH_3CH_2$ | H | H | OH | N—$CH_3$ |
| B528 | CN | $CH_3CH_2$ | H | H | OH | N—$CH_3$ |
| B529 | H | H | H | H | OH | O |
| B530 | $CH_3$ | H | H | H | OH | O |
| B531 | $CH_3CH_2$ | H | H | H | OH | O |
| B532 | $CH_3CH_2CH_2$ | H | H | H | OH | O |
| B533 | $(CH_3)_2CH$ | H | H | H | OH | O |
| B534 | $(CH_3)_3C$ | H | H | H | OH | O |
| B535 | $CH_3S$ | H | H | H | OH | O |
| B536 | $CH_3SO$ | H | H | H | OH | O |
| B537 | $CH_3SO_2$ | H | H | H | OH | O |
| B538 | Ph | H | H | H | OH | O |
| B539 | $CH_3O$ | H | H | H | OH | O |
| B540 | $CH_3OC(O)$ | H | H | H | OH | O |
| B541 | $CH_3CH_2OC(O)$ | H | H | H | OH | O |
| B542 | $CH_2$=$CHCH_2$ | H | H | H | OH | O |
| B543 | $HCCCH_2$ | H | H | H | OH | O |
| B544 | $CF_3$ | H | H | H | OH | O |
| B545 | $(CH_3)_2NSO_2$ | H | H | H | OH | O |
| B546 | $(CH_3)_2N$ | H | H | H | OH | O |
| B547 | PhO | H | H | H | OH | O |
| B548 | PhS | H | H | H | OH | O |
| B549 | PhSO | H | H | H | OH | O |
| B550 | $PhSO_2$ | H | H | H | OH | O |
| B551 | CN | H | H | H | OH | O |
| B552 | $CH_3$ | $CH_3$ | H | H | OH | O |
| B553 | $CH_3CH_2$ | $CH_3$ | H | H | OH | O |
| B554 | $CH_3CH_2CH_2$ | $CH_3$ | H | H | OH | O |
| B555 | $(CH_3)_2CH$ | $CH_3$ | H | H | OH | O |
| B556 | $(CH_3)_3C$ | $CH_3$ | H | H | OH | O |
| B557 | $CH_3S$ | $CH_3$ | H | H | OH | O |
| B558 | $CH_3SO$ | $CH_3$ | H | H | OH | O |
| B559 | $CH_3SO_2$ | $CH_3$ | H | H | OH | O |
| B560 | Ph | $CH_3$ | H | H | OH | O |
| B561 | $CH_3O$ | $CH_3$ | H | H | OH | O |
| B562 | $CH_3OC(O)$ | $CH_3$ | H | H | OH | O |

TABLE 2-continued

Radicals B:

| Radical | $R_6$ | $R_7$ | $R_8$ | $R_9$ | $R_{10}$ | W |
|---|---|---|---|---|---|---|
| B563 | $CH_3CH_2OC(O)$ | $CH_3$ | H | H | OH | O |
| B564 | $CH_2=CHCH_2$ | $CH_3$ | H | H | OH | O |
| B565 | $HCCCH_2$ | $CH_3$ | H | H | OH | O |
| B566 | $CF_3$ | $CH_3$ | H | H | OH | O |
| B567 | $(CH_3)_2NSO_2$ | $CH_3$ | H | H | OH | O |
| B568 | $(CH_3)_2N$ | $CH_3$ | H | H | OH | O |
| B569 | PhO | $CH_3$ | H | H | OH | O |
| B570 | PhS | $CH_3$ | H | H | OH | O |
| B571 | PhSO | $CH_3$ | H | H | OH | O |
| B572 | $PhSO_2$ | $CH_3$ | H | H | OH | O |
| B573 | CN | $CH_3$ | H | H | OH | O |
| B574 | $CH_3$ | H | $CH_3$ | H | OH | O |
| B575 | $CH_3CH_2$ | H | $CH_3$ | H | OH | O |
| B576 | $CH_3CH_2CH_2$ | H | $CH_3$ | H | OH | O |
| B577 | $(CH_3)_2CH$ | H | $CH_3$ | H | OH | O |
| B578 | $(CH_3)_3C$ | H | $CH_3$ | H | OH | O |
| B579 | $CH_3S$ | H | $CH_3$ | H | OH | O |
| B580 | $CH_3SO$ | H | $CH_3$ | H | OH | O |
| B581 | $CH_3SO_2$ | H | $CH_3$ | H | OH | O |
| B582 | Ph | H | $CH_3$ | H | OH | O |
| B583 | $CH_3O$ | H | $CH_3$ | H | OH | O |
| B584 | $CH_3OC(O)$ | H | $CH_3$ | H | OH | O |
| B585 | $CH_3CH_2OC(O)$ | H | $CH_3$ | H | OH | O |
| B586 | $CH_2=CHCH_2$ | H | $CH_3$ | H | OH | O |
| B587 | $HCCCH_2$ | H | $CH_3$ | H | OH | O |
| B588 | $CF_3$ | H | $CH_3$ | H | OH | O |
| B589 | $(CH_3)_2NSO_2$ | H | $CH_3$ | H | OH | O |
| B590 | $(CH_3)_2N$ | H | $CH_3$ | H | OH | O |
| B591 | PhO | H | $CH_3$ | H | OH | O |
| B592 | PhS | H | $CH_3$ | H | OH | O |
| B593 | PhSO | H | $CH_3$ | H | OH | O |
| B594 | $PhSO_2$ | H | $CH_3$ | H | OH | O |
| B595 | CN | H | $CH_3$ | H | OH | O |
| B596 | $CH_3$ | $CH_3$ | $CH_3$ | H | OH | O |
| B597 | $CH_3CH_2$ | $CH_3$ | $CH_3$ | H | OH | O |
| B598 | $CH_3CH_2CH_2$ | $CH_3$ | $CH_3$ | H | OH | O |
| B599 | $(CH_3)_2CH$ | $CH_3$ | $CH_3$ | H | OH | O |
| B600 | $(CH_3)_3C$ | $CH_3$ | $CH_3$ | H | OH | O |
| B601 | $CH_3S$ | $CH_3$ | $CH_3$ | H | OH | O |
| B602 | $CH_3SO$ | $CH_3$ | $CH_3$ | H | OH | O |
| B603 | $CH_3SO_2$ | $CH_3$ | $OH_3$ | H | OH | O |
| B604 | Ph | $CH_3$ | $CH_3$ | H | OH | O |
| B605 | $CH_3O$ | $CH_3$ | $CH_3$ | H | OH | O |
| B606 | $CH_3OC(O)$ | $CH_3$ | $CH_3$ | H | OH | O |
| B607 | $CH_3CH_2OC(O)$ | $CH_3$ | $CH_3$ | H | OH | O |
| B608 | $CH_2=CHCH_2$ | $CH_3$ | $CH_3$ | H | OH | O |
| B609 | $HCCCH_2$ | $CH_3$ | $CH_3$ | H | OH | O |
| B610 | $CF_3$ | $CH_3$ | $CH_3$ | H | OH | O |
| B611 | $(CH_3)_2NSO_2$ | $CH_3$ | $CH_3$ | H | OH | O |
| B612 | $(CH_3)_2N$ | $CH_3$ | $CH_3$ | H | OH | O |
| B613 | PhO | $CH_3$ | $CH_3$ | H | OH | O |
| B614 | PhS | $CH_3$ | $CH_3$ | H | OH | O |
| B615 | PhSO | $CH_3$ | $CH_3$ | H | OH | O |
| B616 | $PhSO_2$ | $CH_3$ | $CH_3$ | H | OH | O |
| B617 | CN | $CH_3$ | $CH_3$ | H | OH | O |
| B618 | $CH_3$ | $CH_3$ | $CH_3$ | $CH_3$ | OH | O |
| B619 | $CH_3CH_2$ | $CH_3$ | $CH_3$ | $CH_3$ | OH | O |
| B620 | $CH_3CH_2CH_2$ | $CH_3$ | $CH_3$ | $CH_3$ | OH | O |
| B621 | $(CH_3)_2CH$ | $CH_3$ | $CH_3$ | $CH_3$ | OH | O |
| B622 | $(CH_3)_3C$ | $CH_3$ | $CH_3$ | $CH_3$ | OH | O |
| B623 | $CH_3S$ | $CH_3$ | $CH_3$ | $CH_3$ | OH | O |
| B624 | $CH_3SO$ | $CH_3$ | $CH_3$ | $CH_3$ | OH | O |
| B625 | $CH_3SO_2$ | $CH_3$ | $CH_3$ | $CH_3$ | OH | O |
| B626 | Ph | $CH_3$ | $CH_3$ | $CH_3$ | OH | O |
| B627 | $CH_3O$ | $CH_3$ | $CH_3$ | $CH_3$ | OH | O |
| B628 | $CH_3OC(O)$ | $CH_3$ | $CH_3$ | $CH_3$ | OH | O |
| B629 | $CH_3CH_2OC(O)$ | $CH_3$ | $CH_3$ | $CH_3$ | OH | O |
| B630 | $CH_2=CHCH_2$ | $CH_3$ | $CH_3$ | $CH_3$ | OH | O |
| B631 | $HCCCH_2$ | $CH_3$ | $CH_3$ | $CH_3$ | OH | O |
| B632 | $CF_3$ | $CH_3$ | $CH_3$ | $CH_3$ | OH | O |
| B633 | $(CH_3)_2NSO_2$ | $CH_3$ | $CH_3$ | $CH_3$ | OH | O |
| B634 | $(CH_3)_2N$ | $CH_3$ | $CH_3$ | $CH_3$ | OH | O |
| B635 | PhO | $CH_3$ | $CH_3$ | $CH_3$ | OH | O |
| B636 | PhS | $CH_3$ | $CH_3$ | $OH_3$ | OH | O |
| B637 | PhSO | $CH_3$ | $CH_3$ | $CH_3$ | OH | O |

TABLE 2-continued

Radicals B:

| Radical | $R_6$ | $R_7$ | $R_8$ | $R_9$ | $R_{10}$ | W |
|---|---|---|---|---|---|---|
| B638 | $PhSO_2$ | $CH_3$ | $CH_3$ | $CH_3$ | OH | O |
| B639 | CN | $CH_3$ | $CH_3$ | $CH_3$ | OH | O |
| B640 | $CH_3CH_2$ | $CH_3CH_2$ | H | H | OH | O |
| B641 | $CH_3CH_2CH_2$ | $CH_3CH_2$ | H | H | OH | O |
| B642 | $(CH_3)_2CH$ | $CH_3CH_2$ | H | H | OH | O |
| B643 | $(CH_3)_3C$ | $CH_3CH_2$ | H | H | OH | O |
| B644 | $CH_3S$ | $CH_3CH_2$ | H | H | OH | O |
| B645 | $CH_3SO$ | $CH_3CH_2$ | H | H | OH | O |
| B646 | $CH_3SO_2$ | $CH_3CH_2$ | H | H | OH | O |
| B647 | Ph | $CH_3CH_2$ | H | H | OH | O |
| B648 | $CH_3O$ | $CH_3CH_2$ | H | H | OH | O |
| B649 | $CH_3OC(O)$ | $CH_3CH_2$ | H | H | OH | O |
| B650 | $CH_3CH_2OC(O)$ | $CH_3CH_2$ | H | H | OH | O |
| B651 | $CH_2=CHCH_2$ | $CH_3CH_2$ | H | H | OH | O |
| B652 | $HCCCH_2$ | $CH_3CH_2$ | H | H | OH | O |
| B653 | $CF_3$ | $CH_3CH_2$ | H | H | OH | O |
| B654 | $(CH_3)_2NSO_2$ | $CH_3CH_2$ | H | H | OH | O |
| B655 | $(CH_3)_2N$ | $CH_3CH_2$ | H | H | OH | O |
| B656 | PhO | $CH_3CH_2$ | H | H | OH | O |
| B657 | PhS | $CH_3CH_2$ | H | H | OH | O |
| B658 | PhSO | $CH_3CH_2$ | H | H | OH | O |
| B659 | $PhSO_2$ | $CH_3CH_2$ | H | H | OH | O |
| B660 | CN | $CH_3CH_2$ | H | H | OH | O |
| B661 | H | H | H | H | OH | S |
| B662 | $CH_3$ | H | H | H | OH | S |
| B663 | $CH_3CH_2$ | H | H | H | OH | S |
| B664 | $CH_3CH_2CH_2$ | H | H | H | OH | S |
| B665 | $(CH_3)_2CH$ | H | H | H | OH | S |
| B666 | $(CH_3)_3C$ | H | H | H | OH | S |
| B667 | $CH_3S$ | H | H | H | OH | S |
| B668 | $CH_3SO$ | H | H | H | OH | S |
| B669 | $CH_3SO_2$ | H | H | H | OH | S |
| B670 | Ph | H | H | H | OH | S |
| B671 | $CH_3O$ | H | H | H | OH | S |
| B672 | $CH_3OC(O)$ | H | H | H | OH | S |
| B673 | $CH_3CH_2OC(O)$ | H | H | H | OH | S |
| B674 | $CH_2=CHCH_2$ | H | H | H | OH | S |
| B675 | $HCCCH_2$ | H | H | H | OH | S |
| B676 | $CF_3$ | H | H | H | OH | S |
| B677 | $(CH_3)_2NSO_2$ | H | H | H | OH | S |
| B678 | $(CH_3)_2N$ | H | H | H | OH | S |
| B679 | PhO | H | H | H | OH | S |
| B680 | PhS | H | H | H | OH | S |
| B681 | PhSO | H | H | H | OH | S |
| B682 | $PhSO_2$ | H | H | H | OH | S |
| B683 | CN | H | H | H | OH | S |
| B684 | $CH_3$ | $CH_3$ | H | H | OH | S |
| B685 | $CH_3CH_2$ | $CH_3$ | H | H | OH | S |
| B686 | $CH_3CH_2CH_2$ | $CH_3$ | H | H | OH | S |
| B687 | $(CH_3)_2CH$ | $CH_3$ | H | H | OH | S |
| B688 | $(CH_3)_3C$ | $CH_3$ | H | H | OH | S |
| B689 | $CH_3S$ | $CH_3$ | H | H | OH | S |
| B690 | $CH_3SO$ | $CH_3$ | H | H | OH | S |
| B691 | $CH_3SO_2$ | $CH_3$ | H | H | OH | S |
| B692 | Ph | $CH_3$ | H | H | OH | S |
| B693 | $CH_3O$ | $CH_3$ | H | H | OH | S |
| B694 | $CH_3OC(O)$ | $CH_3$ | H | H | OH | S |
| B695 | $CH_3CH_2OC(O)$ | $CH_3$ | H | H | OH | S |
| B696 | $CH_2=CHCH_2$ | $CH_3$ | H | H | OH | S |
| B697 | $HCCCH_2$ | $CH_3$ | H | H | OH | S |
| B698 | $CF_3$ | $CH_3$ | H | H | OH | S |
| B699 | $(CH_3)_2NSO_2$ | $CH_3$ | H | H | OH | S |
| B700 | $(CH_3)_2N$ | $CH_3$ | H | H | OH | S |
| B701 | PhO | $CH_3$ | H | H | OH | S |
| B702 | PhS | $CH_3$ | H | H | OH | S |
| B703 | PhSO | $CH_3$ | H | H | OH | S |
| B704 | $PhSO_2$ | $CH_3$ | H | H | OH | S |
| B705 | CN | $CH_3$ | H | H | OH | S |
| B706 | $CH_3$ | H | $CH_3$ | H | OH | S |
| B707 | $CH_3CH_2$ | H | $CH_3$ | H | OH | S |
| B708 | $CH_3CH_2CH_2$ | H | $CH_3$ | H | OH | S |
| B709 | $(CH_3)_2CH$ | H | $CH_3$ | H | OH | S |
| B710 | $(CH_3)_3C$ | H | $CH_3$ | H | OH | S |
| B711 | $CH_3S$ | H | $CH_3$ | H | OH | S |
| B712 | $CH_3SO$ | H | $CH_3$ | H | OH | S |

TABLE 2-continued

Radicals B:

| Radical | $R_6$ | $R_7$ | $R_8$ | $R_9$ | $R_{10}$ | W |
|---|---|---|---|---|---|---|
| B713 | $CH_3SO_2$ | H | $CH_3$ | H | OH | S |
| B714 | Ph | H | $CH_3$ | H | OH | S |
| B715 | $CH_3O$ | H | $CH_3$ | H | OH | S |
| B716 | $CH_3OC(O)$ | H | $CH_3$ | H | OH | S |
| B717 | $CH_3CH_2OC(O)$ | H | $CH_3$ | H | OH | S |
| B718 | $CH_2=CHCH_2$ | H | $CH_3$ | H | OH | S |
| B719 | $HCCCH_2$ | H | $CH_3$ | H | OH | S |
| B720 | $CF_3$ | H | $CH_3$ | H | OH | S |
| B721 | $(CH_3)_2NSO_2$ | H | $CH_3$ | H | OH | S |
| B722 | $(CH_3)_2N$ | H | $CH_3$ | H | OH | S |
| B723 | PhO | H | $CH_3$ | H | OH | S |
| B724 | PhS | H | $CH_3$ | H | OH | S |
| B725 | PhSO | H | $CH_3$ | H | OH | S |
| B726 | $PhSO_2$ | H | $CH_3$ | H | OH | S |
| B727 | CN | H | $CH_3$ | H | OH | S |
| B728 | $CH_3$ | $CH_3$ | $CH_3$ | H | OH | S |
| B729 | $CH_3CH_2$ | $CH_3$ | $CH_3$ | H | OH | S |
| B730 | $CH_3CH_2CH_2$ | $CH_3$ | $CH_3$ | H | OH | S |
| B731 | $(CH_3)_2CH$ | $CH_3$ | $CH_3$ | H | OH | S |
| B732 | $(CH_3)_3C$ | $CH_3$ | $CH_3$ | H | OH | S |
| B733 | $CH_3S$ | $CH_3$ | $CH_3$ | H | OH | S |
| B734 | $CH_3SO$ | $CH_3$ | $CH_3$ | H | OH | S |
| B735 | $CH_3SO_2$ | $CH_3$ | $CH_3$ | H | OH | S |
| B736 | Ph | $CH_3$ | $CH_3$ | H | OH | S |
| B737 | $CH_3O$ | $CH_3$ | $CH_3$ | H | OH | S |
| B738 | $CH_3OC(O)$ | $CH_3$ | $CH_3$ | H | OH | S |
| B739 | $CH_3CH_2OC(O)$ | $CH_3$ | $CH_3$ | H | OH | S |
| B740 | $CH_2=CHCH_2$ | $CH_3$ | $CH_3$ | H | OH | S |
| B741 | $HCCCH_2$ | $CH_3$ | $CH_3$ | H | OH | S |
| B742 | $CF_3$ | $CH_3$ | $CH_3$ | H | OH | S |
| B743 | $(CH_3)_2NSO_2$ | $CH_3$ | $CH_3$ | H | OH | S |
| B744 | $(CH_3)_2N$ | $CH_3$ | $CH_3$ | H | OH | S |
| B745 | PhO | $CH_3$ | $CH_3$ | H | OH | S |
| B746 | PhS | $CH_3$ | $CH_3$ | H | OH | S |
| B747 | PhSO | $CH_3$ | $CH_3$ | H | OH | S |
| B748 | $PhSO_2$ | $CH_3$ | $CH_3$ | H | OH | S |
| B749 | CN | $CH_3$ | $CH_3$ | H | OH | S |
| B750 | $CH_3$ | $CH_3$ | $CH_3$ | $CH_3$ | OH | S |
| B751 | $CH_3CH_2$ | $CH_3$ | $CH_3$ | $CH_3$ | OH | S |
| B752 | $CH_3CH_2CH_2$ | $CH_3$ | $CH_3$ | $CH_3$ | OH | S |
| B753 | $(CH_3)_2CH$ | $CH_3$ | $CH_3$ | $CH_3$ | OH | S |
| B754 | $(CH_3)_3C$ | $CH_3$ | $CH_3$ | $CH_3$ | OH | S |
| B755 | $CH_3S$ | $CH_3$ | $CH_3$ | $CH_3$ | OH | S |
| B756 | $CH_3SO$ | $CH_3$ | $CH_3$ | $CH_3$ | OH | S |
| B757 | $CH_3SO_2$ | $CH_3$ | $CH_3$ | $CH_3$ | OH | S |
| B758 | Ph | $CH_3$ | $CH_3$ | $CH_3$ | OH | S |
| B759 | $CH_3O$ | $CH_3$ | $CH_3$ | $CH_3$ | OH | S |
| B760 | $CH_3OC(O)$ | $CH_3$ | $CH_3$ | $CH_3$ | OH | S |
| B761 | $CH_3CH_2OC(O)$ | $CH_3$ | $CH_3$ | $CH_3$ | OH | S |
| B762 | $CH_2=CHCH_2$ | $CH_3$ | $CH_3$ | $CH_3$ | OH | S |
| B763 | $HCCCH_2$ | $CH_3$ | $CH_3$ | $CH_3$ | OH | S |
| B764 | $CF_3$ | $CH_3$ | $CH_3$ | $CH_3$ | OH | S |
| B765 | $(CH_3)_2NSO_2$ | $CH_3$ | $CH_3$ | $CH_3$ | OH | S |
| B766 | $(CH_3)_2N$ | $CH_3$ | $CH_3$ | $CH_3$ | OH | S |
| B767 | PhO | $CH_3$ | $CH_3$ | $CH_3$ | OH | S |
| B768 | PhS | $CH_3$ | $CH_3$ | $CH_3$ | OH | S |
| B769 | PhSO | $CH_3$ | $CH_3$ | $CH_3$ | OH | S |
| B770 | $PhSO_2$ | $CH_3$ | $CH_3$ | $CH_3$ | OH | S |
| B771 | CN | $CH_3$ | $CH_3$ | $CH_3$ | OH | S |
| B772 | $CH_3CH_2$ | $CH_3CH_2$ | H | H | OH | S |
| B773 | $CH_3CH_2CH_2$ | $CH_3CH_2$ | H | H | OH | S |
| B774 | $(CH_3)_2CH$ | $CH_3CH_2$ | H | H | OH | S |
| B775 | $(CH_3)_3C$ | $CH_3CH_2$ | H | H | OH | S |
| B776 | $CH_3S$ | $CH_3CH_2$ | H | H | OH | S |
| B777 | $CH_3SO$ | $CH_3CH_2$ | H | H | OH | S |
| B778 | $CH_3SO_2$ | $CH_3CH_2$ | H | H | OH | S |
| B779 | Ph | $CH_3CH_2$ | H | H | OH | S |
| B780 | $CH_3O$ | $CH_3CH_2$ | H | H | OH | S |
| B781 | $CH_3OC(O)$ | $CH_3CH_2$ | H | H | OH | S |
| B782 | $CH_3CH_2OC(O)$ | $CH_3CH_2$ | H | H | OH | S |
| B783 | $CH_2=CHCH_2$ | $CH_3CH_2$ | H | H | OH | S |
| B784 | $HCCCH_2$ | $CH_3CH_2$ | H | H | OH | S |
| B785 | $CF_3$ | $CH_3CH_2$ | H | H | OH | S |
| B786 | $(CH_3)_2NSO_2$ | $CH_3CH_2$ | H | H | OH | S |
| B787 | $(CH_3)_2N$ | $CH_3CH_2$ | H | H | OH | S |

TABLE 2-continued

Radicals B:

| Radical | R$_6$ | R$_7$ | R$_8$ | R$_9$ | R$_{10}$ | W |
|---|---|---|---|---|---|---|
| B788 | PhO | CH$_3$CH$_2$ | H | H | OH | S |
| B789 | PhS | CH$_3$CH$_2$ | H | H | OH | S |
| B790 | PhSO | CH$_3$CH$_2$ | H | H | OH | S |
| B791 | PhSO$_2$ | CH$_3$CH$_2$ | H | H | OH | S |
| B792 | CN | CH$_3$CH$_2$ | H | H | OH | S |
| B793 | H | H | H | H | OH | SO$_2$ |
| B794 | CH$_3$ | H | H | H | OH | SO$_2$ |
| B795 | CH$_3$CH$_2$ | H | H | H | OH | SO$_2$ |
| B796 | CH$_3$CH$_2$CH$_2$ | H | H | H | OH | SO$_2$ |
| B797 | (CH$_3$)$_2$CH | H | H | H | OH | SO$_2$ |
| B798 | (CH$_3$)$_3$C | H | H | H | OH | SO$_2$ |
| B799 | CH$_3$S | H | H | H | OH | SO$_2$ |
| B800 | CH$_3$SO | H | H | H | OH | SO$_2$ |
| B801 | CH$_3$SO$_2$ | H | H | H | OH | SO$_2$ |
| B802 | Ph | H | H | H | OH | SO$_2$ |
| B803 | CH$_3$O | H | H | H | OH | SO$_2$ |
| B804 | CH$_3$OC(O) | H | H | H | OH | SO$_2$ |
| B805 | CH$_3$CH$_2$OC(O) | H | H | H | OH | SO$_2$ |
| B806 | CH$_2$=CHCH$_2$ | H | H | H | OH | SO$_2$ |
| B807 | HCCCH$_2$ | H | H | H | OH | SO$_2$ |
| B808 | CF$_3$ | H | H | H | OH | SO$_2$ |
| B809 | (CH$_3$)$_2$NSO$_2$ | H | H | H | OH | SO$_2$ |
| B810 | (CH$_3$)$_2$N | H | H | H | OH | SO$_2$ |
| B811 | PhO | H | H | H | OH | SO$_2$ |
| B812 | PhS | H | H | H | OH | SO$_2$ |
| B813 | PhSO | H | H | H | OH | SO$_2$ |
| B814 | PhSO$_2$ | H | H | H | OH | SO$_2$ |
| B815 | CN | H | H | H | OH | SO$_2$ |
| B816 | CH$_3$ | CH$_3$ | H | H | OH | SO$_2$ |
| B817 | CH$_3$CH$_2$ | CH$_3$ | H | H | OH | SO$_2$ |
| B818 | CH$_3$CH$_2$CH$_2$ | CH$_3$ | H | H | OH | SO$_2$ |
| B819 | (CH$_3$)$_2$CH | CH$_3$ | H | H | OH | SO$_2$ |
| B820 | (CH$_3$)$_3$C | CH$_3$ | H | H | OH | SO$_2$ |
| B821 | CH$_3$S | CH$_3$ | H | H | OH | SO$_2$ |
| B822 | CH$_3$SO | CH$_3$ | H | H | OH | SO$_2$ |
| B823 | CH$_3$SO$_2$ | CH$_3$ | H | H | OH | SO$_2$ |
| B824 | Ph | CH$_3$ | H | H | OH | SO$_2$ |
| B825 | CH$_3$O | CH$_3$ | H | H | OH | SO$_2$ |
| B826 | CH$_3$OC(O) | CH$_3$ | H | H | OH | SO$_2$ |
| B827 | CH$_3$CH$_2$OC(O) | CH$_3$ | H | H | OH | SO$_2$ |
| B828 | CH$_2$=CHCH$_2$ | CH$_3$ | H | H | OH | SO$_2$ |
| B829 | HCCCH$_2$ | CH$_3$ | H | H | OH | SO$_2$ |
| B830 | CF$_3$ | CH$_3$ | H | H | OH | SO$_2$ |
| B831 | (CH$_3$)$_2$NSO$_2$ | CH$_3$ | H | H | OH | SO$_2$ |
| B832 | (CH$_3$)$_2$N | CH$_3$ | H | H | OH | SO$_2$ |
| B833 | PhO | CH$_3$ | H | H | OH | SO$_2$ |
| B834 | PhS | CH$_3$ | H | H | OH | SO$_2$ |
| B835 | PhSO | CH$_3$ | H | H | OH | SO$_2$ |
| B836 | PhSO$_2$ | CH$_3$ | H | H | OH | SO$_2$ |
| B837 | CN | CH$_3$ | H | H | OH | SO$_2$ |
| B838 | CH$_3$ | H | CH$_3$ | H | OH | SO$_2$ |
| B839 | CH$_3$CH$_2$ | H | CH$_3$ | H | OH | SO$_2$ |
| B840 | CH$_3$CH$_2$CH$_2$ | H | CH$_3$ | H | OH | SO$_2$ |
| B841 | (CH$_3$)$_2$CH | H | CH$_3$ | H | OH | SO$_2$ |
| B842 | (CH$_3$)$_3$C | H | CH$_3$ | H | OH | SO$_2$ |
| B843 | CH$_3$S | H | CH$_3$ | H | OH | SO$_2$ |
| B844 | CH$_3$SO | H | CH$_3$ | H | OH | SO$_2$ |
| B845 | CH$_3$SO$_2$ | H | CH$_3$ | H | OH | SO$_2$ |
| B846 | Ph | H | CH$_3$ | H | OH | SO$_2$ |
| B847 | CH$_3$O | H | CH$_3$ | H | OH | SO$_2$ |
| B848 | CH$_3$OC(O) | H | OH$_3$ | H | OH | SO$_2$ |
| B849 | CH$_3$CH$_2$OC(O) | H | CH$_3$ | H | OH | SO$_2$ |
| B850 | CH$_2$=CHCH$_2$ | H | CH$_3$ | H | OH | SO$_2$ |
| B851 | HCCCH$_2$ | H | CH$_3$ | H | OH | SO$_2$ |
| B852 | CF$_3$ | H | CH$_3$ | H | OH | SO$_2$ |
| B853 | (CH$_3$)$_2$NSO$_2$ | H | CH$_3$ | H | OH | SO$_2$ |
| B854 | (CH$_3$)$_2$N | H | CH$_3$ | H | OH | SO$_2$ |
| B855 | PhO | H | CH$_3$ | H | OH | SO$_2$ |
| B856 | PhS | H | CH$_3$ | H | OH | SO$_2$ |
| B857 | PbSO | H | CH$_3$ | H | OH | SO$_2$ |
| B858 | PhSO$_2$ | H | CH$_3$ | H | OH | SO$_2$ |
| B859 | CN | H | CH$_3$ | H | OH | SO$_2$ |
| B860 | CH$_3$ | CH$_3$ | CH$_3$ | H | OH | SO$_2$ |
| B861 | CH$_3$CH$_2$ | CH$_3$ | CH$_3$ | H | OH | SO$_2$ |
| B862 | CH$_3$CH$_2$CH$_2$ | CH$_3$ | CH$_3$ | H | OH | SO$_2$ |

TABLE 2-continued

Radicals B:

| Radical | R$_6$ | R$_7$ | R$_8$ | R$_9$ | R$_{10}$ | W |
|---|---|---|---|---|---|---|
| B863 | (CH$_3$)$_2$CH | CH$_3$ | CH$_3$ | H | OH | SO$_2$ |
| B864 | (CH$_3$)$_3$C | CH$_3$ | CH$_3$ | H | OH | SO$_2$ |
| B865 | CH$_3$S | CH$_3$ | CH$_3$ | H | OH | SO$_2$ |
| B866 | CH$_3$SO | CH$_3$ | CH$_3$ | H | OH | BO$_2$ |
| B867 | CH$_3$SO$_2$ | CH$_3$ | CH$_3$ | H | OH | SO$_2$ |
| B868 | Ph | CH$_3$ | CH$_3$ | H | OH | SO$_2$ |
| B869 | CH$_3$O | CH$_3$ | CH$_3$ | H | OH | SO$_2$ |
| B870 | CH$_3$OC(O) | CH$_3$ | CH$_3$ | H | OH | SO$_2$ |
| B871 | CH$_3$CH$_2$OC(O) | CH$_3$ | CH$_3$ | H | OH | SO$_2$ |
| B872 | CH$_2$=CHCH$_2$ | CH$_3$ | CH$_3$ | H | OH | SO$_2$ |
| B873 | HCCCH$_2$ | CH$_3$ | CH$_3$ | H | OH | SO$_2$ |
| B874 | CF$_3$ | CH$_3$ | CH$_3$ | H | OH | SO$_2$ |
| B875 | (CH$_3$)$_2$NSO$_2$ | CH$_3$ | CH$_3$ | H | OH | SO$_2$ |
| B876 | (CH$_3$)$_2$N | CH$_3$ | CH$_3$ | H | OH | SO$_2$ |
| B877 | PhO | CH$_3$ | CH$_3$ | H | OH | SO$_2$ |
| B878 | PhS | CH$_3$ | CH$_3$ | H | OH | SO$_2$ |
| B879 | PhSO | CH$_3$ | CH$_3$ | H | OH | SO$_2$ |
| B880 | PhSO$_2$ | CH$_3$ | CH$_3$ | H | OH | SO$_2$ |
| B881 | CN | CH$_3$ | CH$_3$ | H | OH | SO$_2$ |
| B882 | CH$_3$ | CH$_3$ | CH$_3$ | CH$_3$ | OH | SO$_2$ |
| B883 | CH$_3$CH$_2$ | CH$_3$ | CH$_3$ | CH$_3$ | OH | SO$_2$ |
| B884 | CH$_3$CH$_2$CH$_2$ | CH$_3$ | CH$_3$ | CH$_3$ | OH | SO$_2$ |
| B885 | (CH$_3$)$_2$CH | CH$_3$ | CH$_3$ | CH$_3$ | OH | SO$_2$ |
| B886 | (CH$_3$)$_3$C | CH$_3$ | CH$_3$ | CH$_3$ | OH | SO$_2$ |
| B887 | CH$_3$S | CH$_3$ | CH$_3$ | CH$_3$ | OH | SO$_2$ |
| B888 | CH$_3$SO | CH$_3$ | CH$_3$ | CH$_3$ | OH | SO$_2$ |
| B889 | CH$_3$SO$_2$ | CH$_3$ | CH$_3$ | CH$_3$ | OH | SO$_2$ |
| B890 | Ph | CH$_3$ | CH$_3$ | CH$_3$ | OH | SO$_2$ |
| B891 | CH$_3$O | CH$_3$ | CH$_3$ | CH$_3$ | OH | SO$_2$ |
| B892 | CH$_3$OC(O) | CH$_3$ | CH$_3$ | CH$_3$ | OH | SO$_2$ |
| B893 | CH$_3$CH$_2$OC(O) | CH$_3$ | CH$_3$ | CH$_3$ | OH | SO$_2$ |
| B894 | CH$_2$=CHCH$_2$ | CH$_3$ | CH$_3$ | CH$_3$ | OH | SO$_2$ |
| B895 | HCCCH$_2$ | CH$_3$ | CH$_3$ | CH$_3$ | OH | SO$_2$ |
| B896 | CF$_3$ | CH$_3$ | CH$_3$ | CH$_3$ | OH | SO$_2$ |
| B897 | (CH$_3$)$_2$NSO$_2$ | CH$_3$ | CH$_3$ | CH$_3$ | OH | SO$_2$ |
| B898 | (CH$_3$)$_2$N | CH$_3$ | CH$_3$ | CH$_3$ | OH | SO$_2$ |
| B899 | PhO | CH$_3$ | CH$_3$ | CH$_3$ | OH | SO$_2$ |
| B900 | PhS | CH$_3$ | CH$_3$ | CH$_3$ | OH | SO$_2$ |
| B901 | PhSO | CH$_3$ | CH$_3$ | CH$_3$ | OH | SO$_2$ |
| B902 | PhSO$_2$ | CH$_3$ | CH$_3$ | CH$_3$ | OH | SO$_2$ |
| B903 | CN | CH$_3$ | CH$_3$ | CH$_3$ | OH | SO$_2$ |
| B904 | CH$_3$CH$_2$ | CH$_3$CH$_2$ | H | H | OH | SO$_2$ |
| B905 | CH$_3$CH$_2$CH$_2$ | CH$_3$CH$_2$ | H | H | OH | SO$_2$ |
| B906 | (CH$_3$)$_2$CH | CH$_3$CH$_2$ | H | H | OH | SO$_2$ |
| B907 | (CH$_3$)$_3$C | CH$_3$CH$_2$ | H | H | OH | SO$_2$ |
| B908 | CH$_3$S | CH$_3$CH$_2$ | H | H | OH | SO$_2$ |
| B909 | CH$_3$SO | CH$_3$CH$_2$ | H | H | OH | SO$_2$ |
| B910 | CH$_3$SO$_2$ | CH$_3$CH$_2$ | H | H | OH | SO$_2$ |
| B911 | Ph | CH$_3$CH$_2$ | H | H | OH | SO$_2$ |
| B912 | CH$_3$O | CH$_3$CH$_2$ | H | H | OH | SO$_2$ |
| B913 | CH$_3$OC(O) | CH$_3$CH$_2$ | H | H | OH | SO$_2$ |
| B914 | CH$_3$CH$_2$OC(O) | CH$_3$CH$_2$ | H | H | OH | SO$_2$ |
| B915 | CH$_2$=CHCH$_2$ | CH$_3$CH$_2$ | H | H | OH | SO$_2$ |
| B916 | HCCCH$_2$ | CH$_3$CH$_2$ | H | H | OH | SO$_2$ |
| B917 | CF$_3$ | CH$_3$CH$_2$ | H | H | OH | SO$_2$ |
| B918 | (CH$_3$)$_2$NSO$_2$ | CH$_3$CH$_2$ | H | H | OH | SO$_2$ |
| B919 | (CH$_3$)$_2$N | CH$_3$CH$_2$ | H | H | OH | SO$_2$ |
| B920 | PhO | CH$_3$CH$_2$ | H | H | OH | SO$_2$ |
| B921 | PhS | CH$_3$CH$_2$ | H | H | OH | SO$_2$ |
| B922 | PhSO | CH$_3$CH$_2$ | H | H | OH | SO$_2$ |
| B923 | PhSO$_2$ | CH$_3$CH$_2$ | H | H | OH | SO$_2$ |
| B924 | CN | CH$_3$CH$_2$ | H | H | OH | SO$_2$ |
| B925 | H | H | H | H | OH | CHC(O)OCH$_2$CH$_3$ |
| B926 | CH$_3$ | H | H | H | OH | CHC(O)OCH$_2$CH$_3$ |
| B927 | CH$_3$CH$_2$ | H | H | H | OH | CHC(O)OCH$_2$CH$_3$ |
| B928 | CH$_3$CH$_2$CH$_2$ | H | H | H | OH | CHC(O)OCH$_2$CH$_3$ |
| B929 | (CH$_3$)$_2$CH | H | H | H | OH | CHC(O)OCH$_2$CH$_3$ |
| B930 | (CH$_3$)$_3$C | H | H | H | OH | CHC(O)OCH$_2$CH$_3$ |
| B931 | CH$_3$S | H | H | H | OH | CHC(O)OCH$_2$CH$_3$ |
| B932 | CH$_3$SO | H | H | H | OH | CHC(O)OCH$_2$CH$_3$ |
| B933 | CH$_3$SO$_2$ | H | H | H | OH | CHC(O)OCH$_2$CH$_3$ |
| B934 | Ph | H | H | H | OH | CHC(O)OCH$_2$CH$_3$ |
| B935 | CH$_3$O | H | H | H | OH | CHC(O)OCH$_2$CH$_3$ |
| B936 | CH$_3$OC(O) | H | H | H | OH | CHC(O)OCH$_2$CH$_3$ |
| B937 | CH$_3$CH$_2$OC(O) | H | H | H | OH | CHC(O)OCH$_2$CH$_3$ |

TABLE 2-continued

Radicals B:

| Radical | R$_6$ | R$_7$ | R$_8$ | R$_9$ | R$_{10}$ | W |
| --- | --- | --- | --- | --- | --- | --- |
| B938 | CH$_2$=CHCH$_2$ | H | H | H | OH | CHC(O)OCH$_2$CH$_3$ |
| B939 | HCCCH$_2$ | H | H | H | OH | CHC(O)OCH$_2$CH$_3$ |
| B940 | CF$_3$ | H | H | H | OH | CHC(O)OCH$_2$CH$_3$ |
| B941 | (CH$_3$)$_2$NSO$_2$ | H | H | H | OH | CHC(O)OCH$_2$CH$_3$ |
| B942 | (CH$_3$)$_2$N | H | H | H | OH | CHC(O)OCH$_2$CH$_3$ |
| B943 | PhO | H | H | H | OH | CHC(O)OCH$_2$CH$_3$ |
| B944 | PhS | H | H | H | OH | CHC(O)OCH$_2$CH$_3$ |
| B945 | PhSO | H | H | H | OH | CHC(O)OCH$_2$CH$_3$ |
| B946 | PhSO$_2$ | H | H | H | OH | CHC(O)OCH$_2$CH$_3$ |
| B947 | CN | H | H | H | OH | CHC(O)OCH$_2$CH$_3$ |
| B948 | CH$_3$ | CH$_3$ | H | H | OH | CHC(O)OCH$_2$CH$_3$ |
| B949 | CH$_3$CH$_2$ | CH$_3$ | H | H | OH | CHC(O)OCH$_2$CH$_3$ |
| B950 | CH$_3$CH$_2$CH$_2$ | CH$_3$ | H | H | OH | CHC(O)OCH$_2$CH$_3$ |
| B951 | (CH$_3$)$_2$CH | CH$_3$ | H | H | OH | CHC(O)OCH$_2$CH$_3$ |
| B952 | (CH$_3$)$_3$C | CH$_3$ | H | H | OH | CHC(O)OCH$_2$CH$_3$ |
| B953 | CH$_3$S | CH$_3$ | H | H | OH | CHC(O)OCH$_2$CH$_3$ |
| B954 | CH$_3$SO | CH$_3$ | H | H | OH | CHC(O)OCH$_2$CH$_3$ |
| B955 | CH$_3$SO$_2$ | CH$_3$ | H | H | OH | CHC(O)OCH$_2$CH$_3$ |
| B956 | Ph | CH$_3$ | H | H | OH | CHC(O)OCH$_2$CH$_3$ |
| B957 | CH$_3$O | CH$_3$ | H | H | OH | CHC(O)OCH$_2$CH$_3$ |
| B958 | CH$_3$OC(O) | CH$_3$ | H | H | OH | CHC(O)OCH$_2$CH$_3$ |
| B959 | CH$_3$CH$_2$OC(O) | CH$_3$ | H | H | OH | CHC(O)OCH$_2$CH$_3$ |
| B960 | CH$_2$=CHCH$_2$ | CH$_3$ | H | H | OH | CHC(O)OCH$_2$CH$_3$ |
| B961 | HCCCH$_2$ | CH$_3$ | H | H | OH | CHC(O)OCH$_2$CH$_3$ |
| B962 | CF$_3$ | CH$_3$ | H | H | OH | CHC(O)OCH$_2$CH$_3$ |
| B963 | (CH$_3$)$_2$NSO$_2$ | CH$_3$ | H | H | OH | CHC(O)OCH$_2$CH$_3$ |
| B964 | (CH$_3$)$_2$N | CH$_3$ | H | H | OH | CHC(O)OCH$_2$CH$_3$ |
| B965 | PhO | CH$_3$ | H | H | OH | CHC(O)OCH$_2$CH$_3$ |
| B966 | PhS | CH$_3$ | H | H | OH | CHC(O)OCH$_2$CH$_3$ |
| B967 | PhSO | CH$_3$ | H | H | OH | CHC(O)OCH$_2$CH$_3$ |
| B968 | PhSO$_2$ | CH$_3$ | H | H | OH | CHC(O)OCH$_2$CH$_3$ |
| B969 | CN | CH$_3$ | H | H | OH | CHC(O)OCH$_2$CH$_3$ |
| B970 | CH$_3$ | H | CH$_3$ | H | OH | CHC(O)OCH$_2$CH$_3$ |
| B971 | CH$_3$CH$_2$ | H | CH$_3$ | H | OH | CHC(O)OCH$_2$CH$_3$ |
| B972 | CH$_3$CH$_2$CH$_2$ | H | CH$_3$ | H | OH | CHC(O)OCH$_2$CH$_3$ |
| B973 | (CH$_3$)$_2$CH | H | CH$_3$ | H | OH | CHC(O)OCH$_2$CH$_3$ |
| B974 | (CH$_3$)$_3$C | H | CH$_3$ | H | OH | CHC(O)OCH$_2$CH$_3$ |
| B975 | CH$_3$S | H | CH$_3$ | H | OH | CHC(O)OCH$_2$CH$_3$ |
| B976 | CH$_3$SO | H | CH$_3$ | H | OH | CHC(O)OCH$_2$CH$_3$ |
| B977 | CH$_3$SO$_2$ | H | CH$_3$ | H | OH | CHC(O)OCH$_2$CH$_3$ |
| B978 | Ph | H | CH$_3$ | H | OH | CHC(O)OCH$_2$CH$_3$ |
| B979 | CH$_3$O | H | CH$_3$ | H | OH | CHC(O)OCH$_2$CH$_3$ |
| B980 | CH$_3$OC(O) | H | CH$_3$ | H | OH | CHC(O)OCH$_2$CH$_3$ |
| B981 | CH$_3$CH$_2$OC(O) | H | CH$_3$ | H | OH | CHC(O)OCH$_2$CH$_3$ |
| B982 | CH$_2$=CHCH$_2$ | H | CH$_3$ | H | OH | CHC(O)OCH$_2$CH$_3$ |
| B983 | HCCCH$_2$ | H | CH$_3$ | H | OH | CHC(O)OCH$_2$CH$_3$ |
| B984 | CF$_3$ | H | CH$_3$ | H | OH | CHC(O)OCH$_2$CH$_3$ |
| B985 | (CH$_3$)$_2$NSO$_2$ | H | CH$_3$ | H | OH | CHC(O)OCH$_2$CH$_3$ |
| B986 | (CH$_3$)$_2$N | H | CH$_3$ | H | OH | CHC(O)OCH$_2$CH$_3$ |
| B987 | PhO | H | CH$_3$ | H | OH | CHC(O)OCH$_2$OH$_3$ |
| B988 | PhS | H | CH$_3$ | H | OH | CHC(O)OCH$_2$CH$_3$ |
| B989 | PhSO | H | CH$_3$ | H | OH | CHC(O)OCH$_2$CH$_3$ |
| B990 | PhSO$_2$ | H | CH$_3$ | H | OH | CHC(O)OCH$_2$CH$_3$ |
| B991 | CN | H | CH$_3$ | H | OH | CHC(O)OCH$_2$CH$_3$ |
| B992 | CH$_3$ | CH$_3$ | CH$_3$ | H | OH | CHC(O)OCH$_2$CH$_3$ |
| B993 | CH$_3$CH$_2$ | CH$_3$ | CH$_3$ | H | OH | CHC(O)OCH$_2$CH$_3$ |
| B994 | CH$_3$CH$_2$CH$_2$ | CH$_3$ | CH$_3$ | H | OH | CHC(O)CCH$_2$CH$_3$ |
| B995 | (CH$_3$)$_2$CH | CH$_3$ | CH$_3$ | H | OH | CHC(O)OCH$_2$CH$_3$ |
| B996 | (CH$_3$)$_3$C | CH$_3$ | CH$_3$ | H | OH | CHC(O)OCH$_2$CH$_3$ |
| B997 | CH$_3$S | CH$_3$ | CH$_3$ | H | OH | CHC(O)OCH$_2$CH$_3$ |
| B998 | CH$_3$SO | CH$_3$ | CH$_3$ | H | OH | CHC(O)OCH$_2$CH$_3$ |
| B999 | CH$_3$SO$_2$ | CH$_3$ | CH$_3$ | H | OH | CHC(O)OCH$_2$CH$_3$ |
| B1000 | Ph | CH$_3$ | CH$_3$ | H | OH | CHC(O)OCH$_2$CH$_3$ |
| B1001 | CH$_3$O | CH$_3$ | CH$_3$ | H | OH | CHC(O)OCH$_2$CH$_3$ |
| B1002 | CH$_3$OC(O) | CH$_3$ | CH$_3$ | H | OH | CHC(O)OCH$_2$CH$_3$ |
| B1003 | CH$_3$CH$_2$OC(O) | CH$_3$ | CH$_3$ | H | OH | CHC(O)OCH$_2$CH$_3$ |
| B1004 | CH$_2$=CHCH$_2$ | CH$_3$ | CH$_3$ | H | OH | CHC(O)OCH$_2$CH$_3$ |
| B1005 | HCCCH$_2$ | CH$_3$ | CH$_3$ | H | OH | CHC(O)OCH$_2$CH$_3$ |
| B1006 | CF$_3$ | CH$_3$ | CH$_3$ | H | OH | CHC(O)OCH$_2$CH$_3$ |
| B1007 | (CH$_3$)$_2$NSO$_2$ | CH$_3$ | CH$_3$ | H | OH | CHC(O)OCH$_2$CH$_3$ |
| B1008 | (CH$_3$)$_2$N | CH$_3$ | CH$_3$ | H | OH | CHC(O)OCH$_2$CH$_3$ |
| B1009 | PhO | CH$_3$ | CH$_3$ | H | OH | CHC(O)OCH$_2$CH$_3$ |
| B1010 | PhS | CH$_3$ | CH$_3$ | H | OH | CHC(O)OCH$_2$CH$_3$ |
| B1011 | PhSO | CH$_3$ | CH$_3$ | H | OH | CHC(O)OCH$_2$CH$_3$ |
| B1012 | PhSO$_2$ | CH$_3$ | CH$_3$ | H | OH | CHC(O)OCH$_2$CH$_3$ |

TABLE 2-continued

Radicals B:

| Radical | R$_6$ | R$_7$ | R$_8$ | R$_9$ | R$_{10}$ | W |
|---|---|---|---|---|---|---|
| B1013 | CN | CH$_3$ | CH$_3$ | H | OH | CHC(O)OCH$_2$CH$_3$ |
| B1014 | CH$_3$ | CH$_3$ | CH$_3$ | CH$_3$ | OH | CHC(O)OCH$_2$CH$_3$ |
| B1015 | CH$_3$CH$_2$ | CH$_3$ | CH$_3$ | CH$_3$ | OH | CHC(O)OCH$_2$CH$_3$ |
| B1016 | CH$_3$CH$_2$CH$_2$ | CH$_3$ | CH$_3$ | CH$_3$ | OH | CHC(O)OCH$_2$CH$_3$ |
| B1017 | (CH$_3$)$_2$CH | CH$_3$ | CH$_3$ | CH$_3$ | OH | CHC(O)OCH$_2$CH$_3$ |
| B1018 | (CH$_3$)$_3$C | CH$_3$ | CH$_3$ | CH$_3$ | OH | CHC(O)OCH$_2$CH$_3$ |
| B1019 | CH$_3$S | CH$_3$ | CH$_3$ | CH$_3$ | OH | CHC(O)OCH$_2$CH$_3$ |
| B1020 | CH$_3$SO | CH$_3$ | CH$_3$ | CH$_3$ | OH | CHC(O)OCH$_2$CH$_3$ |
| B1021 | CH$_3$SO$_2$ | CH$_3$ | CH$_3$ | CH$_3$ | OH | CHC(O)OCH$_2$CH$_3$ |
| B1022 | Ph | CH$_3$ | CH$_3$ | CH$_3$ | OH | CHC(O)OCH$_2$CH$_3$ |
| B1023 | CH$_3$O | CH$_3$ | CH$_3$ | CH$_3$ | OH | CHC(O)OCH$_2$CH$_3$ |
| B1024 | CH$_3$OC(O) | CH$_3$ | CH$_3$ | CH$_3$ | OH | CHC(O)OCH$_2$CH$_3$ |
| B1025 | CH$_3$CH$_2$OC(O) | CH$_3$ | CH$_3$ | CH$_3$ | OH | CHC(O)OCH$_2$CH$_3$ |
| B1026 | CH$_2$=CHCH$_2$ | CH$_3$ | CH$_3$ | CH$_3$ | OH | CHC(O)OCH$_2$CH$_3$ |
| B1027 | HCCCH$_2$ | CH$_3$ | CH$_3$ | CH$_3$ | OH | CHC(O)OCH$_2$CH$_3$ |
| B1028 | CF$_3$ | CH$_3$ | CH$_3$ | CH$_3$ | OH | CHC(O)OCH$_2$CH$_3$ |
| B1029 | (CH$_3$)$_2$NSO$_2$ | CH$_3$ | CH$_3$ | CH$_3$ | OH | CHC(O)OCH$_2$CH$_3$ |
| B1030 | (CH$_3$)$_2$N | CH$_3$ | CH$_3$ | CH$_3$ | OH | CHC(O)OCH$_2$CH$_3$ |
| B1031 | PhO | CH$_3$ | CH$_3$ | CH$_3$ | OH | CHC(O)OCH$_2$CH$_3$ |
| B1032 | PhS | CH$_3$ | CH$_3$ | CH$_3$ | OH | CHC(O)OCH$_2$CH$_3$ |
| B1033 | PhSO | CH$_3$ | CH$_3$ | CH$_3$ | OH | CHC(O)OCH$_2$CH$_3$ |
| B1034 | PhSO$_2$ | CH$_3$ | CH$_3$ | CH$_3$ | OH | CHC(O)OCH$_2$CH$_3$ |
| B1035 | CN | CH$_3$ | CH$_3$ | CH$_3$ | OH | CHC(O)OCH$_2$CH$_3$ |
| B1036 | CH$_3$CH$_2$ | CH$_3$CH$_2$ | H | H | OH | CHC(O)OCH$_2$CH$_3$ |
| B1037 | CH$_3$CH$_2$CH$_2$ | CH$_3$CH$_2$ | H | H | OH | CHC(O)OCH$_2$CH$_3$ |
| B1038 | (CH$_3$)$_2$CH | CH$_3$CH$_2$ | H | H | OH | CHC(O)OCH$_2$CH$_3$ |
| B1039 | (CH$_3$)$_3$C | CH$_3$CH$_2$ | H | H | OH | CHC(O)OCH$_2$CH$_3$ |
| B1040 | CH$_3$S | CH$_3$CH$_2$ | H | H | OH | CHC(O)OCH$_2$CH$_3$ |
| B1041 | CH$_3$SO | CH$_3$CH$_2$ | H | H | OH | CHC(O)OCH$_2$CH$_3$ |
| B1042 | CH$_3$SO$_2$ | CH$_3$CH$_2$ | H | H | OH | CHC(O)OCH$_2$CH$_3$ |
| B1043 | Ph | CH$_3$CH$_2$ | H | H | OH | CHC(O)OCH$_2$CH$_3$ |
| B1044 | CH$_3$O | CH$_3$CH$_2$ | H | H | OH | CHC(O)OCH$_2$CH$_3$ |
| B1045 | CH$_3$OC(O) | CH$_3$CH$_2$ | H | H | OH | CHC(O)OCH$_2$CH$_3$ |
| B1046 | CH$_3$CH$_2$OC(O) | CH$_3$CH$_2$ | H | H | OH | CHC(O)OCH$_2$CH$_3$ |
| B1047 | CH$_2$=CHCH$_2$ | CH$_3$CH$_2$ | H | H | OH | CHC(O)OCH$_2$CH$_3$ |
| B1048 | HCCCH$_2$ | CH$_3$CH$_2$ | H | H | OH | CHC(O)OCH$_2$CH$_3$ |
| B1049 | CF$_3$ | CH$_3$CH$_2$ | H | H | OH | CHC(O)OCH$_2$CH$_3$ |
| B1050 | (CH$_3$)$_2$NSO$_2$ | CH$_3$CH$_2$ | H | H | OH | CHC(O)OCH$_2$CH$_3$ |
| B1051 | (CH$_3$)$_2$N | CH$_3$CH$_2$ | H | H | OH | CHC(O)OCH$_2$CH$_3$ |
| B1052 | PhO | CH$_3$CH$_2$ | H | H | OH | CHC(O)OCH$_2$CH$_3$ |
| B1053 | PhS | CH$_3$CH$_2$ | H | H | OH | CHC(O)OCH$_2$CH$_3$ |
| B1054 | PhSO | CH$_3$CH$_2$ | H | H | OH | CHC(O)OCH$_2$CH$_3$ |
| B1055 | PhSO$_2$ | CH$_3$CH$_2$ | H | H | OH | CHC(O)OCH$_2$CH$_3$ |
| B1056 | CN | CH$_3$CH$_2$ | H | H | OH | CHC(O)OCH$_2$CH$_3$ |
| B1057 | CH$_3$OC(O) | H | H | H | OH | CHPh |
| B1058 | H | H | H | H | OH | CHPh |
| B1059 | H | H | H | H | OH | CH(CH$_2$CH$_3$) |
| B1060 | H | H | H | H | OH | CH(CH$_2$CH$_2$CH$_3$) |
| B1061 | H | H | H | H | OH | CH(CH(CH$_3$)$_2$) |
| B1062 | H | H | H | H | OH | CH(C(CH$_3$)$_3$) |
| B1063 | H | H | H | H | OH | C(CH$_3$)$_2$ |
| B1064 | H | H | H | H | OH | CH(CF$_3$) |
| B1065 | CH$_3$OC(O) | H | H | H | OH | C(CH$_3$)(CF$_3$) |
| B1066 | H | H | H | H | OH | C(CH$_3$)(CF$_3$) |
| B1067 | CH$_3$OC(O) | CH$_3$O | H | H | OH | CH$_2$ |
| B1068 | H | CH$_3$O | H | H | OH | CH$_2$ |
| B1069 | CH$_3$O | CH$_3$OC(O) | H | CH$_3$ | OH | CH$_2$ |
| B1070 | CH$_3$O | H | CH$_3$ | H | OH | CH$_2$ |
| B1071 | Cl | H | H | H | OH | CH$_2$ |
| B1072 | F | H | H | H | OH | CH$_2$ |
| B1073 | H | H | H | H | OH | CH(OCH$_3$)$_2$ |
| B1074 | H | H | H | H | OH | CH$_2$OSO$_2$CH$_3$ |
| B1075 | CH$_3$ | CH$_3$ | CH$_3$ | CH$_3$ | OH | S(O) |
| B1076 | ClCH$_2$CH$_2$ | H | H | H | OH | CH$_2$ |
| B1077 | HO(CH$_2$)$_2$ | H | H | H | OH | CH$_2$ |
| B1078 | MsO(CH$_2$)$_2$ | H | H | H | OH | CH$_2$ |
| B1079 | HOCH(CH$_3$)CH$_2$ | H | H | H | OH | CH$_2$ |
| B1080 | MsOCH(CH$_3$)CH$_2$ | H | H | H | OH | CH$_2$ |
| B1081 | (CH$_3$)$_2$CH | H | CH$_3$ | CH$_3$ | OH | CH$_2$ |
| B1082 | HCCCH$_2$ | H | CH$_3$ | CH$_3$ | OH | CH$_2$ |
| B1083 | H$_2$C=CCH$_2$ | H | CH$_3$ | CH$_3$ | OH | CH$_2$ |
| B1084 | H$_2$C=C(CH$_3$) | H | H | H | OH | CHCH$_3$ |
| B1085 | H | H | H | H | OH | CHCONHCH$_2$Ph |

TABLE 2-continued

Radicals B:

| Radical | R₆ | R₇ | R₈ | R₉ | R₁₀ | W |
|---|---|---|---|---|---|---|
| B1086 | H | H | H | H | OH | 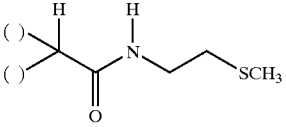 |
| B1087 | CH₃OC(O) | CH₃ | H | H | OH | C(CH₃)₂ |
| B1088 | H | H | H | H | OH | 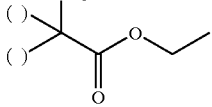 |
| B1089 | CH₃CH₂ | H | CH₃ | CH₃ | OH | CH₂ |
| B1090 | CH₃OC(O) | H | H | H | OH | CF₃CH₂CH₂ |
| B1091 | CH₃CH₂S | CH₃CH₂ | CH₃ | H | OH | CH₂ |
| B1092 | CH₃S | Ph | CH₃ | H | OH | CH₂ |
| B1093 | CH₃CH₂ | CH₃CH₂ | CH₃ | H | OH | CH₂ |
| B1094 | CH₃OC(O) | H | H | H | OH | C(CH₃)₂ |
| B1095 | CH₃ | H | H | H | OH | C(CH₃)₂ |
| B1096 | H | H | H | H | OH | NCOCH₂SCH₃ |
| B1097 | 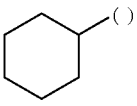 | H | H | H | OH | CH₂ |
| B1098 | 1,1-dimethylvinyl | H | H | H | OH | CH₂ |
| B1099 | 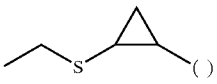 | H | H | H | OH | CH₂ |
| B1100 | H | H | H | H | —ONH+(CH₂CH₃)₃ | CH₂ |
| B1101 | H | H | H | H | —ONH+(CH₂CH₃)₃ | CH(CH₃) |
| B1102 | H | H | H | H | PhS | CH₂ |
| B1103 | H | H | H | H | PhSO | CH₂ |
| B1104 | H | H | H | H | PhSO₂ | CH₂ |
| B1105 | CH₃ | CH₃ | CH₃ | CH₃ | Cl | C=O |
| B1106 | H | H | H | H | OH | CHCH₂CH(CH₃)₂ |
| B1107 | CH₃ | CH₃ | CH₃ | CH₃ | CH₃C(O)O | C=O |
| B1108 | CH₃OC(O)CH₂ | H | H | H | OH | CH₂ |
| B1109 | CH₃OC(O)CH₂ | CH₃ | H | H | OH | CH₂ |
| B1110 | CH₃OC(O)CH₂ | CH₃ | CH₃ | H | OH | CH₂ |
| B1111 | CH₃OC(O)CH₂ | CH₃ | CH₃ | CH₃ | OH | CH₂ |
| B1112 | CH₃OC(O)CH₂ | H | CH₃ | CH₃ | OH | CH₂ |
| B1113 | CH₃CC(O)CH₂ | H | H | H | OH | CH(CH₃) |
| B1114 | CH₃OC(O)CH₂ | CH₃ | H | H | OH | CH(CH₃) |
| B1115 | CH₃OC(O)CH₂ | CH₃ | CH₃ | H | OH | CH(CH₃) |
| B1116 | CH₃OC(O)CH₂ | CH₃ | CH₃ | CH₃ | OH | CH(CH₃) |
| B1117 | CH₃OC(O)CH₂ | H | CH₃ | CH₃ | OH | CH(CH₃) |
| B1118 | CH₃OC(O)CH₂ | H | H | H | OH | C(CH₃)₂ |
| B1119 | CH₃CC(O)CH₂ | CH₃ | H | H | OH | C(CH₃)₂ |
| B1120 | CH₃OC(O)CH₂ | CH₃ | CH₃ | H | OH | C(CH₃)₂ |
| B1121 | CH₃OC(O)CH₂ | CH₃ | CH₃ | CH₃ | OH | C(CH₃)₂ |
| B1122 | CH₃OC(O)CH₂ | H | CH₃ | CH₃ | OH | C(CH₃)₂ |
| B1123 | CH₃CH₂OC(O)CH₂ | H | H | H | OH | CH₂ |
| B1124 | CH₃CH₂OC(O)CH₂ | CH₃ | H | H | OH | CH₂ |
| B1125 | CH₃CH₂OC(O)CH₂ | CH₃ | CH₃ | H | OH | CH₂ |
| B1126 | CH₃CH₂OC(O)CH₂ | CH₃ | CH₃ | CH₃ | OH | CH₂ |
| B1127 | CH₃CH₂OC(O)CH₂ | H | CH₃ | CH₃ | OH | CH₂ |
| B1128 | CH₃CH₂OC(O)CH₂ | H | H | H | OH | CH(CH₃) |
| B1129 | CH₃CH₂OC(O)CH₂ | CH₃ | H | H | OH | CH(CH₃) |
| B1130 | CH₃CH₂OC(O)CH₂ | CH₃ | CH₃ | H | OH | CH(CH₃) |
| B1131 | CH₃CH₂OC(O)CH₂ | CH₃ | CH₃ | CH₃ | OH | CH(CH₃) |
| B1132 | CH₃CH₂OC(O)CH₂ | H | CH₃ | CH₃ | OH | CH(CH₃) |
| B1133 | CH₃CH₂OC(O)CH₂ | H | H | H | OH | C(CH₃)₂ |
| B1134 | CH₃CH₂OC(O)CH₂ | CH₃ | H | H | OH | C(CH₃)₂ |
| B1135 | CH₃CH₂OC(O)CH₂ | CH₃ | CH₃ | H | OH | C(CH₃)₂ |
| B1136 | CH₃CH₂OC(O)CH₂ | CH₃ | CH₃ | CH₃ | OH | C(CH₃)₂ |

TABLE 2-continued

Radicals B:

| Radical | $R_6$ | $R_7$ | $R_8$ | $R_9$ | $R_{10}$ | W |
|---|---|---|---|---|---|---|
| B1137 | $CH_3CH_2OC(O)CH_2$ | H | $CH_3$ | $CH_3$ | OH | $C(CH_3)_2$ |
| B1138 | 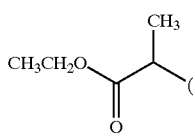 | $CH_3$ | H | H | OH | $CH_2$ |
| B1139 | $CH_3SCH_2$ | H | H | H | OH | $CH_2$ |
| B1140 | $CH_3SCH_2$ | $CH_3$ | H | H | OH | $CH_2$ |
| B1141 | $CH_3SCH_2$ | $CH_3$ | $CH_3$ | H | OH | $CH_2$ |
| B1142 | $CH_3SCH_2$ | $CH_3$ | $CH_3$ | $CH_3$ | OH | $CH_2$ |
| B1143 | $CH_3SCH_2$ | H | $CH_3$ | $CH_3$ | OH | $CH_2$ |
| B1144 | $CH_3SOCH_2$ | H | H | H | OH | $CH_2$ |
| B1145 | $CH_3SOCH_2$ | $CH_3$ | H | H | OH | $CH_2$ |
| B1146 | $CH_3SOCH_2$ | $CH_3$ | $CH_3$ | H | OH | $CH_2$ |
| B1147 | $CH_3SOCH_2$ | $CH_3$ | $CH_3$ | $CH_3$ | OH | $CH_2$ |
| B1148 | $CH_3SOCH_2$ | H | $CH_3$ | $CH_3$ | OH | $CH_2$ |
| B1149 | $CH_3SO_2CH_2$ | H | H | H | OH | $CH_2$ |
| B1150 | $CH_3SO_2CH_2$ | $CH_3$ | H | H | OH | $CH_2$ |
| B1151 | $CH_3SO_2CH_2$ | $CH_3$ | $CH_3$ | H | OH | $CH_2$ |
| B1152 | $CH_3SO_2CH_2$ | $CH_3$ | $CH_3$ | $CH_3$ | OH | $CH_2$ |
| B1153 | $CH_3SO_2CH_2$ | H | $CH_3$ | $CH_3$ | OH | $CH_2$ |
| B1154 | $HOCH_2$ | H | H | H | OH | $CH_2$ |
| B1155 | $HOCH_2$ | $CH_3$ | H | H | OH | $CH_2$ |
| B1156 | $HOCH_2$ | $CH_3$ | $CH_3$ | H | OH | $CH_2$ |
| B1157 | $HOCH_2$ | $CH_3$ | $CH_3$ | $CH_3$ | OH | $CH_2$ |
| B1158 | $HOCH_2$ | H | $CH_3$ | $CH_3$ | OH | $CH_2$ |
| B1159 | $NCCH_2$ | H | H | H | OH | $CH_2$ |
| B1160 | $NCCH_2$ | $CH_3$ | H | H | OH | $CH_2$ |
| B1161 | $NCCH_2$ | $CH_3$ | $CH_3$ | H | OH | $CH_2$ |
| B1162 | $NCCH_2$ | $CH_3$ | $CH_3$ | $CH_3$ | OH | $CH_2$ |
| B1163 | $NCCH_2$ | H | $CH_3$ | $CH_3$ | OH | $CH_2$ |
| B1164 | $CH_3C(O)OCH_2$ | H | H | H | OH | $CH_2$ |
| B1165 | $CH_3C(O)OCH_2$ | $CH_3$ | H | H | OH | $CH_2$ |
| B1166 | $CH_3C(O)OCH_2$ | $CH_3$ | $CH_3$ | H | OH | $CH_2$ |
| B1167 | $CH_3C(O)OCH_2$ | $CH_3$ | $CH_3$ | $CH_3$ | OH | $CH_2$ |
| B1168 | $CH_3C(O)OCH_2$ | H | $CH_3$ | $CH_3$ | OH | $CH_2$ |
| B1169 | $CH_3OCH_2$ | H | H | H | OH | $CH_2$ |
| B1170 | $CH_3OCH_2$ | $CH_3$ | H | H | OH | $CH_2$ |
| B1171 | $CH_3OCH_2$ | $CH_3$ | $CH_3$ | H | OH | $CH_2$ |
| B1172 | $CH_3OCH_2$ | $CH_3$ | $CH_3$ | $CH_3$ | OH | $CH_2$ |
| B1173 | $CH_3OCH_2$ | H | $CH_3$ | $CH_3$ | OH | $CH_2$ |
| B1174 | $PhCH_2$ | H | H | H | OH | $CH_2$ |
| B1175 | $PhCH_2$ | $CH_3$ | H | H | OH | $CH_2$ |
| B1176 | $PhCH_2$ | $CH_3$ | $CH_3$ | H | OH | $CH_2$ |
| B1177 | $PhCH_2$ | $CH_3$ | $CH_3$ | $CH_3$ | OH | $CH_2$ |
| B1178 | $PhCH_2$ | H | $CH_3$ | $CH_3$ | OH | $CH_2$ |
| B1179 | H | H | H | H | O—K+ | $CH_2$ |
| B1180 | H | H | H | H | $S(CH_2)_7CH_3$ | $CH_2$ |
| B1181 | H | H | H | H | $S(CH_2)_7CH_3$ | $CH_2$ |
| B1182 | H | H | H | H | $SO(CH_2)_7CH_3$ | $CH_2$ |
| B1183 | H | H | H | H | $SO_2(CH_2)_7CH_3$ | $CH_2$ |
| B1184 | H | H | H | H | $NHSO_2CH_3$ | $CH_2$ |
| B1185 | H | H | H | H | $NH(CO)S(CH_2)_7CH_3$ | $CH_2$ |
| B1186 | H | H | H | H | Cl | $CH_2$ |
| B1187 | H | H | H | H | $NH_2$ | $CH_2$ |
| B1188 | H | H | H | H | $OC(O)C(CH_3)_3$ | $CH_2$ |
| B1189 | H | H | H | H | $OC(O)CH_3$ | $CH_2$ |
| B1190 | H | H | H | H | $OC(O)Ph$ | $CH_2$ |
| B1191 | H | H | H | H | OC(O)-cyclopropyl | $CH_2$ |
| B1192 | H | H | H | H | $OC(O)CH_2CH_3$ | $CH_2$ |
| B1193 | H | H | H | H | $OC(O)CH=CH_2$ | $CH_2$ |
| B1194 | H | H | H | H | $OC(O)CH=CHCH_3$ | $CH_2$ |
| B1195 | H | H | H | H | $OC(O)SCH_3$ | $CH_2$ |
| B1196 | H | H | H | H | $OC(O)S(CH_2)_7CH_3$ | $CH_2$ |
| B1197 | H | H | H | H | $OC(O)OCH_2CH_3$ | $CH_2$ |
| B1198 | H | H | H | H | $OC(O)N(CH_2CH_3)_2$ | $CH_2$ |
| B1199 | H | H | H | H | S-(4-Cl-phenyl) | $CH_2$ |
| B1200 | H | H | H | H | SO-(4-Cl-phenyl) | $CH_2$ |
| B1201 | H | H | H | H | $SO_2$-(4-Cl-phenyl) | $CH_2$ |
| B1202 | H | H | H | H | S-(4-$CF_3$-phenyl) | $CH_2$ |
| B1203 | H | H | H | H | SO-(4-$CF_3$-phenyl) | $CH_2$ |

TABLE 2-continued

Radicals B:

| Radical | $R_6$ | $R_7$ | $R_8$ | $R_9$ | $R_{10}$ | W |
|---|---|---|---|---|---|---|
| B1204 | H | H | H | H | $SO_2$-(4-$CF_3$-phenyl) | $CH_2$ |
| B1205 | H | H | H | H | S-(4-$NO_2$-phenyl) | $CH_2$ |
| B1206 | H | H | H | H | SO-(4-$NO_2$-phenyl) | $CH_2$ |
| B1207 | H | H | H | H | $SO_2$-(4-$NO_2$-phenyl) | $CH_2$ |
| B1208 | H | H | H | H | S-CH$_2$-(2-furyl) | $CH_2$ |
| B1209 | H | H | H | H | S-(2-(1H-imidazolyl)) | $CH_2$ |
| B1210 | H | H | H | H | S-(4,6-dimethyl-2-pyrimidinyl) | $CH_2$ |
| B1211 | H | H | H | H | S-(5-methylthio-1,3,4-thiadiazol-2-yl) | $CH_2$ |
| B1212 | H | H | H | H | S-(4,6-dimethoxy-2-pyrimidinyl) | $CH_2$ |
| B1179 | $CH_3$ | $CH_3$ | H | H | O—K+ | $CH_2$ |
| B1180 | $CH_3$ | $CH_3$ | H | H | $S(CH_2)_7CH_3$ | $CH_2$ |
| B1181 | $CH_3$ | $CH_3$ | H | H | $S(CH_2)_7CH_3$ | $CH_2$ |
| B1182 | $CH_3$ | $CH_3$ | H | H | $SO(CH_2)_7CH_3$ | $CH_2$ |
| B1183 | $CH_3$ | $CH_3$ | H | H | $SO_2(CH_2)_7CH_3$ | $CH_2$ |
| B1184 | $CH_3$ | $CH_3$ | H | H | $NHSO_2CH_3$ | $CH_2$ |
| B1185 | $CH_3$ | $CH_3$ | H | H | $NH(CO)S(CH_2)_7CH_3$ | $CH_2$ |
| B1186 | $CH_3$ | $CH_3$ | H | H | Cl | $CH_2$ |
| B1187 | $CH_3$ | $CH_3$ | H | H | $NH_2$ | $CH_2$ |
| B1188 | $CH_3$ | $CH_3$ | H | H | $OC(O)C(CH_3)_3$ | $CH_2$ |
| B1189 | $CH_3$ | $CH_3$ | H | H | $OC(O)CH_3$ | $CH_2$ |
| B1190 | $CH_3$ | $CH_3$ | H | H | OC(O)Ph | $CH_2$ |
| B1191 | $CH_3$ | $CH_3$ | H | H | OC(O)-cyclopropyl | $CH_2$ |
| B1192 | $CH_3$ | $CH_3$ | H | H | $OC(O)CH_2CH_3$ | $CH_2$ |
| B1193 | $CH_3$ | $CH_3$ | H | H | $OC(O)CH=CH_2$ | $CH_2$ |
| B1194 | $CH_3$ | $CH_3$ | H | H | $OC(O)CH=CHCH_3$ | $CH_2$ |
| B1195 | $CH_3$ | $CH_3$ | H | H | $OC(O)SCH_3$ | $CH_2$ |
| B1196 | $CH_3$ | $CH_3$ | H | H | $OC(O)S(CH_2)_7CH_3$ | $CH_2$ |
| B1197 | $CH_3$ | $CH_3$ | H | H | $OC(O)OCH_2CH_3$ | $CH_2$ |
| B1198 | $CH_3$ | $CH_3$ | H | H | $OC(O)N(CH_2CH_3)_2$ | $CH_2$ |
| B1199 | $CH_3$ | $CH_3$ | H | H | S-(4-Cl-phenyl) | $CH_2$ |
| B1200 | $CH_3$ | $CH_3$ | H | H | SO-(4-Cl-phenyl) | $CH_2$ |
| B1201 | $CH_3$ | $CH_3$ | H | H | $SO_2$-(4-Cl-phenyl) | $CH_2$ |
| B1202 | $CH_3$ | $CH_3$ | H | H | S-(4-$CF_3$-phenyl) | $CH_2$ |
| B1203 | $CH_3$ | $CH_3$ | H | H | SO-(4-$CF_3$-phenyl) | $CH_2$ |
| B1204 | $CH_3$ | $CH_3$ | H | H | $SO_2$-(4-$CF_3$-phenyl) | $CH_2$ |
| B1205 | $CH_3$ | $CH_3$ | H | H | S-(4-$NO_2$-phenyl) | $CH_2$ |
| B1206 | $CH_3$ | $CH_3$ | H | H | SO-(4-$NO_2$-phenyl) | $CH_2$ |
| B1207 | $CH_3$ | $CH_3$ | H | H | $SO_2$-(4-$NO_2$-phenyl) | $CH_2$ |
| B1208 | $CH_3$ | $CH_3$ | H | H | S-CH$_2$-(2-furyl) | $CH_2$ |

TABLE 2-continued

Radicals B:

| Radical | $R_6$ | $R_7$ | $R_8$ | $R_9$ | $R_{10}$ | W |
|---|---|---|---|---|---|---|
| B1209 | $CH_3$ | $CH_3$ | H | H | 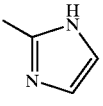 | $CH_2$ |
| B1210 | $CH_3$ | $CH_3$ | H | H | 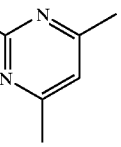 | $CH_2$ |
| B1211 | $CH_3$ | $CH_3$ | H | H | 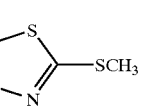 | $CH_2$ |
| B1212 | $CH_3$ | $CH_3$ | H | H | 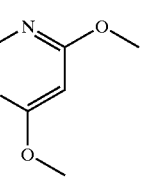 | $CH_2$ |
| B1213 | H | H | H | H | OH | —$CH_2CH_2$— |
| B1214 | $CH_3$ | H | H | H | OH | —$CH_2CH_2$— |
| B1215 | $CH_3$ | $CH_3$ | H | H | OH | —$CH_2CH_2$— |
| B1216 | $CH_3$ | $CH_3$ | $CH_3$ | H | OH | —$CH_2CH_2$— |
| B1217 | $CH_3$ | $CH_3$ | $CH_3$ | $CH_3$ | OH | —$CH_2CH_2$— |

In Table 3 which follows, Q is $Q_2$

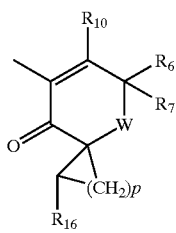

($Q_2$)

and $Q_2$ the radicals C which follow:

TABLE 3

Radicals C:

| Radical | $R_6$ | $R_7$ | $R_{16}$ | $R_{10}$ | p | W |
|---|---|---|---|---|---|---|
| C1 | H | H | H | OH | 1 | $CH_2$ |
| C2 | $CH_3$ | H | H | OH | 1 | $CH_2$ |
| C3 | $CH_3CH_2$ | H | H | OH | 1 | $CH_2$ |
| C4 | $CH_3CH_2CH_2$ | H | H | OH | 1 | $CH_2$ |
| C5 | $(CH_3)_2CH$ | H | H | OH | 1 | $CH_2$ |
| C6 | $(CH_3)_3C$ | H | H | OH | 1 | $CH_2$ |
| C7 | $CH_3S$ | H | H | OH | 1 | $CH_2$ |
| C8 | $CH_3SO$ | H | H | OH | 1 | $CH_2$ |
| C9 | $CH_3SO_2$ | H | H | OH | 1 | $CH_2$ |
| C10 | Ph | H | H | OH | 1 | $CH_2$ |
| C11 | $CH_3O$ | H | H | OH | 1 | $CH_2$ |
| C12 | $CH_3OC(O)$ | H | H | OH | 1 | $CH_2$ |
| C13 | $CH_3CH_2OC(O)$ | H | H | OH | 1 | $CH_2$ |
| C14 | $CH_2$=$CHCH_2$ | H | H | OH | 1 | $CH_2$ |
| C15 | $HCCCH_2$ | H | H | OH | 1 | $CH_2$ |
| C16 | $CF_3$ | H | H | OH | 1 | $CH_2$ |
| C17 | $(CH_3)_2NSO_2$ | H | H | OH | 1 | $CH_2$ |
| C18 | $(CH_3)_2N$ | H | H | OH | 1 | $CH_2$ |
| C19 | PhO | H | H | OH | 1 | $CH_2$ |
| C20 | PhS | H | H | OH | 1 | $CH_2$ |
| C21 | PhSO | H | H | OH | 1 | $CH_2$ |
| C22 | $PhSO_2$ | H | H | OH | 1 | $CH_2$ |
| C23 | CN | H | H | OH | 1 | $CH_2$ |
| C24 | $CH_3$ | $CH_3$ | H | OH | 1 | $CH_2$ |
| C25 | $CH_3CH_2$ | $CH_3$ | H | OH | 1 | $CH_2$ |
| C26 | $CH_3CH_2CH_2$ | $CH_3$ | H | OH | 1 | $CH_2$ |
| C27 | $(CH_3)_2CH$ | $CH_3$ | H | OH | 1 | $CH_2$ |
| C28 | $(CH_3)_3C$ | $CH_3$ | H | OH | 1 | $CH_2$ |
| C29 | $CH_3S$ | $CH_3$ | H | OH | 1 | $CH_2$ |
| C30 | $CH_3SO$ | $CH_3$ | H | OH | 1 | $CH_2$ |
| C31 | $CH_3SO_2$ | $CH_3$ | H | OH | 1 | $CH_2$ |
| C32 | Ph | $CH_3$ | H | OH | 1 | $CH_2$ |
| C33 | $CH_3O$ | $CH_3$ | H | OH | 1 | $CH_2$ |
| C34 | $CH_3OC(O)$ | $CH_3$ | H | OH | 1 | $CH_2$ |
| C35 | $CH_3CH_2OC(O)$ | $CH_3$ | H | OH | 1 | $CH_2$ |
| C36 | $CH_2$=$CHCH_2$ | $CH_3$ | H | OH | 1 | $CH_2$ |
| C37 | $HCCCH_2$ | $CH_3$ | H | OH | 1 | $CH_2$ |
| C38 | $CF_3$ | $CH_3$ | H | OH | 1 | $CH_2$ |
| C39 | $(CH_3)_2NSO_2$ | $CH_3$ | H | OH | 1 | $CH_2$ |
| C40 | $(CH_3)_2N$ | $CH_3$ | H | OH | 1 | $CH_2$ |
| C41 | PhO | $CH_3$ | H | OH | 1 | $CH_2$ |
| C42 | PhS | $CH_3$ | H | OH | 1 | $CH_2$ |
| C43 | PhSO | $CH_3$ | H | OH | 1 | $CH_2$ |
| C44 | $PhSO_2$ | $CH_3$ | H | OH | 1 | $CH_2$ |
| C45 | CN | $CH_3$ | H | OH | 1 | $CH_2$ |

TABLE 3-continued

Radicals C:

| Radical | $R_6$ | $R_7$ | $R_{16}$ | $R_{10}$ | p | W |
|---|---|---|---|---|---|---|
| C46 | H | H | H | OH | 4 | $CH_2$ |
| C47 | $CH_3$ | H | H | OH | 4 | $CH_2$ |
| C48 | $CH_3CH_2$ | H | H | OH | 4 | $CH_2$ |
| C49 | $CH_3CH_2CH_2$ | H | H | OH | 4 | $CH_2$ |
| C50 | $(CH_3)_2CH$ | H | H | OH | 4 | $CH_2$ |
| C51 | $(CH_3)_3C$ | H | H | OH | 4 | $CH_2$ |
| C52 | $CH_3S$ | H | H | OH | 4 | $CH_2$ |
| C53 | $CH_3SO$ | H | H | OH | 4 | $CH_2$ |
| C54 | $CH_3SO_2$ | H | H | OH | 4 | $CH_2$ |
| C55 | Ph | H | H | OH | 4 | $CH_2$ |
| C56 | $CH_3O$ | H | H | OH | 4 | $CH_2$ |
| C57 | $CH_3OC(O)$ | H | H | OH | 4 | $CH_2$ |
| C58 | $CH_3CH_2OC(O)$ | H | H | OH | 4 | $CH_2$ |
| C59 | $CH_2{=}CHCH_2$ | H | H | OH | 4 | $CH_2$ |
| C60 | $HCCCH_2$ | H | H | OH | 4 | $CH_2$ |
| C61 | $CF_3$ | H | H | OH | 4 | $CH_2$ |
| C62 | $(CH_3)_2NSO_2$ | H | H | OH | 4 | $CH_2$ |
| C63 | $(CH_3)_2N$ | H | H | OH | 4 | $CH_2$ |
| C64 | PhO | H | H | OH | 4 | $CH_2$ |
| C65 | PhS | H | H | OH | 4 | $CH_2$ |
| C66 | PhSO | H | H | OH | 4 | $CH_2$ |
| C67 | $PhSO_2$ | H | H | OH | 4 | $CH_2$ |
| C68 | CN | H | H | OH | 4 | $CH_2$ |
| C69 | $CH_3$ | $CH_3$ | H | OH | 4 | $CH_2$ |
| C70 | $CH_3CH_2$ | $CH_3$ | H | OH | 4 | $CH_2$ |
| C71 | $CH_3CH_2CH_2$ | $CH_3$ | H | OH | 4 | $CH_2$ |
| C72 | $(CH_3)_2CH$ | $CH_3$ | H | OH | 4 | $CH_2$ |
| C73 | $(CH_3)_3C$ | $CH_3$ | H | OH | 4 | $CH_2$ |
| C74 | $CH_3S$ | $CH_3$ | H | OH | 4 | $CH_2$ |
| C75 | $CH_3SO$ | $CH_3$ | H | OH | 4 | $CH_2$ |
| C76 | $CH_3SO_2$ | $CH_3$ | H | OH | 4 | $CH_2$ |
| C77 | Ph | $CH_3$ | H | OH | 4 | $CH_2$ |
| C78 | $CH_3O$ | $CH_3$ | H | OH | 4 | $CH_2$ |
| C79 | $CH_3OC(O)$ | $CH_3$ | H | OH | 4 | $CH_2$ |
| C80 | $CH_3CH_2OC(O)$ | $CH_3$ | H | OH | 4 | $CH_2$ |
| C81 | $CH_2{=}CHCH_2$ | $CH_3$ | H | OH | 4 | $CH_2$ |
| C82 | $HCCCH_2$ | $CH_3$ | H | OH | 4 | $CH_2$ |
| C83 | $CF_3$ | $CH_3$ | H | OH | 4 | $CH_2$ |
| C84 | $(CH_3)_2NSO_2$ | $CH_3$ | H | OH | 4 | $CH_2$ |
| C85 | $(CH_3)_2N$ | $CH_3$ | H | OH | 4 | $CH_2$ |
| C86 | PhO | $CH_3$ | H | OH | 4 | $CH_2$ |
| C87 | PhS | $CH_3$ | H | OH | 4 | $CH_2$ |
| C88 | PhSO | $CH_3$ | H | OH | 4 | $CH_2$ |
| C89 | $PhSO_2$ | $CH_3$ | H | OH | 4 | $CH_2$ |
| C90 | CN | $CH_3$ | H | OH | 4 | $CH_2$ |
| C91 | H | H | H | OH | 3 | $CH_2$ |
| C92 | $CH_3$ | H | H | OH | 3 | $CH_2$ |
| C93 | $CH_3CH_2$ | H | H | OH | 3 | $CH_2$ |
| C94 | $CH_3CH_2CH_2$ | H | H | OH | 3 | $CH_2$ |
| C95 | $(CH_3)_2CH$ | H | H | OH | 3 | $CH_2$ |
| C96 | $(CH_3)_3C$ | H | H | OH | 3 | $CH_2$ |
| C97 | $CH_3S$ | H | H | OH | 3 | $CH_2$ |
| C98 | $CH_3SO$ | H | H | OH | 3 | $CH_2$ |
| C99 | $CH_3SO_2$ | H | H | OH | 3 | $CH_2$ |
| C100 | Ph | H | H | OH | 3 | $CH_2$ |
| C101 | $CH_3O$ | H | H | OH | 3 | $CH_2$ |
| C102 | $CH_3OC(O)$ | H | H | OH | 3 | $CH_2$ |
| C103 | $CH_3CH_2OC(O)$ | H | H | OH | 3 | $CH_2$ |
| C104 | $CH_2{=}CHCH_2$ | H | H | OH | 3 | $CH_2$ |
| C105 | $HCCCH_2$ | H | H | OH | 3 | $CH_2$ |
| C106 | $CF_3$ | H | H | OH | 3 | $CH_2$ |
| C107 | $(CH_3)_2NSO_2$ | H | H | OH | 3 | $CH_2$ |
| C108 | $(CH_3)_2N$ | H | H | OH | 3 | $CH_2$ |
| C109 | PhO | H | H | OH | 3 | $CH_2$ |
| C110 | PhS | H | H | OH | 3 | $CH_2$ |
| C111 | PhSO | H | H | OH | 3 | $CH_2$ |
| C112 | $PhSO_2$ | H | H | OH | 3 | $CH_2$ |
| C113 | CN | H | H | OH | 3 | $CH_2$ |
| C114 | $CH_3$ | $CH_3$ | H | OH | 3 | $CH_2$ |
| C115 | $CH_3CH_2$ | $CH_3$ | H | OH | 3 | $CH_2$ |
| C116 | $CH_3CH_2CH_2$ | $CH_3$ | H | OH | 3 | $CH_2$ |
| C117 | $(CH_3)_2CH$ | $CH_3$ | H | OH | 3 | $CH_2$ |
| C118 | $(CH_3)_3C$ | $CH_3$ | H | OH | 3 | $CH_2$ |
| C119 | $CH_3S$ | $CH_3$ | H | OH | 3 | $CH_2$ |
| C120 | $CH_3SO$ | $CH_3$ | H | OH | 3 | $CH_2$ |
| C121 | $CH_3SO_2$ | $CH_3$ | H | OH | 3 | $CH_2$ |
| C122 | Ph | $CH_3$ | H | OH | 3 | $CH_2$ |
| C123 | $CH_3O$ | $CH_3$ | H | OH | 3 | $CH_2$ |
| C124 | $CH_3OC(O)$ | $CH_3$ | H | OH | 3 | $CH_2$ |
| C125 | $CH_3CH_2OC(O)$ | $CH_3$ | H | OH | 3 | $CH_2$ |
| C126 | $CH_2{=}CHCH_2$ | $CH_3$ | H | OH | 3 | $CH_2$ |
| C127 | $HCCCH_2$ | $CH_3$ | H | OH | 3 | $CH_2$ |
| C128 | $CF_3$ | $CH_3$ | H | OH | 3 | $CH_2$ |
| C129 | $(CH_3)_2NSO_2$ | $CH_3$ | H | OH | 3 | $CH_2$ |
| C130 | $(CH_3)_2N$ | $CH_3$ | H | OH | 3 | $CH_2$ |
| C131 | PhO | $CH_3$ | H | OH | 3 | $CH_2$ |
| C132 | PhS | $CH_3$ | H | OH | 3 | $CH_2$ |
| C133 | PhSO | $CH_3$ | H | OH | 3 | $CH_2$ |
| C134 | $PhSO_2$ | $CH_3$ | H | OH | 3 | $CH_2$ |
| C135 | CN | $CH_3$ | H | OH | 3 | $CH_2$ |
| C136 | $CH_3CH_2$ | $CH_3CH_2$ | H | OH | 1 | $CH_2$ |
| C137 | H | H | H | OH | 1 | $CH(CH_3)$ |
| C138 | $CH_3$ | H | H | OH | 1 | $CH(CH_3)$ |
| C139 | $CH_3$ | $CH_3$ | H | OH | 1 | $CH(CH_3)$ |
| C140 | $CH_{2CH3}$ | H | H | OH | 1 | $CH(CH_3)$ |
| C141 | $CH_{2CH3}$ | $CH_3$ | H | OH | 1 | $CH(CH_3)$ |
| C142 | $CH_3CH_2$ | $CH_3CH_2$ | H | OH | 1 | $CH(CH_3)$ |
| C143 | H | H | $CH_3$ | OH | 1 | $CH_2$ |
| C144 | $CH_3$ | $CH_3$ | $CH_3$ | OH | 1 | $CH_2$ |
| C145 | $CH_3CH_2$ | $CH_3CH_2$ | $CH_3$ | OH | 1 | $CH_2$ |
| C146 | H | H | H | OH | 2 | $CH_2$ |
| C147 | $CH_3$ | $CH_3$ | H | OH | 2 | $CH_2$ |
| C148 | $CH_3CH_2$ | $CH_3CH_2$ | H | OH | 2 | $CH_2$ |
| C149 | H | H | H | OH | 5 | $CH_2$ |
| C150 | $CH_3$ | $CH_3$ | H | OH | 5 | $CH_2$ |
| C151 | $CH_3CH_2$ | $CH_3CH_2$ | H | OH | 5 | $CH_2$ |
| C152 | $CH_3$ | H | H | OH | 2 | $CH_2$ |

In Table 4 which follows, Q is $Q_3$ $$(Q_3)$$

and $Q_3$ the following radicals D:

TABLE 4

Radicals D:

| Radical | $R_6$ | $R_7$ | $R_8$ | $R_{12}$ | $R_{10}$ | o |
|---|---|---|---|---|---|---|
| D1 | H | H | H | H | OH | 2 |
| D2 | $CH_3$ | H | H | H | OH | 2 |
| D3 | $CH_3CH_2$ | H | H | H | OH | 2 |
| D4 | $CH_3CH_2CH_2$ | H | H | H | OH | 2 |
| D5 | $(CH_3)_2CH$ | H | H | H | OH | 2 |
| D6 | $(CH_3)_3C$ | H | H | H | OH | 2 |
| D7 | $CH_3S$ | H | H | H | OH | 2 |
| D8 | $CH_3SO$ | H | H | H | OH | 2 |
| D9 | $CH_3SO_2$ | H | H | H | OH | 2 |
| D10 | Ph | H | H | H | OH | 2 |
| D11 | $CH_3O$ | H | H | H | OH | 2 |
| D12 | $CH_2{=}CHCH_2$ | H | H | H | OH | 2 |
| D13 | $HCCCH_2$ | H | H | H | OH | 2 |
| D14 | $CF_3$ | H | H | H | OH | 2 |
| D15 | PhO | H | H | H | OH | 2 |
| D16 | PhS | H | H | H | OH | 2 |
| D17 | PhSO | H | H | H | OH | 2 |
| D18 | $PhSO_2$ | H | H | H | OH | 2 |

TABLE 4-continued

Radicals D:

| Radical | $R_6$ | $R_7$ | $R_8$ | $R_{12}$ | $R_{10}$ | o |
|---|---|---|---|---|---|---|
| D19 | $CH_3$ | $CH_3$ | H | H | OH | 2 |
| D20 | $CH_3CH_2$ | $CH_3$ | H | H | OH | 2 |
| D21 | $CH_3CH_2CH_2$ | $CH_3$ | H | H | OH | 2 |
| D22 | $(CH_3)_2CH$ | $CH_3$ | H | H | OH | 2 |
| D23 | $(CH_3)_3C$ | $CH_3$ | H | H | OH | 2 |
| D24 | $CH_3S$ | $CH_3$ | H | H | OH | 2 |
| D25 | $CH_3SO$ | $CH_3$ | H | H | OH | 2 |
| D26 | $CH_3SO_2$ | $CH_3$ | H | H | OH | 2 |
| D27 | Ph | $CH_3$ | H | H | OH | 2 |
| D28 | $CH_3O$ | $CH_3$ | H | H | OH | 2 |
| D29 | $CH_2=CHCH_2$ | $CH_3$ | H | H | OH | 2 |
| D30 | $HCCCH_2$ | $CH_3$ | H | H | OH | 2 |
| D31 | $CF_3$ | $CH_3$ | H | H | OH | 2 |
| D32 | PhO | $CH_3$ | H | H | OH | 2 |
| D33 | PhS | $CH_3$ | H | H | OH | 2 |
| D34 | PhSO | $CH_3$ | H | H | OH | 2 |
| D35 | $PhSO_2$ | $CH_3$ | H | H | OH | 2 |
| D36 | H | H | H | H | OH | 3 |
| D37 | $CH_3$ | H | H | H | OH | 3 |
| D38 | $CH_3CH_2$ | H | H | H | OH | 3 |
| D39 | $CH_3CH_2CH_2$ | H | H | H | OH | 3 |
| D40 | $(CH_3)_2CH$ | H | H | H | OH | 3 |
| D41 | $(CH_3)_3C$ | H | H | H | OH | 3 |
| D42 | $CH_3S$ | H | H | H | OH | 3 |
| D43 | $CH_3SO$ | H | H | H | OH | 3 |
| D44 | $CH_3SO_2$ | H | H | H | OH | 3 |
| D45 | Ph | H | H | H | OH | 3 |
| D46 | $CH_3O$ | H | H | H | OH | 3 |
| D47 | $CH_2=CHCH_2$ | H | H | H | OH | 3 |
| D48 | $HCCCH_2$ | H | H | H | OH | 3 |
| D49 | $CF_3$ | H | H | H | OH | 3 |
| D50 | PhO | H | H | H | OH | 3 |
| D51 | PhS | H | H | H | OH | 3 |
| D52 | PhSO | H | H | H | OH | 3 |
| D53 | $PhSO_2$ | H | H | H | OH | 3 |
| D54 | $CH_3$ | $CH_3$ | H | H | OH | 3 |
| D55 | $CH_3CH_2$ | $CH_3$ | H | H | OH | 3 |
| D56 | $CH_3CH_2CH_2$ | $CH_3$ | H | H | OH | 3 |
| D57 | $(CH_3)_2CH$ | $CH_3$ | H | H | OH | 3 |
| D58 | $(CH_3)_3C$ | $CH_3$ | H | H | OH | 3 |
| D59 | $CH_3S$ | $CH_3$ | H | H | OH | 3 |
| D60 | $CH_3SO$ | $CH_3$ | H | H | OH | 3 |
| D61 | $CH_3SO_2$ | $CH_3$ | H | H | OH | 3 |
| D62 | Ph | $CH_3$ | H | H | OH | 3 |
| D63 | $CH_3O$ | $CH_3$ | H | H | OH | 3 |
| D64 | $CH_2=CHCH_2$ | $CH_3$ | H | H | OH | 3 |
| D65 | $HCCCH_2$ | $CH_3$ | H | H | OH | 3 |
| D66 | $CF_3$ | $CH_3$ | H | H | OH | 3 |
| D67 | PhO | $CH_3$ | H | H | OH | 3 |
| D68 | PhS | $CH_3$ | H | H | OH | 3 |
| D69 | PhSO | $CH_3$ | H | H | OH | 3 |
| D70 | $PhSO_2$ | $CH_3$ | H | H | OH | 3 |
| D71 | H | H | H | H | OH | 4 |
| D72 | $CH_3$ | H | H | H | OH | 4 |
| D73 | $CH_3CH_2$ | H | H | H | OH | 4 |
| D74 | $CH_3CH_2CH_2$ | H | H | H | OH | 4 |
| D75 | $(CH_3)_2CH$ | H | H | H | OH | 4 |
| D76 | $(CH_3)_3C$ | H | H | H | OH | 4 |
| D77 | $CH_3S$ | H | H | H | OH | 4 |
| D78 | $CH_3SO$ | H | H | H | OH | 4 |
| D79 | $CH_3SO_2$ | H | H | H | OH | 4 |
| D80 | Ph | H | H | H | OH | 4 |
| D81 | $CH_3O$ | H | H | H | OH | 4 |
| D82 | $CH_2=CHCH_2$ | H | H | H | OH | 4 |
| D83 | $HCCCH_2$ | H | H | H | OH | 4 |
| D84 | $CF_3$ | H | H | H | OH | 4 |
| D85 | PhO | H | H | H | OH | 4 |
| D86 | PhS | H | H | H | OH | 4 |
| D87 | PhSO | H | H | H | OH | 4 |
| D88 | $PhSO_2$ | H | H | H | OH | 4 |
| D89 | $CH_3$ | $CH_3$ | H | H | OH | 4 |
| D90 | $CH_3CH_2$ | $CH_3$ | H | H | OH | 4 |
| D91 | $CH_3CH_2CH_2$ | $CH_3$ | H | H | OH | 4 |
| D92 | $(CH_3)_2CH$ | $CH_3$ | H | H | OH | 4 |
| D93 | $(CH_3)_3C$ | $CH_3$ | H | H | OH | 4 |

TABLE 4-continued

Radicals D:

| Radical | $R_6$ | $R_7$ | $R_8$ | $R_{12}$ | $R_{10}$ | o |
|---|---|---|---|---|---|---|
| D94 | $CH_3S$ | $CH_3$ | H | H | OH | 4 |
| D95 | $CH_3SO$ | $CH_3$ | H | H | OH | 4 |
| D96 | $CH_3SO_2$ | $CH_3$ | H | H | OH | 4 |
| D97 | Ph | $CH_3$ | H | H | OH | 4 |
| D98 | $CH_3O$ | $CH_3$ | H | H | OH | 4 |
| D99 | $CH_2=CHCH_2$ | $CH_3$ | H | H | OH | 4 |
| D100 | $HCCCH_2$ | $CH_3$ | H | H | OH | 4 |
| D101 | $CF_3$ | $CH_3$ | H | H | OH | 4 |
| D102 | PhO | $CH_3$ | H | H | OH | 4 |
| D103 | PhS | $CH_3$ | H | H | OH | 4 |
| D104 | PhSO | $CH_3$ | H | H | OH | 4 |
| D105 | $PhSO_2$ | $CH_3$ | H | H | OH | 4 |
| D106 | H | H | H | $CH_3$ | OH | 4 |
| D107 | H | H | H | $CH_3$ | OH | 3 |
| D108 | H | H | H | H | OH | 1 |
| D109 | $CH_3$ | H | H | H | OH | 1 |
| D110 | $CH_3OC(O)$ | $CH_3$ | H | H | OH | 1 |
| D111 | $CH_3CH_2OC(O)$ | $CH_3$ | H | H | OH | 1 |
| D112 | $CH_3O$ | $CH_3$ | H | H | OH | 1 |
| D113 | $CH_3S$ | $CH_3$ | H | H | OH | 1 |
| D114 | $CH_3SO$ | $CH_3$ | H | H | OH | 1 |
| D115 | $CH_3SO_2$ | $CH_3$ | H | H | OH | 1 |
| D116 | $CH_3CH_2$ | H | H | H | OH | 1 |
| D117 | $CH_3OC(O)$ | $CH_3CH_2$ | H | H | OH | 1 |
| D118 | $CH_3CH_2OC(O)$ | $CH_3CH_2$ | H | H | OH | 1 |
| D119 | $CH_3O$ | $CH_3CH_2$ | H | H | OH | 1 |
| D120 | $CH_3S$ | $CH_3CH_2$ | H | H | OH | 1 |
| D121 | $CH_3SO$ | $CH_3CH_2$ | H | H | OH | 1 |
| D122 | $CH_3SO_2$ | $CH_3CH_2$ | H | H | OH | 1 |
| D123 | $CH_3CH_2S$ | $CH_3$ | H | H | OH | 1 |
| D124 | $CH_3CH_2SO$ | $CH_3$ | H | H | OH | 1 |
| D125 | $CH_3CH_2SO_2$ | $CH_3$ | H | H | OH | 1 |
| D126 | $CH_3CH_2S$ | $CH_3CH_2$ | H | H | OH | 1 |
| D127 | $CH_3CH_2SO$ | $CH_3CH_2$ | H | H | OH | 1 |
| D128 | $CH_3CH_2SO_2$ | $CH_3CH_2$ | H | H | OH | 1 |
| D129 | H | H | $CH_3$ | H | OH | 1 |
| D130 | $CH_3$ | H | $CH_3$ | H | OH | 1 |
| D131 | $CH_3OC(O)$ | $CH_3$ | $CH_3$ | H | OH | 1 |
| D132 | $CH_3CH_2OC(O)$ | $CH_3$ | $CH_3$ | H | OH | 1 |
| D133 | $CH_3O$ | $CH_3$ | $CH_3$ | H | OH | 1 |
| D134 | $CH_3S$ | $CH_3$ | $CH_3$ | H | OH | 1 |
| 0135 | $CH_3SO$ | $CH_3$ | $CH_3$ | H | OH | 1 |
| D136 | $CH_3SO_2$ | $CH_3$ | $CH_3$ | H | OH | 1 |
| D137 | H | H | H | $CH_3$ | OH | 1 |
| D138 | $CH_3$ | H | H | $CH_3$ | OH | 1 |
| D139 | H | H | $CH_3$ | $CH_3$ | OH | 1 |
| D140 | $CH_3CH_2OC(O)$ | $CH_3$ | H | H | OH | 4 |

In Table 5 which follows, 0 is $Q_4$

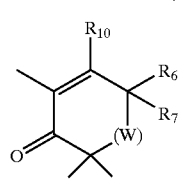

(Q_4)

and $Q_4$ the following radicals E:

TABLE 5

Radicals E:

| Radical | $R_6$ | $R_7$ | $R_{10}$ | X | Y | W | q |
|---|---|---|---|---|---|---|---|
| E1 | H | H | OH | S | $CH_2$ | $CH_2$ | 2 |
| E2 | $CH_3$ | H | OH | S | $CH_2$ | $CH_2$ | 2 |
| E3 | $CH_3$ | $CH_3$ | OH | S | $CH_2$ | $CH_2$ | 2 |
| E4 | $CH_3OC(O)$ | H | OH | S | $CH_2$ | $CH_2$ | 2 |
| E5 | $CH_3$ | $CH_3OC(O)$ | OH | S | $CH_2$ | $CH_2$ | 2 |

TABLE 5-continued

| | Radicals E: | | | | | | |
|---|---|---|---|---|---|---|---|
| Radical | $R_6$ | $R_7$ | $R_{10}$ | X | Y | W | q |
| E6  | H          | H          | OH | SO   | $CH_2$ | $CH_2$ | 2 |
| E7  | $CH_3$     | H          | OH | SO   | $CH_2$ | $CH_2$ | 2 |
| E8  | $CH_3$     | $CH_3$     | OH | SO   | $CH_2$ | $CH_2$ | 2 |
| E9  | $CH_3OC(O)$| H          | OH | SO   | $CH_2$ | $CH_2$ | 2 |
| E10 | $CH_3$     | $CH_3OC(O)$| OH | SO   | $CH_2$ | $CH_2$ | 2 |
| E11 | H          | H          | OH | $SO_2$ | $CH_2$ | $CH_2$ | 2 |
| E12 | $CH_3$     | H          | OH | $SO_2$ | $CH_2$ | $CH_2$ | 2 |
| E13 | $CH_3$     | $CH_3$     | OH | $SO_2$ | $CH_2$ | $CH_2$ | 2 |
| E14 | $CH_3OC(O)$| H          | OH | $SO_2$ | $CH_2$ | $CH_2$ | 2 |
| E15 | $CH_3$     | $CH_3OC(O)$| OH | $SO_2$ | $CH_2$ | $CH_2$ | 2 |
| E16 | H          | H          | OH | CO   | O | $CH_2$ | 2 |
| E17 | $CH_3$     | H          | OH | CO   | O | $CH_2$ | 2 |
| E18 | $CH_3$     | $CH_3$     | OH | CO   | O | $CH_2$ | 2 |
| E19 | $CH_3OC(O)$| H          | OH | CO   | O | $CH_2$ | 2 |
| E20 | $CH_3$     | $CH_3OC(O)$| OH | CO   | O | $CH_2$ | 2 |
| E21 | H          | H          | OH | CO   | O | $CH_2$ | 2 |
| E22 | $CH_3$     | H          | OH | CO   | O | $CH_2$ | 2 |
| E23 | $CH_3$     | $CH_3$     | OH | CO   | O | $CH_2$ | 2 |
| E24 | $CH_3OC(O)$| H          | OH | CO   | O | $CH_2$ | 2 |
| E25 | $CH_3$     | $CH_3OC(O)$| OH | CO   | O | $CH_2$ | 2 |
| E26 | H          | H          | OH | CO   | O | $CH_2$ | 2 |
| E27 | $CH_3$     | H          | OH | CO   | O | $CH_2$ | 2 |
| E28 | $CH_3$     | $CH_3$     | OH | CO   | O | $CH_2$ | 2 |
| E29 | $CH_3OC(O)$| H          | OH | CO   | O | $CH_2$ | 2 |
| E30 | $CH_3$     | $CH_3OC(O)$| OH | CO   | O | $CH_2$ | 2 |

In Table 6 which follows, Q is $Q_5$

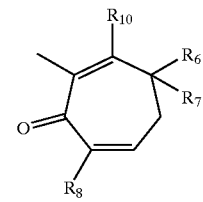

(Q5)

and $Q_5$ the radicals F which follow:

TABLE 6

| | Radicals F: | | | |
|---|---|---|---|---|
| Radical | $R_6$ | $R_7$ | $R_8$ | $R_{10}$ |
| F1 | H      | H      | H      | OH |
| F2 | $CH_3$ | H      | H      | OH |
| F3 | $CH_3$ | $CH_3$ | H      | OH |
| F4 | $CH_3$ | $CH_3$ | $CH_3$ | OH |
| F5 | H      | H      | $CH_3$ | OH |
| F6 | H      | $CH_3$ | $CH_3$ | OH |

TABLE 7

Compounds of the formula Ia

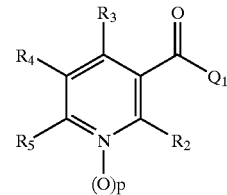

(Ia)

| Comp. No. | $R_2$ | $R_3$ | $R_4$ | $R_5$ | $Q_1$ | p |
|---|---|---|---|---|---|---|
| A1  | H               | H | H | $CF_3$ | B24 | 0 |
| A2  | $CH_3$          | H | H | $CF_3$ | B24 | 0 |
| A3  | $CH_3CH_2$      | H | H | $CF_3$ | B24 | 0 |
| A4  | $(CH_3)_2CH$    | H | H | $CF_3$ | B24 | 0 |
| A5  | $(CH_3)_3C$     | H | H | $CF_3$ | B24 | 0 |
| A6  | cyclopropyl     | H | H | $CF_3$ | B24 | 0 |
| A7  | $CH_3(CH_2)_2$  | H | H | $CF_3$ | B24 | 0 |
| A8  | $CH_3OCH_2$     | H | H | $CF_3$ | B24 | 0 |
| A9  | $CH_3O(CH_2)_2$ | H | H | $CF_3$ | B24 | 0 |
| A10 | Ph              | H | H | $CF_3$ | B24 | 0 |
| A11 | PhO             | H | H | $CF_3$ | B24 | 0 |
| A12 | PhS             | H | H | $CF_3$ | B24 | 0 |
| A13 | PhSO            | H | H | $CF_3$ | B24 | 0 |
| A14 | $PhSO_2$        | H | H | $CF_3$ | B24 | 0 |
| A15 | $CH_3S$         | H | H | $CF_3$ | B24 | 0 |
| A16 | $CH_3SO$        | H | H | $CF_3$ | B24 | 0 |
| A17 | $CF_3$          | H | H | $CF_3$ | B24 | 0 |
| A18 | $F_2CH$         | H | H | $CF_3$ | B24 | 0 |
| A19 | HCC             | H | H | $CF_3$ | B24 | 0 |
| A20 | $CH_3CC$        | H | H | $CF_3$ | B24 | 0 |
| A21 | $CH_2$=CH       | H | H | $CF_3$ | B24 | 0 |
| A22 | $CH_2$=$CHCH_2$ | H | H | $CF_3$ | B24 | 0 |
| A23 | $CH_3SO_2N(CH_3)$ | H | H | $CF_3$ | B24 | 0 |

TABLE 7-continued

Compounds of the formula Ia (Ia)

| Comp. No. | R$_2$ | R$_3$ | R$_4$ | R$_5$ | Q$_1$ | p |
|---|---|---|---|---|---|---|
| A24 | (CH$_3$)$_2$N | H | H | CF$_3$ | B24 | 0 |
| A25 | (CH$_3$)$_2$NSO$_2$ | H | H | CF$_3$ | B24 | 0 |
| A26 | ClCH$_2$ | H | H | CF$_3$ | B24 | 0 |
| A27 | CH$_3$SCH$_2$ | H | H | CF$_3$ | B24 | 0 |
| A28 | CH$_3$SOCH$_2$ | H | H | CF$_3$ | B24 | 0 |
| A29 | CH$_3$SO$_2$CH$_2$ | H | H | CF$_3$ | B24 | 0 |
| A30 | [1.2.4]-triazol-1-ylmethyl | H | H | CF$_3$ | B24 | 0 |
| A31 | CH$_3$ | CF$_3$ | H | CH$_3$ | B24 | 0 |
| A32 | CH$_3$ | CH$_3$ | H | CF$_3$ | B24 | 0 |
| A33 | H | H | H | CF$_3$CF$_2$ | B24 | 0 |
| A34 | CH$_3$ | H | H | CF$_3$CF$_2$ | B24 | 0 |
| A35 | CH$_3$CH$_2$ | H | H | CF$_3$CF$_2$ | B24 | 0 |
| A36 | cyclopropyl | H | H | CF$_3$CF$_2$ | B24 | 0 |
| A37 | (CH$_3$)$_3$C | H | H | CF$_3$CF$_2$ | B24 | 0 |
| A38 | (CH$_3$)$_2$CH | H | H | CF$_3$CF$_2$ | B24 | 0 |
| A39 | CH$_3$(CH$_2$)$_2$ | H | H | CF$_3$CF$_2$ | B24 | 0 |
| A40 | CH$_3$OCH$_2$ | H | H | CF$_3$CF$_2$ | B24 | 0 |
| A41 | CH$_3$O(CH$_2$)$_2$ | H | H | CF$_3$CF$_2$ | B24 | 0 |
| A42 | Ph | H | H | CF$_3$CF$_2$ | B24 | 0 |
| A43 | PhO | H | H | CF$_3$CF$_2$ | B24 | 0 |
| A44 | PhS | H | H | CF$_3$CF$_2$ | B24 | 0 |
| A45 | PhSO | H | H | CF$_3$CF$_2$ | B24 | 0 |
| A46 | PhSO$_2$ | H | H | CF$_3$CF$_2$ | B24 | 0 |
| A47 | CH$_3$S | H | H | CF$_3$CF$_2$ | B24 | 0 |
| A48 | CH$_3$SO | H | H | CF$_3$CF$_2$ | B24 | 0 |
| A49 | CF$_3$ | H | H | CF$_3$CF$_2$ | B24 | 0 |
| A50 | F$_2$CH | H | H | CF$_3$CF$_2$ | B24 | 0 |
| A51 | HCC | H | H | CF$_3$CF$_2$ | B24 | 0 |
| A52 | CH$_3$CC | H | H | CF$_3$CF$_2$ | B24 | 0 |
| A53 | CH$_2$=CH | H | H | CF$_3$CF$_2$ | B24 | 0 |
| A54 | CH$_2$=CHCH$_2$ | H | H | CF$_3$CF$_2$ | B24 | 0 |
| A55 | CH$_3$SO$_2$N(CH$_3$) | H | H | CF$_3$CF$_2$ | B24 | 0 |
| A56 | (CH$_3$)$_2$N | H | H | CF$_3$CF$_2$ | B24 | 0 |
| A57 | (CH$_3$)$_2$NSO$_2$ | H | H | CF$_3$CF$_2$ | B24 | 0 |
| A58 | ClCH$_2$ | H | H | CF$_3$CF$_2$ | B24 | 0 |
| A59 | CH$_3$SCH$_2$ | H | H | CF$_3$CF$_2$ | B24 | 0 |
| A60 | CH$_3$SOCH$_2$ | H | H | CF$_3$CF$_2$ | B24 | 0 |
| A61 | CH$_3$SO$_2$CH$_2$ | H | H | CF$_3$CF$_2$ | B24 | 0 |
| A62 | [1.2.4]-triazol-1-ylmethyl | H | H | CF$_3$CF$_2$ | B24 | 0 |
| A63 | H | H | H | CF$_3$CF$_2$CF$_2$ | B24 | 0 |
| A64 | CH$_3$ | H | H | CF$_3$CF$_2$CF$_2$ | B24 | 0 |
| A65 | CH$_3$CH$_2$ | H | H | CF$_3$CF$_2$CF$_2$ | B24 | 0 |
| A66 | cyclopropyl | H | H | CF$_3$CF$_2$CF$_2$ | B24 | 0 |
| A67 | (CH$_3$)$_3$C | H | H | CF$_3$CF$_2$CF$_2$ | B24 | 0 |
| A68 | (CH$_3$)$_2$CH | H | H | CF$_3$CF$_2$CF$_2$ | B24 | 0 |
| A69 | CH$_3$(CH$_2$)$_2$ | H | H | CF$_3$CF$_2$CF$_2$ | B24 | 0 |
| A70 | CH$_3$OCH$_2$ | H | H | CF$_3$CF$_2$CF$_2$ | B24 | 0 |
| A71 | CH$_3$O(CH$_2$)$_2$ | H | H | CF$_3$CF$_2$CF$_2$ | B24 | 0 |
| A72 | Ph | H | H | CF$_3$CF$_2$CF$_2$ | B24 | 0 |
| A73 | PhO | H | H | CF$_3$CF$_2$CF$_2$ | B24 | 0 |
| A74 | PhS | H | H | CF$_3$CF$_2$CF$_2$ | B24 | 0 |
| A75 | PhSO | H | H | CF$_3$CF$_2$CF$_2$ | B24 | 0 |
| A76 | PhSO$_2$ | H | H | CF$_3$CF$_2$CF$_2$ | B24 | 0 |
| A77 | CH$_3$S | H | H | CF$_3$CF$_2$CF$_2$ | B24 | 0 |
| A78 | CH$_3$SO | H | H | CF$_3$CF$_2$CF$_2$ | B24 | 0 |
| A79 | CF$_3$ | H | H | CF$_3$CF$_2$CF$_2$ | B24 | 0 |
| A80 | F$_2$CH | H | H | CF$_3$CF$_2$CF$_2$ | B24 | 0 |
| A81 | HCC | H | H | CF$_3$CF$_2$CF$_2$ | B24 | 0 |
| A82 | CH$_3$CC | H | H | CF$_3$CF$_2$CF$_2$ | B24 | 0 |
| A83 | CH$_2$=CH | H | H | CF$_3$CF$_2$CF$_2$ | B24 | 0 |
| A84 | CH$_2$=CHCH$_2$ | H | H | CF$_3$CF$_2$CF$_2$ | B24 | 0 |

TABLE 7-continued

Compounds of the formula Ia (Ia)

| Comp. No. | $R_2$ | $R_3$ | $R_4$ | $R_5$ | $Q_1$ | p |
|---|---|---|---|---|---|---|
| A85 | $CH_3SO_2N(CH_3)$ | H | H | $CF_3CF_2CF_2$ | B24 | 0 |
| A86 | $(CH_3)_2N$ | H | H | $CF_3CF_2CF_2$ | B24 | 0 |
| A87 | $(CH_3)_2NSO_2$ | H | H | $CF_3CF_2CF_2$ | B24 | 0 |
| A88 | $ClCH_2$ | H | H | $CF_3CF_2CF_2$ | B24 | 0 |
| A89 | $CH_3SCH_2$ | H | H | $CF_3CF_2CF_2$ | B24 | 0 |
| A90 | $CH_3SOCH_2$ | H | H | $CF_3CF_2CF_2$ | B24 | 0 |
| A91 | $CH_3SO_2CH_2$ | H | H | $CF_3CF_2CF_2$ | B24 | 0 |
| A92 | [1.2.4]-triazol-1-ylmethyl | H | H | $CF_3CF_2CF_2$ | B24 | 0 |
| A93 | H | H | H | $CF_2Cl$ | B24 | 0 |
| A94 | $CH_3$ | H | H | $CF_2Cl$ | B24 | 0 |
| A95 | $CH_3CH_2$ | H | H | $CF_2Cl$ | B24 | 0 |
| A96 | cyclopropyl | H | H | $CF_2Cl$ | B24 | 0 |
| A97 | $(CH_3)_3C$ | H | H | $CF_2Cl$ | B24 | 0 |
| A98 | $(CH_3)_2CH$ | H | H | $CF_2Cl$ | B24 | 0 |
| A99 | $CH_3(CH_2)_2$ | H | H | $CF_2Cl$ | B24 | 0 |
| A100 | $CH_3OCH_2$ | H | H | $CF_2Cl$ | B24 | 0 |
| A101 | $CH_3O(CH_2)_2$ | H | H | $CF_2Cl$ | B24 | 0 |
| A102 | Ph | H | H | $CF_2Cl$ | B24 | 0 |
| A103 | PhO | H | H | $CF_2Cl$ | B24 | 0 |
| A104 | PhS | H | H | $CF_2Cl$ | B24 | 0 |
| A105 | PhSO | H | H | $CF_2Cl$ | B24 | 0 |
| A106 | $PhSO_2$ | H | H | $CF_2Cl$ | B24 | 0 |
| A107 | $CH_3S$ | H | H | $CF_2Cl$ | B24 | 0 |
| A108 | $CH_3SO$ | H | H | $CF_2Cl$ | B24 | 0 |
| A109 | $CF_3$ | H | H | $CF_2Cl$ | B24 | 0 |
| A110 | $F_2CH$ | H | H | $CF_2Cl$ | B24 | 0 |
| A111 | HCC | H | H | $CF_2Cl$ | B24 | 0 |
| A112 | $CH_3CC$ | H | H | $CF_2Cl$ | B24 | 0 |
| A113 | $CH_2=CH$ | H | H | $CF_2Cl$ | B24 | 0 |
| A114 | $CH_2=CHCH_2$ | H | H | $CF_2Cl$ | B24 | 0 |
| A115 | $CH_3SO_2N(CH_3)$ | H | H | $CF_2Cl$ | B24 | 0 |
| A116 | $(CH_3)_2N$ | H | H | $CF_2Cl$ | B24 | 0 |
| A117 | $(CH_3)_2NSO_2$ | H | H | $CF_2Cl$ | B24 | 0 |
| A118 | $ClCH_2$ | H | H | $CF_2Cl$ | B24 | 0 |
| A119 | $CH_3SCH_2$ | H | H | $CF_2Cl$ | B24 | 0 |
| A120 | $CH_3SOCH_2$ | H | H | $CF_2Cl$ | B24 | 0 |
| A121 | $CH_3SO_2CH_2$ | H | H | $CF_2Cl$ | B24 | 0 |
| A122 | [1.2.4]-triazol-1-ylmethyl | H | H | $CF_2Cl$ | B24 | 0 |
| A123 | H | H | H | $CHF_2$ | B24 | 0 |
| A124 | $CH_3$ | H | H | $CHF_2$ | B24 | 0 |
| A125 | $CH_3CH_2$ | H | H | $CHF_2$ | B24 | 0 |
| A126 | cyclopropyl | H | H | $CHF_2$ | B24 | 0 |
| A127 | $(CH_3)_3C$ | H | H | $CHF_2$ | B24 | 0 |
| A128 | $(CH_3)_2CH$ | H | H | $CHF_2$ | B24 | 0 |
| A129 | $CH_3(CH_2)_2$ | H | H | $CHF_2$ | B24 | 0 |
| A130 | $CH_3OCH_2$ | H | H | $CHF_2$ | B24 | 0 |
| A131 | $CH_3O(CH_2)_2$ | H | H | $CHF_2$ | B24 | 0 |
| A132 | Ph | H | H | $CHF_2$ | B24 | 0 |
| A133 | PhO | H | H | $CHF_2$ | B24 | 0 |
| A134 | PhS | H | H | $CHF_2$ | B24 | 0 |
| A135 | PhSO | H | H | $CHF_2$ | B24 | 0 |
| A136 | $PhSO_2$ | H | H | $CHF_2$ | B24 | 0 |
| A137 | $CH_3S$ | H | H | $CHF_2$ | B24 | 0 |
| A138 | $CH_3SO$ | H | H | $CHF_2$ | B24 | 0 |
| A139 | $CF_3$ | H | H | $CHF_2$ | B24 | 0 |
| A140 | $F_2CH$ | H | H | $CHF_2$ | B24 | 0 |
| A141 | HCC | H | H | $CHF_2$ | B24 | 0 |
| A142 | $CH_3CC$ | H | H | $CHF_2$ | B24 | 0 |
| A143 | $CH_2=CH$ | H | H | $CHF_2$ | B24 | 0 |
| A144 | $CH_2=CHCH_2$ | H | H | $CHF_2$ | B24 | 0 |
| A145 | $CH_3SO_2N(CH_3)$ | H | H | $CHF_2$ | B24 | 0 |

TABLE 7-continued

Compounds of the formula Ia (Ia)

| Comp. No. | R$_2$ | R$_3$ | R$_4$ | R$_5$ | Q$_1$ | p |
|---|---|---|---|---|---|---|
| A146 | (CH$_3$)$_2$N | H | H | CHF$_2$ | B24 | 0 |
| A147 | (CH$_3$)$_2$NSO$_2$ | H | H | CHF$_2$ | B24 | 0 |
| A148 | ClCH$_2$ | H | H | CHF$_2$ | B24 | 0 |
| A149 | CH$_3$SCH$_2$ | H | H | CHF$_2$ | B24 | 0 |
| A150 | CH$_3$SOCH$_2$ | H | H | CHF$_2$ | B24 | 0 |
| A151 | CH$_3$SO$_2$CH$_2$ | H | H | CHF$_2$ | B24 | 0 |
| A152 | [1.2.4]-triazol-1-ylmethyl | H | H | CHF$_2$ | B24 | 0 |
| A153 | H | H | H | CCl$_3$ | B24 | 0 |
| A154 | CH$_3$ | H | H | CCl$_3$ | B24 | 0 |
| A155 | CH$_3$CH$_2$ | H | H | CCl$_3$ | B24 | 0 |
| A156 | cyclopropyl | H | H | CCl$_3$ | B24 | 0 |
| A157 | (CH$_3$)$_3$C | H | H | CCl$_3$ | B24 | 0 |
| A158 | (CH$_3$)$_2$CH | H | H | CCl$_3$ | B24 | 0 |
| A159 | CH$_3$(CH$_2$)$_2$ | H | H | CCl$_3$ | B24 | 0 |
| A160 | CH$_3$OCH$_2$ | H | H | CCl$_3$ | B24 | 0 |
| A161 | CH$_3$O(CH$_2$)$_2$ | H | H | CCl$_3$ | B24 | 0 |
| A162 | Ph | H | H | CCl$_3$ | B24 | 0 |
| A163 | PhO | H | H | CCl$_3$ | B24 | 0 |
| A164 | PhS | H | H | CCl$_3$ | B24 | 0 |
| A165 | PhSO | H | H | CCl$_3$ | B24 | 0 |
| A166 | PhSO$_2$ | H | H | CCl$_3$ | B24 | 0 |
| A167 | CH$_3$S | H | H | CCl$_3$ | B24 | 0 |
| A168 | CH$_3$SO | H | H | CCl$_3$ | B24 | 0 |
| A169 | CF$_3$ | H | H | CCl$_3$ | B24 | 0 |
| A170 | F$_2$CH | H | H | CCl$_3$ | B24 | 0 |
| A171 | HCC | H | H | CCl$_3$ | B24 | 0 |
| A172 | CH$_3$CC | H | H | CCl$_3$ | B24 | 0 |
| A173 | CH$_2$=CH | H | H | CCl$_3$ | B24 | 0 |
| A174 | CH$_2$=CHCH$_2$ | H | H | CCl$_3$ | B24 | 0 |
| A175 | CH$_3$SO$_2$N(CH$_3$) | H | H | CCl$_3$ | B24 | 0 |
| A176 | (CH$_3$)$_2$N | H | H | CCl$_3$ | B24 | 0 |
| A177 | (CH$_3$)$_2$NSO$_2$ | H | H | CCl$_3$ | B24 | 0 |
| A178 | ClCH$_2$ | H | H | CCl$_3$ | B24 | 0 |
| A179 | CH$_3$SCH$_2$ | H | H | CCl$_3$ | B24 | 0 |
| A180 | CH$_3$SOCH$_2$ | H | H | CCl$_3$ | B24 | 0 |
| A181 | CH$_3$SO$_2$CH$_2$ | H | H | CCl$_3$ | B24 | 0 |
| A182 | [1.2.4]-triazol-1-ylmethyl | H | H | CCl$_3$ | B24 | 0 |
| A183 | H | H | CH$_3$ | CF$_3$ | B24 | 0 |
| A184 | CH$_3$ | H | CH$_3$ | CF$_3$ | B24 | 0 |
| A185 | CH$_3$CH$_2$ | H | CH$_3$ | CF$_3$ | B24 | 0 |
| A186 | cyclopropyl | H | CH$_3$ | CF$_3$ | B24 | 0 |
| A187 | (CH$_3$)$_3$C | H | CH$_3$ | CF$_3$ | B24 | 0 |
| A188 | (CH$_3$)$_2$CH | H | CH$_3$ | CF$_3$ | B24 | 0 |
| A189 | CH$_3$(CH$_2$)$_2$ | H | CH$_3$ | CF$_3$ | B24 | 0 |
| A190 | CH$_3$OCH$_2$ | H | CH$_3$ | CF$_3$ | B24 | 0 |
| A191 | CH$_3$O(CH$_2$)$_2$ | H | CH$_3$ | CF$_3$ | B24 | 0 |
| A192 | Ph | H | CH$_3$ | CF$_3$ | B24 | 0 |
| A193 | PhO | H | CH$_3$ | CF$_3$ | B24 | 0 |
| A194 | PhS | H | CH$_3$ | CF$_3$ | B24 | 0 |
| A195 | PhSO | H | CH$_3$ | CF$_3$ | B24 | 0 |
| A196 | PhSO$_2$ | H | CH$_3$ | CF$_3$ | B24 | 0 |
| A197 | CH$_3$S | H | CH$_3$ | CF$_3$ | B24 | 0 |
| A198 | CH$_3$SO | H | CH$_3$ | CF$_3$ | B24 | 0 |
| A199 | CF$_3$ | H | CH$_3$ | CF$_3$ | B24 | 0 |
| A200 | F$_2$CH | H | CH$_3$ | CF$_3$ | B24 | 0 |
| A201 | HCC | H | CH$_3$ | CF$_3$ | B24 | 0 |
| A202 | CH$_3$CC | H | CH$_3$ | CF$_3$ | B24 | 0 |
| A203 | CH$_2$=CH | H | CH$_3$ | CF$_3$ | B24 | 0 |
| A204 | CH$_2$=CHCH$_2$ | H | CH$_3$ | CF$_3$ | B24 | 0 |
| A205 | CH$_3$SO$_2$N(CH$_3$) | H | CH$_3$ | CF$_3$ | B24 | 0 |
| A206 | (CH$_3$)$_2$N | H | CH$_3$ | CF$_3$ | B24 | 0 |

TABLE 7-continued

Compounds of the formula Ia (Ia)

| Comp. No. | $R_2$ | $R_3$ | $R_4$ | $R_5$ | $Q_1$ | p |
|---|---|---|---|---|---|---|
| A207 | $(CH_3)_2NSO_2$ | H | $CH_3$ | $CF_3$ | B24 | 0 |
| A208 | $ClCH_2$ | H | $CH_3$ | $CF_3$ | B24 | 0 |
| A209 | $CH_3SCH_2$ | H | $CH_3$ | $CF_3$ | B24 | 0 |
| A210 | $CH_3SOCH_2$ | H | $CH_3$ | $CF_3$ | B24 | 0 |
| A211 | $CH_3SO_2CH_2$ | H | $CH_3$ | $CF_3$ | B24 | 0 |
| A212 | H | H | $CH_3$ | $CF_3CF_2$ | B24 | 0 |
| A213 | $CH_3$ | H | $CH_3$ | $CF_3CF_2$ | B24 | 0 |
| A214 | $CH_3CH_2$ | H | $CH_3$ | $CF_3CF_2$ | B24 | 0 |
| A215 | cyclopropyl | H | $CH_3$ | $CF_3CF_2$ | B24 | 0 |
| A216 | $(CH_3)_3C$ | H | $CH_3$ | $CF_3CF_2$ | B24 | 0 |
| A217 | $(CH_3)_2CH$ | H | $CH_3$ | $CF_3CF_2$ | B24 | 0 |
| A218 | $CH_3(CH_2)_2$ | H | $CH_3$ | $CF_3CF_2$ | B24 | 0 |
| A219 | $CH_3OCH_2$ | H | $CH_3$ | $CF_3CF_2$ | B24 | 0 |
| A220 | $CH_3O(CH_2)_2$ | H | $CH_3$ | $CF_3CF_2$ | B24 | 0 |
| A221 | Ph | H | $CH_3$ | $CF_3CF_2$ | B24 | 0 |
| A222 | PhO | H | $CH_3$ | $CF_3CF_2$ | B24 | 0 |
| A223 | PhS | H | $CH_3$ | $CF_3CF_2$ | B24 | 0 |
| A224 | PhSO | H | $CH_3$ | $CF_3CF_2$ | B24 | 0 |
| A225 | $PhSO_2$ | H | $CH_3$ | $CF_3CF_2$ | B24 | 0 |
| A226 | $CH_3S$ | H | $CH_3$ | $CF_3CF_2$ | B24 | 0 |
| A227 | $CH_3SO$ | H | $CH_3$ | $CF_3CF_2$ | B24 | 0 |
| A228 | $CF_3$ | H | $CH_3$ | $CF_3CF_2$ | B24 | 0 |
| A229 | $F_2CH$ | H | $CH_3$ | $CF_3CF_2$ | B24 | 0 |
| A230 | HCC | H | $CH_3$ | $CF_3CF_2$ | B24 | 0 |
| A231 | $CH_3CC$ | H | $CH_3$ | $CF_3CF_2$ | B24 | 0 |
| A232 | $CH_2=CH$ | H | $CH_3$ | $CF_3CF_2$ | B24 | 0 |
| A233 | $CH_2=CHCH_2$ | H | $CH_3$ | $CF_3CF_2$ | B24 | 0 |
| A234 | $CH_3SO_2N(CH_3)$ | H | $CH_3$ | $CF_3CF_2$ | B24 | 0 |
| A235 | $(CH_3)_2N$ | H | $CH_3$ | $CF_3CF_2$ | B24 | 0 |
| A236 | $(CH_3)_2NSO_2$ | H | $CH_3$ | $CF_3CF_2$ | B24 | 0 |
| A237 | $ClCH_2$ | H | $CH_3$ | $CF_3CF_2$ | B24 | 0 |
| A238 | $CH_3SCH_2$ | H | $CH_3$ | $CF_3CF_2$ | B24 | 0 |
| A239 | $CH_3SOCH_2$ | H | $CH_3$ | $CF_3CF_2$ | B24 | 0 |
| A240 | $CH_3SO_2CH_2$ | H | $CH_3$ | $CF_3CF_2$ | B24 | 0 |
| A241 | H | H | $CH_3$ | $CF_3CF_2CF_2$ | B24 | 0 |
| A242 | $CH_3$ | H | $CH_3$ | $CF_3CF_2CF_2$ | B24 | 0 |
| A243 | $CH_3CH_2$ | H | $CH_3$ | $CF_3CF_2CF_2$ | B24 | 0 |
| A244 | cyclopropyl | H | $CH_3$ | $CF_3CF_2CF_2$ | B24 | 0 |
| A245 | $(CH_3)_3C$ | H | $CH_3$ | $CF_3CF_2CF_2$ | B24 | 0 |
| A246 | $(CH_3)_2CH$ | H | $CH_3$ | $CF_3CF_2CF_2$ | B24 | 0 |
| A247 | $CH_3(CH_2)_2$ | H | $CH_3$ | $CF_3CF_2CF_2$ | B24 | 0 |
| A248 | $CH_3OCH_2$ | H | $CH_3$ | $CF_3CF_2CF_2$ | B24 | 0 |
| A249 | $CH_3O(CH_2)_2$ | H | $CH_3$ | $CF_3CF_2CF_2$ | B24 | 0 |
| A250 | Ph | H | $CH_3$ | $CF_3CF_2CF_2$ | B24 | 0 |
| A251 | PhO | H | $CH_3$ | $CF_3CF_2CF_2$ | B24 | 0 |
| A252 | PhS | H | $CH_3$ | $CF_3CF_2CF_2$ | B24 | 0 |
| A253 | PhSO | H | $CH_3$ | $CF_3CF_2CF_2$ | B24 | 0 |
| A254 | $PhSO_2$ | H | $CH_3$ | $CF_3CF_2CF_2$ | B24 | 0 |
| A255 | $CH_3S$ | H | $CH_3$ | $CF_3CF_2CF_2$ | B24 | 0 |
| A256 | $CH_3SO$ | H | $CH_3$ | $CF_3CF_2CF_2$ | B24 | 0 |
| A257 | $CF_3$ | H | $CH_3$ | $CF_3CF_2CF_2$ | B24 | 0 |
| A258 | $F_2CH$ | H | $CH_3$ | $CF_3CF_2CF_2$ | B24 | 0 |
| A259 | HCC | H | $CH_3$ | $CF_3CF_2CF_2$ | B24 | 0 |
| A260 | $CH_3CC$ | H | $CH_3$ | $CF_3CF_2CF_2$ | B24 | 0 |
| A261 | $CH_2=CH$ | H | $CH_3$ | $CF_3CF_2CF_2$ | B24 | 0 |
| A262 | $CH_2=CHCH_2$ | H | $CH_3$ | $CF_3CF_2CF_2$ | B24 | 0 |
| A263 | $CH_3SO_2N(CH_3)$ | H | $CH_3$ | $CF_3CF_2CF_2$ | B24 | 0 |
| A264 | $(CH_3)_2N$ | H | $CH_3$ | $CF_3CF_2CF_2$ | B24 | 0 |
| A265 | $(CH_3)_2NSO_2$ | H | $CH_3$ | $CF_3CF_2CF_2$ | B24 | 0 |
| A266 | $ClCH_2$ | H | $CH_3$ | $CF_3CF_2CF_2$ | B24 | 0 |
| A267 | $CH_3SCH_2$ | H | $CH_3$ | $CF_3CF_2CF_2$ | B24 | 0 |
| A268 | $CH_3SOCH_2$ | H | $CH_3$ | $CF_3CF_2CF_2$ | B24 | 0 |
| A269 | $CH_3SO_2CH_2$ | H | $CH_3$ | $CF_3CF_2CF_2$ | B24 | 0 |

TABLE 7-continued

Compounds of the formula Ia $$\text{(Ia)}$$

Structure: Pyridine ring with $R_3$ at position 4, $R_4$ at position 5, $R_5$ at position 6, $R_2$ at position 2, and $C(=O)Q_1$ at position 3. N-oxide designated as $(O)_p$.

| Comp. No. | $R_2$ | $R_3$ | $R_4$ | $R_5$ | $Q_1$ | p |
|---|---|---|---|---|---|---|
| A270 | H | H | CH$_3$ | CF$_2$Cl | B24 | 0 |
| A271 | CH$_3$ | H | CH$_3$ | CF$_2$Cl | B24 | 0 |
| A272 | CH$_3$CH$_2$ | H | CH$_3$ | CF$_2$Cl | B24 | 0 |
| A273 | cyclopropyl | H | CH$_3$ | CF$_2$Cl | B24 | 0 |
| A274 | (CH$_3$)$_3$C | H | CH$_3$ | CF$_2$Cl | B24 | 0 |
| A275 | (CH$_3$)$_2$CH | H | CH$_3$ | CF$_2$Cl | B24 | 0 |
| A276 | CH$_3$(CH$_2$)$_2$ | H | CH$_3$ | CF$_2$Cl | B24 | 0 |
| A277 | CH$_3$OCH$_2$ | H | CH$_3$ | CF$_2$Cl | B24 | 0 |
| A278 | CH$_3$O(CH$_2$)$_2$ | H | CH$_3$ | CF$_2$Cl | B24 | 0 |
| A279 | Ph | H | CH$_3$ | CF$_2$Cl | B24 | 0 |
| A280 | PhO | H | CH$_3$ | CF$_2$Cl | B24 | 0 |
| A281 | PhS | H | CH$_3$ | CF$_2$Cl | B24 | 0 |
| A282 | PhSO | H | CH$_3$ | CF$_2$Cl | B24 | 0 |
| A283 | PhSO$_2$ | H | CH$_3$ | CF$_2$Cl | B24 | 0 |
| A284 | CH$_3$S | H | CH$_3$ | CF$_2$Cl | B24 | 0 |
| A285 | CH$_3$SO | H | CH$_3$ | CF$_2$Cl | B24 | 0 |
| A286 | CF$_3$ | H | CH$_3$ | CF$_2$Cl | B24 | 0 |
| A287 | F$_2$CH | H | CH$_3$ | CF$_2$Cl | B24 | 0 |
| A288 | HCC | H | CH$_3$ | CF$_2$Cl | B24 | 0 |
| A289 | CH$_3$CC | H | CH$_3$ | CF$_2$Cl | B24 | 0 |
| A290 | CH$_2$=CH | H | CH$_3$ | CF$_2$Cl | B24 | 0 |
| A291 | CH$_2$=CHCH$_2$ | H | CH$_3$ | CF$_2$Cl | B24 | 0 |
| A292 | CH$_3$SO$_2$N(CH$_3$) | H | CH$_3$ | CF$_2$Cl | B24 | 0 |
| A293 | (CH$_3$)$_2$N | H | CH$_3$ | CF$_2$Cl | B24 | 0 |
| A294 | (CH$_3$)$_2$NSO$_2$ | H | CH$_3$ | CF$_2$Cl | B24 | 0 |
| A295 | ClCH$_2$ | H | CH$_3$ | CF$_2$Cl | B24 | 0 |
| A296 | CH$_3$SCH$_2$ | H | CH$_3$ | CF$_2$Cl | B24 | 0 |
| A297 | CH$_3$SOCH$_2$ | H | CH$_3$ | CF$_2$Cl | B24 | 0 |
| A298 | CH$_3$SO$_2$CH$_2$ | H | CH$_3$ | CF$_2$Cl | B24 | 0 |
| A299 | H | H | CH$_3$ | CHF$_2$ | B24 | 0 |
| A300 | CH$_3$ | H | CH$_3$ | CHF$_2$ | B24 | 0 |
| A301 | CH$_3$CH$_2$ | H | CH$_3$ | CHF$_2$ | B24 | 0 |
| A302 | cyclopropyl | H | CH$_3$ | CHF$_2$ | B24 | 0 |
| A303 | (CH$_3$)$_3$C | H | CH$_3$ | CHF$_2$ | B24 | 0 |
| A304 | (CH$_3$)$_2$CH | H | CH$_3$ | CHF$_2$ | B24 | 0 |
| A305 | CH$_3$(CH$_2$)$_2$ | H | CH$_3$ | CHF$_2$ | B24 | 0 |
| A306 | CH$_3$OCH$_2$ | H | CH$_3$ | CHF$_2$ | B24 | 0 |
| A307 | CH$_3$O(CH$_2$)$_2$ | H | CH$_3$ | CHF$_2$ | B24 | 0 |
| A308 | Ph | H | CH$_3$ | CHF$_2$ | B24 | 0 |
| A309 | PhO | H | CH$_3$ | CHF$_2$ | B24 | 0 |
| A310 | PhS | H | CH$_3$ | CHF$_2$ | B24 | 0 |
| A311 | PhSO | H | CH$_3$ | CHF$_2$ | B24 | 0 |
| A312 | PhSO$_2$ | H | CH$_3$ | CHF$_2$ | B24 | 0 |
| A313 | CH$_3$S | H | CH$_3$ | CHF$_2$ | B24 | 0 |
| A314 | CH$_3$SO | H | CH$_3$ | CHF$_2$ | B24 | 0 |
| A315 | CF$_3$ | H | CH$_3$ | CHF$_2$ | B24 | 0 |
| A316 | F$_2$CH | H | CH$_3$ | CHF$_2$ | B24 | 0 |
| A317 | HCC | H | CH$_3$ | CHF$_2$ | B24 | 0 |
| A318 | CH$_3$CC | H | CH$_3$ | CHF$_2$ | B24 | 0 |
| A319 | CH$_2$=CH | H | CH$_3$ | CHF$_2$ | B24 | 0 |
| A320 | CH$_2$=CHCH$_2$ | H | CH$_3$ | CHF$_2$ | B24 | 0 |
| A321 | CH$_3$SO$_2$N(CH$_3$) | H | CH$_3$ | CHF$_2$ | B24 | 0 |
| A322 | (CH$_3$)$_2$N | H | CH$_3$ | CHF$_2$ | B24 | 0 |
| A323 | (CH$_3$)$_2$NSO$_2$ | H | CH$_3$ | CHF$_2$ | B24 | 0 |
| A324 | ClCH$_2$ | H | CH$_3$ | CHF$_2$ | B24 | 0 |
| A325 | CH$_3$SCH$_2$ | H | CH$_3$ | CHF$_2$ | B24 | 0 |
| A326 | CH$_3$SOCH$_2$ | H | CH$_3$ | CHF$_2$ | B24 | 0 |
| A327 | CH$_3$SO$_2$CH$_2$ | H | CH$_3$ | CHF$_2$ | B24 | 0 |
| A328 | H | H | CH$_3$ | CCl$_3$ | B24 | 0 |
| A329 | CH$_3$ | H | CH$_3$ | CCl$_3$ | B24 | 0 |
| A330 | CH$_3$CH$_2$ | H | CH$_3$ | CCl$_3$ | B24 | 0 |
| A331 | (CH$_3$)$_3$C | H | CH$_3$ | CCl$_3$ | B24 | 0 |
| A332 | (CH$_3$)$_2$CH | H | CH$_3$ | CCl$_3$ | B24 | 0 |

TABLE 7-continued

Compounds of the formula Ia (Ia)

$$\text{structure with } R_3, R_4, R_5 \text{ on pyridine ring, } R_2, Q_1\text{C(=O)}, \text{N-(O)}_p$$

| Comp. No. | $R_2$ | $R_3$ | $R_4$ | $R_5$ | $Q_1$ | p |
|---|---|---|---|---|---|---|
| A333 | cyclopropyl | H | $CH_3$ | $CCl_3$ | B24 | 0 |
| A334 | $CH_3(CH_2)_2$ | H | $CH_3$ | $CCl_3$ | B24 | 0 |
| A335 | $CH_3OCH_2$ | H | $CH_3$ | $CCl_3$ | B24 | 0 |
| A336 | $CH_3O(CH_2)_2$ | H | $CH_3$ | $CCl_3$ | B24 | 0 |
| A337 | Ph | H | $CH_3$ | $CCl_3$ | B24 | 0 |
| A338 | PhO | H | $CH_3$ | $CCl_3$ | B24 | 0 |
| A339 | PhS | H | $CH_3$ | $CCl_3$ | B24 | 0 |
| A340 | PhSO | H | $CH_3$ | $CCl_3$ | B24 | 0 |
| A341 | $PhSO_2$ | H | $CH_3$ | $CCl_3$ | B24 | 0 |
| A342 | $CH_3S$ | H | $CH_3$ | $CCl_3$ | B24 | 0 |
| A343 | $CH_3SO$ | H | $CH_3$ | $CCl_3$ | B24 | 0 |
| A344 | $CF_3$ | H | $CH_3$ | $CCl_3$ | B24 | 0 |
| A345 | $F_2CH$ | H | $CH_3$ | $CCl_3$ | B24 | 0 |
| A346 | HCC | H | $CH_3$ | $CCl_3$ | B24 | 0 |
| A347 | $CH_3CC$ | H | $CH_3$ | $CCl_3$ | B24 | 0 |
| A348 | $CH_2$=CH | H | $CH_3$ | $CCl_3$ | B24 | 0 |
| A349 | $CH_2$=CHCH$_2$ | H | $CH_3$ | $CCl_3$ | B24 | 0 |
| A350 | $CH_3SO_2N(CH_3)$ | H | $CH_3$ | $CCl_3$ | B24 | 0 |
| A351 | $(CH_3)_2N$ | H | $CH_3$ | $CCl_3$ | B24 | 0 |
| A352 | $(CH_3)_2NSO_2$ | H | $CH_3$ | $CCl_3$ | B24 | 0 |
| A353 | $ClCH_2$ | H | $CH_3$ | $CCl_3$ | B24 | 0 |
| A354 | $CH_3SCH_2$ | H | $CH_3$ | $CCl_3$ | B24 | 0 |
| A355 | $CH_3SOCH_2$ | H | $CH_3$ | $CCl_3$ | B24 | 0 |
| A356 | $CH_3SO_2CH_2$ | H | $CH_3$ | $CCl_3$ | B24 | 0 |
| A357 | H | H | Ph | $CF_3$ | B24 | 0 |
| A358 | $CH_3$ | H | Ph | $CF_3$ | B24 | 0 |
| A359 | $CH_3CH_2$ | H | Ph | $CF_3$ | B24 | 0 |
| A360 | cyclopropyl | H | Ph | $CF_3$ | B24 | 0 |
| A361 | $(CH_3)_3C$ | H | Ph | $CF_3$ | B24 | 0 |
| A362 | $(CH_3)_2CH$ | H | Ph | $CF_3$ | B24 | 0 |
| A363 | $CH_3(CH_2)_2$ | H | Ph | $CF_3$ | B24 | 0 |
| A364 | $CH_3OCH_2$ | H | Ph | $CF_3$ | B24 | 0 |
| A365 | $CH_3O(CH_2)_2$ | H | Ph | $CF_3$ | B24 | 0 |
| A366 | Ph | H | Ph | $CF_3$ | B24 | 0 |
| A367 | PhO | H | Ph | $CF_3$ | B24 | 0 |
| A368 | PhS | H | Ph | $CF_3$ | B24 | 0 |
| A369 | PhSO | H | Ph | $CF_3$ | B24 | 0 |
| A370 | $PhSO_2$ | H | Ph | $CF_3$ | B24 | 0 |
| A371 | $CH_3S$ | H | Ph | $CF_3$ | B24 | 0 |
| A372 | $CH_3SO$ | H | Ph | $CF_3$ | B24 | 0 |
| A373 | $CF_3$ | H | Ph | $CF_3$ | B24 | 0 |
| A374 | $F_2CH$ | H | Ph | $CF_3$ | B24 | 0 |
| A375 | HCC | H | Ph | $CF_3$ | B24 | 0 |
| A376 | $CH_3CC$ | H | Ph | $CF_3$ | B24 | 0 |
| A377 | $CH_2$=CH | H | Ph | $CF_3$ | B24 | 0 |
| A378 | $CH_2$=CHCH$_2$ | H | Ph | $CF_3$ | B24 | 0 |
| A379 | $CH_3SO_2N(CH_3)$ | H | Ph | $CF_3$ | B24 | 0 |
| A380 | $(CH_3)_2N$ | H | Ph | $CF_3$ | B24 | 0 |
| A381 | $(CH_3)_2NSO_2$ | H | Ph | $CF_3$ | B24 | 0 |
| A382 | $ClCH_2$ | H | Ph | $CF_3$ | B24 | 0 |
| A383 | $CH_3SCH_2$ | H | Ph | $CF_3$ | B24 | 0 |
| A384 | $CH_3SOCH_2$ | H | Ph | $CF_3$ | B24 | 0 |
| A385 | $CH_3SO_2CH_2$ | H | Ph | $CF_3$ | B24 | 0 |
| A386 | H | H | Ph | $CF_3CF_2$ | B24 | 0 |
| A387 | $CH_3$ | H | Ph | $CF_3CF_2$ | B24 | 0 |
| A388 | $CH_3CH_2$ | H | Ph | $CF_3CF_2$ | B24 | 0 |
| A389 | cyclopropyl | H | Ph | $CF_3CF_2$ | B24 | 0 |
| A390 | $(CH_3)_3C$ | H | Ph | $CF_3CF_2$ | B24 | 0 |
| A391 | $(CH_3)_2CH$ | H | Ph | $CF_3CF_2$ | B24 | 0 |
| A392 | $CH_3(CH_2)_2$ | H | Ph | $CF_3CF_2$ | B24 | 0 |
| A393 | $CH_3OCH_2$ | H | Ph | $CF_3CF_2$ | B24 | 0 |
| A394 | $CH_3O(CH_2)_2$ | H | Ph | $CF_3CF_2$ | B24 | 0 |
| A395 | Ph | H | Ph | $CF_3CF_2$ | B24 | 0 |

TABLE 7-continued

Compounds of the formula Ia (Ia)

| Comp. No. | R$_2$ | R$_3$ | R$_4$ | R$_5$ | Q$_1$ | p |
|---|---|---|---|---|---|---|
| A396 | PhO | H | Ph | CF$_3$CF$_2$ | B24 | 0 |
| A397 | PhS | H | Ph | CF$_3$CF$_2$ | B24 | 0 |
| A398 | PhSO | H | Ph | CF$_3$CF$_2$ | B24 | 0 |
| A399 | PhSO$_2$ | H | Ph | CF$_3$CF$_2$ | B24 | 0 |
| A400 | CH$_3$S | H | Ph | CF$_3$CF$_2$ | B24 | 0 |
| A401 | CH$_3$SO | H | Ph | CF$_3$CF$_2$ | B24 | 0 |
| A402 | CF$_3$ | H | Ph | CF$_3$CF$_2$ | B24 | 0 |
| A403 | F$_2$CH | H | Ph | CF$_3$CF$_2$ | B24 | 0 |
| A404 | HCC | H | Ph | CF$_3$CF$_2$ | B24 | 0 |
| A405 | CH$_3$CC | H | Ph | CF$_3$CF$_2$ | B24 | 0 |
| A406 | CH$_2$=CH | H | Ph | CF$_3$CF$_2$ | B24 | 0 |
| A407 | CH$_2$=CHCH$_2$ | H | Ph | CF$_3$CF$_2$ | B24 | 0 |
| A408 | CH$_3$SO$_2$N(CH$_3$) | H | Ph | CF$_3$CF$_2$ | B24 | 0 |
| A409 | (CH$_3$)$_2$N | H | Ph | CF$_3$CF$_2$ | B24 | 0 |
| A410 | (CH$_3$)$_2$NSO$_2$ | H | Ph | CF$_3$CF$_2$ | B24 | 0 |
| A411 | ClCH$_2$ | H | Ph | CF$_3$CF$_2$ | B24 | 0 |
| A412 | CH$_3$SCH$_2$ | H | Ph | CF$_3$CF$_2$ | B24 | 0 |
| A413 | CH$_3$SOCH$_2$ | H | Ph | CF$_3$CF$_2$ | B24 | 0 |
| A414 | CH$_3$SO$_2$CH$_2$ | H | Ph | CF$_3$CF$_2$ | B24 | 0 |
| A415 | H | H | Ph | CF$_3$CF$_2$CF$_2$ | B24 | 0 |
| A416 | CH$_3$ | H | Ph | CF$_3$CF$_2$CF$_2$ | B24 | 0 |
| A417 | CH$_3$CH$_2$ | H | Ph | CF$_3$CF$_2$CF$_2$ | B24 | 0 |
| A418 | cyclopropyl | H | Ph | CF$_3$CF$_2$CF$_2$ | B24 | 0 |
| A419 | (CH$_3$)$_3$C | H | Ph | CF$_3$CF$_2$CF$_2$ | B24 | 0 |
| A420 | (CH$_3$)$_2$CH | H | Ph | CF$_3$CF$_2$CF$_2$ | B24 | 0 |
| A421 | CH$_3$(CH$_2$)$_2$ | H | Ph | CF$_3$CF$_2$CF$_2$ | B24 | 0 |
| A422 | CH$_3$OCH$_2$ | H | Ph | CF$_3$CF$_2$CF$_2$ | B24 | 0 |
| A423 | CH$_3$O(CH$_2$)$_2$ | H | Ph | CF$_3$CF$_2$CF$_2$ | B24 | 0 |
| A424 | Ph | H | Ph | CF$_3$CF$_2$CF$_2$ | B24 | 0 |
| A425 | PhO | H | Ph | CF$_3$CF$_2$CF$_2$ | B24 | 0 |
| A426 | PhS | H | Ph | CF$_3$CF$_2$CF$_2$ | B24 | 0 |
| A427 | PhSO | H | Ph | CF$_3$CF$_2$CF$_2$ | B24 | 0 |
| A428 | PhSO$_2$ | H | Ph | CF$_3$CF$_2$CF$_2$ | B24 | 0 |
| A429 | CH$_3$S | H | Ph | CF$_3$CF$_2$CF$_2$ | B24 | 0 |
| A430 | CH$_3$SO | H | Ph | CF$_3$CF$_2$CF$_2$ | B24 | 0 |
| A431 | CF$_3$ | H | Ph | CF$_3$CF$_2$CF$_2$ | B24 | 0 |
| A432 | F$_2$CH | H | Ph | CF$_3$CF$_2$CF$_2$ | B24 | 0 |
| A433 | HCC | H | Ph | CF$_3$CF$_2$CF$_2$ | B24 | 0 |
| A434 | CH$_3$CC | H | Ph | CF$_3$CF$_2$CF$_2$ | B24 | 0 |
| A435 | CH$_2$=CH | H | Ph | CF$_3$CF$_2$CF$_2$ | B24 | 0 |
| A436 | CH$_2$=CHCH$_2$ | H | Ph | CF$_3$CF$_2$CF$_2$ | B24 | 0 |
| A437 | CH$_3$SO$_2$N(CH$_3$) | H | Ph | CF$_3$CF$_2$CF$_2$ | B24 | 0 |
| A438 | (CH$_3$)$_2$N | H | Ph | CF$_3$CF$_2$CF$_2$ | B24 | 0 |
| A439 | (CH$_3$)$_2$NSO$_2$ | H | Ph | CF$_3$CF$_2$CF$_2$ | B24 | 0 |
| A440 | ClCH$_2$ | H | Ph | CF$_3$CF$_2$CF$_2$ | B24 | 0 |
| A441 | CH$_3$SCH$_2$ | H | Ph | CF$_3$CF$_2$CF$_2$ | B24 | 0 |
| A442 | CH$_3$SOCH$_2$ | H | Ph | CF$_3$CF$_2$CF$_2$ | B24 | 0 |
| A443 | CH$_3$SO$_2$CH$_2$ | H | Ph | CF$_3$CF$_2$CF$_2$ | B24 | 0 |
| A444 | H | H | Ph | CF$_2$Cl | B24 | 0 |
| A445 | CH$_3$ | H | Ph | CF$_2$Cl | B24 | 0 |
| A446 | CH$_3$CH$_2$ | H | Ph | CF$_2$Cl | B24 | 0 |
| A447 | cyclopropyl | H | Ph | CF$_2$Cl | B24 | 0 |
| A448 | (CH$_3$)$_3$C | H | Ph | CF$_2$Cl | B24 | 0 |
| A449 | (CH$_3$)$_2$CH | H | Ph | CF$_2$Cl | B24 | 0 |
| A450 | CH$_3$(CH$_2$)$_2$ | H | Ph | CF$_2$Cl | B24 | 0 |
| A451 | CH$_3$OCH$_2$ | H | Ph | CF$_2$Cl | B24 | 0 |
| A452 | CH$_3$O(CH$_2$)$_2$ | H | Ph | CF$_2$Cl | B24 | 0 |
| A453 | Ph | H | Ph | CF$_2$Cl | B24 | 0 |
| A454 | PhO | H | Ph | CF$_2$Cl | B24 | 0 |
| A455 | PhS | H | Ph | CF$_2$Cl | B24 | 0 |
| A456 | PhSO | H | Ph | CF$_2$Cl | B24 | 0 |
| A457 | PhSO$_2$ | H | Ph | CF$_2$Cl | B24 | 0 |
| A458 | CH$_3$S | H | Ph | CF$_2$Cl | B24 | 0 |

TABLE 7-continued

Compounds of the formula Ia (Ia)

| Comp. No. | $R_2$ | $R_3$ | $R_4$ | $R_5$ | $Q_1$ | p |
|---|---|---|---|---|---|---|
| A459 | $CH_3SO$ | H | Ph | $CF_2Cl$ | B24 | 0 |
| A460 | $CF_3$ | H | Ph | $CF_2Cl$ | B24 | 0 |
| A461 | $F_2CH$ | H | Ph | $CF_2Cl$ | B24 | 0 |
| A462 | HCC | H | Ph | $CF_2Cl$ | B24 | 0 |
| A463 | $CH_3CC$ | H | Ph | $CF_2Cl$ | B24 | 0 |
| A464 | $CH_2$=CH | H | Ph | $CF_2Cl$ | B24 | 0 |
| A465 | $CH_2$=$CHCH_2$ | H | Ph | $CF_2Cl$ | B24 | 0 |
| A466 | $CH_3SO_2N(CH_3)$ | H | Ph | $CF_2Cl$ | B24 | 0 |
| A467 | $(CH_3)_2N$ | H | Ph | $CF_2Cl$ | B24 | 0 |
| A468 | $(CH_3)_2NSO_2$ | H | Ph | $CF_2Cl$ | B24 | 0 |
| A469 | $ClCH_2$ | H | Ph | $CF_2Cl$ | B24 | 0 |
| A470 | $CH_3SCH_2$ | H | Ph | $CF_2Cl$ | B24 | 0 |
| A471 | $CH_3SOCH_2$ | H | Ph | $CF_2Cl$ | B24 | 0 |
| A472 | $CH_3SO_2CH_2$ | H | Ph | $CF_2Cl$ | B24 | 0 |
| A473 | H | H | Ph | $CHF_2$ | B24 | 0 |
| A474 | $CH_3$ | H | Ph | $CHF_2$ | B24 | 0 |
| A475 | $CH_3CH_2$ | H | Ph | $CHF_2$ | B24 | 0 |
| A476 | cyclopropyl | H | Ph | $CHF_2$ | B24 | 0 |
| A477 | $(CH_3)_3C$ | H | Ph | $CHF_2$ | B24 | 0 |
| A478 | $(CH_3)_2CH$ | H | Ph | $CHF_2$ | B24 | 0 |
| A479 | $CH_3(CH_2)_2$ | H | Ph | $CHF_2$ | B24 | 0 |
| A480 | $CH_3OCH_2$ | H | Ph | $CHF_2$ | B24 | 0 |
| A481 | $CH_3O(CH_2)_2$ | H | Ph | $CHF_2$ | B24 | 0 |
| A482 | Ph | H | Ph | $CHF_2$ | B24 | 0 |
| A483 | PhO | H | Ph | $CHF_2$ | B24 | 0 |
| A484 | PhS | H | Ph | $CHF_2$ | B24 | 0 |
| A485 | PhSO | H | Ph | $CHF_2$ | B24 | 0 |
| A486 | $PhSO_2$ | H | Ph | $CHF_2$ | B24 | 0 |
| A487 | $CH_3S$ | H | Ph | $CHF_2$ | B24 | 0 |
| A488 | $CH_3SO$ | H | Ph | $CHF_2$ | B24 | 0 |
| A489 | $CF_3$ | H | Ph | $CHF_2$ | B24 | 0 |
| A490 | $F_2CH$ | H | Ph | $CHF_2$ | B24 | 0 |
| A491 | HCC | H | Ph | $CHF_2$ | B24 | 0 |
| A492 | $CH_3CC$ | H | Ph | $CHF_2$ | B24 | 0 |
| A493 | $CH_2$=CH | H | Ph | $CHF_2$ | B24 | 0 |
| A494 | $CH_2$=$CHCH_2$ | H | Ph | $CHF_2$ | B24 | 0 |
| A495 | $CH_3SO_2N(CH_3)$ | H | Ph | $CHF_2$ | B24 | 0 |
| A496 | $(CH_3)_2N$ | H | Ph | $CHF_2$ | B24 | 0 |
| A497 | $(CH_3)_2NSO_2$ | H | Ph | $CHF_2$ | B24 | 0 |
| A498 | $ClCH_2$ | H | Ph | $CHF_2$ | B24 | 0 |
| A499 | $CH_3SCH_2$ | H | Ph | $CHF_2$ | B24 | 0 |
| A500 | $CH_3SOCH_2$ | H | Ph | $CHF_2$ | B24 | 0 |
| A501 | $CH_3SO_2CH_2$ | H | Ph | $CHF_2$ | B24 | 0 |
| A502 | H | H | Ph | $CCl_3$ | B24 | 0 |
| A503 | $CH_3$ | H | Ph | $CCl_3$ | B24 | 0 |
| A504 | $CH_3CH_2$ | H | Ph | $CCl_3$ | B24 | 0 |
| A505 | cyclopropyl | H | Ph | $CCl_3$ | B24 | 0 |
| A506 | $(CH_3)_3C$ | H | Ph | $CCl_3$ | B24 | 0 |
| A507 | $(CH_3)_2CH$ | H | Ph | $CCl_3$ | B24 | 0 |
| A508 | $CH_3(CH_2)_2$ | H | Ph | $CCl_3$ | B24 | 0 |
| A509 | $CH_3OCH_2$ | H | Ph | $CCl_3$ | B24 | 0 |
| A510 | $CH_3O(CH_2)_2$ | H | Ph | $CCl_3$ | B24 | 0 |
| A511 | Ph | H | Ph | $CCl_3$ | B24 | 0 |
| A512 | PhO | H | Ph | $CCl_3$ | B24 | 0 |
| A513 | PhS | H | Ph | $CCl_3$ | B24 | 0 |
| A514 | PhSO | H | Ph | $CCl_3$ | B24 | 0 |
| A515 | $PhSO_2$ | H | Ph | $CCl_3$ | B24 | 0 |
| A516 | $CH_3S$ | H | Ph | $CCl_3$ | B24 | 0 |
| A517 | $CH_3SO$ | H | Ph | $CCl_3$ | B24 | 0 |
| A518 | $CF_3$ | H | Ph | $CCl_3$ | B24 | 0 |
| A519 | $F_2CH$ | H | Ph | $CCl_3$ | B24 | 0 |
| A520 | HCC | H | Ph | $CCl_3$ | B24 | 0 |
| A521 | $CH_3CC$ | H | Ph | $CCl_3$ | B24 | 0 |

TABLE 7-continued

Compounds of the formula Ia (Ia)

| Comp. No. | R$_2$ | R$_3$ | R$_4$ | R$_5$ | Q$_1$ | p |
|---|---|---|---|---|---|---|
| A522 | CH$_2$=CH | H | Ph | CCl$_3$ | B24 | 0 |
| A523 | CH$_2$=CHCH$_2$ | H | Ph | CCl$_3$ | B24 | 0 |
| A524 | CH$_3$SO$_2$N(CH$_3$) | H | Ph | CCl$_3$ | B24 | 0 |
| A525 | (CH$_3$)$_2$N | H | Ph | CCl$_3$ | B24 | 0 |
| A526 | (CH$_3$)$_2$NSO$_2$ | H | Ph | CCl$_3$ | B24 | 0 |
| A527 | ClCH$_2$ | H | Ph | CCl$_3$ | B24 | 0 |
| A528 | CH$_3$SCH$_2$ | H | Ph | CCl$_3$ | B24 | 0 |
| A529 | CH$_3$SOCH$_2$ | H | Ph | CCl$_3$ | B24 | 0 |
| A530 | CH$_3$SO$_2$CH$_2$ | H | Ph | CCl$_3$ | B24 | 0 |
| A531 | H | CH$_3$ | H | CF$_3$ | B24 | 0 |
| A532 | H | CH$_3$CH$_2$ | H | CF$_3$ | B24 | 0 |
| A533 | H | cyclopropyl | H | CF$_3$ | B24 | 0 |
| A534 | H | (CH$_3$)$_3$CH | H | CF$_3$ | B24 | 0 |
| A535 | H | (CH$_3$)$_2$CH | H | CF$_3$ | B24 | 0 |
| A536 | H | CH$_3$(CH$_2$)$_2$ | H | CF$_3$ | B24 | 0 |
| A537 | H | CH$_3$OCH$_2$ | H | CF$_3$ | B24 | 0 |
| A538 | H | CH$_3$O(CH$_2$)$_2$ | H | CF$_3$ | B24 | 0 |
| A539 | H | Ph | H | CF$_3$ | B24 | 0 |
| A540 | H | PhO | H | CF$_3$ | B24 | 0 |
| A541 | H | PhS | H | CF$_3$ | B24 | 0 |
| A542 | H | PhSO | H | CF$_3$ | B24 | 0 |
| A543 | H | PhSO$_2$ | H | CF$_3$ | B24 | 0 |
| A544 | H | CH$_3$S | H | CF$_3$ | B24 | 0 |
| A545 | H | CH$_3$SO | H | CF$_3$ | B24 | 0 |
| A546 | H | CF$_3$ | H | CF$_3$ | B24 | 0 |
| A547 | H | F$_2$CH | H | CF$_3$ | B24 | 0 |
| A548 | H | HCC | H | CF$_3$ | B24 | 0 |
| A549 | H | CH$_3$CC | H | CF$_3$ | B24 | 0 |
| A550 | H | CH$_2$=CH | H | CF$_3$ | B24 | 0 |
| A551 | H | CH$_2$=CHCH$_2$ | H | CF$_3$ | B24 | 0 |
| A552 | H | CH$_3$SO$_2$N(CH$_3$) | H | CF$_3$ | B24 | 0 |
| A553 | H | (CH$_3$)$_2$N | H | CF$_3$ | B24 | 0 |
| A554 | H | (CH$_3$)$_2$NSO$_2$ | H | CF$_3$ | B24 | 0 |
| A555 | H | CH$_3$SCH$_2$ | H | CF$_3$ | B24 | 0 |
| A556 | H | CH$_3$SOCH$_2$ | H | CF$_3$ | B24 | 0 |
| A557 | H | CH$_3$SO$_2$CH$_2$ | H | CF$_3$ | B24 | 0 |
| A558 | H | CH$_3$ | H | CF$_3$CF$_2$ | B24 | 0 |
| A559 | H | CH$_3$CH$_2$ | H | CF$_3$CF$_2$ | B24 | 0 |
| A560 | H | cyclopropyl | H | CF$_3$CF$_2$ | B24 | 0 |
| A561 | H | (CH$_3$)$_3$C | H | CF$_3$CF$_2$ | B24 | 0 |
| A562 | H | (CH$_3$)$_2$CH | H | CF$_3$CF$_2$ | B24 | 0 |
| A563 | H | CH$_3$(CH$_2$)$_2$ | H | CF$_3$CF$_2$ | B24 | 0 |
| A564 | H | CH$_3$OCH$_2$ | H | CF$_3$CF$_2$ | B24 | 0 |
| A565 | H | CH$_3$O(CH$_2$)$_2$ | H | CF$_3$CF$_2$ | B24 | 0 |
| A566 | H | Ph | H | CF$_3$CF$_2$ | B24 | 0 |
| A567 | H | PhO | H | CF$_3$CF$_2$ | B24 | 0 |
| A568 | H | PhS | H | CF$_3$CF$_2$ | B24 | 0 |
| A569 | H | PhSO | H | CF$_3$CF$_2$ | B24 | 0 |
| A570 | H | PhSO$_2$ | H | CF$_3$CF$_2$ | B24 | 0 |
| A571 | H | CH$_3$S | H | CF$_3$CF$_2$ | B24 | 0 |
| A572 | H | CH$_3$SO | H | CF$_3$CF$_2$ | B24 | 0 |
| A573 | H | CF$_3$ | H | CF$_3$CF$_2$ | B24 | 0 |
| A574 | H | F$_2$CH | H | CF$_3$CF$_2$ | B24 | 0 |
| A575 | H | HCC | H | CF$_3$CF$_2$ | B24 | 0 |
| A576 | H | CH$_3$CC | H | CF$_3$CF$_2$ | B24 | 0 |
| A577 | H | CH$_2$=CH | H | CF$_3$CF$_2$ | B24 | 0 |
| A578 | H | CH$_2$=CHCH$_2$ | H | CF$_3$CF$_2$ | B24 | 0 |
| A579 | H | CH$_3$SO$_2$N(CH$_3$) | H | CF$_3$CF$_2$ | B24 | 0 |
| A580 | H | (CH$_3$)$_2$N | H | CF$_3$CF$_2$ | B24 | 0 |
| A581 | H | (CH$_3$)$_2$NSO$_2$ | H | CF$_3$CF$_2$ | B24 | 0 |
| A582 | H | CH$_3$SCH$_2$ | H | CF$_3$CF$_2$ | B24 | 0 |
| A583 | H | CH$_3$SOCH$_2$ | H | CF$_3$CF$_2$ | B24 | 0 |
| A584 | H | CH$_3$SO$_2$CH$_2$ | H | CF$_3$CF$_2$ | B24 | 0 |

TABLE 7-continued

Compounds of the formula Ia

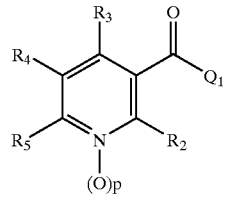

(Ia)

| Comp. No. | $R_2$ | $R_3$ | $R_4$ | $R_5$ | $Q_1$ | p |
|---|---|---|---|---|---|---|
| A585 | H | $CH_3$ | H | $CF_3CF_2CF_2$ | B24 | 0 |
| A586 | H | $CH_3CH_2$ | H | $CF_3CF_2CF_2$ | B24 | 0 |
| A587 | H | cyclopropyl | H | $CF_3CF_2CF_2$ | B24 | 0 |
| A588 | H | $(CH_3)_3C$ | H | $CF_3CF_2CF_2$ | B24 | 0 |
| A589 | H | $(CH_3)_2CH$ | H | $CF_3CF_2CF_2$ | B24 | 0 |
| A590 | H | $CH_3(CH_2)_2$ | H | $CF_3CF_2CF_2$ | B24 | 0 |
| A591 | H | $CH_3OCH_2$ | H | $CF_3CF_2CF_2$ | B24 | 0 |
| A592 | H | $CH_3O(CH_2)_2$ | H | $CF_3CF_2CF_2$ | B24 | 0 |
| A593 | H | Ph | H | $CF_3CF_2CF_2$ | B24 | 0 |
| A594 | H | PhO | H | $CF_3CF_2CF_2$ | B24 | 0 |
| A595 | H | PhS | H | $CF_3CF_2CF_2$ | B24 | 0 |
| A596 | H | PhSO | H | $CF_3CF_2CF_2$ | B24 | 0 |
| A597 | H | $PhSO_2$ | H | $CF_3CF_2CF_2$ | B24 | 0 |
| A598 | H | $CH_3S$ | H | $CF_3CF_2CF_2$ | B24 | 0 |
| A599 | H | $CH_3SO$ | H | $CF_3CF_2CF_2$ | B24 | 0 |
| A600 | H | $CF_3$ | H | $CF_3CF_2CF_2$ | B24 | 0 |
| A601 | H | $F_2CH$ | H | $CF_3CF_2CF_2$ | B24 | 0 |
| A602 | H | HCC | H | $CF_3CF_2CF_2$ | B24 | 0 |
| A603 | H | $CH_3CC$ | H | $CF_3CF_2CF_2$ | B24 | 0 |
| A604 | H | $CH_2$=CH | H | $CF_3CF_2CF_2$ | B24 | 0 |
| A605 | H | $CH_2$=$CHCH_2$ | H | $CF_3CF_2CF_2$ | B24 | 0 |
| A606 | H | $CH_3SO_2N(CH_3)$ | H | $CF_3CF_2CF_2$ | B24 | 0 |
| A607 | H | $(CH_3)_2N$ | H | $CF_3CF_2CF_2$ | B24 | 0 |
| A608 | H | $(CH_3)_2NSO_2$ | H | $CF_3CF_2CF_2$ | B24 | 0 |
| A609 | H | $CH_3SCH_2$ | H | $CF_3CF_2CF_2$ | B24 | 0 |
| A610 | H | $CH_3SOCH_2$ | H | $CF_3CF_2CF_2$ | B24 | 0 |
| A611 | H | $CH_3SO_2CH_2$ | H | $CF_3CF_2CF_2$ | B24 | 0 |
| A612 | H | $CH_3$ | H | $CF_2Cl$ | B24 | 0 |
| A613 | H | $CH_3CH_2$ | H | $CF_2Cl$ | B24 | 0 |
| A614 | H | cyclopropyl | H | $CF_2Cl$ | B24 | 0 |
| A615 | H | $(CH_3)_3C$ | H | $CF_2Cl$ | B24 | 0 |
| A616 | H | $(CH_3)_2CH$ | H | $CF_2Cl$ | B24 | 0 |
| A617 | H | $CH_3(CH_2)_2$ | H | $CF_2Cl$ | B24 | 0 |
| A618 | H | $CH_3OCH_2$ | H | $CF_2Cl$ | B24 | 0 |
| A619 | H | $CH_3O(CH_2)_2$ | H | $CF_2Cl$ | B24 | 0 |
| A620 | H | Ph | H | $CF_2Cl$ | B24 | 0 |
| A621 | H | PhO | H | $CF_2Cl$ | B24 | 0 |
| A622 | H | PhS | H | $CF_2Cl$ | B24 | 0 |
| A623 | H | PhSO | H | $CF_2Cl$ | B24 | 0 |
| A624 | H | $PhSO_2$ | H | $CF_2Cl$ | B24 | 0 |
| A625 | H | $CH_3S$ | H | $CF_2Cl$ | B24 | 0 |
| A626 | H | $CH_3SO$ | H | $CF_2Cl$ | B24 | 0 |
| A627 | H | $CF_3$ | H | $CF_2Cl$ | B24 | 0 |
| A628 | H | $F_2CH$ | H | $CF_2Cl$ | B24 | 0 |
| A629 | H | HCC | H | $CF_2Cl$ | B24 | 0 |
| A630 | H | $CH_3CC$ | H | $CF_2Cl$ | B24 | 0 |
| A631 | H | $CH_2$=CH | H | $CF_2Cl$ | B24 | 0 |
| A632 | H | $CH_2$=$CHCH_2$ | H | $CF_2Cl$ | B24 | 0 |
| A633 | H | $CH_3SO_2N(CH_3)$ | H | $CF_2Cl$ | B24 | 0 |
| A634 | H | $(CH_3)_2N$ | H | $CF_2Cl$ | B24 | 0 |
| A635 | H | $(CH_3)_2NSO_2$ | H | $CF_2Cl$ | B24 | 0 |
| A636 | H | $CH_3SCH_2$ | H | $CF_2Cl$ | B24 | 0 |
| A637 | H | $CH_3SOCH_2$ | H | $CF_2Cl$ | B24 | 0 |
| A638 | H | $CH_3SO_2CH_2$ | H | $CF_2Cl$ | B24 | 0 |
| A639 | H | $CH_3$ | H | $CHF_2$ | B24 | 0 |
| A640 | H | $CH_3CH_2$ | H | $CHF_2$ | B24 | 0 |
| A641 | H | cyclopropyl | H | $CHF_2$ | B24 | 0 |
| A642 | H | $(CH_3)_3C$ | H | $CHF_2$ | B24 | 0 |
| A643 | H | $(CH_3)_2CH$ | H | $CHF_2$ | B24 | 0 |
| A644 | H | $CH_3(CH_2)_2$ | H | $CHF_2$ | B24 | 0 |
| A645 | H | $CH_3OCH_2$ | H | $CHF_2$ | B24 | 0 |
| A646 | H | $CH_3O(CH_2)_2$ | H | $CHF_2$ | B24 | 0 |
| A647 | H | Ph | H | $CHF_2$ | B24 | 0 |

TABLE 7-continued

Compounds of the formula Ia (Ia)

| Comp. No. | R$_2$ | R$_3$ | R$_4$ | R$_5$ | Q$_1$ | p |
|---|---|---|---|---|---|---|
| A648 | H | PhO | H | CHF$_2$ | B24 | 0 |
| A649 | H | PhS | H | CHF$_2$ | B24 | 0 |
| A650 | H | PhSO | H | CHF$_2$ | B24 | 0 |
| A651 | H | PhSO$_2$ | H | CHF$_2$ | B24 | 0 |
| A652 | H | CH$_3$S | H | CHF$_2$ | B24 | 0 |
| A653 | H | CH$_3$SO | H | CHF$_2$ | B24 | 0 |
| A654 | H | CF$_3$ | H | CHF$_2$ | B24 | 0 |
| A655 | H | F$_2$CH | H | CHF$_2$ | B24 | 0 |
| A656 | H | HCC | H | CHF$_2$ | B24 | 0 |
| A657 | H | CH$_3$CC | H | CHF$_2$ | B24 | 0 |
| A658 | H | CH$_2$=CH | H | CHF$_2$ | B24 | 0 |
| A659 | H | CH$_2$=CHCH$_2$ | H | CHF$_2$ | B24 | 0 |
| A660 | H | CH$_3$SO$_2$N(CH$_3$) | H | CHF$_2$ | B24 | 0 |
| A661 | H | (CH$_3$)$_2$N | H | CHF$_2$ | B24 | 0 |
| A662 | H | (CH$_3$)$_2$NSO$_2$ | H | CHF$_2$ | B24 | 0 |
| A663 | H | CH$_3$SCH$_2$ | H | CHF$_2$ | B24 | 0 |
| A664 | H | CH$_3$SOCH$_2$ | H | CHF$_2$ | B24 | 0 |
| A665 | H | CH$_3$SO$_2$CH$_2$ | H | CHF$_2$ | B24 | 0 |
| A666 | H | CH$_3$ | H | CCl$_3$ | B24 | 0 |
| A667 | H | CH$_3$CH$_2$ | H | CCl$_3$ | B24 | 0 |
| A668 | H | cyclopropyl | H | CCl$_3$ | B24 | 0 |
| A669 | H | (CH$_3$)$_3$C | H | CCl$_3$ | B24 | 0 |
| A670 | H | (CH$_3$)$_2$CH | H | CCl$_3$ | B24 | 0 |
| A671 | H | CH$_3$(CH$_2$)$_2$ | H | CCl$_3$ | B24 | 0 |
| A672 | H | CH$_3$OCH$_2$ | H | CCl$_3$ | B24 | 0 |
| A673 | H | CH$_3$O(CH$_2$)$_2$ | H | CCl$_3$ | B24 | 0 |
| A674 | H | Ph | H | CCl$_3$ | B24 | 0 |
| A675 | H | PhO | H | CCl$_3$ | B24 | 0 |
| A676 | H | PhS | H | CCl$_3$ | B24 | 0 |
| A677 | H | PhSO | H | CCl$_3$ | B24 | 0 |
| A678 | H | PhSO$_2$ | H | CCl$_3$ | B24 | 0 |
| A679 | H | CH$_3$S | H | CCl$_3$ | B24 | 0 |
| A680 | H | CH$_3$SO | H | CCl$_3$ | B24 | 0 |
| A681 | H | CF$_3$ | H | CCl$_3$ | B24 | 0 |
| A682 | H | F$_2$CH | H | CCl$_3$ | B24 | 0 |
| A683 | H | HCC | H | CCl$_3$ | B24 | 0 |
| A684 | H | CH$_3$CC | H | CCl$_3$ | B24 | 0 |
| A685 | H | CH$_2$=CH | H | CCl$_3$ | B24 | 0 |
| A686 | H | CH$_2$=CHCH$_2$ | H | CCl$_3$ | B24 | 0 |
| A687 | H | CH$_3$SO$_2$N(CH$_3$) | H | CCl$_3$ | B24 | 0 |
| A688 | H | (CH$_3$)$_2$N | H | CCl$_3$ | B24 | 0 |
| A689 | H | (CH$_3$)$_2$NSO$_2$ | H | CCl$_3$ | B24 | 0 |
| A690 | H | CH$_3$SCH$_2$ | H | CCl$_3$ | B24 | 0 |
| A691 | H | CH$_3$SOCH$_2$ | H | CCl$_3$ | B24 | 0 |
| A692 | H | CH$_3$SO$_2$CH$_2$ | H | CCl$_3$ | B24 | 0 |
| A693 | H | CH$_3$ | CH$_3$ | CF$_3$ | B24 | 0 |
| A694 | H | CH$_3$CH$_2$ | CH$_3$ | CF$_3$ | B24 | 0 |
| A695 | H | cyclopropyl | CH$_3$ | CF$_3$ | B24 | 0 |
| A696 | H | (CH$_3$)$_3$C | CH$_3$ | CF$_3$ | B24 | 0 |
| A697 | H | (CH$_3$)$_2$CH | CH$_3$ | CF$_3$ | B24 | 0 |
| A698 | H | CH$_3$(CH$_2$)$_2$ | CH$_3$ | CF$_3$ | B24 | 0 |
| A699 | H | CH$_3$OCH$_2$ | CH$_3$ | CF$_3$ | B24 | 0 |
| A700 | H | CH$_3$O(CH$_2$)$_2$ | CH$_3$ | CF$_3$ | B24 | 0 |
| A701 | H | Ph | CH$_3$ | CF$_3$ | B24 | 0 |
| A702 | H | PhO | CH$_3$ | CF$_3$ | B24 | 0 |
| A703 | H | PhS | CH$_3$ | CF$_3$ | B24 | 0 |
| A704 | H | PhSO | CH$_3$ | CF$_3$ | B24 | 0 |
| A705 | H | PhSO$_2$ | CH$_3$ | CF$_3$ | B24 | 0 |
| A706 | H | CH$_3$S | CH$_3$ | CF$_3$ | B24 | 0 |
| A707 | H | CH$_3$SO | CH$_3$ | CF$_3$ | B24 | 0 |
| A708 | H | CF$_3$ | CH$_3$ | CF$_3$ | B24 | 0 |
| A709 | H | F$_2$CH | CH$_3$ | CF$_3$ | B24 | 0 |
| A710 | H | HCC | CH$_3$ | CF$_3$ | B24 | 0 |

TABLE 7-continued

Compounds of the formula Ia $$\text{(Ia)}$$

| Comp. No. | $R_2$ | $R_3$ | $R_4$ | $R_5$ | $Q_1$ | p |
|---|---|---|---|---|---|---|
| A711 | H | CH$_3$CC | CH$_3$ | CF$_3$ | B24 | 0 |
| A712 | H | CH$_2$=CH | CH$_3$ | CF$_3$ | B24 | 0 |
| A713 | H | CH$_2$=CHCH$_2$ | CH$_3$ | CF$_3$ | B24 | 0 |
| A714 | H | CH$_3$SO$_2$N(CH$_3$) | CH$_3$ | CF$_3$ | B24 | 0 |
| A715 | H | (CH$_3$)$_2$N | CH$_3$ | CF$_3$ | B24 | 0 |
| A716 | H | (CH$_3$)$_2$NSO$_2$ | CH$_3$ | CF$_3$ | B24 | 0 |
| A717 | H | CH$_3$SCH$_2$ | CH$_3$ | CF$_3$ | B24 | 0 |
| A718 | H | CH$_3$SOCH$_2$ | CH$_3$ | CF$_3$ | B24 | 0 |
| A719 | H | CH$_3$SO$_2$CH$_2$ | CH$_3$ | CF$_3$ | B24 | 0 |
| A720 | H | CH$_3$ | CH$_3$ | CF$_3$CF$_2$ | B24 | 0 |
| A721 | H | CH$_3$CH$_2$ | CH$_3$ | CF$_3$CF$_2$ | B24 | 0 |
| A722 | H | cyclopropyl | CH$_3$ | CF$_3$CF$_2$ | B24 | 0 |
| A723 | H | (CH$_3$)$_3$C | CH$_3$ | CF$_3$CF$_2$ | B24 | 0 |
| A724 | H | (CH$_3$)$_2$CH | CH$_3$ | CF$_3$CF$_2$ | B24 | 0 |
| A725 | H | CH$_3$(CH$_2$)$_2$ | CH$_3$ | CF$_3$CF$_2$ | B24 | 0 |
| A726 | H | CH$_3$OCH$_2$ | CH$_3$ | CF$_3$CF$_2$ | B24 | 0 |
| A727 | H | CH$_3$O(CH$_2$)$_2$ | CH$_3$ | CF$_3$CF$_2$ | B24 | 0 |
| A728 | H | Ph | CH$_3$ | CF$_3$CF$_2$ | B24 | 0 |
| A729 | H | PhO | CH$_3$ | CF$_3$CF$_2$ | B24 | 0 |
| A730 | H | PhS | CH$_3$ | CF$_3$CF$_2$ | B24 | 0 |
| A731 | H | PhSO | CH$_3$ | CF$_3$CF$_2$ | B24 | 0 |
| A732 | H | PhSO$_2$ | CH$_3$ | CF$_3$CF$_2$ | B24 | 0 |
| A733 | H | CH$_3$S | CH$_3$ | CF$_3$CF$_2$ | B24 | 0 |
| A734 | H | CH$_3$SO | CH$_3$ | CF$_3$CF$_2$ | B24 | 0 |
| A735 | H | CF$_3$ | CH$_3$ | CF$_3$CF$_2$ | B24 | 0 |
| A736 | H | F$_2$CH | CH$_3$ | CF$_3$CF$_2$ | B24 | 0 |
| A737 | H | HCC | CH$_3$ | CF$_3$CF$_2$ | B24 | 0 |
| A738 | H | CH$_3$CC | CH$_3$ | CF$_3$CF$_2$ | B24 | 0 |
| A739 | H | CH$_2$=CH | CH$_3$ | CF$_3$CF$_2$ | B24 | 0 |
| A740 | H | CH$_2$=CHCH$_2$ | CH$_3$ | CF$_3$CF$_2$ | B24 | 0 |
| A741 | H | CH$_3$SO$_2$N(CH$_3$) | CH$_3$ | CF$_3$CF$_2$ | B24 | 0 |
| A742 | H | (CH$_3$)$_2$N | CH$_3$ | CF$_3$CF$_2$ | B24 | 0 |
| A743 | H | (CH$_3$)$_2$NSO$_2$ | CH$_3$ | CF$_3$CF$_2$ | B24 | 0 |
| A744 | H | CH$_3$SCH$_2$ | CH$_3$ | CF$_3$CF$_2$ | B24 | 0 |
| A745 | H | CH$_3$SOCH$_2$ | CH$_3$ | CF$_3$CF$_2$ | B24 | 0 |
| A746 | H | CH$_3$SO$_2$CH$_2$ | CH$_3$ | CF$_3$CF$_2$ | B24 | 0 |
| A747 | H | CH$_3$ | CH$_3$ | CF$_3$CF$_2$CF$_2$ | B24 | 0 |
| A748 | H | CH$_3$CH$_2$ | CH$_3$ | CF$_3$CF$_2$CF$_2$ | B24 | 0 |
| A749 | H | cyclopropyl | CH$_3$ | CF$_3$CF$_2$CF$_2$ | B24 | 0 |
| A750 | H | (CH$_3$)$_3$C | CH$_3$ | CF$_3$CF$_2$CF$_2$ | B24 | 0 |
| A751 | H | (CH$_3$)$_2$CH | CH$_3$ | CF$_3$CF$_2$CF$_2$ | B24 | 0 |
| A752 | H | CH$_3$(CH$_2$)$_2$ | CH$_3$ | CF$_3$CF$_2$CF$_2$ | B24 | 0 |
| A753 | H | CH$_3$OCH$_2$ | CH$_3$ | CF$_3$CF$_2$CF$_2$ | B24 | 0 |
| A754 | H | CH$_3$O(CH$_2$)$_2$ | CH$_3$ | CF$_3$CF$_2$CF$_2$ | B24 | 0 |
| A755 | H | Ph | CH$_3$ | CF$_3$CF$_2$CF$_2$ | B24 | 0 |
| A756 | H | PhO | CH$_3$ | CF$_3$CF$_2$CF$_2$ | B24 | 0 |
| A757 | H | PhS | CH$_3$ | CF$_3$CF$_2$CF$_2$ | B24 | 0 |
| A758 | H | PhSO | CH$_3$ | CF$_3$CF$_2$CF$_2$ | B24 | 0 |
| A759 | H | PhSO$_2$ | CH$_3$ | CF$_3$CF$_2$CF$_2$ | B24 | 0 |
| A760 | H | CH$_3$S | CH$_3$ | CF$_3$CF$_2$CF$_2$ | B24 | 0 |
| A761 | H | CH$_3$SO | CH$_3$ | CF$_3$CF$_2$CF$_2$ | B24 | 0 |
| A762 | H | CF$_3$ | CH$_3$ | CF$_3$CF$_2$CF$_2$ | B24 | 0 |
| A763 | H | F$_2$CH | CH$_3$ | CF$_3$CF$_2$CF$_2$ | B24 | 0 |
| A764 | H | HCC | CH$_3$ | CF$_3$CF$_2$CF$_2$ | B24 | 0 |
| A765 | H | CH$_3$CC | CH$_3$ | CF$_3$CF$_2$CF$_2$ | B24 | 0 |
| A766 | H | CH$_2$=CH | CH$_3$ | CF$_3$CF$_2$CF$_2$ | B24 | 0 |
| A767 | H | CH$_2$=CHCH$_2$ | CH$_3$ | CF$_3$CF$_2$CF$_2$ | B24 | 0 |
| A768 | H | CH$_3$SO$_2$N(CH$_3$) | CH$_3$ | CF$_3$CF$_2$CF$_2$ | B24 | 0 |
| A769 | H | (CH$_3$)$_2$N | CH$_3$ | CF$_3$CF$_2$CF$_2$ | B24 | 0 |
| A770 | H | (CH$_3$)$_2$NSO$_2$ | CH$_3$ | CF$_3$CF$_2$CF$_2$ | B24 | 0 |
| A771 | H | CH$_3$SCH$_2$ | CH$_3$ | CF$_3$CF$_2$CF$_2$ | B24 | 0 |
| A772 | H | CH$_3$SOCH$_2$ | CH$_3$ | CF$_3$CF$_2$CF$_2$ | B24 | 0 |
| A773 | H | CH$_3$SO$_2$CH$_2$ | CH$_3$ | CF$_3$CF$_2$CF$_2$ | B24 | 0 |

TABLE 7-continued

Compounds of the formula Ia (Ia)

$$\text{structure with } R_3, R_4, R_5, R_2, Q_1, O, N, (O)_p$$

| Comp. No. | $R_2$ | $R_3$ | $R_4$ | $R_5$ | $Q_1$ | p |
|---|---|---|---|---|---|---|
| A774 | H | $CH_3$ | $CH_3$ | $CF_2Cl$ | B24 | 0 |
| A775 | H | $CH_3CH_2$ | $CH_3$ | $CF_2Cl$ | B24 | 0 |
| A776 | H | cyclopropyl | $CH_3$ | $CF_2Cl$ | B24 | 0 |
| A777 | H | $(CH_3)_3C$ | $CH_3$ | $CF_2Cl$ | B24 | 0 |
| A778 | H | $(CH_3)_2CH$ | $CH_3$ | $CF_2Cl$ | B24 | 0 |
| A779 | H | $CH_3(CH_2)_2$ | $CH_3$ | $CF_2Cl$ | B24 | 0 |
| A780 | H | $CH_3OCH_2$ | $CH_3$ | $CF_2Cl$ | B24 | 0 |
| A781 | H | $CH_3O(CH_2)_2$ | $CH_3$ | $CF_2Cl$ | B24 | 0 |
| A782 | H | Ph | $CH_3$ | $CF_2Cl$ | B24 | 0 |
| A783 | H | PhO | $CH_3$ | $CF_2Cl$ | B24 | 0 |
| A784 | H | PhS | $CH_3$ | $CF_2Cl$ | B24 | 0 |
| A785 | H | PhSO | $CH_3$ | $CF_2Cl$ | B24 | 0 |
| A786 | H | $PhSO_2$ | $CH_3$ | $CF_2Cl$ | B24 | 0 |
| A787 | H | $CH_3S$ | $CH_3$ | $CF_2Cl$ | B24 | 0 |
| A788 | H | $CH_3SO$ | $CH_3$ | $CF_2Cl$ | B24 | 0 |
| A789 | H | $CF_3$ | $CH_3$ | $CF_2Cl$ | B24 | 0 |
| A790 | H | $F_2CH$ | $CH_3$ | $CF_2Cl$ | B24 | 0 |
| A791 | H | HCC | $CH_3$ | $CF_2Cl$ | B24 | 0 |
| A792 | H | $CH_3CC$ | $CH_3$ | $CF_2Cl$ | B24 | 0 |
| A793 | H | $CH_2=CH$ | $CH_3$ | $CF_2Cl$ | B24 | 0 |
| A794 | H | $CH_2=CHCH_2$ | $CH_3$ | $CF_2Cl$ | B24 | 0 |
| A795 | H | $CH_3SO_2N(CH_3)$ | $CH_3$ | $CF_2Cl$ | B24 | 0 |
| A796 | H | $(CH_3)_2N$ | $CH_3$ | $CF_2Cl$ | B24 | 0 |
| A797 | H | $(CH_3)_2NSO_2$ | $CH_3$ | $CF_2Cl$ | B24 | 0 |
| A798 | H | $CH_3SCH_2$ | $CH_3$ | $CF_2Cl$ | B24 | 0 |
| A799 | H | $CH_3SOCH_2$ | $CH_3$ | $CF_2Cl$ | B24 | 0 |
| A800 | H | $CH_3SO_2CH_2$ | $CH_3$ | $CF_2Cl$ | B24 | 0 |
| A801 | H | $CH_3$ | $CH_3$ | $CHF_2$ | B24 | 0 |
| A802 | H | $CH_3CH_2$ | $CH_3$ | $CHF_2$ | B24 | 0 |
| A803 | H | cyclopropyl | $CH_3$ | $CHF_2$ | B24 | 0 |
| A804 | H | $(CH_3)_3C$ | $CH_3$ | $CHF_2$ | B24 | 0 |
| A805 | H | $(CH_3)_2CH$ | $CH_3$ | $CHF_2$ | B24 | 0 |
| A806 | H | $CH_3(CH_2)_2$ | $CH_3$ | $CHF_2$ | B24 | 0 |
| A807 | H | $CH_3OCH_2$ | $CH_3$ | $CHF_2$ | B24 | 0 |
| A808 | H | $CH_3O(CH_2)_2$ | $CH_3$ | $CHF_2$ | B24 | 0 |
| A809 | H | Ph | $CH_3$ | $CHF_2$ | B24 | 0 |
| A810 | H | PhO | $CH_3$ | $CHF_2$ | B24 | 0 |
| A811 | H | PhS | $CH_3$ | $CHF_2$ | B24 | 0 |
| A812 | H | PhSO | $CH_3$ | $CHF_2$ | B24 | 0 |
| A813 | H | $PhSO_2$ | $CH_3$ | $CHF_2$ | B24 | 0 |
| A814 | H | $CH_3S$ | $CH_3$ | $CHF_2$ | B24 | 0 |
| A815 | H | $CH_3SO$ | $CH_3$ | $CHF_2$ | B24 | 0 |
| A816 | H | $CF_3$ | $CH_3$ | $CHF_2$ | B24 | 0 |
| A817 | H | $F_2CH$ | $CH_3$ | $CHF_2$ | B24 | 0 |
| A818 | H | HCC | $CH_3$ | $CHF_2$ | B24 | 0 |
| A819 | H | $CH_3CC$ | $CH_3$ | $CHF_2$ | B24 | 0 |
| A820 | H | $CH_2=CH$ | $CH_3$ | $CHF_2$ | B24 | 0 |
| A821 | H | $CH_2=CHCH_2$ | $CH_3$ | $CHF_2$ | B24 | 0 |
| A822 | H | $CH_3SO_2N(CH_3)$ | $CH_3$ | $CHF_2$ | B24 | 0 |
| A823 | H | $(CH_3)_2N$ | $CH_3$ | $CHF_2$ | B24 | 0 |
| A824 | H | $(CH_3)_2NSO_2$ | $CH_3$ | $CHF_2$ | B24 | 0 |
| A825 | H | $CH_3SCH_2$ | $CH_3$ | $CHF_2$ | B24 | 0 |
| A826 | H | $CH_3SOCH_2$ | $CH_3$ | $CHF_2$ | B24 | 0 |
| A827 | H | $CH_3SO_2CH_2$ | $CH_3$ | $CHF_2$ | B24 | 0 |
| A828 | H | $CH_3$ | $CH_3$ | $CCl_3$ | B24 | 0 |
| A829 | H | $CH_3CH_2$ | $CH_3$ | $CCl_3$ | B24 | 0 |
| A830 | H | cyclopropyl | $CH_3$ | $CCl_3$ | B24 | 0 |
| A831 | H | $(CH_3)_3C$ | $CH_3$ | $CCl_3$ | B24 | 0 |
| A832 | H | $(CH_3)_2CH$ | $CH_3$ | $CCl_3$ | B24 | 0 |
| A833 | H | $CH_3(CH_2)_2$ | $CH_3$ | $CCl_3$ | B24 | 0 |
| A834 | H | $CH_3OCH_2$ | $CH_3$ | $CCl_3$ | B24 | 0 |
| A835 | H | $CH_3O(CH_2)_2$ | $CH_3$ | $CCl_3$ | B24 | 0 |
| A836 | H | Ph | $CH_3$ | $CCl_3$ | B24 | 0 |

TABLE 7-continued

Compounds of the formula Ia (Ia)

| Comp. No. | $R_2$ | $R_3$ | $R_4$ | $R_5$ | $Q_1$ | p |
|---|---|---|---|---|---|---|
| A837 | H | PhO | $CH_3$ | $CCl_3$ | B24 | 0 |
| A838 | H | PhS | $CH_3$ | $CCl_3$ | B24 | 0 |
| A839 | H | PhSO | $CH_3$ | $CCl_3$ | B24 | 0 |
| A840 | H | $PhSO_2$ | $CH_3$ | $CCl_3$ | B24 | 0 |
| A841 | H | $CH_3S$ | $CH_3$ | $CCl_3$ | B24 | 0 |
| A842 | H | $CH_3SO$ | $CH_3$ | $CCl_3$ | B24 | 0 |
| A843 | H | $CF_3$ | $CH_3$ | $CCl_3$ | B24 | 0 |
| A844 | H | $F_2CH$ | $CH_3$ | $CCl_3$ | B24 | 0 |
| A845 | H | HCC | $CH_3$ | $CCl_3$ | B24 | 0 |
| A846 | H | $CH_3CC$ | $CH_3$ | $CCl_3$ | B24 | 0 |
| A847 | H | $CH_2$=CH | $CH_3$ | $CCl_3$ | B24 | 0 |
| A848 | H | $CH_2$=$CHCH_2$ | $CH_3$ | $CCl_3$ | B24 | 0 |
| A849 | H | $CH_3SO_2N(CH_3)$ | $CH_3$ | $CCl_3$ | B24 | 0 |
| A850 | H | $(CH_3)_2N$ | $CH_3$ | $CCl_3$ | B24 | 0 |
| A851 | H | $(CH_3)_2NSO_2$ | $CH_3$ | $CCl_3$ | B24 | 0 |
| A852 | H | $CH_3SCH_2$ | $CH_3$ | $CCl_3$ | B24 | 0 |
| A853 | H | $CH_3SOCH_2$ | $CH_3$ | $CCl_3$ | B24 | 0 |
| A854 | H | $CH_3SO_2CH_2$ | $CH_3$ | $CCl_3$ | B24 | 0 |
| A855 | H | $CH_3$ | Ph | $CF_3$ | B24 | 0 |
| A856 | H | $CH_3CH_2$ | Ph | $CF_3$ | B24 | 0 |
| A857 | H | $(CH_3)_2CH$ | Ph | $CF_3$ | B24 | 0 |
| A858 | H | $(CH_3)_2CH$ | Ph | $CF_3$ | B24 | 0 |
| A859 | H | cyclopropyl | Ph | $CF_3$ | B24 | 0 |
| A860 | H | $CH_3(CH_2)_2$ | Ph | $CF_3$ | B24 | 0 |
| A861 | H | $CH_3OCH_2$ | Ph | $CF_3$ | B24 | 0 |
| A862 | H | $CH_3O(CH_2)_2$ | Ph | $CF_3$ | B24 | 0 |
| A863 | H | Ph | Ph | $CF_3$ | B24 | 0 |
| A864 | H | PhO | Ph | $CF_3$ | B24 | 0 |
| A865 | H | PhS | Ph | $CF_3$ | B24 | 0 |
| A866 | H | PhSO | Ph | $CF_3$ | B24 | 0 |
| A867 | H | $PhSO_2$ | Ph | $CF_3$ | B24 | 0 |
| A868 | H | $CH_3S$ | Ph | $CF_3$ | B24 | 0 |
| A869 | H | $CH_3SO$ | Ph | $CF_3$ | B24 | 0 |
| A870 | H | $CF_3$ | Ph | $CF_3$ | B24 | 0 |
| A871 | H | $F_2CH$ | Ph | $CF_3$ | B24 | 0 |
| A872 | H | HCC | Ph | $CF_3$ | B24 | 0 |
| A873 | H | $CH_3CC$ | Ph | $CF_3$ | B24 | 0 |
| A874 | H | $CH_2$=CH | Ph | $CF_3$ | B24 | 0 |
| A875 | H | $CH_2$=$CHCH_2$ | Ph | $CF_3$ | B24 | 0 |
| A876 | H | $CH_3SO_2N(CH_3)$ | Ph | $CF_3$ | B24 | 0 |
| A877 | H | $(CH_3)_2N$ | Ph | $CF_3$ | B24 | 0 |
| A878 | H | $(CH_3)_2NSO_2$ | Ph | $CF_3$ | B24 | 0 |
| A879 | H | $CH_3SCH_2$ | Ph | $CF_3$ | B24 | 0 |
| A880 | H | $CH_3SOCH_2$ | Ph | $CF_3$ | B24 | 0 |
| A881 | H | $CH_3SO_2CH_2$ | Ph | $CF_3$ | B24 | 0 |
| A882 | H | $CH_3$ | Ph | $CF_3CF_2$ | B24 | 0 |
| A883 | H | $CH_3CH_2$ | Ph | $CF_3CF_2$ | B24 | 0 |
| A884 | H | cyclopropyl | Ph | $CF_3CF_2$ | B24 | 0 |
| A885 | H | $(CH_3)_3C$ | Ph | $CF_3CF_2$ | B24 | 0 |
| A886 | H | $(CH_3)_2CH$ | Ph | $CF_3CF_2$ | B24 | 0 |
| A887 | H | $CH_3(CH_2)_2$ | Ph | $CF_3CF_2$ | B24 | 0 |
| A888 | H | $CH_3OCH_2$ | Ph | $CF_3CF_2$ | B24 | 0 |
| A889 | H | $CH_3O(CH_2)_2$ | Ph | $CF_3CF_2$ | B24 | 0 |
| A890 | H | Ph | Ph | $CF_3CF_2$ | B24 | 0 |
| A891 | H | PhO | Ph | $CF_3CF_2$ | B24 | 0 |
| A892 | H | PhS | Ph | $CF_3CF_2$ | B24 | 0 |
| A893 | H | PhSO | Ph | $CF_3CF_2$ | B24 | 0 |
| A894 | H | $PhSO_2$ | Ph | $CF_3CF_2$ | B24 | 0 |
| A895 | H | $CH_3S$ | Ph | $CF_3CF_2$ | B24 | 0 |
| A896 | H | $CH_3SO$ | Ph | $CF_3CF_2$ | B24 | 0 |
| A897 | H | $CF_3$ | Ph | $CF_3CF_2$ | B24 | 0 |
| A898 | H | $F_2CH$ | Ph | $CF_3CF_2$ | B24 | 0 |
| A899 | H | HCC | Ph | $CF_3CF_2$ | B24 | 0 |

TABLE 7-continued

Compounds of the formula Ia $$\text{(Ia)}$$

| Comp. No. | $R_2$ | $R_3$ | $R_4$ | $R_5$ | $Q_1$ | p |
|---|---|---|---|---|---|---|
| A900 | H | CH$_3$CC | Ph | CF$_3$CF$_2$ | B24 | 0 |
| A901 | H | CH$_2$=CH | Ph | CF$_3$CF$_2$ | B24 | 0 |
| A902 | H | CH$_2$=CHCH$_2$ | Ph | CF$_3$CF$_2$ | B24 | 0 |
| A903 | H | CH$_3$SO$_2$N(CH$_3$) | Ph | CF$_3$CF$_2$ | B24 | 0 |
| A904 | H | (CH$_3$)$_2$N | Ph | CF$_3$CF$_2$ | B24 | 0 |
| A905 | H | (CH$_3$)$_2$NSO$_2$ | Ph | CF$_3$CF$_2$ | B24 | 0 |
| A906 | H | CH$_3$SCH$_2$ | Ph | CF$_3$CF$_2$ | B24 | 0 |
| A907 | H | CH$_3$SOCH$_2$ | Ph | CF$_3$CF$_2$ | B24 | 0 |
| A908 | H | CH$_3$SO$_2$CH$_2$ | Ph | CF$_3$CF$_2$ | B24 | 0 |
| A909 | H | CH$_3$ | Ph | CF$_3$CF$_2$CF$_2$ | B24 | 0 |
| A910 | H | CH$_3$CH$_2$ | Ph | CF$_3$CF$_2$CF$_2$ | B24 | 0 |
| A911 | H | cyclopropyl | Ph | CF$_3$CF$_2$CF$_2$ | B24 | 0 |
| A912 | H | (CH$_3$)$_3$C | Ph | CF$_3$CF$_2$CF$_2$ | B24 | 0 |
| A913 | H | (CH$_3$)$_2$CH | Ph | CF$_3$CF$_2$CF$_2$ | B24 | 0 |
| A914 | H | CH$_3$(CH$_2$)$_2$ | Ph | CF$_3$CF$_2$CF$_2$ | B24 | 0 |
| A915 | H | CH$_3$OCH$_2$ | Ph | CF$_3$CF$_2$CF$_2$ | B24 | 0 |
| A916 | H | CH$_3$O(CH$_2$)$_2$ | Ph | CF$_3$CF$_2$CF$_2$ | B24 | 0 |
| A917 | H | Ph | Ph | CF$_3$CF$_2$CF$_2$ | B24 | 0 |
| A918 | H | PhO | Ph | CF$_3$CF$_2$CF$_2$ | B24 | 0 |
| A919 | H | PhS | Ph | CF$_3$CF$_2$CF$_2$ | B24 | 0 |
| A920 | H | PhSO | Ph | CF$_3$CF$_2$CF$_2$ | B24 | 0 |
| A921 | H | PhSO$_2$ | Ph | CF$_3$CF$_2$CF$_2$ | B24 | 0 |
| A922 | H | CH$_3$S | Ph | CF$_3$CF$_2$CF$_2$ | B24 | 0 |
| A923 | H | CH$_3$SO | Ph | CF$_3$CF$_2$CF$_2$ | B24 | 0 |
| A924 | H | CF$_3$ | Ph | CF$_3$CF$_2$CF$_2$ | B24 | 0 |
| A925 | H | F$_2$CH | Ph | CF$_3$CF$_2$CF$_2$ | B24 | 0 |
| A926 | H | HCC | Ph | CF$_3$CF$_2$CF$_2$ | B24 | 0 |
| A927 | H | CH$_3$CC | Ph | CF$_3$CF$_2$CF$_2$ | B24 | 0 |
| A928 | H | CH$_2$=CH | Ph | CF$_3$CF$_2$CF$_2$ | B24 | 0 |
| A929 | H | CH$_2$=CHCH$_2$ | Ph | CF$_3$CF$_2$CF$_2$ | B24 | 0 |
| A930 | H | CH$_3$SO$_2$N(CH$_3$) | Ph | CF$_3$CF$_2$CF$_2$ | B24 | 0 |
| A931 | H | (CH$_3$)$_2$N | Ph | CF$_3$CF$_2$CF$_2$ | B24 | 0 |
| A932 | H | (CH$_3$)$_2$NSO$_2$ | Ph | CF$_3$CF$_2$CF$_2$ | B24 | 0 |
| A933 | H | CH$_3$SCH$_2$ | Ph | CF$_3$CF$_2$CF$_2$ | B24 | 0 |
| A934 | H | CH$_3$SOCH$_2$ | Ph | CF$_3$CF$_2$CF$_2$ | B24 | 0 |
| A935 | H | CH$_3$SO$_2$CH$_2$ | Ph | CF$_3$CF$_2$CF$_2$ | B24 | 0 |
| A936 | H | CH$_3$ | Ph | CF$_2$Cl | B24 | 0 |
| A937 | H | CH$_3$CH$_2$ | Ph | CF$_2$Cl | B24 | 0 |
| A938 | H | cyclopropyl | Ph | CF$_2$Cl | B24 | 0 |
| A939 | H | (CH$_3$)$_3$C | Ph | CF$_2$Cl | B24 | 0 |
| A940 | H | (CH$_3$)$_2$CH | Ph | CF$_2$Cl | B24 | 0 |
| A941 | H | CH$_3$(CH$_2$)$_2$ | Ph | CF$_2$Cl | B24 | 0 |
| A942 | H | CH$_3$OCH$_2$ | Ph | CF$_2$Cl | B24 | 0 |
| A943 | H | CH$_3$O(CH$_2$)$_2$ | Ph | CF$_2$Cl | B24 | 0 |
| A944 | H | Ph | Ph | CF$_2$Cl | B24 | 0 |
| A945 | H | PhO | Ph | CF$_2$Cl | B24 | 0 |
| A946 | H | PhS | Ph | CF$_2$Cl | B24 | 0 |
| A947 | H | PhSO | Ph | CF$_2$Cl | B24 | 0 |
| A948 | H | PhSO$_2$ | Ph | CF$_2$Cl | B24 | 0 |
| A949 | H | CH$_3$S | Ph | CF$_2$Cl | B24 | 0 |
| A950 | H | CH$_3$SO | Ph | CF$_2$Cl | B24 | 0 |
| A951 | H | CF$_3$ | Ph | CF$_2$Cl | B24 | 0 |
| A952 | H | F$_2$CH | Ph | CF$_2$Cl | B24 | 0 |
| A953 | H | HCC | Ph | CF$_2$Cl | B24 | 0 |
| A954 | H | CH$_3$CC | Ph | CF$_2$Cl | B24 | 0 |
| A955 | H | CH$_2$=CH | Ph | CF$_2$Cl | B24 | 0 |
| A956 | H | CH$_2$=CHCH$_2$ | Ph | CF$_2$Cl | B24 | 0 |
| A957 | H | CH$_3$SO$_2$N(CH$_3$) | Ph | CF$_2$Cl | B24 | 0 |
| A958 | H | (CH$_3$)$_2$N | Ph | CF$_2$Cl | B24 | 0 |
| A959 | H | (CH$_3$)$_2$NSO$_2$ | Ph | CF$_2$Cl | B24 | 0 |
| A960 | H | CH$_3$SCH$_2$ | Ph | CF$_2$Cl | B24 | 0 |
| A961 | H | CH$_3$SOCH$_2$ | Ph | CF$_2$Cl | B24 | 0 |
| A962 | H | CH$_3$SO$_2$CH$_2$ | Ph | CF$_2$Cl | B24 | 0 |

TABLE 7-continued

Compounds of the formula Ia $$\text{(Ia)}$$

| Comp. No. | $R_2$ | $R_3$ | $R_4$ | $R_5$ | $Q_1$ | p |
|---|---|---|---|---|---|---|
| A963 | H | $CH_3$ | Ph | $CHF_2$ | B24 | 0 |
| A964 | H | $CH_3CH_2$ | Ph | $CHF_2$ | B24 | 0 |
| A965 | H | $(CH_3)_3C$ | Ph | $CHF_2$ | B24 | 0 |
| A966 | H | $(CH_3)_2CH$ | Ph | $CHF_2$ | B24 | 0 |
| A967 | H | cyclopropyl | Ph | $CHF_2$ | B24 | 0 |
| A968 | H | $CH_3(CH_2)_2$ | Ph | $CHF_2$ | B24 | 0 |
| A969 | H | $CH_3OCH_2$ | Ph | $CHF_2$ | B24 | 0 |
| A970 | H | $CH_3O(CH_2)_2$ | Ph | $CHF_2$ | B24 | 0 |
| A971 | H | Ph | Ph | $CHF_2$ | B24 | 0 |
| A972 | H | PhO | Ph | $CHF_2$ | B24 | 0 |
| A973 | H | PhS | Ph | $CHF_2$ | B24 | 0 |
| A974 | H | PhSO | Ph | $CHF_2$ | B24 | 0 |
| A975 | H | $PhSO_2$ | Ph | $CHF_2$ | B24 | 0 |
| A976 | H | $CH_3S$ | Ph | $CHF_2$ | B24 | 0 |
| A977 | H | $CH_3SO$ | Ph | $CHF_2$ | B24 | 0 |
| A978 | H | $CF_3$ | Ph | $CHF_2$ | B24 | 0 |
| A979 | H | $F_2CH$ | Ph | $CHF_2$ | B24 | 0 |
| A980 | H | HCC | Ph | $CHF_2$ | B24 | 0 |
| A981 | H | $CH_3CC$ | Ph | $CHF_2$ | B24 | 0 |
| A982 | H | $CH_2=CH$ | Ph | $CHF_2$ | B24 | 0 |
| A983 | H | $CH_2=CHCH_2$ | Ph | $CHF_2$ | B24 | 0 |
| A984 | H | $CH_3SO_2N(CH_3)$ | Ph | $CHF_2$ | B24 | 0 |
| A985 | H | $(CH_3)_2N$ | Ph | $CHF_2$ | B24 | 0 |
| A986 | H | $(CH_3)_2NSO_2$ | Ph | $CHF_2$ | B24 | 0 |
| A987 | H | $CH_3SCH_2$ | Ph | $CHF_2$ | B24 | 0 |
| A988 | H | $CH_3SOCH_2$ | Ph | $CHF_2$ | B24 | 0 |
| A989 | H | $CH_3SO_2CH_2$ | Ph | $CHF_2$ | B24 | 0 |
| A990 | H | $CH_3$ | Ph | $CCl_3$ | B24 | 0 |
| A991 | H | $CH_3CH_2$ | Ph | $CCl_3$ | B24 | 0 |
| A992 | H | $(CH_3)_3C$ | Ph | $CCl_3$ | B24 | 0 |
| A993 | H | $(CH_3)_2CH$ | Ph | $CCl_3$ | B24 | 0 |
| A994 | H | cyclopropyl | Ph | $CCl_3$ | B24 | 0 |
| A995 | H | $CH_3(CH_2)_2$ | Ph | $CCl_3$ | B24 | 0 |
| A996 | H | $CH_3OCH_2$ | Ph | $CCl_3$ | B24 | 0 |
| A997 | H | $CH_3O(CH_2)_2$ | Ph | $CCl_3$ | B24 | 0 |
| A998 | H | Ph | Ph | $CCl_3$ | B24 | 0 |
| A999 | H | PhO | Ph | $CCl_3$ | B24 | 0 |
| A1000 | H | PhS | Ph | $CCl_3$ | B24 | 0 |
| A1001 | H | PhSO | Ph | $CCl_3$ | B24 | 0 |
| A1002 | H | $PhSO_2$ | Ph | $CCl_3$ | B24 | 0 |
| A1003 | H | $CH_3S$ | Ph | $CCl_3$ | B24 | 0 |
| A1004 | H | $CH_3SO$ | Ph | $CCl_3$ | B24 | 0 |
| A1005 | H | $CF_3$ | Ph | $CCl_3$ | B24 | 0 |
| A1006 | H | $F_2CH$ | Ph | $CCl_3$ | B24 | 0 |
| A1007 | H | HCC | Ph | $CCl_3$ | B24 | 0 |
| A1008 | H | $CH_3CC$ | Ph | $CCl_3$ | B24 | 0 |
| A1009 | H | $CH_2=CH$ | Ph | $CCl_3$ | B24 | 0 |
| A1010 | H | $CH_2=CHCH_2$ | Ph | $CCl_3$ | B24 | 0 |
| A1011 | H | $CH_3SO_2N(CH_3)$ | Ph | $CCl_3$ | B24 | 0 |
| A1012 | H | $(CH_3)_2N$ | Ph | $CCl_3$ | B24 | 0 |
| A1013 | H | $(CH_3)_2NSO_2$ | Ph | $CCl_3$ | B24 | 0 |
| A1014 | H | $CH_3SCH_2$ | Ph | $CCl_3$ | B24 | 0 |
| A1015 | H | $CH_3SOCH_2$ | Ph | $CCl_3$ | B24 | 0 |
| A1016 | H | $CH_3SO_2CH_2$ | Ph | $CCl_3$ | B24 | 0 |
| A1017 | F | H | H | $CF_3$ | B24 | 0 |
| A1018 | Cl | H | H | $CF_3$ | B24 | 0 |
| A1019 | Br | H | H | $CF_3$ | B24 | 0 |
| A1020 | NC | H | H | $CF_3$ | B24 | 0 |
| A1021 | $CH_3SO_2O$ | H | H | $CF_3$ | B24 | 0 |
| A1022 | $CH_3O$ | H | H | $CF_3$ | B24 | 0 |
| A1023 | $CH_3CH_2O$ | H | H | $CF_3$ | B24 | 0 |
| A1024 | $CH_2CH=CH_2O$ | H | H | $CF_3$ | B24 | 0 |
| A1025 | $HCCCH_2O$ | H | H | $CF_3$ | B24 | 0 |

TABLE 7-continued

Compounds of the formula Ia (Ia)

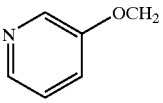

| Comp. No. | $R_2$ | $R_3$ | $R_4$ | $R_5$ | $Q_1$ | p |
|---|---|---|---|---|---|---|
| A1026 | PhCH$_2$S | H | H | CF$_3$ | B24 | 0 |
| A1027 | PhCH$_2$SO$_2$ | H | H | CF$_3$ | B24 | 0 |
| A1028 | ClCH$_2$CH$_2$ | H | H | CF$_3$ | B24 | 0 |
| A1029 | BrCH$_2$ | H | H | CF$_3$ | B24 | 0 |
| A1030 | FCH$_2$ | H | H | CF$_3$ | B24 | 0 |
| A1031 | CHF$_2$CH$_2$ | H | H | CF$_3$ | B24 | 0 |
| A1032 | CF$_3$CH$_2$ | H | H | CF$_3$ | B24 | 0 |
| A1033 | [1,3]-imidazol-1-ylmethyl | H | H | CF$_3$ | B24 | 0 |
| A1034 | CHCl$_2$CH$_2$ | H | H | CF$_3$ | B24 | 0 |
| A1035 | ClCH=CH | H | H | CF$_3$ | B24 | 0 |
| A1036 | Cl$_2$C=CH | H | H | CF$_3$ | B24 | 0 |
| A1037 | CF$_3$CH=CH | H | H | CF$_3$ | B24 | 0 |
| A1038 | ClCC | H | H | CF$_3$ | B24 | 0 |
| A1039 | PhCH$_2$ | H | H | CF$_3$ | B24 | 0 |
| A1040 | CH$_3$CH$_2$ | CH$_3$ | H | CF$_3$ | B24 | 0 |
| A1041 | CH$_3$ | OH | H | CF$_3$ | B24 | 0 |
| A1042 | CH$_3$ | F | H | CF$_3$ | B24 | 0 |
| A1043 | CH$_3$ | Cl | H | CF$_3$ | B24 | 0 |
| A1044 | F | CH$_3$ | H | CF$_3$ | B24 | 0 |
| A1045 | Cl | CH$_3$ | H | CF$_3$ | B24 | 0 |
| A1046 | H | F | H | CF$_3$ | B24 | 0 |
| A1047 | H | Cl | H | CF$_3$ | B24 | 0 |
| A1048 | H | Br | H | CF$_3$ | B24 | 0 |
| A1049 | H | OH | H | CF$_3$ | B24 | 0 |
| A1050 | H | OCH$_3$ | H | CF$_3$ | B24 | 0 |
| A1051 | H | OCHF$_2$ | H | CF$_3$ | B24 | 0 |
| A1052 | H | OSO$_2$CH$_3$ | H | CF$_3$ | B24 | 0 |
| A1053 | H | OSO$_2$CF$_3$ | H | CF$_3$ | B24 | 0 |
| A1054 | H | ClCH$_2$ | H | CF$_3$ | B24 | 0 |
| A1055 | H | BrCH$_2$ | H | CF$_3$ | B24 | 0 |
| A1056 | H | FCH$_2$ | H | CF$_3$ | B24 | 0 |
| A1057 | H | CHF$_2$CH$_2$ | H | CF$_3$ | B24 | 0 |
| A1058 | H | CF$_3$CH$_2$ | H | CF$_3$ | B24 | 0 |
| A1059 | H | triazolylmethyl | H | CF$_3$ | B24 | 0 |
| A1060 | H | CHCl$_2$CH$_2$ | H | CF$_3$ | B24 | 0 |
| A1061 | H | ClCH=CH | H | CF$_3$ | B24 | 0 |
| A1062 | H | Cl$_2$C=CH | H | CF$_3$ | B24 | 0 |
| A1063 | H | CF$_3$CH=CH | H | CF$_3$ | B24 | 0 |
| A1064 | H | ClCC | H | CF$_3$ | B24 | 0 |
| A1065 | H | CH$_3$C(O) | H | CF$_3$ | B24 | 0 |
| A1066 | H | Ph | H | CF$_3$ | B24 | 0 |
| A1067 | H | SO$_2$CH$_3$ | H | CF$_3$ | B24 | 0 |
| A1068 | H | SO$_2$CF$_3$ | H | CF$_3$ | B24 | 0 |
| A1069 | H | NC | H | CF$_3$ | B24 | 0 |
| A1070 | H | NO$_2$ | H | CF$_3$ | B24 | 0 |
| A1071 | CH$_3$ | H | F | CF$_3$ | B24 | 0 |
| A1072 | CH$_3$ | H | Cl | CF$_3$ | B24 | 0 |
| A1073 | CH$_3$ | H | Br | CF$_3$ | B24 | 0 |
| A1074 | CH$_3$ | H | NC | CF$_3$ | B24 | 0 |
| A1075 | CH$_3$ | H | CH$_3$O | CF$_3$ | B24 | 0 |
| A1076 | CH$_3$ | H | CH$_3$S | CF$_3$ | B24 | 0 |
| A1077 | CH$_3$ | H | CH$_3$SO | CF$_3$ | B24 | 0 |
| A1078 | CH$_3$ | H | CH$_3$SO$_2$ | CF$_3$ | B24 | 0 |
| A1079 | CH$_3$CH$_2$OCH$_2$ | H | H | CF$_3$ | B24 | 0 |
| A1080 | PhOCH$_2$ | H | H | CF$_3$ | B24 | 0 |
| A1081 | (pyridin-3-yl)OCH$_2$ | H | H | CF$_3$ | B24 | 0 |

TABLE 7-continued
Compounds of the formula Ia
(Ia)
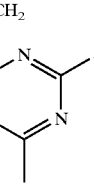
| Comp. No. | R₂ | R₃ | R₄ | R₅ | Q₁ | p |
|---|---|---|---|---|---|---|
| A1082 | (CH₃)₂CH₂OCH₂ | H | H | CF₃ | B24 | 0 |
| A1083 | BrCH₂CH₂ | H | H | CF₃ | B24 | 0 |
| A1084 | FCH₂CH₂ | H | H | CF₃ | B24 | 0 |
| A1085 | 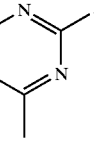 | H | H | CF₃ | | 0 |
| A1086 | 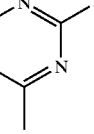 | H | H | CF₃ | B24 | 0 |
| A1087 | 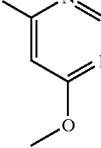 | H | H | CF₃ | B24 | 0 |
| A1088 | 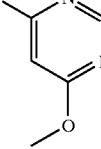 | H | H | CF₃ | B24 | 0 |
| A1089 | 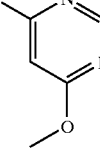 | H | H | CF₃ | B24 | 0 |
| A1090 |  | H | H | CF₃ | B24 | 0 |
| A1091 | cyclopropyl-CH₂ | H | H | CF₃ | B24 | 0 |
| A1092 | 2,2-dichlorocycloprop-1-yl | H | H | CF₃ | B24 | 0 |
| A1093 | CH₃OC(O)CH=CH | H | H | CF₃ | B24 | 0 |
| A1094 | CH₃CH₂OC(O)CH=CH | H | H | CF₃ | B24 | 0 |
| A1095 | ClCH₂CH=CH | H | H | CF₃ | | 0 |
| A1096 | CH=C=CH | H | H | CF₃ | B24 | 0 |
| A1097 | (CH₃)₂NCH₂ | H | H | CF₃ | B24 | 0 |
| A1098 | HOCH₂ | H | H | CF₃ | B24 | 0 |

TABLE 7-continued

Compounds of the formula Ia

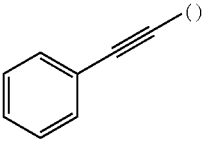

(Ia)

| Comp. No. | R₂ | R₃ | R₄ | R₅ | Q₁ | p |
|---|---|---|---|---|---|---|
| A1099 | CH₃C(O)OCH₂ | H | H | CF₃ | B24 | 0 |
| A1100 | PhC(O)OCH₂ | H | H | CF₃ | B24 | 0 |
| A1101 | PhCH₂CH₂ | H | H | CF₃ | B24 | 0 |
| A1102 | CH₃OC(O)CH₂ | H | H | CF₃ | B24 | 0 |
| A1103 | NCCH₂ | H | H | CF₃ | B24 | 0 |
| A1104 | CH₃(CH₂)₇SCH₂ | H | H | CF₃ | B24 | 0 |
| A1105 | CH₃(CH₂)₇SOCH₂ | H | H | CF₃ | B24 | 0 |
| A1106 | CH₃(CH₂)₇SO₂CH₂ | H | H | CF₃ | B24 | 0 |
| A1107 |  | H | H | CF₃ | B24 | 0 |
| A1108 | ClCH₂CC | H | H | CF₃ | B24 | 0 |
| A1109 | CHF₂CH₂CH₂ | H | H | CF₃ | B24 | 0 |
| A1110 | CHCl₂CH₂CH₂ | H | H | CF₃ | B24 | 0 |
| A1111 | CF₃SO₂O | H | H | CF₃ | B24 | 0 |
| A1112 |  | H | H | CF₃ | B24 | 0 |
| A1113 |  | H | H | CF₃ | B24 | 0 |
| A1114 | 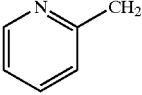 | H | H | CF₃ | B24 | 0 |
| A1115 | 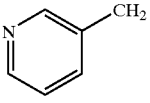 | H | H | CF₃ | B24 | 0 |
| A1116 | 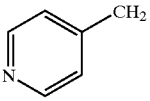 | H | H | CF₃ | B24 | 0 |
| A1117 |  | H | H | CF₃ | B24 | 0 |
| A1118 | CH₃ON=CHCH₂ | H | H | CF₃ | B24 | 0 |

TABLE 7-continued

Compounds of the formula Ia (Ia)

| Comp. No. | R₂ | R₃ | R₄ | R₅ | Q₁ | p |
|---|---|---|---|---|---|---|
| A1119 | O=CHCH₂ | H | H | CF₃ | B24 | 0 |
| A1120 | CH₃CH₂OCH₂ | H | H | CF₂Cl | B24 | 0 |
| A1121 | PhOCH₂ | H | H | CF₂Cl | B24 | 0 |
| A1122 | pyridin-3-yl-OCH₂ | H | H | CF₂Cl | B24 | 0 |
| A1123 | (CH₃)₂CH₂OCH₂ | H | H | CF₂Cl | B24 | 0 |
| A1124 | BrCH₂ | H | H | CF₂Cl | B24 | 0 |
| A1125 | FCH₂ | H | H | CF₂Cl | B24 | 0 |
| A1126 | (4,6-dimethylpyrimidin-2-yl)SCH₂ | H | H | CF₂Cl | B24 | 0 |
| A1127 | (4,6-dimethylpyrimidin-2-yl)SOCH₂ | H | H | CF₂Cl | B24 | 0 |
| A1128 | (4,6-dimethylpyrimidin-2-yl)SO₂CH₂ | H | H | CF₂Cl | B24 | 0 |
| A1129 | (4,6-dimethoxypyrimidin-2-yl)SCH₂ | H | H | CF₂Cl | B24 | 0 |
| A1130 | (4,6-dimethoxypyrimidin-2-yl)SOCH₂ | H | H | CF₂Cl | B24 | 0 |
| A1131 | (4,6-dimethoxypyrimidin-2-yl)SO₂CH₂ | H | H | CF₂Cl | B24 | 0 |

TABLE 7-continued

Compounds of the formula Ia

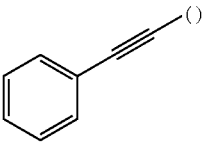

(Ia)

| Comp. No. | R₂ | R₃ | R₄ | R₅ | Q₁ | p |
|---|---|---|---|---|---|---|
| A1132 | cyclopropyl-CH₂ | H | H | CF₂Cl | B24 | 0 |
| A1133 | 2,2-dichlorocycloprop-1-yl | H | H | CF₂Cl | B24 | 0 |
| A1134 | CH₃OC(O)CH=CH | H | H | CF₂Cl | B24 | 0 |
| A1135 | CH₃CH₂OC(O)CH=CH | H | H | CF₂Cl | B24 | 0 |
| A1136 | ClCH₂CH=CH | H | H | CF₂Cl | B24 | 0 |
| A1137 | CH=C=CH | H | H | CF₂Cl | B24 | 0 |
| A1138 | (CH₃)₂NCH₂ | H | H | CF₂Cl | B24 | 0 |
| A1139 | HOCH₂ | H | H | CF₂Cl | B24 | 0 |
| A1140 | CH₃C(O)OCH₂ | H | H | CF₂Cl | B24 | 0 |
| A1141 | PhC(O)OCH₂ | H | H | CF₂Cl | B24 | 0 |
| A1142 | PhCH₂ | H | H | CF₂Cl | B24 | 0 |
| A1143 | CH₃OC(O)CH₂ | H | H | CF₂Cl | B24 | 0 |
| A1144 | NCCH₂ | H | H | CF₂Cl | B24 | 0 |
| A1145 | CH₃(CH₂)₇SCH₂ | H | H | CF₂C: | B24 | 0 |
| A1146 | CH₃(CH₂)₇SOCH₂ | H | H | CF₂Cl | B24 | 0 |
| A1147 | CH₃(CH₂)₇SO₂CH₂ | H | H | CF₂Cl | B24 | 0 |
| A1148 | 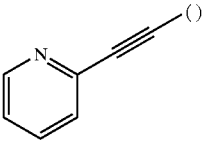 | H | H | CF₂Cl | B24 | 0 |
| A1149 | ClCH₂CC | H | H | CF₂Cl | B24 | 0 |
| A1150 | Br | H | H | CF₂Cl | B24 | 0 |
| A1151 | Cl | H | H | CF₂Cl | B24 | 0 |
| A1152 | CF₃SO₂O | H | H | CF₂Cl | B24 | 0 |
| A1153 | 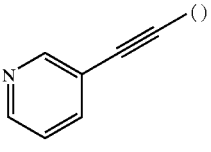 | H | H | CF₂Cl | B24 | 0 |
| A1154 | 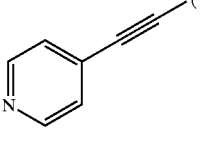 | H | H | CF₂Cl | B24 | 0 |
| A1155 | 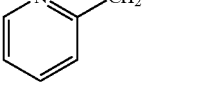 | H | H | CF₂Cl | B24 | 0 |
| A1156 |  | H | H | CF₂Cl | B24 | 0 |

TABLE 7-continued
Compounds of the formula Ia
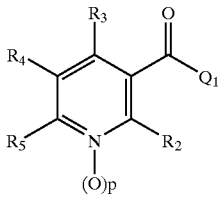
(Ia)
| Comp. No. | R$_2$ | R$_3$ | R$_4$ | R$_5$ | Q$_1$ | p |
|---|---|---|---|---|---|---|
| A1157 | 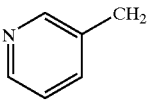 | H | H | CF$_2$Cl | B24 | 0 |
| A1158 | 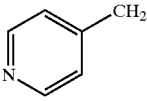 | H | H | CF$_2$Cl | B24 | 0 |
| A1159 | CH$_3$ON=CHCH$_2$ | H | H | CF$_2$Cl | B24 | 0 |
| A1160 | O=CHCH$_2$ | H | H | CF$_2$Cl | B24 | 0 |
| A1161 | CH$_3$CH$_2$OCH$_2$ | H | H | CF$_2$H | B24 | 0 |
| A1162 | PhOCH$_2$ | H | H | CF$_2$H | B24 | 0 |
| A1163 | 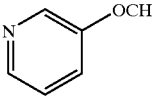 | H | H | CF$_2$H | B24 | 0 |
| A1164 | (CH$_3$)$_2$CH$_2$OCH$_2$ | H | H | CF$_2$H | B24 | 0 |
| A1165 | BrCH$_2$ | H | H | CF$_2$H | B24 | 0 |
| A1166 | FCH$_2$ | H | H | CF$_2$H | B24 | 0 |
| A1167 | 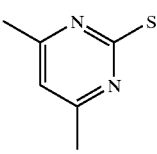 | H | H | CF$_2$H | B24 | 0 |
| A1168 | 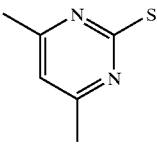 | H | H | CF$_2$H | B24 | 0 |
| A1169 | 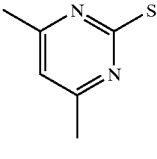 | H | H | CF$_2$H | B24 | 0 |
| A1170 | 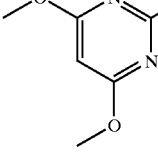 | H | H | CF$_2$H | B24 | 0 |

TABLE 7-continued

Compounds of the formula Ia (Ia)

| Comp. No. | R$_2$ | R$_3$ | R$_4$ | R$_5$ | Q$_1$ | p |
|---|---|---|---|---|---|---|
| A1171 | 2-(methylsulfinylmethyl)-4,6-dimethoxypyrimidine | H | H | CF$_2$H | B24 | 0 |
| A1172 | 2-(methylsulfonylmethyl)-4,6-dimethoxypyrimidine | H | H | CF$_2$H | B24 | 0 |
| A1173 | cyclopropyl-CH$_2$ | H | H | CF$_2$H | B24 | 0 |
| A1174 | 2,2-dichlorocycloprop-1-yl | H | H | CF$_2$H | B24 | 0 |
| A1175 | CH$_3$OC(O)CH=CH | H | H | CF$_2$H | B24 | 0 |
| A1176 | CH$_3$CH$_2$OC(O)CH=CH | H | H | CF$_2$H | B24 | 0 |
| A1177 | ClCH$_2$CH=CH | H | H | CF$_2$H | B24 | 0 |
| A1178 | CH=C=CH | H | H | CF$_2$H | B24 | 0 |
| A1179 | (CH$_3$)$_2$NCH$_2$ | H | H | CF$_2$H | B24 | 0 |
| A1180 | HOCH$_2$ | H | H | CF$_2$H | B24 | 0 |
| A1181 | CH$_3$C(O)OCH$_2$ | H | H | CF$_2$H | B24 | 0 |
| A1182 | PhC(O)OCH$_2$ | H | H | CF$_2$H | B24 | 0 |
| A1183 | PhCH$_2$ | H | H | CF$_2$H | B24 | 0 |
| A1184 | CH$_3$OC(O)CH$_2$ | H | H | CF$_2$H | B24 | 0 |
| A1185 | NCCH$_2$ | H | H | CF$_2$H | B24 | 0 |
| A1186 | CH$_3$(CH$_2$)$_7$SCH$_2$ | H | H | CF$_2$H | B24 | 0 |
| A1187 | CH$_3$(CH$_2$)$_7$SOCH$_2$ | H | H | CF$_2$H | B24 | 0 |
| A1188 | CH$_3$(CH$_2$)$_7$SO$_2$CH$_2$ | H | H | CF$_2$H | B24 | 0 |
| A1189 | phenyl-C≡C- | H | H | CF$_2$H | B24 | 0 |
| A1190 | ClCH$_2$CC | H | H | CF$_2$H | B24 | 0 |
| A1191 | Br | H | H | CF$_2$H | B24 | 0 |
| A1192 | Cl | H | H | CF$_2$H | B24 | 0 |
| A1193 | CF$_3$SO$_2$O | H | H | CF$_2$H | B24 | 0 |
| A1194 | pyridin-2-yl-C≡C- | H | H | CF$_2$H | B24 | 0 |
| A1195 | pyridin-3-yl-C≡C- | H | H | CF$_2$H | B24 | 0 |

TABLE 7-continued

Compounds of the formula Ia

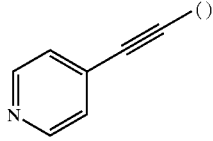

(Ia)

| Comp. No. | R₂ | R₃ | R₄ | R₅ | Q₁ | p |
|---|---|---|---|---|---|---|
| A1196 | 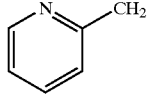 | H | H | CF₂H | B24 | 0 |
| A1197 | 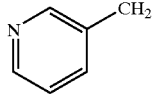 | H | H | CF₂H | B24 | 0 |
| A1198 | 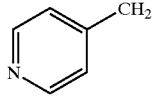 | H | H | CF₂H | B24 | 0 |
| A1199 | 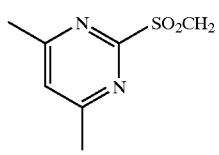 | H | H | CF₂H | B24 | 0 |
| A1200 | CH₃ON=CHCH₂ | H | H | CF₂H | B24 | 0 |
| A1201 | O=CHCH₂ | H | H | CF₂H | B24 | 0 |
| A1202 | CH₃CH=CH | H | H | CF₃ | B24 | 0 |
| A1203 | CH₃SO₂NH | H | H | CF₃ | B24 | 0 |
| A1204 | CH₃CH₂CH₂O | H | CH₃ | CF₃ | B24 | 0 |
| A1205 | Cl | CH₃ | H | CF₃ | B24 | 0 |
| A1206 | F₂CHO | H | H | CF₃ | B24 | 0 |
| A1207 | CH₃CH₂C(O)OCH₂ | H | H | CF₃ | B24 | 0 |
| A1208 | CH₃CH₂OC(O)OCH₂ | H | H | CF₃ | B24 | 0 |
| A1209 | CH₃OCH₂OCH₂ | H | H | CF₃ | B24 | 0 |
| A1210 | CH₃ | H | H | CF₃ | B24 | 1 |
| A1211 | CH₃CH₂ | H | H | CF₃ | B24 | 1 |
| A1212 | cyclopropyl | H | H | CF₃ | B24 | 1 |
| A1213 | CH₃(CH₂)₂ | H | H | CF₃ | B24 | 1 |
| A1214 | CH₃OCH₂ | H | H | CF₃ | B24 | 1 |
| A1215 | CF₃ | H | H | CF₃ | B24 | 1 |
| A1216 | F₂CH | H | H | CF₃ | B24 | 1 |
| A1217 | ClCH₂ | H | H | CF₃ | B24 | 1 |
| A1218 | CH₃SO₂CH₂ | H | H | CF₃ | B24 | 1 |
| A1219 | CH₃ | CF₃ | H | CH₃ | B24 | 1 |
| A1220 | CH₃CH₂OCH₂ | H | H | CF₃ | B24 | 1 |
| A1221 | PhOCH₂ | H | H | CF₃ | B24 | 1 |
| A1222 | (CH₃)₂CH₂OCH₂ | H | H | CF₃ | B24 | 1 |
| A1223 | BrCH₂ | H | H | CF₃ | B24 | 1 |
| A1224 | FCH₂ | H | H | CF₃ | B24 | 1 |
| A1225 |  | H | H | CF₃ | B24 | 1 |

TABLE 7-continued

Compounds of the formula Ia (Ia)

| Comp. No. | $R_2$ | $R_3$ | $R_4$ | $R_5$ | $Q_1$ | p |
|---|---|---|---|---|---|---|
| A1226 | 4,6-dimethoxypyrimidin-2-yl-SO$_2$CH$_2$ | H | H | $CF_3$ | B24 | 1 |
| A1227 | cyclopropyl-CH$_2$ | H | H | $CF_3$ | B24 | 1 |
| A1228 | 2,2-dichlorocycloprop-1-yl | H | H | $CF_3$ | B24 | 1 |
| A1229 | (CH$_3$)$_2$NCH$_2$ | H | H | $CF_3$ | B24 | 1 |
| A1230 | HOCH$_2$ | H | H | $CF_3$ | B24 | 1 |
| A1231 | CH$_3$C(O)OCH$_2$ | H | H | $CF_3$ | B24 | 1 |
| A1232 | PhC(O)OCH$_2$ | H | H | $CF_3$ | B24 | 1 |
| A1233 | PhCH$_2$ | H | H | $CF_3$ | B24 | 1 |
| A1234 | CH$_3$OC(O)CH$_2$ | H | H | $CF_3$ | B24 | 1 |
| A1235 | NCCH$_2$ | H | H | $CF_3$ | B24 | 1 |
| A1236 | CH$_3$(CH$_2$)$_7$SO$_2$CH$_2$ | H | H | $CF_3$ | B24 | 1 |
| A1237 | Br | H | H | $CF_3$ | B24 | 1 |
| A1238 | Cl | H | H | $CF_3$ | B24 | 1 |
| A1239 | O=CHCH$_2$ | H | H | $CF_3$ | B24 | 1 |
| A1240 | CH$_3$ | H | H | $CF_2Cl$ | B24 | 1 |
| A1241 | CH$_3$CH$_2$ | H | H | $CF_2Cl$ | B24 | 1 |
| A1242 | cyclopropyl | H | H | $CF_2Cl$ | B24 | 1 |
| A1243 | CH$_3$(CH$_2$)$_2$ | H | H | $CF_2Cl$ | B24 | 1 |
| A1244 | CH$_3$OCH$_2$ | H | H | $CF_2Cl$ | B24 | 1 |
| A1245 | CF$_3$ | H | H | $CF_2Cl$ | B24 | 1 |
| A1246 | F$_2$CH | H | H | $CF_2Cl$ | B24 | 1 |
| A1247 | ClCH$_2$ | H | H | $CF_2Cl$ | B24 | 1 |
| A1248 | CH$_3$SO$_2$CH$_2$ | H | H | $CF_2Cl$ | B24 | 1 |
| A1249 | CH$_3$ | CF$_3$ | H | $CF_2Cl$ | B24 | 1 |
| A1250 | CH$_3$CH$_2$OCH$_2$ | H | H | $CF_2Cl$ | B24 | 1 |
| A1251 | PhOCH$_2$ | H | H | $CF_2Cl$ | B24 | 1 |
| A1252 | (CH$_3$)$_2$CH$_2$OCH$_2$ | H | H | $CF_2Cl$ | B24 | 1 |
| A1253 | BrCH$_2$ | H | H | $CF_2Cl$ | B24 | 1 |
| A1254 | FCH$_2$ | H | H | $CF_2Cl$ | B24 | 1 |
| A1255 | 4,6-dimethylpyrimidin-2-yl-SO$_2$CH$_2$ | H | H | $CF_2Cl$ | B24 | 1 |
| A1256 | 4,6-dimethoxypyrimidin-2-yl-SO$_2$CH$_2$ | H | H | $CF_2Cl$ | B24 | 1 |
| A1257 | cyclopropyl-CH$_2$ | H | H | $CF_2Cl$ | B24 | 1 |
| A1258 | 2,2-dichlorocycloprop-1-yl | H | H | $CF_2Cl$ | B24 | 1 |
| A1259 | (CH$_3$)$_2$NCH$_2$ | H | H | $CF_2Cl$ | B24 | 1 |
| A1260 | HOCH$_2$ | H | H | $CF_2Cl$ | B24 | 1 |
| A1261 | CH$_3$C(O)OCH$_2$ | H | H | $CF_2Cl$ | B24 | 1 |
| A1262 | PhC(O)OCH$_2$ | H | H | $CF_2Cl$ | B24 | 1 |
| A1263 | PhCH$_2$ | H | H | $CF_2Cl$ | B24 | 1 |

TABLE 7-continued

Compounds of the formula Ia (Ia)

| Comp. No. | $R_2$ | $R_3$ | $R_4$ | $R_5$ | $Q_1$ | p |
|---|---|---|---|---|---|---|
| A1264 | $CH_3OC(O)CH_2$ | H | H | $CF_2Cl$ | B24 | 1 |
| A1265 | $NCCH_2$ | H | H | $CF_2Cl$ | B24 | 1 |
| A1266 | $CH_3(CH_2)_7SO_2CH_2$ | H | H | $CF_2Cl$ | B24 | 1 |
| A1267 | Br | H | H | $CF_2Cl$ | B24 | 1 |
| A1268 | Cl | H | H | $CF_2Cl$ | B24 | 1 |
| A1269 | $O=CHCH_2$ | H | H | $CF_2Cl$ | B24 | 1 |
| A1270 | $CH_3$ | H | H | $CF_2H$ | B24 | 1 |
| A1271 | $CH_3CH_2$ | H | H | $CF_2H$ | B24 | 1 |
| A1272 | cyclopropyl | H | H | $CF_2H$ | B24 | 1 |
| A1273 | $CH_3(CH_2)_2$ | H | H | $CF_2H$ | B24 | 1 |
| A1274 | $CH_3OCH_2$ | H | H | $CF_2H$ | B24 | 1 |
| A1275 | $CF_3$ | H | H | $CF_2H$ | B24 | 1 |
| A1276 | $F_2CH$ | H | H | $CF_2H$ | B24 | 1 |
| A1277 | $ClCH_2$ | H | H | $CF_2H$ | B24 | 1 |
| A1278 | $CH_3SO_2CH_2$ | H | H | $CF_2H$ | B24 | 1 |
| A1279 | $CH_3$ | $CF_3$ | H | $CF_2H$ | B24 | 1 |
| A1280 | $CH_3CH_2OCH_2$ | H | H | $CF_2H$ | B24 | 1 |
| A1281 | $PhOCH_2$ | H | H | $CF_2H$ | B24 | 1 |
| A1282 | $(CH_3)_2CH_2OCH_2$ | H | H | $CF_2H$ | B24 | 1 |
| A1283 | $BrCH_2$ | H | H | $CF_2H$ | B24 | 1 |
| A1284 | $FCH_2$ | H | H | $CF_2H$ | B24 | 1 |
| A1285 | 4,6-dimethylpyrimidin-2-yl-SO$_2$CH$_2$ | H | H | $CF_2H$ | B24 | 1 |
| A1286 | 4,6-dimethoxypyrimidin-2-yl-SO$_2$CH$_2$ | H | H | $CF_2H$ | B24 | 1 |
| A1287 | cyclopropyl-$CH_2$ | H | H | $CF_2H$ | B24 | 1 |
| A1288 | 2,2-dichlorocycloprop-1-yl | H | H | $CF_2H$ | B24 | 1 |
| A1289 | $(CH_3)_2NCH_2$ | H | H | $CF_2H$ | B24 | 1 |
| A1290 | $HOCH_2$ | H | H | $CF_2H$ | B24 | 1 |
| A1291 | $CH_3C(O)OCH_2$ | H | H | $CF_2H$ | B24 | 1 |
| A1292 | $PhC(O)OCH_2$ | H | H | $CF_2H$ | B24 | 1 |
| A1293 | $PhCH_2$ | H | H | $CF_2H$ | B24 | 1 |
| A1294 | $CH_3OC(O)CH_2$ | H | H | $CF_2H$ | B24 | 1 |
| A1295 | $NCCH_2$ | H | H | $CF_2H$ | B24 | 1 |
| A1296 | $CH_3(CH_2)_7SO_2CH_2$ | H | H | $CF_2H$ | B24 | 1 |
| A1297 | Br | H | H | $CF_2H$ | B24 | 1 |
| A1298 | Cl | H | H | $CF_2H$ | B24 | 1 |
| A1299 | $O=CHCH_2$ | H | H | $CF_2H$ | B24 | 1 |
| A1300 | $CH_3$ | H | H | $CF_3CF_2$ | B24 | 1 |
| A1301 | HO | H | Ph | $CF_3$ | B24 | 0 |
| A1302 | $CH_3$ | H | $CH_2=CH$ | $CF_3$ | B24 | 0 |
| A1303 | $CH_3$ | H | $CH_3CH_2O$ | $CF_3$ | B24 | 0 |
| A1304 | HO | $CH_3$ | H | $CF_3$ | B24 | 0 |
| A1305 | HO | H | H | $CF_3$ | B24 | 0 |
| A1306 | $(CH_3CH_2)_2N(O)CO$ | H | H | $CF_3$ | B24 | 0 |
| A1307 | $CH_3$ | H | tosyl-O | $CF_3$ | B24 | 0 |
| A1308 | $CH_3$ | H | $CH_3CC$ | $CF_3$ | B24 | 0 |
| A1309 | $CH_3$ | H | HCC | $CF_3$ | B24 | 0 |
| A1310 | $CH_3$ | H | $ClCH_2CC$ | $CF_3$ | B24 | 0 |

TABLE 7-continued

Compounds of the formula Ia (Ia)

| Comp. No. | R$_2$ | R$_3$ | R$_4$ | R$_5$ | Q$_1$ | p |
|---|---|---|---|---|---|---|
| A1311 | CH$_3$ | H | PhCH$_2$O | CF$_3$ | B24 | 0 |
| A1312 | CH$_3$ | H | CF$_3$SO$_2$O | CF$_3$ | B24 | 0 |
| A1313 | CH$_3$ | H | (CH$_3$)$_2$N | CF$_3$ | B24 | 0 |
| A1314 | CH$_3$ | H | CH$_3$C(O)O | CF$_3$ | B24 | 0 |
| A1315 | CH$_3$ | H | CH$_3$CH$_2$C(O)O | CF$_3$ | B24 | 0 |
| A1316 | CH$_3$ | H | PhC(O)O | CF$_3$ | B24 | 0 |
| A1317 | CH$_3$ | H | 3-pyridyl | CF$_3$ | B24 | 0 |
| A1318 | CH$_3$OCH$_2$OCH$_2$ | H | H | CF$_2$Cl | B24 | 0 |
| A1319 | CH$_3$OCH$_2$OCH$_2$ | H | H | CF$_2$H | B24 | 0 |
| A1320 | CH$_3$OCH$_2$OCH$_2$ | H | H | CF$_2$CF$_3$ | B24 | 0 |
| A1321 | CH$_3$OCH$_2$OCH$_2$ | H | H | CF$_3$ | B24 | 1 |
| A1322 | CH$_3$O | H | CH$_3$ | CF$_3$ | B24 | 0 |

In the formulaic representations of the tables (for example Table 7, compound A 1088, substituent R$_2$), the linkage site with the pyridine ring is on the right-hand side of the formulaic representation. Terminal valencies are a methyl group.

TABLE 8

Compounds of the formula Ib (p is 0 or 1):

(Ib)

| Q$_1$ | Q$_1$ | Q$_1$ | Q$_1$ | Q$_1$ | Q$_1$ | Q$_1$ | Q$_1$ | Q$_1$ | Q$_1$ | Q$_1$ | Q$_1$ |
|---|---|---|---|---|---|---|---|---|---|---|---|
| B1 | B2 | B3 | B4 | B5 | B6 | B7 | B8 | B9 | B10 | B11 | B12 |
| B13 | B14 | B15 | B16 | B17 | B18 | B19 | B20 | B21 | B22 | B23 | — |
| B25 | B26 | B27 | B28 | B29 | B30 | B31 | B32 | B33 | B34 | B35 | B36 |
| B37 | B38 | B39 | B40 | B41 | B42 | B43 | B44 | B45 | B46 | B47 | B48 |
| B49 | B50 | B51 | B52 | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | B95 | B96 |
| B97 | B98 | B99 | B100 | B101 | B102 | B103 | B104 | B105 | B106 | B107 | B108 |
| B109 | B110 | B111 | B112 | B113 | B114 | B115 | B116 | B117 | B118 | B119 | B120 |
| B121 | B122 | B123 | B124 | B125 | B126 | B127 | B128 | B129 | B130 | B131 | B132 |
| B133 | B134 | B135 | B136 | B137 | B138 | B139 | B140 | B141 | B142 | B143 | B144 |
| B145 | B146 | B147 | B148 | B149 | B150 | B151 | B152 | B153 | B154 | B155 | B156 |
| B157 | B158 | B159 | B160 | B161 | B162 | B163 | B164 | B165 | B166 | B167 | B168 |
| B169 | B170 | B171 | B172 | B173 | B174 | B175 | B176 | B177 | B178 | B179 | B180 |
| B181 | B182 | B183 | B184 | B185 | B186 | B187 | B188 | B189 | B190 | B191 | B192 |
| B193 | B194 | B195 | B196 | B197 | B198 | B199 | B200 | B201 | B202 | B203 | B204 |
| B205 | B206 | B207 | B208 | B209 | B210 | B211 | B212 | B213 | B214 | B215 | B216 |
| B217 | B218 | B219 | B220 | B221 | B222 | B223 | B224 | B225 | B226 | B227 | B228 |
| B229 | B230 | B231 | B232 | B233 | B234 | B235 | B236 | B237 | B238 | B239 | B240 |
| B241 | B242 | B243 | B244 | B245 | B246 | B247 | B248 | B249 | B250 | B251 | B252 |
| B253 | B254 | B255 | B256 | B257 | B258 | B259 | B260 | B261 | B262 | B263 | B264 |
| B265 | B266 | B267 | B268 | B269 | B270 | B271 | B272 | B273 | B274 | B275 | B276 |

TABLE 8-continued

Compounds of the formula Ib (p is 0 or 1):

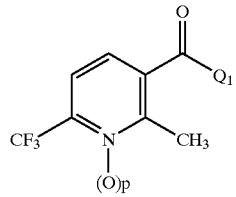

(Ib)

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B277 | B278 | B279 | B280 | B281 | B282 | B283 | B284 | B285 | B286 | B287 | B288 |
| B289 | B290 | B291 | B292 | B293 | B294 | B295 | B296 | B297 | B298 | B299 | B300 |
| B301 | B302 | B303 | B304 | B305 | B306 | B307 | B308 | B309 | B310 | B311 | B312 |
| B313 | B314 | B315 | B316 | B317 | B318 | B319 | B320 | B321 | B322 | B323 | B324 |
| B325 | B326 | B327 | B328 | B329 | B330 | B331 | B332 | B333 | B334 | B335 | B336 |
| B337 | B338 | B339 | B340 | B341 | B342 | B343 | B344 | B345 | B346 | B347 | B348 |
| B349 | B350 | B351 | B352 | B353 | B354 | B355 | B356 | B357 | B358 | B359 | B360 |
| B361 | B362 | B363 | B364 | B365 | B366 | B367 | B368 | B369 | B370 | B371 | B372 |
| B373 | B374 | B375 | B376 | B377 | B378 | B379 | B380 | B381 | B382 | B383 | B384 |
| B385 | B386 | B387 | B388 | B389 | B390 | B391 | B392 | B393 | B394 | B395 | B396 |
| B397 | B398 | B399 | B400 | B401 | B402 | B403 | B404 | B405 | B406 | B407 | B408 |
| B409 | B410 | B411 | B412 | B413 | B414 | B415 | B416 | B417 | B418 | B419 | B420 |
| B421 | B422 | B423 | B424 | B425 | B426 | B427 | B428 | B429 | B430 | B431 | B432 |
| B433 | B434 | B435 | B436 | B437 | B438 | B439 | B440 | B441 | B442 | B443 | B444 |
| B445 | B446 | B447 | B448 | B449 | B450 | B451 | B452 | B453 | B454 | B455 | B456 |
| B457 | B458 | B459 | B460 | B461 | B462 | B463 | B464 | B465 | B466 | B467 | B468 |
| B469 | B470 | B471 | B472 | B473 | B474 | B475 | B476 | B477 | B478 | B479 | B480 |
| B481 | B482 | B483 | B484 | B485 | B486 | B487 | B488 | B489 | B490 | B491 | B492 |
| B493 | B494 | B495 | B496 | B497 | B498 | B499 | B500 | B501 | B502 | B503 | B504 |
| B505 | B506 | B507 | B508 | B509 | B510 | B511 | B512 | B513 | B514 | B515 | B516 |
| B517 | B518 | B519 | B520 | B521 | B522 | B523 | B524 | B525 | B526 | B527 | B528 |
| B529 | B530 | B531 | B532 | B533 | B534 | B535 | B536 | B537 | B538 | B539 | B540 |
| B541 | B542 | B543 | B544 | B545 | B546 | B547 | B548 | B549 | B550 | B551 | B552 |
| B553 | B554 | B555 | B556 | B557 | B558 | B559 | B560 | B561 | B562 | B563 | B564 |
| B565 | B566 | B567 | B568 | B569 | B570 | B571 | B572 | B573 | B574 | B575 | B576 |
| B577 | B578 | B579 | B580 | B581 | B582 | B583 | B584 | B585 | B586 | B587 | B588 |
| B589 | B590 | B591 | B592 | B593 | B594 | B595 | B596 | B597 | B598 | B599 | B600 |
| B601 | B602 | B603 | B604 | B605 | B606 | B607 | B608 | B609 | B610 | B611 | B612 |
| B613 | B614 | B615 | B616 | B617 | B618 | B619 | B620 | B621 | B622 | B623 | B624 |
| B625 | B626 | B627 | B628 | B629 | B630 | B631 | B632 | B633 | B634 | B635 | B636 |
| B637 | B638 | B639 | B640 | B641 | B642 | B643 | B644 | B645 | B646 | B647 | B648 |
| B649 | B650 | B651 | B652 | B653 | B654 | B655 | B656 | B657 | B658 | B659 | B660 |
| B661 | B662 | B663 | B664 | B665 | B666 | B667 | B668 | B669 | B670 | B671 | B672 |
| B773 | B774 | B775 | B776 | B777 | B778 | B779 | B786 | B781 | B782 | B783 | B784 |
| B785 | B786 | B787 | B788 | B789 | B790 | B791 | B792 | B793 | B794 | B795 | B796 |
| B797 | B798 | B799 | B800 | B801 | B802 | B803 | B804 | B805 | B806 | B807 | B808 |
| B809 | B810 | B811 | B812 | B813 | B814 | B815 | B816 | B817 | B818 | B819 | B820 |
| B821 | B822 | B823 | B824 | B825 | B826 | B827 | B828 | B829 | B830 | B831 | B832 |
| B833 | B834 | B835 | B836 | B837 | B838 | B839 | B840 | B841 | B842 | B843 | B844 |
| B845 | B846 | B847 | B848 | B849 | B850 | B851 | B852 | B853 | B854 | B855 | B856 |
| B857 | B858 | B859 | B860 | B861 | B862 | B863 | B864 | B865 | B866 | B867 | B868 |
| B869 | B870 | B871 | B872 | B873 | B874 | B875 | B876 | B877 | B878 | B879 | B880 |
| B881 | B882 | B883 | B884 | B885 | B886 | B887 | B888 | B889 | B890 | B891 | B892 |
| B893 | B894 | B895 | B896 | B897 | B898 | B899 | B900 | B901 | B902 | B903 | B904 |
| B905 | B906 | B907 | B908 | B909 | B910 | B911 | B912 | B913 | B914 | B915 | B916 |
| B917 | B918 | B919 | B920 | B921 | B922 | B923 | B924 | B925 | B926 | B927 | B928 |
| B929 | B930 | B931 | B932 | B933 | B934 | B935 | B936 | B937 | B938 | B939 | B940 |
| B941 | B942 | B943 | B944 | B945 | B946 | B947 | B948 | B949 | B950 | B951 | B952 |
| B953 | B954 | B955 | B956 | B957 | B958 | B959 | B960 | B961 | B962 | B963 | B964 |
| B965 | B966 | B967 | B968 | B969 | B970 | B971 | B972 | B973 | B974 | B975 | B976 |
| B977 | B978 | B979 | B980 | B981 | B982 | B983 | B984 | B985 | B986 | B987 | B988 |
| B989 | B990 | B991 | B992 | B993 | B994 | B995 | B996 | B997 | B998 | B999 | B1000 |
| B1001 | B1002 | B1003 | B1004 | B1005 | B1006 | B1007 | B1008 | B1009 | B1010 | B1011 | B1012 |
| B1013 | B1014 | B1015 | B1016 | B1017 | B1018 | B1019 | B1020 | B1021 | B1022 | B1023 | B1024 |
| B1025 | B1026 | B1027 | B1028 | B1029 | B1030 | B1031 | B1032 | B1033 | B1034 | B1035 | B1036 |
| B1037 | B1038 | B1039 | B1040 | B1041 | B1042 | B1043 | B1044 | B1045 | B1046 | B1047 | B1048 |
| B1049 | B1050 | B1051 | B1052 | B1053 | B1054 | B1055 | B1056 | B1057 | B1058 | B1059 | B1060 |
| B1061 | B1062 | B1063 | B1064 | B1065 | B1066 | B1067 | B1068 | B1069 | B1070 | B1071 | B1072 |
| B1073 | B1074 | B1075 | B1076 | B1077 | B1078 | B1079 | B1080 | B1081 | B1082 | B1083 | B1084 |
| B1085 | B1086 | B1087 | B1088 | B1089 | B1090 | B1091 | B1092 | B1093 | B1094 | B1095 | B1096 |
| B1097 | B1098 | B1099 | B1100 | B1101 | B1102 | B1103 | B1104 | B1105 | B1106 | B1107 | B1108 |
| B1109 | B1110 | B1111 | B1112 | B1113 | B1114 | B1115 | B1116 | B1117 | B1118 | B1119 | B1120 |
| B1121 | B1122 | B1123 | B1124 | B1125 | B1126 | B1127 | B1128 | B1129 | B1130 | B1131 | B1132 |
| B1133 | B1134 | B1135 | B1136 | B1137 | B1138 | B1139 | B1140 | B1141 | B1142 | B1143 | B1144 |

TABLE 8-continued

Compounds of the formula Ib (p is 0 or 1):

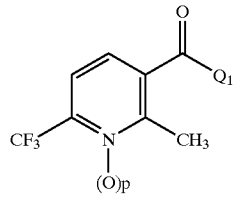

(Ib)

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B1145 | B1146 | B1147 | B1148 | B1149 | B1150 | B1151 | B1152 | B1153 | B1154 | B1155 | B1156 |
| B1157 | B1158 | B1159 | B1160 | B1161 | B1162 | B1163 | B1164 | B1165 | B1166 | B1167 | B1168 |
| B1169 | B1170 | B1171 | B1172 | B1173 | B1174 | B1175 | B1176 | B1177 | B1178 | B1179 | B1180 |
| B1181 | B1182 | B1183 | B1184 | B1185 | B1186 | B1187 | B1188 | B1189 | B1190 | B1191 | B1192 |
| B1193 | B1194 | B1195 | B1196 | B1197 | B1198 | B1199 | B1200 | B1201 | B1202 | B1203 | B1204 |
| B1205 | B1206 | B1207 | B1208 | B1209 | B1210 | B1211 | B1212 | B1213 | B1214 | B1215 | B1216 |
| B1217 | | | | | | | | | | | |

TABLE 9

Compounds of the formula Ic (p is 0 or 1):

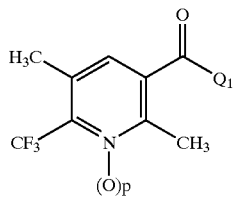

(Ic)

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B1 | B2 | B3 | B4 | B5 | B6 | B7 | B8 | B9 | B10 | B11 | B12 |
| B13 | B14 | B15 | B16 | B17 | B18 | B19 | B20 | B21 | B22 | B23 | — |
| B25 | B26 | B27 | B28 | B29 | B30 | B31 | B32 | B33 | B34 | B35 | B36 |
| B37 | B38 | B39 | B40 | B41 | B42 | B43 | B44 | B45 | B46 | B47 | B48 |
| B49 | B50 | B51 | B52 | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | B95 | B96 |
| B97 | B98 | B99 | B100 | B101 | B102 | B103 | B104 | B105 | B106 | B107 | B108 |
| B109 | B110 | B111 | B112 | B113 | B114 | B115 | B116 | B117 | B118 | B119 | B120 |
| B121 | B122 | B123 | B124 | B125 | B126 | B127 | B128 | B129 | B130 | B131 | B132 |
| B133 | B134 | B135 | B136 | B137 | B138 | B139 | B140 | B141 | B142 | B143 | B144 |
| B145 | B146 | B147 | B148 | B149 | B150 | B151 | B152 | B153 | B154 | B155 | B156 |
| B157 | B158 | B159 | B160 | B161 | B162 | B163 | B164 | B165 | B166 | B167 | B168 |
| B169 | B170 | B171 | B172 | B173 | B174 | B175 | B176 | B177 | B178 | B179 | B180 |
| B181 | B182 | B183 | B184 | B185 | B186 | B187 | B188 | B189 | B190 | B191 | B192 |
| B193 | B194 | B195 | B196 | B197 | B198 | B199 | B200 | B201 | B202 | B203 | B204 |
| B205 | B206 | B207 | B208 | B209 | B210 | B211 | B212 | B213 | B214 | B215 | B216 |
| B217 | B218 | B219 | B220 | B221 | B222 | B223 | B224 | B225 | B226 | B227 | B228 |
| B229 | B230 | B231 | B232 | B233 | B234 | B235 | B236 | B237 | B238 | B239 | B240 |
| B241 | B242 | B243 | B244 | B245 | B246 | B247 | B248 | B249 | B250 | B251 | B252 |
| B253 | B254 | B255 | B256 | B257 | B258 | B259 | B260 | B261 | B262 | B263 | B264 |
| B265 | B266 | B267 | B268 | B269 | B270 | B271 | B272 | B273 | B274 | B275 | B276 |
| B277 | B278 | B279 | B280 | B281 | B282 | B283 | B284 | B285 | B286 | B287 | B288 |
| B289 | B290 | B291 | B292 | B293 | B294 | B295 | B296 | B297 | B298 | B299 | B300 |
| B301 | B302 | B303 | B304 | B305 | B306 | B307 | B308 | B309 | B310 | B311 | B312 |
| B313 | B314 | B315 | B316 | B317 | B318 | B319 | B320 | B321 | B322 | B323 | B324 |
| B325 | B326 | B327 | B328 | B329 | B330 | B331 | B332 | B333 | B334 | B335 | B336 |
| B337 | B338 | B339 | B340 | B341 | B342 | B343 | B344 | B345 | B346 | B347 | B348 |
| B349 | B350 | B351 | B352 | B353 | B354 | B355 | B356 | B357 | B358 | B359 | B360 |
| B361 | B362 | B363 | B364 | B365 | B366 | B367 | B368 | B369 | B370 | B371 | B372 |
| B373 | B374 | B375 | B376 | B377 | B378 | B379 | B380 | B381 | B382 | B383 | B384 |
| B385 | B386 | B387 | B388 | B389 | B390 | B391 | B392 | B393 | B394 | B395 | B396 |
| B397 | B398 | B399 | B400 | B401 | B402 | B403 | B404 | B405 | B406 | B407 | B408 |
| B409 | B410 | B411 | B412 | B413 | B414 | B415 | B416 | B417 | B418 | B419 | B420 |
| B421 | B422 | B423 | B424 | B425 | B426 | B427 | B428 | B429 | B430 | B431 | B432 |
| B433 | B434 | B435 | B436 | B437 | B438 | B439 | B440 | B441 | B442 | B443 | B444 |
| B445 | B446 | B447 | B448 | B449 | B450 | B451 | B452 | B453 | B454 | B455 | B456 |

TABLE 9-continued

Compounds of the formula Ic (p is 0 or 1):

(Ic)

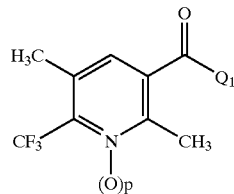

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B457 | B458 | B459 | B460 | B461 | B462 | B463 | B464 | B465 | B466 | B467 | B468 |
| B469 | B470 | B471 | B472 | B473 | B474 | B475 | B476 | B477 | B478 | B479 | B480 |
| B4B1 | B4B2 | B483 | B484 | B485 | B486 | B487 | B488 | B489 | B490 | B491 | B492 |
| B493 | B494 | B495 | B496 | B497 | B498 | B499 | B500 | B501 | B502 | B503 | B504 |
| B505 | B506 | B507 | B508 | B509 | B510 | B511 | B512 | B513 | B514 | B515 | B516 |
| B517 | B518 | B519 | B520 | B521 | B522 | B523 | B524 | B525 | B526 | B527 | B528 |
| B529 | B530 | B531 | B532 | B533 | B534 | B535 | B536 | B537 | B538 | B539 | B540 |
| B541 | B542 | B543 | B544 | B545 | B546 | B547 | B548 | B549 | B550 | B551 | B552 |
| B553 | B554 | B555 | B556 | B557 | B558 | B559 | B560 | B561 | B562 | B563 | B564 |
| B565 | B566 | B567 | B568 | B569 | B570 | B571 | B572 | B573 | B574 | B575 | B576 |
| B577 | B578 | B579 | B580 | B581 | B582 | B583 | B584 | B585 | B586 | B587 | B588 |
| B589 | B590 | B591 | B592 | B593 | B594 | B595 | B596 | B597 | B598 | B599 | B600 |
| B601 | B602 | B603 | B604 | B605 | B606 | B607 | B608 | B609 | B610 | B611 | B612 |
| B613 | B614 | B615 | B616 | B617 | B618 | B619 | B620 | B621 | B622 | B623 | B624 |
| B625 | B626 | B627 | B628 | B629 | B630 | B631 | B632 | B633 | B634 | B635 | B636 |
| B637 | B638 | B639 | B640 | B641 | B642 | B643 | B644 | B645 | B646 | B647 | B648 |
| B649 | B650 | B651 | B652 | B653 | B654 | B655 | B556 | B657 | B658 | B659 | B660 |
| B661 | B662 | B663 | B664 | B665 | B666 | B667 | B668 | B669 | B670 | B671 | B672 |
| B773 | B774 | B775 | B776 | B777 | B778 | B779 | B780 | B781 | B782 | B783 | B784 |
| B785 | B786 | B787 | B788 | B789 | B790 | B791 | B792 | B793 | B794 | B795 | B796 |
| B797 | B798 | B799 | B800 | B801 | B802 | B803 | B804 | B805 | B806 | B807 | B808 |
| B809 | B810 | B811 | B812 | B813 | B814 | B815 | B816 | B817 | B818 | B819 | B820 |
| B821 | B822 | B823 | B824 | B825 | B826 | B827 | B828 | B829 | B830 | B831 | B832 |
| B833 | B834 | B835 | B836 | B837 | B838 | B839 | B840 | B841 | B842 | B843 | B844 |
| B845 | B846 | B847 | B848 | B849 | B850 | B851 | B852 | B853 | B854 | B855 | B856 |
| B857 | B858 | B859 | B860 | B861 | B862 | B863 | B864 | B865 | B866 | B867 | B868 |
| B869 | B870 | B871 | B872 | B873 | B874 | B875 | B876 | B877 | B878 | B879 | B880 |
| B881 | B882 | B883 | B884 | B885 | B886 | B887 | B888 | B889 | B890 | B891 | B892 |
| B893 | B894 | B895 | B896 | B897 | B898 | B899 | B900 | B901 | B902 | B903 | B904 |
| B905 | B906 | B907 | B908 | B909 | B910 | B911 | B912 | B913 | B914 | B915 | B916 |
| B917 | B918 | B919 | B920 | B921 | B922 | B923 | B924 | B925 | B926 | B927 | B928 |
| B929 | B930 | B931 | B932 | B933 | B934 | B935 | B936 | B937 | B938 | B939 | B940 |
| B941 | B942 | B943 | B944 | B945 | B946 | B947 | B948 | B949 | B950 | B951 | B952 |
| B953 | B954 | B955 | B956 | B957 | B958 | B959 | B960 | B961 | B962 | B963 | B964 |
| B965 | B966 | B967 | B968 | B969 | B970 | B971 | B972 | B973 | B974 | B975 | B976 |
| B977 | B978 | B979 | B980 | B981 | B982 | B983 | B984 | B985 | B986 | B987 | B988 |
| B989 | B990 | B991 | B992 | B993 | B994 | B995 | B996 | B997 | B998 | B999 | B1000 |
| B1001 | B1002 | B1003 | B1004 | B1005 | B1006 | B1007 | B1008 | B1009 | B1010 | B1011 | B1012 |
| B1013 | B1014 | B1015 | B1016 | B1017 | B1018 | B1019 | B1020 | B1021 | B1022 | B1023 | B1024 |
| B1025 | B1026 | B1027 | B1028 | B1029 | B1030 | B1031 | B1032 | B1033 | B1034 | B1035 | B1036 |
| B1037 | B1038 | B1039 | B1040 | B1041 | B1042 | B1043 | B1044 | B1045 | B1046 | B1047 | B1048 |
| B1049 | B1050 | B1051 | B1052 | B1053 | B1054 | B1055 | B1056 | B1057 | B1058 | B1059 | B1060 |
| B1061 | B1062 | B1063 | B1064 | B1065 | B1066 | B1067 | B1068 | B1069 | B1070 | B1071 | B1072 |
| B1073 | B1074 | B1075 | B1076 | B1077 | B1078 | B1079 | B1080 | B1081 | B1082 | B1083 | B1084 |
| B1085 | B1086 | B1087 | B1088 | B1089 | B1090 | B1091 | B1092 | B1093 | B1094 | B1095 | B1096 |
| B1097 | B1098 | B1099 | B1100 | B1101 | B1102 | B1103 | B1104 | B1105 | B1106 | B1107 | B1108 |
| B1109 | B1110 | B1111 | B1112 | B1113 | B1114 | B1115 | B1116 | B1117 | B1118 | B1119 | B1120 |
| B1121 | B1122 | B1123 | B1124 | B1125 | B1126 | B1127 | B1128 | B1129 | B1130 | B1131 | B1132 |
| B1133 | B1134 | B1135 | B1136 | B1137 | B1138 | B1139 | B1140 | B1141 | B1142 | B1143 | B1144 |
| B1145 | B1146 | B1147 | B1148 | B1149 | B1150 | B1151 | B1152 | B1153 | B1154 | B1155 | B1156 |
| B1157 | B1158 | B1159 | B1160 | B1161 | B1162 | B1163 | B1164 | B1165 | B1166 | B1167 | B1168 |
| B1169 | B1170 | B1171 | B1172 | B1173 | B1174 | B1175 | B1176 | B1177 | B1178 | B1179 | B1180 |
| B1181 | B1182 | B1183 | B1184 | B1185 | B1186 | B1187 | B1188 | B1189 | B1190 | B1191 | B1192 |
| B1193 | B1194 | B1195 | B1196 | B1197 | B1198 | B1199 | B1200 | B1201 | B1202 | B1203 | B1204 |
| B1205 | B1206 | B1207 | B1208 | B1209 | B1210 | B1211 | B1212 | B1213 | B1214 | B1215 | B1216 |
| B1217 | | | | | | | | | | | |

TABLE 10

Compounds of the formula Id (p is 0 or 1):

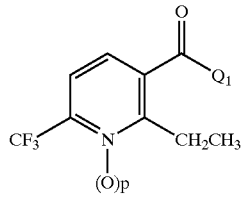

(Id)

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B1 | B2 | B3 | B4 | B5 | B6 | B7 | B8 | B9 | B10 | B11 | B12 |
| B13 | B14 | B15 | B16 | B17 | B18 | B19 | B20 | B21 | B22 | B23 | — |
| B25 | B26 | B27 | B28 | B29 | B30 | B31 | B32 | B33 | B34 | B35 | B36 |
| B37 | B38 | B39 | B40 | B41 | B42 | B43 | B44 | B45 | B46 | B47 | B48 |
| B49 | B50 | B51 | B52 | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | B95 | B96 |
| B97 | B98 | B99 | B100 | B101 | B102 | B103 | B104 | B105 | B106 | B107 | B108 |
| B109 | B110 | B111 | B112 | B113 | B114 | B115 | B116 | B117 | B118 | B119 | B120 |
| B121 | B122 | B123 | B124 | B125 | B126 | B127 | B128 | B129 | B130 | B131 | B132 |
| B133 | B134 | B135 | B136 | B137 | B138 | B139 | B140 | B141 | B142 | B143 | B144 |
| B145 | B146 | B147 | B148 | B149 | B150 | B151 | B152 | B153 | B154 | B155 | B156 |
| B157 | B158 | B159 | B160 | B161 | B162 | B163 | B164 | B165 | B166 | B167 | B168 |
| B169 | B170 | B171 | B172 | B173 | B174 | B175 | B176 | B177 | B178 | B179 | B180 |
| B181 | B182 | B183 | B184 | B185 | B186 | B187 | B188 | B189 | B190 | B191 | B192 |
| B193 | B194 | B195 | B196 | B197 | B198 | B199 | B200 | B201 | B202 | B203 | B204 |
| B205 | B206 | B207 | B208 | B209 | B210 | B211 | B212 | B213 | B214 | B215 | B216 |
| B217 | B218 | B219 | B220 | B221 | B222 | B223 | B224 | B225 | B226 | B227 | B228 |
| B229 | B230 | B231 | B232 | B233 | B234 | B235 | B236 | B237 | B238 | B239 | B240 |
| B241 | B242 | B243 | B244 | B245 | B246 | B247 | B248 | B249 | B250 | B251 | B252 |
| B253 | B254 | B255 | B256 | B257 | B258 | B259 | B260 | B261 | B262 | B263 | B264 |
| B265 | B266 | B267 | B268 | B269 | B270 | B271 | B272 | B273 | B274 | B275 | B276 |
| B277 | B278 | B279 | B280 | B281 | B282 | B283 | B284 | B285 | B286 | B287 | B288 |
| B289 | B290 | B291 | B292 | B293 | B294 | B295 | B296 | B297 | B298 | B299 | B300 |
| B301 | B302 | B303 | B304 | B305 | B306 | B307 | B308 | B309 | B310 | B311 | B312 |
| B313 | B314 | B315 | B316 | B317 | B318 | B319 | B320 | B321 | B322 | B323 | B324 |
| B325 | B326 | B327 | B328 | B329 | B330 | B331 | B332 | B333 | B334 | B335 | B336 |
| B337 | B338 | B339 | B340 | B341 | B342 | B343 | B344 | B345 | B346 | B347 | B348 |
| B349 | B350 | B351 | B352 | B353 | B354 | B355 | B356 | B357 | B358 | B359 | B360 |
| B361 | B362 | B363 | B364 | B365 | B366 | B367 | B368 | B369 | B370 | B371 | B372 |
| B373 | B374 | B375 | B376 | B377 | B378 | B379 | B380 | B381 | B382 | B383 | B384 |
| B385 | B386 | B387 | B388 | B389 | B390 | B391 | B392 | B393 | B394 | B395 | B396 |
| B397 | B398 | B399 | B400 | B401 | B402 | B403 | B404 | B405 | B406 | B407 | B408 |
| B409 | B410 | B411 | B412 | B413 | B414 | B415 | B416 | B417 | B418 | B419 | B420 |
| B421 | B422 | B423 | B424 | B425 | B426 | B427 | B428 | B429 | B430 | B431 | B432 |
| B433 | B434 | B435 | B436 | B437 | B438 | B439 | B440 | B441 | B442 | B443 | B444 |
| B445 | B446 | B447 | B448 | B449 | B450 | B451 | B452 | B453 | B454 | B455 | B456 |
| B457 | B458 | B459 | B460 | B461 | B462 | B463 | B464 | B465 | B466 | B467 | B468 |
| B469 | B470 | B471 | B472 | B473 | B474 | B475 | B476 | B477 | B478 | B479 | B480 |
| B481 | B4B2 | B4B3 | B484 | B485 | B486 | B487 | B488 | B489 | B490 | B491 | B492 |
| B493 | B494 | B495 | B496 | B497 | B498 | B499 | B500 | B501 | B502 | B503 | B504 |
| B505 | B506 | B507 | B508 | B509 | B510 | B511 | B512 | B513 | B514 | B515 | B516 |
| B517 | B518 | B519 | B520 | B521 | B522 | B523 | B524 | B525 | B526 | B527 | B528 |
| B529 | B530 | B531 | B532 | B533 | B534 | B535 | B536 | B537 | B538 | B539 | B540 |
| B541 | B542 | B543 | B544 | B545 | B546 | B547 | B548 | B549 | B550 | B551 | B552 |
| B553 | B554 | B555 | B556 | B557 | B558 | B559 | B560 | B561 | B562 | B563 | B564 |
| B565 | B566 | B567 | B568 | B569 | B570 | B571 | B572 | B573 | B574 | B575 | B576 |
| B577 | B578 | B579 | B580 | B581 | B582 | B583 | B584 | B585 | B586 | B587 | B588 |
| B589 | B590 | B591 | B592 | B593 | B594 | B595 | B596 | B597 | B598 | B599 | B600 |
| B601 | B602 | B603 | B604 | B605 | B606 | B607 | B608 | B609 | B610 | B611 | B612 |
| B613 | B614 | B615 | B616 | B617 | B618 | B619 | B620 | B621 | B622 | B623 | B624 |
| B625 | B626 | B627 | B628 | B629 | B630 | B631 | B632 | B633 | B634 | B635 | B636 |
| B637 | B638 | B639 | B640 | B641 | B642 | B643 | B644 | B645 | B646 | B647 | B648 |
| B649 | B650 | B651 | B652 | B653 | B654 | B655 | B656 | B657 | B658 | B659 | B660 |
| B661 | B662 | B663 | B664 | B665 | B666 | B667 | B668 | B669 | B670 | B671 | B672 |
| B773 | B774 | B775 | B776 | B777 | B778 | B779 | B780 | B781 | B782 | B783 | B784 |
| B785 | B786 | B787 | B788 | B789 | B790 | B791 | B792 | B793 | B794 | B795 | B796 |
| B797 | B798 | B799 | B800 | B801 | B802 | B803 | B804 | B805 | B806 | B807 | B808 |
| B809 | B810 | B811 | B812 | B813 | B814 | B815 | B816 | B817 | B818 | B819 | B820 |
| B821 | B822 | B823 | B824 | B825 | B826 | B827 | B828 | B829 | B830 | B831 | B832 |
| B833 | B834 | B835 | B836 | B837 | B838 | B839 | B840 | B841 | B842 | B843 | B844 |
| B845 | B846 | B847 | B848 | B849 | B850 | B851 | B852 | B853 | B854 | B855 | B856 |
| B857 | B858 | B859 | B860 | B861 | B862 | B863 | B864 | B865 | B866 | B867 | B868 |

TABLE 10-continued

Compounds of the formula Id (p is 0 or 1):

(Id)

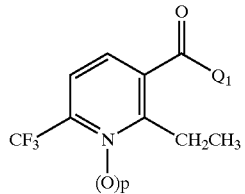

| Q₁ | Q₁ | Q₁ | Q₁ | Q₁ | Q₁ | Q₁ | Q₁ | Q₁ | Q₁ | Q₁ | Q₁ |
|---|---|---|---|---|---|---|---|---|---|---|---|
| B869 | B870 | B871 | B872 | B873 | B874 | B875 | B876 | B877 | B878 | B879 | B880 |
| B881 | B882 | B883 | B884 | B885 | B886 | B887 | B888 | B889 | B890 | B891 | B892 |
| B893 | B894 | B895 | B896 | B897 | B898 | B899 | B900 | B901 | B902 | B903 | B904 |
| B905 | B906 | B907 | B908 | B909 | B910 | B911 | B912 | B913 | B914 | B915 | B916 |
| B917 | B918 | B919 | B920 | B921 | B922 | B923 | B924 | B925 | B926 | B927 | B928 |
| B929 | B930 | B931 | B932 | B933 | B934 | B935 | B936 | B937 | B938 | B939 | B940 |
| B941 | B942 | B943 | B944 | B945 | B946 | B947 | B948 | B949 | B950 | B951 | B952 |
| B953 | B954 | B955 | B956 | B957 | B958 | B959 | B960 | B961 | B962 | B963 | B964 |
| B965 | B966 | B967 | B968 | B969 | B970 | B971 | B972 | B973 | B974 | B975 | B976 |
| B977 | B978 | B979 | B980 | B981 | B982 | B983 | B984 | B985 | B986 | B987 | B988 |
| B989 | B990 | B991 | B992 | B993 | B994 | B995 | B996 | B997 | B998 | B999 | B1000 |
| B1001 | B1002 | B1003 | B1004 | B1005 | B1006 | B1007 | B1008 | B1009 | B1010 | B1011 | B1012 |
| B1013 | B1014 | B1015 | B1016 | B1017 | B1018 | B1019 | B1020 | B1021 | B1022 | B1023 | B1024 |
| B1025 | B1026 | B1027 | B1028 | B1029 | B1030 | B1031 | B1032 | B1033 | B1034 | B1035 | B1036 |
| B1037 | B1038 | B1039 | B1040 | B1041 | B1042 | B1043 | B1044 | B1045 | B1046 | B1047 | B1048 |
| B1049 | B1050 | B1051 | B1052 | B1053 | B1054 | B1055 | B1056 | B1057 | B1058 | B1059 | B1060 |
| B1061 | B1062 | B1063 | B1064 | B1065 | B1066 | B1067 | B1068 | B1069 | B1070 | B1071 | B1072 |
| B1073 | B1074 | B1075 | B1076 | B1077 | B1078 | B1079 | B1080 | B1081 | B1082 | B1083 | B1084 |
| B1085 | B1086 | B1087 | B1088 | B1089 | B1090 | B1091 | B1092 | B1093 | B1094 | B1095 | B1096 |
| B1097 | B1098 | B1099 | B1100 | B1101 | B1102 | B1103 | B1104 | B1105 | B1106 | B1107 | B1108 |
| B1109 | B1110 | B1111 | B1112 | B1113 | B1114 | B1115 | B1116 | B1117 | B1118 | B1119 | B1120 |
| B1121 | B1122 | B1123 | B1124 | B1125 | B1126 | B1127 | B1128 | B1129 | B1130 | B1131 | B1132 |
| B1133 | B1134 | B1135 | B1136 | B1137 | B1138 | B1139 | B1140 | B1141 | B1142 | B1143 | B1144 |
| B1145 | B1146 | B1147 | B1148 | B1149 | B1150 | B1151 | B1152 | B1153 | B1154 | B1155 | B1156 |
| B1157 | B1158 | B1159 | B1160 | B1161 | B1162 | B1163 | B1164 | B1165 | B1166 | B1167 | B1168 |
| B1169 | B1170 | B1171 | B1172 | B1173 | B1174 | B1175 | B1176 | B1177 | B1178 | B1179 | B1180 |
| B1181 | B1182 | B1183 | B1184 | B1185 | B1186 | B1187 | B1188 | B1189 | B1190 | B1191 | B1192 |
| B1193 | B1194 | B1195 | B1196 | B1197 | B1198 | B1199 | B1200 | B1201 | B1202 | B1203 | B1204 |
| B1205 | B1206 | B1207 | B1208 | B1209 | B1210 | B1211 | B1212 | B1213 | B1214 | B1215 | B1216 |
| B1217 | | | | | | | | | | | |

TABLE 11

Compounds of the formula Ie (p is 0 or 1):

(Ie)

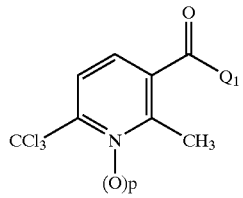

| Q₁ | Q₁ | Q₁ | Q₁ | Q₁ | Q₁ | Q₁ | Q₁ | Q₁ | Q₁ | Q₁ | Q₁ |
|---|---|---|---|---|---|---|---|---|---|---|---|
| B1 | B2 | B3 | B4 | B5 | B6 | B7 | B8 | B9 | B10 | B11 | B12 |
| B13 | B14 | B15 | B16 | B17 | B18 | B19 | B20 | B2 | B22 | B23 | — |
| B25 | B26 | B27 | B28 | B29 | B30 | B31 | B32 | B33 | B34 | B35 | B36 |
| B37 | B38 | B39 | B40 | B41 | B42 | B43 | B44 | B45 | B46 | B47 | B48 |
| B49 | B50 | B51 | B52 | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | B95 | B96 |
| B97 | B98 | B99 | B100 | B101 | B102 | B103 | B104 | B105 | B106 | B107 | B108 |
| B109 | B110 | B111 | B112 | B113 | B114 | B115 | B116 | B117 | B118 | B119 | B120 |
| B121 | B122 | B123 | B124 | B125 | B126 | B127 | B128 | B129 | B130 | B131 | B132 |
| B133 | B134 | B135 | B136 | B137 | B138 | B139 | B140 | B141 | B142 | B143 | B144 |
| B145 | B146 | B147 | B148 | B149 | B150 | B151 | B152 | B153 | B154 | B155 | B156 |
| B157 | B158 | B159 | B160 | B161 | B162 | B163 | B164 | B165 | B166 | B167 | B168 |
| B169 | B170 | B171 | B172 | B173 | B174 | B175 | B176 | B177 | B178 | B179 | B180 |

TABLE 11-continued

Compounds of the formula Ie (p is 0 or 1):

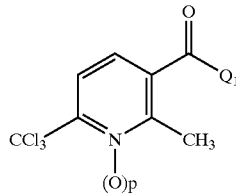

(Ie)

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B181 | B182 | B183 | B184 | B185 | B186 | B187 | B188 | B189 | B190 | B191 | B192 |
| B193 | B194 | B195 | B196 | B197 | B198 | B199 | B200 | B201 | B202 | B203 | B204 |
| B205 | B206 | B207 | B208 | B209 | B210 | B211 | B212 | B213 | B214 | B215 | B216 |
| B217 | B218 | B219 | B220 | B221 | B222 | B223 | B224 | B225 | B226 | B227 | B228 |
| B229 | B230 | B231 | B232 | B233 | B234 | B235 | B236 | B237 | B238 | B239 | B240 |
| B241 | B242 | B243 | B244 | B245 | B246 | B247 | B248 | B249 | B250 | B251 | B252 |
| B253 | B254 | B255 | B256 | B257 | B258 | B259 | B260 | B261 | B262 | B263 | B264 |
| B265 | B266 | B267 | B268 | B269 | B270 | B271 | B272 | B273 | B274 | B275 | B276 |
| B277 | B278 | B279 | B280 | B281 | B282 | B283 | B284 | B285 | B286 | B287 | B288 |
| B289 | B290 | B291 | B292 | B293 | B294 | B295 | B296 | B297 | B298 | B299 | B300 |
| B301 | B302 | B303 | B304 | B305 | B306 | B307 | B308 | B309 | B310 | B311 | B312 |
| B313 | B314 | B315 | B316 | B317 | B318 | B319 | B320 | B321 | B322 | B323 | B324 |
| B325 | B326 | B327 | B328 | B329 | B330 | B331 | B332 | B333 | B334 | B335 | B336 |
| B337 | B338 | B339 | B340 | B341 | B342 | B343 | B344 | B345 | B346 | B347 | B348 |
| B349 | B350 | B351 | B452 | B353 | B354 | B355 | B356 | B357 | B358 | B359 | B360 |
| B361 | B362 | B363 | B364 | B365 | B366 | B367 | B368 | B369 | B370 | B371 | B372 |
| B373 | B374 | B375 | B376 | B377 | B378 | B379 | B380 | B381 | B382 | B383 | B384 |
| B385 | B386 | B4B7 | B388 | B389 | B390 | B391 | B392 | B393 | B394 | B395 | B396 |
| B397 | B398 | B399 | B400 | B401 | B402 | B403 | B404 | B405 | B406 | B407 | B408 |
| B409 | B410 | B411 | B412 | B413 | B414 | B415 | B416 | B417 | B418 | B419 | B420 |
| B421 | B422 | B423 | B424 | B425 | B426 | B427 | B428 | B429 | B430 | B431 | B432 |
| B433 | B434 | B435 | B436 | B437 | B438 | B439 | B440 | B441 | B442 | B443 | B444 |
| B445 | B446 | B447 | B448 | B449 | B450 | B451 | B452 | B453 | B454 | B455 | B456 |
| B457 | B458 | B459 | B460 | B461 | B462 | B463 | B464 | B465 | B466 | B467 | B468 |
| B469 | B470 | B471 | B472 | B473 | B474 | B475 | B476 | B477 | B478 | B479 | B480 |
| B481 | B482 | B483 | B484 | B485 | B486 | B487 | B488 | B489 | B490 | B491 | B492 |
| B493 | B494 | B495 | B496 | B497 | B498 | B499 | B500 | B501 | B502 | B503 | B504 |
| B505 | B506 | B507 | B508 | B509 | B510 | B511 | B512 | B513 | B514 | B515 | B516 |
| B517 | B518 | B519 | B520 | B521 | B522 | B523 | B524 | B525 | B526 | B527 | B528 |
| B529 | B530 | B531 | B532 | B533 | B534 | B535 | B536 | B537 | B538 | B539 | B540 |
| B541 | B542 | B543 | B544 | B545 | B546 | B547 | B548 | B549 | B550 | B551 | B552 |
| B553 | B554 | B555 | B556 | B557 | B558 | B559 | B560 | B561 | B562 | B563 | B564 |
| B565 | B566 | B567 | B568 | B569 | B570 | B571 | B572 | B573 | B574 | B575 | B576 |
| B577 | B578 | B579 | B580 | B581 | B582 | B583 | B584 | B585 | B586 | B587 | B588 |
| B589 | B590 | B591 | B592 | B593 | B594 | B595 | B596 | B597 | B598 | B599 | B600 |
| B601 | B602 | B603 | B604 | B605 | B606 | B607 | B608 | B609 | B610 | B611 | B612 |
| B613 | B614 | B615 | B616 | B617 | B618 | B619 | B620 | B621 | B622 | B623 | B624 |
| B625 | B626 | B627 | B628 | B629 | B630 | B631 | B632 | B633 | B634 | B635 | B636 |
| B637 | B638 | B639 | B640 | B641 | B642 | B643 | B644 | B645 | B646 | B647 | B648 |
| B649 | B650 | B651 | B652 | B653 | B654 | B655 | B656 | B657 | B658 | B659 | B660 |
| B661 | B662 | B663 | B664 | B665 | B666 | B667 | B668 | B669 | B670 | B671 | B672 |
| B773 | B774 | B775 | B776 | B777 | B778 | B779 | B780 | B781 | B782 | B783 | B784 |
| B785 | B786 | B787 | B788 | B789 | B790 | B791 | B792 | B793 | B794 | B795 | B796 |
| B797 | B798 | B799 | B800 | B801 | B802 | B803 | B804 | B805 | B806 | B807 | B808 |
| B809 | B810 | B811 | B812 | B813 | B814 | B815 | B816 | B817 | B818 | B819 | B820 |
| B821 | B822 | B823 | B824 | B825 | B826 | B827 | B828 | B829 | B830 | B831 | B832 |
| B833 | B834 | B835 | B836 | B837 | B838 | B839 | B840 | B841 | B842 | B843 | B844 |
| B845 | B846 | B847 | B848 | B849 | B850 | B851 | B852 | B853 | B854 | B855 | B856 |
| B857 | B858 | B859 | B860 | B861 | B862 | B863 | B864 | B865 | B866 | B867 | B868 |
| B869 | B870 | B871 | B872 | B873 | B874 | B875 | B876 | B877 | B878 | B879 | B880 |
| B881 | B882 | B883 | B884 | B885 | B886 | B887 | B888 | B889 | B890 | B891 | B892 |
| B893 | B894 | B895 | B896 | B897 | B898 | B899 | B900 | B901 | B902 | B903 | B904 |
| B905 | B906 | B907 | B908 | B909 | B910 | B911 | B912 | B913 | B914 | B915 | B916 |
| B917 | B918 | B919 | B920 | B921 | B922 | B923 | B924 | B925 | B926 | B927 | B928 |
| B929 | B930 | B931 | B932 | B933 | B934 | B935 | B936 | B937 | B938 | B939 | B940 |
| B941 | B942 | B943 | B944 | B945 | B946 | B947 | B948 | B949 | B950 | B951 | B952 |
| B953 | B954 | B955 | B956 | B957 | B958 | B959 | B960 | B961 | B962 | B963 | B964 |
| B965 | B966 | B967 | B968 | B969 | B970 | B971 | B972 | B973 | B974 | B975 | B976 |
| B977 | B978 | B979 | B980 | B981 | B982 | B983 | B984 | B985 | B986 | B987 | B988 |
| B989 | B990 | B991 | B992 | B993 | B994 | B995 | B996 | B997 | B998 | B999 | B1000 |
| B1001 | B1002 | B1003 | B1004 | B1005 | B1006 | B1007 | B1008 | B1009 | B1010 | B1011 | B1012 |
| B1013 | B1014 | B1015 | B1016 | B1017 | B1018 | B1019 | B1020 | B1021 | B1022 | B1023 | B1024 |
| B1025 | B1026 | B1027 | B1028 | B1029 | B1030 | B1031 | B1032 | B1033 | B1034 | B1035 | B1036 |
| B1037 | B1038 | B1039 | B1040 | B1041 | B1042 | B1043 | B1044 | B1045 | B1046 | B1047 | B1048 |

TABLE 11-continued

Compounds of the formula Ie (p is 0 or 1):

(Ie)

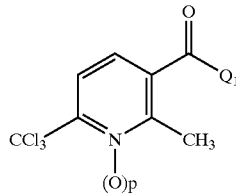

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B1049 | B1050 | B1051 | B1052 | B1053 | B1054 | B1055 | B1056 | B1057 | B1058 | B1059 | B1060 |
| B1061 | B1062 | B1063 | B1064 | B1065 | B1066 | B1067 | B1068 | B1069 | B1070 | B1071 | B1072 |
| B1073 | B1074 | B1075 | B1076 | B1077 | B1078 | B1079 | B1080 | B1081 | B1082 | B1083 | B1084 |
| B1085 | B1086 | B1087 | B1088 | B1089 | B1090 | B1091 | B1092 | B1093 | B1094 | B1095 | B1096 |
| B1097 | B1098 | B1099 | B1100 | B1101 | B1102 | B1103 | B1104 | B1105 | B1106 | B1107 | B1108 |
| B1109 | B1110 | B1111 | B1112 | B1113 | B1114 | B1115 | B1116 | B1117 | B1118 | B1119 | B1120 |
| B1121 | B1122 | B1123 | B1124 | B1125 | B1126 | B1127 | B1128 | B1129 | B1130 | B1131 | B1132 |
| B1133 | B1134 | B1135 | B1136 | B1137 | B1138 | B1139 | B1140 | B1141 | B1142 | B1143 | B1144 |
| B1145 | B1146 | B1147 | B1148 | B1149 | B1150 | B1151 | B1152 | B1153 | B1154 | B1155 | B1156 |
| B1157 | B1158 | B1159 | B1160 | B1161 | B1162 | B1163 | B1164 | B1165 | B1166 | B1167 | B1168 |
| B1169 | B1170 | B1171 | B1172 | B1173 | B1174 | B1175 | B1176 | B1177 | B1178 | B1179 | B1180 |
| B1181 | B1182 | B1183 | B1184 | B1185 | B1186 | B1187 | B1188 | B1189 | B1190 | B1191 | B1192 |
| B1193 | B1194 | B1195 | B1196 | B1197 | B1198 | B1199 | B1200 | B1201 | B1202 | B1203 | B1204 |
| B1205 | B1206 | B1207 | B1208 | B1209 | B1210 | B1211 | B1212 | B1213 | B1214 | B1215 | B1216 |
| B1217 | | | | | | | | | | | |

TABLE 12

Compounds of the formula If (p is 0 or 1):

(If)

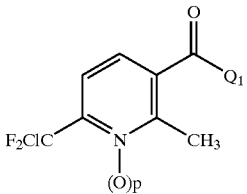

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B1 | B2 | B3 | B4 | B5 | B6 | B7 | B8 | B9 | B10 | B11 | B12 |
| B13 | B14 | B15 | B16 | B17 | B18 | B19 | B20 | B21 | B22 | B23 | — |
| B25 | B26 | B27 | B28 | B29 | B30 | B31 | B32 | B33 | B34 | B35 | B36 |
| B37 | B38 | B39 | B40 | B41 | B42 | B43 | B44 | B45 | B46 | B47 | B48 |
| B49 | B50 | B51 | B52 | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | B95 | B96 |
| B97 | B98 | B99 | B100 | B101 | B102 | B103 | B104 | B105 | B106 | B107 | B108 |
| B109 | B110 | B111 | B112 | B113 | B114 | B115 | B116 | B117 | B118 | B119 | B120 |
| B121 | B122 | B123 | B124 | B125 | B126 | B127 | B128 | B129 | B130 | B131 | B132 |
| B133 | B134 | B135 | B136 | B137 | B138 | B139 | B140 | B141 | B142 | B143 | B144 |
| B145 | B146 | B147 | B148 | B149 | B150 | B151 | B152 | B153 | B154 | B155 | B156 |
| B157 | B158 | B159 | B160 | B161 | B162 | B163 | B164 | B165 | B166 | B167 | B168 |
| B169 | B170 | B171 | B172 | B173 | B174 | B175 | B176 | B177 | B178 | B179 | B180 |
| B181 | B182 | B183 | B184 | B185 | B186 | B187 | B188 | B189 | B190 | B191 | B192 |
| B193 | B194 | B195 | B196 | B197 | B198 | B199 | B200 | B201 | B202 | B203 | B204 |
| B205 | B206 | B207 | B208 | B209 | B210 | B211 | B212 | B213 | B214 | B215 | B216 |
| B217 | B218 | B219 | B220 | B221 | B222 | B223 | B224 | B225 | B226 | B227 | B228 |
| B229 | B230 | B231 | B232 | B233 | B234 | B235 | B236 | B237 | B238 | B239 | B240 |
| B241 | B242 | B243 | B244 | B245 | B246 | B247 | B248 | B249 | B250 | B251 | B252 |
| B253 | B254 | B255 | B256 | B257 | B258 | B259 | B260 | B261 | B262 | B263 | B264 |
| B265 | B266 | B267 | B268 | B269 | B270 | B271 | B272 | B273 | B274 | B275 | B276 |
| B277 | B278 | B279 | B280 | B281 | B282 | B283 | B284 | B285 | B286 | B287 | B288 |
| B289 | B290 | B291 | B292 | B293 | B294 | B295 | B296 | B297 | B298 | B299 | B300 |
| B301 | B302 | B303 | B304 | B305 | B306 | B307 | B308 | B309 | B310 | B311 | B312 |
| B313 | B314 | B315 | B316 | B317 | B318 | B319 | B320 | B321 | B322 | B323 | B324 |
| B325 | B326 | B327 | B328 | B329 | B330 | B331 | B332 | B333 | B334 | B335 | B336 |
| B337 | B338 | B339 | B340 | B341 | B342 | B343 | B344 | B345 | B346 | B347 | B348 |
| B349 | B350 | B351 | B352 | B353 | B354 | B355 | B356 | B357 | B358 | B359 | B360 |

TABLE 12-continued

Compounds of the formula If (p is 0 or 1):

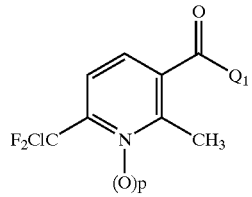

(If)

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B361 | B362 | B363 | B364 | B365 | B366 | B367 | B368 | B369 | B370 | B371 | B372 |
| B373 | B374 | B375 | B376 | B377 | B378 | B379 | B380 | B381 | B382 | B383 | B384 |
| B385 | B386 | B387 | B388 | B389 | B390 | B391 | B392 | B393 | B394 | B395 | B396 |
| B397 | B398 | B399 | B400 | B401 | B402 | B403 | B404 | B405 | B406 | B407 | B408 |
| B409 | B410 | B411 | B412 | B413 | B414 | B415 | B416 | B417 | B418 | B419 | B420 |
| B421 | B422 | B423 | B424 | B425 | B426 | B427 | B428 | B429 | B430 | B431 | B432 |
| B433 | B434 | B435 | B436 | B437 | B438 | B439 | B440 | B441 | B442 | B443 | B444 |
| B445 | B446 | B447 | B448 | B449 | B450 | B451 | B452 | B453 | B454 | B455 | B456 |
| B457 | B458 | B459 | B460 | B461 | B462 | B463 | B464 | B465 | B466 | B467 | B468 |
| B469 | B470 | B471 | B472 | B473 | B474 | B475 | B476 | B477 | B478 | B479 | B480 |
| B481 | B482 | B483 | B484 | B485 | B486 | B487 | B488 | B489 | B490 | B491 | B492 |
| B493 | B494 | B495 | B496 | B497 | B498 | B499 | B500 | B501 | B502 | B503 | B504 |
| B505 | B506 | B507 | B508 | B509 | B510 | B511 | B512 | B513 | B514 | B515 | B516 |
| B517 | B518 | B519 | B520 | B521 | B522 | B523 | B524 | B525 | B526 | B527 | B528 |
| B529 | B530 | B531 | B532 | B533 | B534 | B535 | B536 | B537 | B538 | B539 | B540 |
| B541 | B542 | B543 | B544 | B545 | B546 | B547 | B548 | B549 | B550 | B551 | B552 |
| B553 | B554 | B555 | B556 | B557 | B558 | B559 | B560 | B561 | B562 | B563 | B564 |
| B565 | B566 | B567 | B568 | B569 | B570 | B571 | B572 | B573 | B574 | B575 | B576 |
| B577 | B578 | B579 | B580 | B581 | B582 | B583 | B584 | B585 | B586 | B587 | B588 |
| B589 | B590 | B591 | B592 | B593 | B594 | B595 | B596 | B597 | B598 | B599 | B600 |
| B601 | B602 | B603 | B604 | B605 | B606 | B607 | B608 | B609 | B610 | B611 | B612 |
| B613 | B614 | B615 | B616 | B617 | B618 | B619 | B620 | B621 | B622 | B623 | B624 |
| B625 | B626 | B627 | B628 | B629 | B630 | B631 | B632 | B633 | B634 | B635 | B636 |
| B637 | B638 | B639 | B640 | B641 | B642 | B643 | B644 | B645 | B646 | B647 | B648 |
| B649 | B650 | B651 | B652 | B653 | B654 | B655 | B656 | B657 | B658 | B659 | B660 |
| B661 | B662 | B663 | B664 | B665 | B666 | B667 | B668 | B669 | B670 | B671 | B672 |
| B773 | B774 | B775 | B776 | B777 | B778 | B779 | B780 | B781 | B782 | B783 | B784 |
| B785 | B786 | B787 | B788 | B789 | B790 | B791 | B792 | B793 | B794 | B795 | B796 |
| B797 | B798 | B799 | B800 | B801 | B802 | B803 | B804 | B805 | B806 | B807 | B808 |
| B809 | B810 | B811 | B812 | B813 | B814 | B815 | B816 | B817 | B818 | B819 | B820 |
| B821 | B822 | B823 | B824 | B825 | B826 | B827 | B828 | B829 | B830 | B831 | B832 |
| B833 | B834 | B835 | B836 | B837 | B838 | B839 | B840 | B841 | B842 | B843 | B844 |
| B845 | B846 | B847 | B848 | B849 | B850 | B851 | B852 | B853 | B854 | B855 | B856 |
| B857 | B858 | B859 | B860 | B861 | B862 | B863 | B864 | B865 | B866 | B867 | B868 |
| B869 | B870 | B871 | B872 | B873 | B874 | B875 | B876 | B877 | B878 | B879 | B880 |
| B881 | B882 | B883 | B884 | B885 | B886 | B887 | B888 | B889 | B890 | B891 | B892 |
| B893 | B894 | B895 | B896 | B897 | B898 | B899 | B900 | B901 | B902 | B903 | B904 |
| B905 | B906 | B907 | B908 | B909 | B910 | B911 | B912 | B913 | B914 | B915 | B916 |
| B917 | B918 | B919 | B920 | B921 | B922 | B923 | B924 | B925 | B926 | B927 | B928 |
| B929 | B930 | B931 | B932 | B933 | B934 | B935 | B936 | B937 | B938 | B939 | B940 |
| B941 | B942 | B943 | B944 | B945 | B946 | B947 | B948 | B949 | B950 | B951 | B952 |
| B953 | B954 | B955 | B956 | B957 | B958 | B959 | B960 | B961 | B962 | B963 | B964 |
| B965 | B966 | B967 | B968 | B969 | B970 | B971 | B972 | B973 | B974 | B975 | B976 |
| B977 | B978 | B979 | B980 | B981 | B982 | B983 | B984 | B985 | B986 | B987 | B988 |
| B989 | B990 | B991 | B992 | B993 | B994 | B995 | B996 | B997 | B998 | B999 | B1000 |
| B1001 | B1002 | B1003 | B1004 | B1005 | B1006 | B1007 | B1008 | B1009 | B1010 | B1011 | B1012 |
| B1013 | B1014 | B1015 | B1016 | B1017 | B1018 | B1019 | B1020 | B1021 | B1022 | B1023 | B1024 |
| B1025 | B1026 | B1027 | B1028 | B1029 | B1030 | B1031 | B1032 | B1033 | B1034 | B1035 | B1036 |
| B1037 | B1038 | B1039 | B1040 | B1041 | B1042 | B1043 | B1044 | B1045 | B1046 | B1047 | B1048 |
| B1049 | B1050 | B1051 | B1052 | B1053 | B1054 | B1055 | B1056 | B1057 | B1056 | B1059 | B1060 |
| B1061 | B1062 | B1063 | B1064 | B1065 | B1066 | B1067 | B1068 | B1069 | B1070 | B1071 | B1072 |
| B1073 | B1074 | B1075 | B1076 | B1077 | B1078 | B1079 | B1080 | B1081 | B1082 | B1083 | B1084 |
| B1685 | B1086 | B1087 | B1088 | B1089 | B1090 | B1091 | B1092 | B1093 | B1094 | B1095 | B1096 |
| B1097 | B1098 | B1099 | B1100 | B1101 | B1102 | B1103 | B1104 | B1105 | B1106 | B1107 | B1108 |
| B1109 | B1110 | B1111 | B1112 | B1113 | B1114 | B1115 | B1116 | B1117 | B1118 | B1119 | B1120 |
| B1121 | B1122 | B1123 | B1124 | B1125 | B1126 | B1127 | B1128 | B1129 | B1130 | B1131 | B1132 |
| B1133 | B1134 | B1135 | B1136 | B1137 | B1138 | B1139 | B1140 | B1141 | B1142 | B1143 | B1144 |
| B1145 | B1146 | B1147 | B1148 | B1149 | B1150 | B1151 | B1152 | B1153 | B1154 | B1155 | B1156 |
| B1157 | B1158 | B1159 | B1160 | B1161 | B1162 | B1163 | B1164 | B1165 | B1166 | B1167 | B1168 |
| B1169 | B1170 | B1171 | B1172 | B1173 | B1174 | B1175 | B1176 | B1177 | B1178 | B1179 | B1180 |
| B1181 | B1182 | B1183 | B1184 | B1185 | B1186 | B1187 | B1188 | B1189 | B1190 | B1191 | B1192 |

TABLE 12-continued

Compounds of the formula If (p is 0 or 1):

(If)

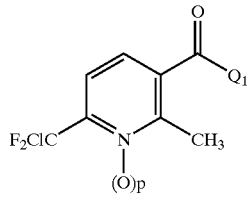

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B1193 | B1194 | B1195 | B1196 | B1197 | B1198 | B1199 | B1200 | B1201 | B1202 | B1203 | B1204 |
| B1205 | B1206 | B1207 | B1208 | B1209 | B1210 | B1211 | B1212 | B1213 | B1214 | B1215 | B1216 |
| B1217 | | | | | | | | | | | |

TABLE 13

Compounds of the formula Ig (p is 0 or 1):

(Ig)

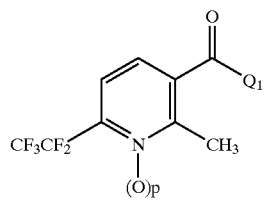

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B1 | B2 | B3 | B4 | B5 | B6 | B7 | B8 | B9 | B10 | B11 | B12 |
| B13 | B14 | B15 | B16 | B17 | B18 | B19 | B20 | B21 | B22 | B23 | — |
| B25 | B26 | B27 | B28 | B29 | B30 | B31 | B32 | B33 | B34 | B35 | B36 |
| B37 | B38 | B39 | B40 | B41 | B42 | B43 | B44 | B45 | B46 | B47 | B48 |
| B49 | B50 | B51 | B52 | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | B95 | B96 |
| B97 | B98 | B99 | B100 | B101 | B102 | B103 | B104 | B105 | B106 | B107 | B108 |
| B109 | B110 | B111 | B112 | B113 | B114 | B115 | B116 | B117 | B118 | B119 | B120 |
| B121 | B122 | B123 | B124 | B125 | B126 | B127 | B128 | B129 | B130 | B131 | B132 |
| B133 | B134 | B135 | B136 | B137 | B138 | B139 | B140 | B141 | B142 | B143 | B144 |
| B145 | B146 | B147 | B148 | B149 | B150 | B151 | B152 | B153 | B154 | B155 | B156 |
| B157 | B158 | B159 | B160 | B161 | B162 | B163 | B164 | B165 | B166 | B167 | B168 |
| B169 | B170 | B171 | B172 | B173 | B174 | B175 | B176 | B177 | B178 | B179 | B180 |
| B181 | B182 | B183 | B184 | B185 | B186 | B187 | B188 | B189 | B190 | B191 | B192 |
| B193 | B194 | B195 | B196 | B197 | B198 | B199 | B200 | B201 | B202 | B203 | B204 |
| B205 | B206 | B207 | B208 | B209 | B210 | B211 | B212 | B213 | B214 | B215 | B216 |
| B217 | B218 | B219 | B220 | B221 | B222 | B223 | B224 | B225 | B226 | B227 | B228 |
| B229 | B230 | B231 | B232 | B233 | B234 | B235 | B236 | B237 | B238 | B239 | B240 |
| B241 | B242 | B243 | B244 | B245 | B246 | B247 | B248 | B249 | B250 | B251 | B252 |
| B253 | B254 | B255 | B256 | B257 | B258 | B259 | B260 | B261 | B262 | B263 | B264 |
| B265 | B266 | B267 | B268 | B269 | B270 | B271 | B272 | B273 | B274 | B275 | B276 |
| B277 | B278 | B279 | B280 | B281 | B282 | B283 | B284 | B285 | B286 | B287 | B288 |
| B289 | B290 | B291 | B292 | B293 | B294 | B295 | B296 | B297 | B298 | B299 | B300 |
| B301 | B302 | B303 | B304 | B305 | B306 | B307 | B308 | B309 | B310 | B311 | B312 |
| B312 | B314 | B315 | B316 | B317 | B318 | B319 | B320 | B321 | B322 | B323 | B324 |
| B325 | B326 | B327 | B328 | B329 | B330 | B331 | B332 | B333 | B334 | B335 | B336 |
| B337 | B338 | B339 | B340 | B341 | B342 | B343 | B344 | B345 | B346 | B347 | B348 |
| B349 | B350 | B351 | B352 | B353 | B354 | B355 | B356 | B357 | B358 | B359 | B360 |
| B361 | B362 | B363 | B364 | B365 | B366 | B367 | B368 | B369 | B370 | B371 | B372 |
| B373 | B374 | B375 | B376 | B377 | B378 | B379 | B380 | B381 | B382 | B383 | B384 |
| B385 | B386 | B387 | B388 | B389 | B390 | B391 | B392 | B393 | B394 | B395 | B396 |
| B397 | B398 | B399 | B400 | B401 | B402 | B403 | B404 | B405 | B406 | B407 | B408 |
| B409 | B410 | B411 | B412 | B413 | B414 | B415 | B416 | B417 | B418 | B419 | B420 |
| B421 | B422 | B423 | B424 | B425 | B426 | B427 | B428 | B429 | B430 | B431 | B432 |
| B433 | B434 | B435 | B436 | B437 | B438 | B439 | B440 | B441 | B442 | B443 | B444 |
| B445 | B446 | B447 | B448 | B449 | B450 | B451 | B452 | B453 | B454 | B455 | B456 |
| B457 | B458 | B459 | B460 | B461 | B462 | B463 | B464 | B465 | B466 | B467 | B468 |
| B469 | B470 | B471 | B472 | B473 | B474 | B475 | B476 | B477 | B478 | B479 | B480 |
| B481 | B482 | B483 | B484 | B485 | B486 | B487 | B488 | B489 | B490 | B401 | B492 |
| B493 | B494 | B495 | B496 | B497 | B498 | B499 | B500 | B501 | B502 | B503 | B504 |

TABLE 13-continued

Compounds of the formula Ig (p is 0 or 1):

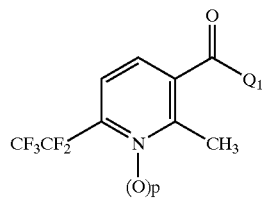

(Ig)

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B505 | B506 | B507 | B508 | B509 | B510 | B511 | B512 | B513 | B514 | B515 | B516 |
| B517 | B518 | B519 | B520 | B521 | B522 | B523 | B524 | B525 | B526 | B527 | B528 |
| B529 | B530 | B531 | B532 | B533 | B534 | B535 | B536 | B537 | B538 | B539 | B540 |
| B541 | B542 | B543 | B544 | B545 | B546 | B547 | B548 | B549 | B550 | B551 | B552 |
| B553 | B554 | B555 | B556 | B557 | B558 | B559 | B560 | B561 | B562 | B563 | B564 |
| B565 | B566 | B567 | B568 | B569 | B570 | B571 | B572 | B573 | B574 | B575 | B576 |
| B577 | B578 | B579 | B580 | B581 | B582 | B583 | B584 | B585 | B586 | B587 | B588 |
| B589 | B590 | B591 | B592 | B593 | B594 | B595 | B596 | B597 | B598 | B599 | B600 |
| B601 | B602 | B603 | B604 | B605 | B606 | B607 | B608 | B609 | B610 | B611 | B612 |
| B613 | B614 | B615 | B616 | B617 | B618 | B619 | B620 | B621 | B622 | B623 | B624 |
| B625 | B626 | B627 | B628 | B629 | B630 | B631 | B632 | B633 | B634 | B635 | B636 |
| B637 | B638 | B639 | B&40 | B641 | B642 | B643 | B644 | B645 | B646 | B647 | B648 |
| B649 | B659 | B651 | B652 | B653 | B654 | B655 | B656 | B657 | B658 | B659 | B660 |
| B661 | B662 | B663 | B664 | B665 | B666 | B667 | B668 | B669 | B670 | B671 | B672 |
| B773 | B774 | B775 | B776 | B777 | B778 | B779 | B780 | B781 | B782 | B783 | B784 |
| B785 | B786 | B787 | B788 | B789 | B790 | B791 | B792 | B793 | B794 | B795 | B796 |
| B797 | B798 | B799 | B800 | B801 | B802 | B803 | B804 | B805 | B806 | B807 | B808 |
| B809 | B810 | B811 | B812 | B813 | B814 | B815 | B816 | B817 | B818 | B819 | B820 |
| B821 | B822 | B823 | B824 | B825 | B826 | B827 | B828 | B829 | B830 | B831 | B832 |
| B833 | B834 | B835 | B836 | B837 | B838 | B839 | B840 | B841 | B842 | B843 | B844 |
| B845 | B846 | B847 | B848 | B849 | B850 | B851 | B852 | B853 | B854 | B855 | B856 |
| B857 | B858 | B859 | B860 | B861 | B862 | B863 | B864 | B865 | B866 | B867 | B868 |
| B869 | B870 | B871 | B872 | B873 | B874 | B875 | B876 | B877 | B878 | B879 | B880 |
| B881 | B882 | B883 | B884 | B885 | B886 | B887 | B888 | B889 | B890 | B891 | B892 |
| B893 | B894 | B895 | B896 | B897 | B898 | B899 | B900 | B901 | B902 | B903 | B904 |
| B905 | B906 | B907 | B908 | B909 | B910 | B911 | B912 | B913 | B914 | B915 | B916 |
| B917 | B918 | B919 | B920 | B921 | B922 | B923 | B924 | B925 | B926 | B927 | B928 |
| B929 | B930 | B931 | B932 | B933 | B934 | B935 | B936 | B937 | B938 | B939 | B940 |
| B941 | B942 | B943 | B944 | B945 | B946 | B947 | B948 | B949 | B950 | B951 | B952 |
| B953 | B954 | B955 | B956 | B957 | B958 | B959 | B960 | B961 | B962 | B963 | B964 |
| B965 | B966 | B967 | B968 | B969 | B970 | B971 | B972 | B973 | B974 | B975 | B976 |
| B977 | B978 | B979 | B980 | B981 | B982 | B983 | B984 | B985 | B986 | B987 | B988 |
| B989 | B990 | B991 | B992 | B993 | B994 | B995 | B996 | B997 | B998 | B999 | B1000 |
| B1001 | B1002 | B1003 | B1004 | B1005 | B1006 | B1007 | B1008 | B1009 | B1010 | B1011 | B1012 |
| B1013 | B1014 | B1015 | B1016 | B1017 | B1018 | B1019 | B1020 | B1021 | B1022 | B1023 | B1024 |
| B1025 | B1026 | B1027 | B1028 | B1029 | B1030 | B1031 | B1032 | B1033 | B1034 | B1035 | B1036 |
| B1037 | B1038 | B1039 | B1040 | B1041 | B1042 | B1043 | B1044 | B1045 | B1046 | B1047 | B1048 |
| B1049 | B1050 | B1051 | B1052 | B1053 | B1054 | B1055 | B1056 | B1057 | B1058 | B1059 | B1060 |
| B1061 | B1062 | B1063 | B1064 | B1065 | B1066 | B1067 | B1068 | B1069 | B1070 | B1071 | B1072 |
| B1073 | B1074 | B1075 | B1076 | B1077 | B1078 | B1079 | B1080 | B1081 | B1082 | B1083 | B1084 |
| B1085 | B1086 | B1087 | B1088 | B1089 | B1090 | B1091 | B1092 | B1093 | B1094 | B1095 | B1096 |
| B1097 | B1098 | B1099 | B1100 | B1101 | B1102 | B1103 | B1104 | B1105 | B1106 | B1107 | B1108 |
| B1109 | B1110 | B1111 | B1112 | B1113 | B1114 | B1115 | B1116 | B1117 | B1118 | B1119 | B1120 |
| B1121 | B1122 | B1123 | B1124 | B1125 | B1126 | B1127 | B1128 | B1129 | B1130 | B1131 | B1132 |
| B1133 | B1134 | B1135 | B1136 | B1137 | B1138 | B1139 | B1140 | B1141 | B1142 | B1143 | B1144 |
| B1145 | B1146 | B1147 | B1148 | B1149 | B1150 | B1151 | B1152 | B1153 | B1154 | B1155 | B1156 |
| B1157 | B1158 | B1159 | B1160 | B1161 | B1162 | B1163 | B1164 | B1165 | B1166 | B1167 | B1168 |
| B1169 | B1170 | B1171 | B1172 | B1173 | B1174 | B1175 | B1176 | B1177 | B1178 | B1179 | B1180 |
| B1181 | B1182 | B1183 | B1184 | B1185 | B1186 | B1187 | B1188 | B1189 | B1190 | B1191 | B1192 |
| B1193 | B1194 | B1195 | B1196 | B1197 | B1198 | B1199 | B1200 | B1201 | B1202 | B1203 | B1204 |
| B1205 | B1206 | B1207 | B1208 | B1209 | B1210 | B1211 | B1212 | B1213 | B1214 | B1215 | B1216 |
| B1217 | | | | | | | | | | | |

TABLE 14

Compounds of the formula Ih (p is 0 or 1):

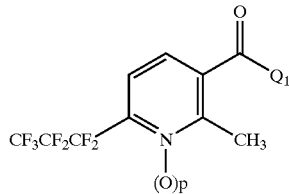

(Ih)

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B1 | B2 | B3 | B4 | B5 | B6 | B7 | B8 | B9 | B10 | B11 | B12 |
| B13 | B14 | B15 | B16 | B17 | B18 | B19 | B20 | B21 | B22 | B23 | — |
| B25 | B26 | B27 | B28 | B29 | B30 | B31 | B32 | B33 | B34 | B35 | B36 |
| B37 | B38 | B39 | B40 | B41 | B42 | B43 | B44 | B45 | B46 | B47 | B48 |
| B49 | B50 | B51 | B52 | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | B95 | B96 |
| B97 | B98 | B99 | B100 | B101 | B102 | B103 | B104 | B105 | B106 | B107 | B108 |
| B109 | B110 | B111 | B112 | B113 | B114 | B115 | B116 | B117 | B118 | B119 | B120 |
| B121 | B122 | B123 | B124 | B125 | B126 | B127 | B128 | B129 | B130 | B131 | B132 |
| B133 | B134 | B135 | B136 | B137 | B138 | B139 | B140 | B141 | B142 | B143 | B144 |
| B145 | B146 | B147 | B148 | B149 | B150 | B151 | B152 | B153 | B154 | B155 | B156 |
| B157 | B158 | B159 | B160 | B161 | B162 | B163 | B164 | B165 | B166 | B167 | B168 |
| B169 | B170 | B171 | B172 | B173 | B174 | B175 | B176 | B177 | B178 | B179 | B180 |
| B181 | B182 | B183 | B184 | B185 | B186 | B187 | B188 | B189 | B190 | B191 | B192 |
| B193 | B194 | B195 | B196 | B197 | B198 | B199 | B200 | B201 | B202 | B203 | B204 |
| B205 | B206 | B207 | B208 | B209 | B210 | B211 | B212 | B213 | B214 | B215 | B216 |
| B217 | B218 | B219 | B220 | B221 | B222 | B223 | B224 | B225 | B226 | B227 | B228 |
| B229 | B230 | B231 | B232 | B233 | B234 | B235 | B236 | B237 | B238 | B239 | B240 |
| B241 | B242 | B243 | B244 | B245 | B246 | B247 | B248 | B249 | B250 | B251 | B252 |
| B253 | B254 | B255 | B256 | B257 | B258 | B259 | B260 | B261 | B262 | B263 | B264 |
| B265 | B266 | B267 | B268 | B269 | B270 | B271 | B272 | B273 | B274 | B275 | B276 |
| B277 | B278 | B279 | B280 | B281 | B282 | B283 | B284 | B285 | B286 | B287 | B288 |
| B289 | B290 | B291 | B292 | B293 | B294 | B295 | B296 | B297 | B298 | B299 | B300 |
| B301 | B302 | B303 | B304 | B305 | B306 | B307 | B308 | B309 | B310 | B311 | B312 |
| B313 | B314 | B315 | B316 | B317 | B318 | B319 | B320 | B321 | B322 | B323 | B324 |
| B325 | B326 | B327 | B328 | B329 | B330 | B331 | B332 | B333 | B334 | B335 | B336 |
| B337 | B338 | B339 | B340 | B341 | B342 | B343 | B344 | B345 | B346 | B347 | B348 |
| B349 | B350 | B351 | B352 | B353 | B354 | B355 | B356 | B357 | B358 | B359 | B360 |
| B361 | B362 | B363 | B364 | B365 | B366 | B367 | B368 | B369 | B370 | B371 | B372 |
| B373 | B374 | B375 | B376 | B377 | B378 | B379 | B380 | B381 | B382 | B383 | B384 |
| B385 | B386 | B387 | B388 | B389 | B390 | B391 | B392 | B393 | B394 | B395 | B396 |
| B397 | B398 | B399 | B400 | B401 | B402 | B403 | B404 | B405 | B406 | B407 | B408 |
| B409 | B410 | B411 | B412 | B413 | B414 | B415 | B416 | B417 | B418 | B419 | B420 |
| B421 | B422 | B423 | B424 | B425 | B426 | B427 | B428 | B429 | B430 | B431 | B432 |
| B433 | B434 | B435 | B436 | B437 | B438 | B439 | B440 | B441 | B442 | B443 | B444 |
| B445 | B446 | B447 | B448 | B449 | B450 | B451 | B452 | B453 | B454 | B455 | B456 |
| B457 | B458 | B459 | B460 | B461 | B462 | B463 | B464 | B465 | B466 | B467 | B468 |
| B469 | B470 | B471 | B472 | B473 | B474 | B475 | B476 | B477 | B478 | B479 | B480 |
| B4B1 | B482 | B483 | B484 | B485 | B486 | B487 | B488 | B489 | B490 | B491 | B492 |
| B493 | B494 | B495 | B496 | B497 | B498 | B499 | B500 | B501 | B502 | B503 | B504 |
| B505 | B506 | B507 | B508 | B509 | B510 | B511 | B512 | B513 | B514 | B515 | B516 |
| B517 | B518 | B519 | B520 | B521 | B522 | B523 | B524 | B525 | B526 | B527 | B528 |
| B529 | B530 | B531 | B532 | B533 | B534 | B535 | B536 | B537 | B538 | B539 | B540 |
| B541 | B542 | B543 | B544 | B545 | B546 | B547 | B548 | B549 | B550 | B551 | B552 |
| B553 | B554 | B555 | B556 | B557 | B558 | B559 | B560 | B561 | B562 | B563 | B564 |
| B565 | B566 | B567 | B568 | B569 | B570 | B571 | B572 | B573 | B574 | B575 | B576 |
| B577 | B578 | B579 | B580 | B581 | B582 | B583 | B584 | B585 | B586 | B587 | B588 |
| B589 | B590 | B591 | B592 | B593 | B594 | B595 | B596 | B597 | B598 | B599 | B600 |
| B601 | B602 | B603 | B604 | B605 | B606 | B607 | B608 | B609 | B610 | B611 | B612 |
| B613 | B614 | B615 | B616 | B617 | B618 | B619 | B620 | B621 | B622 | B623 | B624 |
| B625 | B626 | B627 | B628 | B629 | B630 | B631 | B632 | B633 | B634 | B635 | B636 |
| B637 | B638 | B639 | B640 | B641 | B642 | B643 | B644 | B645 | B646 | B647 | B648 |
| B649 | B650 | B651 | B652 | B653 | B654 | B655 | B656 | B657 | B658 | B659 | B660 |
| B661 | B662 | B663 | B664 | B665 | B666 | B667 | B668 | B669 | B670 | B671 | B672 |
| B773 | B774 | B775 | B776 | B777 | B778 | B779 | B780 | B781 | B782 | B783 | B784 |
| B785 | B786 | B787 | B788 | B789 | B790 | B791 | B792 | B793 | B794 | B795 | B796 |
| B797 | B798 | B799 | B800 | B801 | B802 | B803 | B804 | B805 | B806 | B807 | B808 |
| B809 | B810 | B811 | B812 | B813 | B814 | B815 | B816 | B817 | B818 | B819 | B820 |
| B821 | B822 | B823 | B824 | B825 | B826 | B827 | B828 | B829 | B830 | B831 | B832 |
| B833 | B834 | B835 | B836 | B837 | B838 | B839 | B840 | B841 | B842 | B843 | B844 |
| B845 | B846 | B847 | B848 | B849 | B850 | B851 | B852 | B853 | B854 | B855 | B856 |
| B857 | B858 | B859 | B860 | B861 | B862 | B863 | B864 | B865 | B866 | B867 | B868 |

TABLE 14-continued

Compounds of the formula Ih (p is 0 or 1):

(Ih)

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B869 | B870 | B871 | B872 | B873 | B874 | B875 | B876 | B877 | B878 | B879 | B880 |
| B881 | B882 | B883 | B884 | B885 | B886 | B887 | B888 | B889 | B890 | B891 | B892 |
| B893 | B894 | B895 | B896 | B897 | B898 | B899 | B900 | B901 | B902 | B903 | B904 |
| B905 | B906 | B907 | B908 | B909 | B910 | B911 | B912 | B913 | B914 | B915 | B916 |
| B917 | B918 | B919 | B920 | B921 | B922 | B923 | B924 | B925 | B926 | B927 | B928 |
| B929 | B930 | B931 | B932 | B933 | B934 | B935 | B936 | B937 | B938 | B939 | B940 |
| B941 | B942 | B943 | B944 | B945 | B946 | B947 | B948 | B949 | B950 | B951 | B952 |
| B953 | B954 | B955 | B956 | B957 | B958 | B959 | B960 | B961 | B962 | B963 | B964 |
| B965 | B966 | B967 | B968 | B969 | B970 | B971 | B972 | B973 | B974 | B975 | B976 |
| B977 | B978 | B979 | B980 | B981 | B982 | B983 | B984 | B985 | B986 | B987 | B988 |
| B989 | B990 | B991 | B992 | B993 | B994 | B995 | B996 | B997 | B998 | B999 | B1000 |
| B1001 | B1002 | B1003 | B1004 | B1005 | B1006 | B1007 | B1008 | B1009 | B1010 | B1011 | B1012 |
| B1013 | B1014 | B1015 | B1016 | B1017 | B1018 | B1019 | B1020 | B1021 | B1022 | B1023 | B1024 |
| B1025 | B1026 | B1027 | B1028 | B1029 | B1030 | B1031 | B1032 | B1033 | B1034 | B1035 | B1036 |
| B1037 | B1038 | B1039 | B1040 | B1041 | B1042 | B1043 | B1044 | B1045 | B1046 | B1047 | B1048 |
| B1049 | B1050 | B1051 | B1052 | B1053 | B1054 | B1055 | B1056 | B1057 | B1058 | B1059 | B1060 |
| B1061 | B1062 | B1063 | B1064 | B1065 | B1066 | B1067 | B1068 | B1069 | B1070 | B1071 | B1072 |
| B1073 | B1074 | B1075 | B1076 | B1077 | B1078 | B1079 | B1080 | B1081 | B1082 | B1083 | B1084 |
| B1085 | B1086 | B1087 | B1088 | B1089 | B1090 | B1091 | B1092 | B1093 | B1094 | B1095 | B1096 |
| B1097 | B1098 | B1099 | B1100 | B1101 | B1102 | B1103 | B1104 | B1105 | B1106 | B1107 | B1108 |
| B1109 | B1110 | B1111 | B1112 | B1113 | B1114 | B1115 | B1116 | B1117 | B1118 | B1119 | B1120 |
| B1121 | B1122 | B1123 | B1124 | B1125 | B1126 | B1127 | B1128 | B1129 | B1130 | B1131 | B1132 |
| B1133 | B1134 | B1135 | B1136 | B1137 | B1138 | B1139 | B1140 | B1141 | B1142 | B1143 | B1144 |
| B1145 | B1146 | B1147 | B1148 | B1149 | B1150 | B1151 | B1152 | B1153 | B1154 | B1155 | B1156 |
| B1157 | B1158 | B1159 | B1160 | B1161 | B1162 | B1163 | B1164 | B1165 | B1166 | B1167 | B1168 |
| B1169 | B1170 | B1171 | B1172 | B1173 | B1174 | B1175 | B1176 | B1177 | B1178 | B1179 | B1180 |
| B1181 | B1182 | B1183 | B1184 | B1185 | B1186 | B1187 | B1188 | B1189 | B1190 | B1191 | B1192 |
| B1193 | B1194 | B1195 | B1196 | B1197 | B1198 | B1199 | B1200 | B1201 | B1202 | B1203 | B1204 |
| B1205 | B1206 | B1207 | B1208 | B1209 | B1210 | B1211 | B1212 | B1213 | B1214 | B1215 | B1216 |
| B1217 | | | | | | | | | | | |

TABLE 15

Compounds of the formula Ik (p is 0 or 1):

(Ik)

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B1 | B2 | B3 | B4 | B5 | B6 | B7 | B8 | B9 | B10 | B11 | B12 |
| B13 | B14 | B15 | B16 | B1Y | B18 | B19 | B20 | B21 | B22 | B23 | — |
| B25 | B26 | B27 | B28 | B29 | B30 | B31 | B32 | B33 | B34 | B35 | B36 |
| B37 | B38 | B39 | B40 | B41 | B42 | B43 | B44 | B45 | B46 | B47 | B48 |
| B49 | B50 | B51 | B52 | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | B95 | B96 |
| B97 | B98 | B99 | B100 | B101 | B102 | B103 | B104 | B105 | B106 | B107 | B108 |
| B109 | B110 | B111 | B112 | B113 | B114 | B115 | B116 | B117 | B118 | B119 | B120 |
| B121 | B122 | B123 | B124 | B125 | B126 | B127 | B128 | B129 | B130 | B131 | B132 |
| B133 | B134 | B135 | B136 | B137 | B138 | B139 | B140 | B141 | B142 | B143 | B144 |
| B145 | B146 | B147 | B148 | B149 | B150 | B151 | B152 | B153 | B154 | B155 | B156 |
| B157 | B158 | B159 | B160 | B161 | B162 | B163 | B164 | B165 | B166 | B167 | B168 |
| B169 | B170 | B171 | B172 | B173 | B174 | B175 | B176 | B177 | B178 | B179 | B180 |

TABLE 15-continued

Compounds of the formula Ik (p is 0 or 1):

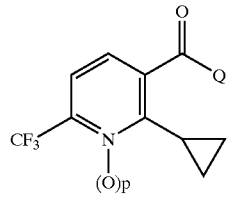

(Ik)

| Q₁ | Q₁ | Q₁ | Q₁ | Q₁ | Q₁ | Q₁ | Q₁ | Q₁ | Q₁ | Q₁ | Q₁ |
|---|---|---|---|---|---|---|---|---|---|---|---|
| B181 | B182 | B183 | B184 | B185 | B186 | B187 | B188 | B189 | B190 | B191 | B192 |
| B193 | B194 | B195 | B196 | B197 | B198 | B199 | B200 | B201 | B202 | B203 | B204 |
| B205 | B206 | B207 | B208 | B209 | B210 | B211 | B212 | B213 | B214 | B215 | B216 |
| B217 | B218 | B219 | B220 | B221 | B222 | B223 | B224 | B225 | B226 | B227 | B228 |
| B229 | B230 | B231 | B232 | B233 | B234 | B235 | B236 | B237 | B238 | B239 | B240 |
| B241 | B242 | B243 | B244 | B245 | B246 | B247 | B248 | B249 | B250 | B251 | B252 |
| B253 | B254 | B255 | B256 | B257 | B258 | B259 | B260 | B261 | B262 | B263 | B264 |
| B265 | B266 | B267 | B268 | B269 | B270 | B271 | B272 | B273 | B274 | B275 | B276 |
| B277 | B278 | B279 | B280 | B281 | B282 | B283 | B284 | B285 | B286 | B287 | B288 |
| B289 | B290 | B291 | B292 | B293 | B294 | B295 | B296 | B297 | B298 | B299 | B300 |
| B301 | B302 | B303 | B304 | B305 | B306 | B307 | B308 | B309 | B310 | B311 | B312 |
| B313 | B314 | B315 | B316 | B317 | B318 | B319 | B320 | B321 | B322 | B323 | B324 |
| B325 | B326 | B327 | B328 | B329 | B330 | B331 | B332 | B333 | B334 | B335 | B336 |
| B337 | B338 | B339 | B340 | B341 | B342 | B343 | B344 | B345 | B346 | B347 | B348 |
| B349 | B350 | B351 | B352 | B353 | B354 | B355 | B356 | B357 | B358 | B359 | B360 |
| B361 | B362 | B363 | B364 | B365 | B366 | B367 | B368 | B369 | B370 | B371 | B372 |
| B373 | B374 | B375 | B376 | B377 | B378 | B379 | B380 | B381 | B382 | B383 | B384 |
| B385 | B386 | B387 | B388 | B389 | B390 | B391 | B392 | B393 | B394 | B395 | B396 |
| B397 | B398 | B399 | B400 | B401 | B402 | B403 | B404 | B405 | B406 | B407 | B408 |
| B409 | B410 | B411 | B412 | B413 | B414 | B415 | B416 | B417 | B418 | B419 | B420 |
| B421 | B422 | B423 | B424 | B425 | B426 | B427 | B428 | B429 | B430 | B431 | B432 |
| B433 | B434 | B435 | B436 | B437 | B438 | B439 | B440 | B441 | B442 | B443 | B444 |
| B445 | B446 | B447 | B448 | B449 | B450 | B451 | B452 | B453 | B454 | B455 | B456 |
| B457 | B458 | B459 | B460 | B461 | B462 | B463 | B464 | B465 | B466 | B467 | B468 |
| B469 | B470 | B471 | B472 | B473 | B474 | B475 | B476 | B477 | B478 | B479 | B480 |
| B481 | B482 | B483 | B484 | B485 | B486 | B487 | B488 | B489 | B490 | B491 | B492 |
| B493 | B494 | B495 | B496 | B497 | B498 | B499 | B500 | B501 | B502 | B503 | B504 |
| B505 | B506 | B507 | B508 | B509 | B510 | B511 | B512 | B513 | B514 | B515 | B516 |
| B517 | B518 | B519 | B520 | B521 | B522 | B523 | B524 | B525 | B526 | B527 | B528 |
| B529 | B530 | B531 | B532 | B533 | B534 | B535 | B536 | B537 | B538 | B539 | B540 |
| B541 | B542 | B543 | B544 | B545 | B546 | B547 | B548 | B549 | B550 | B551 | B552 |
| B553 | B554 | B555 | B556 | B557 | B558 | B559 | B560 | B561 | B562 | B563 | B564 |
| B565 | B566 | B567 | B568 | B569 | B570 | B571 | B572 | B573 | B574 | B575 | B576 |
| B577 | B578 | B579 | B580 | B581 | B582 | B583 | B584 | B585 | B586 | B587 | B588 |
| B589 | B590 | B591 | B592 | B593 | B594 | B595 | B596 | B597 | B598 | B599 | B600 |
| B601 | B602 | B603 | B604 | B605 | B606 | B607 | B608 | B609 | B610 | B611 | B612 |
| B613 | B614 | B615 | B616 | B617 | B618 | B619 | B620 | B621 | B622 | B623 | B624 |
| B625 | B626 | B627 | B628 | B629 | B630 | B631 | B632 | B633 | B634 | B635 | B636 |
| B637 | B638 | B639 | B640 | B641 | B642 | B643 | B644 | B645 | B646 | B647 | B648 |
| B649 | B650 | B651 | B652 | B653 | B654 | B655 | B656 | B657 | B658 | B659 | B660 |
| B661 | B662 | B663 | B664 | B665 | B666 | B667 | B668 | B669 | B670 | B671 | B672 |
| B773 | B774 | B775 | B776 | B777 | B778 | B779 | B780 | B781 | B782 | B783 | B784 |
| B785 | B786 | B787 | B788 | B789 | B790 | B791 | B792 | B793 | B794 | B795 | B796 |
| B797 | B798 | B799 | B800 | B801 | B802 | B803 | B804 | B805 | B806 | B807 | B808 |
| B809 | B810 | B811 | B812 | B813 | B814 | B815 | B816 | B817 | B818 | B819 | B820 |
| B821 | B822 | B823 | B824 | B825 | B826 | B827 | B828 | B829 | B830 | B831 | B832 |
| B833 | B834 | B835 | B836 | B837 | B838 | B839 | B840 | B841 | B842 | B843 | B844 |
| B845 | B846 | B847 | B848 | B849 | B850 | B851 | B852 | B853 | B854 | B855 | B856 |
| B857 | B858 | B859 | B860 | B861 | B862 | B863 | B864 | B865 | B866 | B867 | B868 |
| B869 | B870 | B871 | B872 | B873 | B874 | B875 | B876 | B877 | B878 | B879 | B880 |
| B881 | B882 | B883 | B884 | B885 | B886 | B887 | B888 | B889 | B890 | B891 | B892 |
| B893 | B894 | B895 | B896 | B897 | B898 | B899 | B900 | B901 | B902 | B903 | B904 |
| B905 | B906 | B907 | B908 | B909 | B910 | B911 | B912 | B913 | B914 | B915 | B916 |
| B917 | B918 | B919 | B920 | B921 | B922 | B923 | B924 | B925 | B926 | B927 | B928 |
| B929 | B930 | B931 | B932 | B933 | B934 | B935 | B936 | B937 | B938 | B939 | B940 |
| B941 | B942 | B943 | B944 | B945 | B946 | B947 | B948 | B949 | B950 | B951 | B952 |
| B953 | B954 | B955 | B956 | B957 | B958 | B959 | B960 | B961 | B962 | B963 | B964 |
| B965 | B966 | B967 | B968 | B969 | B970 | B971 | B972 | B973 | B974 | B975 | B976 |
| B977 | B978 | B979 | B980 | B981 | B982 | B983 | B984 | B985 | B986 | B987 | B988 |
| B989 | B990 | B991 | B992 | B993 | B994 | B995 | B996 | B997 | B998 | B999 | B1000 |
| B1001 | B1002 | B1003 | B1004 | B1005 | B1006 | B1007 | B1008 | B1009 | B1010 | B1011 | B1012 |
| B1013 | B1014 | B1015 | B1016 | B1017 | B1018 | B1019 | B1020 | B1021 | B1022 | B1023 | B1024 |
| B1025 | B1026 | B1027 | B1028 | B1029 | B1030 | B1031 | B1032 | B1033 | B1034 | B1035 | B1036 |
| B1037 | B1038 | B1039 | B1040 | B1041 | B1042 | B1043 | B1044 | B1045 | B1046 | B1047 | B1048 |

TABLE 15-continued

Compounds of the formula Ik (p is 0 or 1):

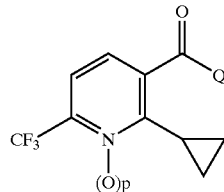

(Ik)

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B1049 | B1050 | B1051 | B1052 | B1053 | B1054 | B1055 | B1056 | B1057 | B1058 | B1059 | B1060 |
| B1061 | B1062 | B1063 | B1064 | B1065 | B1066 | B1067 | B1068 | B1069 | B1070 | B1071 | B1072 |
| B1073 | B1074 | B1075 | B1076 | B1077 | B1078 | B1079 | B1080 | B1081 | B1082 | B1083 | B1084 |
| B1085 | B1086 | B1087 | B1088 | B1089 | B1090 | B1091 | B1092 | B1093 | B1094 | B1095 | B1096 |
| B1097 | B1098 | B1099 | B1100 | B1101 | B1102 | B1103 | B1104 | B1105 | B1106 | B1107 | B1108 |
| B1109 | B1110 | B1111 | B1112 | B1113 | B1114 | B1115 | B1116 | B1117 | B1118 | B1119 | B1120 |
| B1121 | B1122 | B1123 | B1124 | B1125 | B1126 | B1127 | B1128 | B1129 | B1130 | B1131 | B1132 |
| B1133 | B1134 | B1135 | B1136 | B1137 | B1138 | B1139 | B1140 | B1141 | B1142 | B1143 | B1144 |
| B1145 | B1146 | B1147 | B1148 | B1149 | B1150 | B1151 | B1152 | B1153 | B1154 | B1155 | B1156 |
| B1157 | B1158 | B1159 | B1160 | B1161 | B1162 | B1163 | B1164 | B1165 | B1166 | B1167 | B1168 |
| B1169 | B1170 | B1171 | B1172 | B1173 | B1174 | B1175 | B1176 | B1177 | B1178 | B1179 | B1180 |
| B1181 | B1182 | B1183 | B1184 | B1185 | B1186 | B1187 | B1188 | B1189 | B1190 | B1191 | B1192 |
| B1193 | B1194 | B1195 | B1196 | B1197 | B1198 | B1199 | B1200 | B1201 | B1202 | B1203 | B1204 |
| B1205 | B1206 | B1207 | B1208 | B1209 | B1210 | B1211 | B1212 | B1213 | B1214 | B1215 | B1216 |
| B1217 | | | | | | | | | | | |

TABLE 16

Compounds of the formula Im (p is 0 or 1):

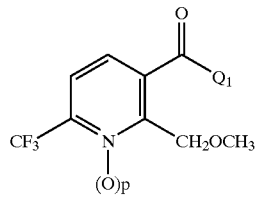

(Im)

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B1 | B2 | B3 | B4 | B5 | B6 | B7 | B8 | B9 | B10 | B11 | B12 |
| B13 | B14 | B15 | B16 | B17 | B18 | B19 | B20 | B21 | B22 | B23 | — |
| B25 | B26 | B27 | B28 | B29 | B30 | B31 | B32 | B33 | B34 | B35 | B36 |
| B37 | B38 | B39 | B40 | B41 | B42 | B43 | B44 | B45 | B46 | B47 | B48 |
| B49 | B50 | B51 | B52 | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | B95 | B96 |
| B97 | B98 | B99 | B100 | B101 | B102 | B103 | B104 | B105 | B106 | B107 | B108 |
| B109 | B110 | B111 | B112 | B113 | B114 | B115 | B116 | B117 | B118 | B119 | B120 |
| B121 | B122 | B123 | B124 | B125 | B126 | B127 | B128 | B129 | B130 | B131 | B132 |
| B133 | B134 | B135 | B136 | B137 | B138 | B139 | B140 | B141 | B142 | B143 | B144 |
| B145 | B146 | B147 | B148 | B149 | B150 | B151 | B152 | B153 | B154 | B155 | B156 |
| B157 | B158 | B159 | B160 | B161 | B162 | B163 | B164 | B165 | B166 | B167 | B168 |
| B169 | B170 | B171 | B172 | B173 | B174 | B175 | B176 | B177 | B178 | B179 | B180 |
| B181 | B182 | B183 | B184 | B185 | B186 | B187 | B188 | B189 | B190 | B191 | B192 |
| B193 | B194 | B195 | B196 | B197 | B198 | B199 | B200 | B201 | B202 | B203 | B204 |
| B205 | B206 | B207 | B208 | B209 | B210 | B211 | B212 | B213 | B214 | B215 | B216 |
| B217 | B218 | B219 | B220 | B221 | B222 | B223 | B224 | B225 | B226 | B227 | B228 |
| B229 | B230 | B231 | B232 | B233 | B234 | B235 | B236 | B237 | B238 | B239 | B240 |
| B241 | B242 | B243 | B244 | B245 | B246 | B247 | B248 | B249 | B250 | B251 | B252 |
| B253 | B254 | B255 | B256 | B257 | B258 | B259 | B260 | B261 | B262 | B263 | B264 |
| B265 | B266 | B267 | B268 | B269 | B270 | B271 | B272 | B273 | B274 | B275 | B276 |
| B277 | B278 | B279 | B280 | B281 | B282 | B283 | B284 | B285 | B286 | B287 | B288 |
| B289 | B290 | B291 | B292 | B293 | B294 | B295 | B296 | B297 | B298 | B299 | B300 |
| B301 | B302 | B303 | B304 | B305 | B306 | B307 | B308 | B309 | B310 | B311 | B312 |
| B313 | B314 | B315 | B316 | B317 | B318 | B319 | B320 | B321 | B322 | B323 | B324 |
| B325 | B326 | B327 | B328 | B329 | B330 | B331 | B332 | B333 | B334 | B335 | B336 |
| B337 | B338 | B339 | B440 | B341 | B342 | B343 | B344 | B345 | B346 | B347 | B348 |
| B349 | B350 | B351 | B352 | B353 | B354 | B355 | B356 | B357 | B358 | B359 | B360 |
| B361 | B362 | B363 | B364 | B365 | B366 | B367 | B368 | B369 | B370 | B371 | B372 |

TABLE 16-continued

Compounds of the formula Im (p is 0 or 1):

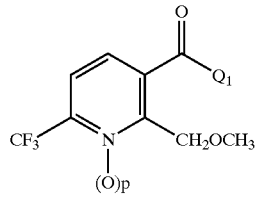

(Im)

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B373 | B374 | B375 | B376 | B377 | B378 | B379 | B380 | B381 | B382 | B383 | B384 |
| B385 | B386 | B387 | B388 | B389 | B390 | B391 | B392 | B393 | B394 | B395 | B396 |
| B397 | B398 | B399 | B400 | B401 | B402 | B403 | B404 | B405 | B406 | B407 | B408 |
| B409 | B410 | B411 | B412 | B413 | B414 | B415 | B416 | B417 | B418 | B419 | B420 |
| B421 | B422 | B423 | B424 | B425 | B426 | B427 | B428 | B429 | B430 | B431 | B432 |
| B433 | B434 | B435 | B436 | B437 | B438 | B439 | B440 | B441 | B442 | B443 | B444 |
| B445 | B446 | B447 | B448 | B449 | B450 | B451 | B452 | B453 | B454 | B455 | B456 |
| B457 | B458 | B459 | B460 | B461 | B462 | B463 | B464 | B465 | B466 | B467 | B468 |
| B469 | B470 | B471 | B472 | B473 | B474 | B475 | B476 | B477 | B478 | B479 | B480 |
| B481 | B4B2 | B4B3 | B4B4 | B4B5 | B4B6 | B4B7 | B488 | B489 | B490 | B491 | B492 |
| B493 | B494 | B495 | B496 | B497 | B498 | B499 | B500 | B501 | B502 | B503 | B504 |
| B505 | B506 | B507 | B508 | B509 | B510 | B511 | B512 | B513 | B514 | B515 | B516 |
| B517 | B518 | B519 | B520 | B521 | B522 | B523 | B524 | B525 | B526 | B527 | B528 |
| B529 | B530 | B531 | B532 | B533 | B534 | B535 | B536 | B537 | B538 | B539 | B540 |
| B541 | B542 | B543 | B544 | B545 | B546 | B547 | B548 | B549 | B550 | B551 | B552 |
| B553 | B554 | B555 | B556 | B557 | B558 | B559 | B560 | B561 | B562 | B563 | B564 |
| B565 | B566 | B567 | B568 | B569 | B570 | B571 | B572 | B573 | B574 | B575 | B576 |
| B577 | B578 | B579 | B580 | B581 | B582 | B583 | B584 | B585 | B586 | B587 | B588 |
| B589 | B590 | B591 | B592 | B593 | B594 | B595 | B596 | B597 | B598 | B599 | B600 |
| B601 | B602 | B603 | B604 | B605 | B606 | B607 | B608 | B609 | B610 | B611 | B612 |
| B613 | B614 | B615 | B616 | B617 | B618 | B619 | B620 | B621 | B622 | B623 | B624 |
| B625 | B626 | B627 | B628 | B629 | B630 | B631 | B632 | B633 | B634 | B635 | B636 |
| B637 | B638 | B639 | B640 | B641 | B642 | B643 | B644 | B645 | B646 | B647 | B648 |
| B649 | B650 | B651 | B652 | B653 | B654 | B655 | B656 | B657 | B658 | B659 | B660 |
| B661 | B662 | B663 | B664 | B665 | B666 | B667 | B668 | B669 | B670 | B671 | B672 |
| B773 | B774 | B775 | B776 | B777 | B775 | B779 | B780 | B781 | B782 | B783 | B784 |
| B785 | B786 | B787 | B788 | B789 | B790 | B791 | B792 | B793 | B794 | B795 | B796 |
| B797 | B798 | B799 | B800 | B801 | B802 | B803 | B804 | B805 | B806 | B807 | B808 |
| B809 | B810 | B811 | B812 | B813 | B814 | B815 | B816 | B817 | B818 | B819 | B820 |
| B821 | B822 | B823 | B824 | B825 | B826 | B827 | B828 | B829 | B830 | B831 | B832 |
| B833 | B834 | B835 | B836 | B837 | B838 | B839 | B840 | B841 | B842 | B843 | B844 |
| B845 | B846 | B847 | B848 | B849 | B850 | B851 | B852 | B853 | B854 | B855 | B856 |
| B857 | B858 | B859 | B860 | B861 | B862 | B863 | B864 | B865 | B866 | B867 | B868 |
| B869 | B870 | B871 | B872 | B873 | B874 | B875 | B876 | B877 | B878 | B879 | B880 |
| B881 | B882 | B883 | B884 | B885 | B886 | B887 | B888 | B889 | B890 | B891 | B892 |
| B893 | B894 | B895 | B896 | B897 | B898 | B899 | B900 | B901 | B902 | B903 | B904 |
| B905 | B906 | B907 | B908 | B909 | B910 | B911 | B912 | B913 | B914 | B915 | B916 |
| B917 | B918 | B919 | B920 | B921 | B922 | B923 | B924 | B925 | B926 | B927 | B928 |
| B929 | B930 | B931 | B932 | B933 | B934 | B935 | B936 | B937 | B938 | B939 | B940 |
| B941 | B942 | B943 | B944 | B945 | B946 | B947 | B948 | B949 | B950 | B951 | B952 |
| B953 | B954 | B955 | B956 | B957 | B958 | B959 | B960 | B961 | B962 | B963 | B964 |
| B965 | B966 | B967 | B968 | B969 | B970 | B971 | B972 | B973 | B974 | B975 | B976 |
| B977 | B978 | B979 | B980 | B981 | B982 | B983 | B984 | B985 | B986 | B987 | B988 |
| B989 | B990 | B991 | B992 | B993 | B994 | B995 | B996 | B997 | B998 | B999 | B1000 |
| B1001 | B1002 | B1003 | B1004 | B1005 | B1006 | B1007 | B1008 | B1009 | B1010 | B1011 | B1012 |
| B1013 | B1014 | B1015 | B1016 | B1017 | B1018 | B1019 | B1020 | B1021 | B1022 | B1023 | B1024 |
| B1025 | B1026 | B1027 | B1028 | B1029 | B1030 | B1031 | B1032 | B1033 | B1034 | B1035 | B1036 |
| B1037 | B1038 | B1039 | B1040 | B1041 | B1042 | B1043 | B1044 | B1045 | B1046 | B1047 | B1048 |
| B1049 | B1050 | B1051 | B1052 | B1053 | B1054 | B1055 | B1056 | B1057 | B1058 | B1059 | B1060 |
| B1061 | B1062 | B1063 | B1064 | B1065 | B1066 | B1067 | B1068 | B1069 | B1070 | B1071 | B1072 |
| B1073 | B1074 | B1075 | B1076 | B1077 | B1078 | B1079 | B1080 | B1081 | B1082 | B1083 | B1084 |
| B1085 | B1086 | B1087 | B1088 | B1089 | B1090 | B1091 | B1092 | B1093 | B1094 | B1095 | B1096 |
| B1097 | B1098 | B1099 | B1100 | B1101 | B1102 | B1103 | B1104 | B1105 | B1106 | B1107 | B1108 |
| B1109 | B1110 | B1111 | B1112 | B1113 | B1114 | B1115 | B1116 | B1117 | B1118 | B1119 | B1120 |
| B1121 | B1122 | B1123 | B1124 | B1125 | B1126 | B1127 | B1128 | B1129 | B1130 | B1131 | B1132 |
| B1133 | B1134 | B1135 | B1136 | B1137 | B1138 | B1139 | B1140 | B1141 | B1142 | B1143 | B1144 |
| B1145 | B1146 | B1147 | B1148 | B1149 | B1150 | B1151 | B1152 | B1153 | B1154 | B1155 | B1156 |
| B1157 | B1158 | B1159 | B1160 | B1161 | B1162 | B1163 | B1164 | B1165 | B1166 | B1167 | B1168 |
| B1169 | B1170 | B1171 | B1172 | B1173 | B1174 | B1175 | B1176 | B1177 | B1178 | B1179 | B1180 |
| B1181 | B1182 | B1183 | B1184 | B1185 | B1186 | B1187 | B1188 | B1189 | B1190 | B1191 | B1192 |
| B1193 | B1194 | B1195 | B1196 | B1197 | B1198 | B1199 | B1200 | B1201 | B1202 | B1203 | B1204 |
| B1205 | B1206 | B1207 | B1208 | B1209 | B1210 | B1211 | B1212 | B1213 | B1214 | B1215 | B1216 |
| B1217 | | | | | | | | | | | |

TABLE 17

Compounds of the formula In (p is 0 or 1):

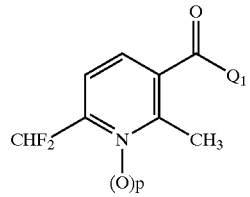

(In)

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B1 | B2 | B3 | B4 | B5 | B6 | B7 | B8 | B9 | B10 | B11 | B12 |
| B13 | B14 | B15, | B16 | B17 | B18 | B19 | B20 | B21 | B22 | B23 | — |
| B25 | B26 | B27 | B28 | B29 | B30 | B31 | B32 | B33 | B34 | B35 | B36 |
| B37 | B38 | B39 | B40 | B41 | B42 | B43 | B44 | B45 | B46 | B47 | B48 |
| B49 | B50 | B51 | B52 | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | B95 | B96 |
| B97 | B98 | B99 | B100 | B101 | B102 | B103 | B104 | B105 | B106 | B107 | B108 |
| B109 | B110 | B111 | B112 | B113 | B114 | B115 | B116 | B117 | B118 | B119 | B120 |
| B121 | B122 | B123 | B124 | B125 | B126 | B127 | B128 | B129 | B130 | B131 | B132 |
| B133 | B134 | B135 | B136 | B137 | B138 | B139 | B140 | B141 | B142 | B143 | B144 |
| B145 | B146 | B147 | B148 | B149 | B150 | B151 | B152 | B153 | B154 | B155 | B156 |
| B157 | B158 | B159 | B160 | B161 | B162 | B163 | B164 | B165 | B166 | B167 | B168 |
| B169 | B170 | B171 | B172 | B173 | B174 | B175 | B176 | B177 | B178 | B179 | B180 |
| B181 | B182 | B183 | B184 | B185 | B186 | B187 | B188 | B189 | B190 | B191 | B192 |
| B193 | B194 | B195 | B196 | B197 | B198 | B199 | B200 | B201 | B202 | B203 | B204 |
| B205 | B206 | B207 | B208 | B209 | B210 | B211 | B212 | B213 | B214 | B215 | B216 |
| B217 | B218 | B219 | B220 | B221 | B222 | B223 | B224 | B225 | B226 | B227 | B228 |
| B229 | B230 | B231 | B232 | B233 | B234 | B235 | B236 | B237 | B238 | B239 | B240 |
| B241 | B242 | B243 | B244 | B245 | B246 | B247 | B248 | B249 | B250 | B251 | B252 |
| B253 | B254 | B255 | B256 | B257 | B258 | B259 | B260 | B261 | B262 | B263 | B264 |
| B265 | B266 | B267 | B268 | B269 | B270 | B271 | B272 | B273 | B274 | B275 | B276 |
| B277 | B278 | B279 | B280 | B281 | B282 | B283 | B284 | B285 | B286 | B287 | B288 |
| B289 | B290 | B291 | B292 | B293 | B294 | B295 | B296 | B297 | B298 | B299 | B300 |
| B301 | B302 | B303 | B304 | B305 | B306 | B307 | B308 | B309 | B310 | B311 | B312 |
| B313 | B314 | B315 | B316 | B317 | B318 | B319 | B320 | B321 | B322 | B323 | B324 |
| B325 | B326 | B327 | B328 | B329 | B330 | B331 | B332 | B333 | B334 | B335 | B336 |
| B337 | B338 | B339 | B340 | B341 | B342 | B343 | B344 | B345 | B346 | B347 | B348 |
| B349 | B350 | B351 | B352 | B353 | B354 | B355 | B356 | B357 | B358 | B359 | B360 |
| B361 | B362 | B363 | B364 | B365 | B366 | B367 | B368 | B369 | B370 | B371 | B372 |
| B373 | B374 | B375 | B376 | B377 | B378 | B379 | B380 | B381 | B382 | B383 | B384 |
| B385 | B386 | B387 | B388 | B389 | B390 | B391 | B392 | B393 | B394 | B395 | B396 |
| B397 | B398 | B399 | B400 | B401 | B402 | B403 | B404 | B405 | B406 | B407 | B408 |
| B409 | B410 | B411 | B412 | B413 | B414 | B415 | B416 | B417 | B418 | B419 | B420 |
| B421 | B422 | B423 | B424 | B425 | B426 | B427 | B428 | B429 | B430 | B431 | B432 |
| B433 | B434 | B435 | B436 | B437 | B438 | B439 | B440 | B441 | B442 | B443 | B444 |
| B445 | B446 | B447 | B448 | B449 | B450 | B451 | B452 | B453 | B454 | B455 | B456 |
| B457 | B458 | B459 | B460 | B461 | B462 | B463 | B464 | B465 | B466 | B467 | B468 |
| B469 | B470 | B471 | B472 | B473 | B474 | B475 | B476 | B477 | B478 | B479 | B480 |
| B481 | B482 | B483 | B484 | B485 | B4B6 | B487 | B488 | B489 | B490 | B491 | B492 |
| B493 | B494 | B495 | B496 | B497 | B498 | B499 | B500 | B501 | B502 | B503 | B504 |
| B505 | B506 | B507 | B508 | B509 | B510 | B511 | B512 | B513 | B514 | B515 | B516 |
| B517 | B518 | B519 | B520 | B521 | B522 | B523 | B524 | B525 | B526 | B527 | B528 |
| B529 | B530 | B531 | B532 | B533 | B534 | B535 | B536 | B537 | B538 | B539 | B540 |
| B541 | B542 | B543 | B544 | B545 | B546 | B547 | B548 | B549 | B550 | B551 | B552 |
| B553 | B554 | B555 | B556 | B557 | B558 | B559 | B560 | B561 | B562 | B563 | B564 |
| B565 | B566 | B567 | B568 | B569 | B570 | B571 | B572 | B573 | B574 | B575 | B576 |
| B577 | B578 | B579 | B580 | B581 | B582 | B583 | B584 | B585 | B586 | B587 | B588 |
| B589 | B590 | B591 | B592 | B593 | B594 | B595 | B596 | B597 | B598 | B599 | B600 |
| B601 | B602 | B603 | B604 | B605 | B606 | B607 | B608 | B609 | B610 | B611 | B612 |
| B613 | B614 | B615 | B616 | B617 | B618 | B619 | B620 | B621 | B622 | B623 | B624 |
| B625 | B626 | B627 | B628 | B629 | B630 | B631 | B632 | B633 | B634 | B635 | B636 |
| B637 | B638 | B639 | B640 | B641 | B642 | B643 | B644 | B645 | B646 | B647 | B648 |
| B649 | B650 | B651 | B652 | B653 | B654 | B655 | B656 | B657 | B658 | B659 | B660 |
| B661 | B662 | B663 | B664 | B665 | B666 | B667 | B668 | B669 | B670 | B671 | B672 |
| B773 | B774 | B775 | B776 | B777 | B778 | B779 | B780 | B781 | B782 | B783 | B784 |
| B785 | B786 | B787 | B788 | B789 | B790 | B791 | B792 | B793 | B794 | B795 | B796 |
| B797 | B798 | B799 | B800 | B801 | B802 | B803 | B804 | B805 | B806 | B807 | B808 |
| B809 | B810 | B811 | B812 | B813 | B814 | B815 | B816 | B817 | B818 | B819 | B820 |
| B821 | B822 | B823 | B824 | B825 | B826 | B827 | B828 | B829 | B830 | B831 | B832 |
| B833 | B834 | B835 | B836 | B837 | B838 | B839 | B840 | B841 | B842 | B843 | B844 |
| B845 | B846 | B847 | B848 | B849 | B850 | B851 | B852 | B853 | B854 | B855 | B856 |
| B857 | B858 | B859 | B860 | B861 | B862 | B863 | B864 | B865 | B866 | B867 | B868 |

TABLE 17-continued

Compounds of the formula In (p is 0 or 1):

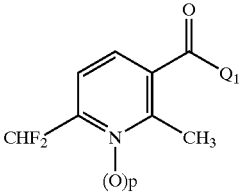

(In)

| $Q_1$ | $Q_1$ | $Q_1$ | $Q_1$ | $Q_1$ | $Q_1$ | $Q_1$ | $Q_1$ | $Q_1$ | $Q_1$ | $Q_1$ | $Q_1$ |
|---|---|---|---|---|---|---|---|---|---|---|---|
| B869 | B870 | B871 | B872 | B873 | B874 | B875 | B876 | B877 | B878 | B879 | B880 |
| B881 | B882 | B883 | B884 | B885 | B886 | B887 | B888 | B889 | B890 | B891 | B892 |
| B893 | B894 | B895 | B896 | B897 | B898 | B899 | B900 | B901 | B902 | B903 | B904 |
| B905 | B906 | B907 | B908 | B909 | B910 | B911 | B912 | B913 | B914 | B915 | B916 |
| B917 | B918 | B919 | B920 | B921 | B922 | B923 | B924 | B925 | B926 | B927 | B928 |
| B929 | B930 | B931 | B932 | B933 | B934 | B935 | B936 | B937 | B938 | B939 | B940 |
| B941 | B942 | B943 | B944 | B945 | B946 | B947 | B948 | B949 | B950 | B951 | B952 |
| B953 | B954 | B955 | B956 | B957 | B958 | B959 | B960 | B961 | B962 | B963 | B964 |
| B965 | B966 | B967 | B968 | B969 | B970 | B971 | B972 | B973 | B974 | B975 | B976 |
| B977 | B978 | B979 | B980 | B981 | B982 | B983 | B984 | B985 | B986 | B987 | B988 |
| B989 | B990 | B991 | B992 | B993 | B994 | B995 | B996 | B997 | B998 | B999 | B1000 |
| B1001 | B1002 | B1003 | B1004 | B1005 | B1006 | B1007 | B1008 | B1009 | B1010 | B1011 | B1012 |
| B1013 | B1014 | B1015 | B1016 | B1017 | B1018 | B1019 | B1020 | B1021 | B1022 | B1023 | B1024 |
| B1025 | B1026 | B1027 | B1028 | B1029 | B1030 | B1031 | B1032 | B1033 | B1034 | B1035 | B1036 |
| B1037 | B1038 | B1039 | B1040 | B1041 | B1042 | B1043 | B1044 | B1045 | B1046 | B1047 | B1048 |
| B1049 | B1050 | B1051 | B1052 | B1053 | B1054 | B1055 | B1056 | B1057 | B1058 | B1059 | B1060 |
| B1061 | B1062 | B1063 | B1064 | B1065 | B1066 | B1067 | B1068 | B1069 | B1070 | B1071 | B1072 |
| B1073 | B1074 | B1075 | B1076 | B1077 | B1078 | B1079 | B1080 | B1081 | B1082 | B1083 | B1084 |
| B1085 | B1086 | B1087 | B1088 | B1089 | B1090 | B1091 | B1092 | B1093 | B1094 | B1095 | B1096 |
| B1097 | B1098 | B1099 | B1100 | B1101 | B1102 | B1103 | B1104 | B1105 | B1106 | B1107 | B1108 |
| B1109 | B1110 | B1111 | B1112 | B1113 | B1114 | B1115 | B1116 | B1117 | B1118 | B1119 | B1120 |
| B1121 | B1122 | B1123 | B1124 | B1125 | B1126 | B1127 | B1128 | B1129 | B1130 | B1131 | B1132 |
| B1133 | B1134 | B1135 | B1136 | B1137 | B1138 | B1139 | B1140 | B1141 | B1142 | B1143 | B1144 |
| B1145 | B1146 | B1147 | B1148 | B1149 | B1150 | B1151 | B1152 | B1153 | B1154 | B1155 | B1156 |
| B1157 | B1158 | B1159 | B1160 | B1161 | B1162 | B1163 | B1164 | B1165 | B1166 | B1167 | B1168 |
| B1169 | B1170 | B1171 | B1172 | B1173 | B1174 | B1175 | B1176 | B1177 | B1178 | B1179 | B1180 |
| B1181 | B1182 | B1183 | B1184 | B1185 | B1186 | B1187 | B1188 | B1189 | B1190 | B1191 | B1192 |
| B1193 | B1194 | B1195 | B1196 | B1197 | B1198 | B1199 | B1200 | B1201 | B1202 | B1203 | B1204 |
| B1205 | B1206 | B1207 | B1208 | B1209 | B1210 | B1211 | B1212 | B1213 | B1214 | B1215 | B1216 |
| B1217 | | | | | | | | | | | |

TABLE 18

Compounds of the formula Io (p is 0 or 1):

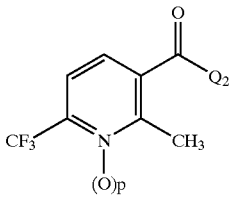

(Io)

| $Q_2$ | $Q_2$ | $Q_2$ | $Q_2$ | $Q_2$ | $Q_2$ | $Q_2$ | $Q_2$ | $Q_2$ | $Q_2$ | $Q_2$ | $Q_2$ |
|---|---|---|---|---|---|---|---|---|---|---|---|
| C1 | C2 | C3 | C4 | C5 | C6 | C7 | C8 | C9 | C10 | C11 | C12 |
| C13 | C14 | C15 | C16 | C17 | C18 | C19 | C20 | C21 | C22 | C23 | C24 |
| C25 | C26 | C27 | C28 | C29 | C30 | C31 | C32 | C33 | C34 | C35 | C36 |
| C37 | C38 | C39 | C40 | C41 | C42 | C43 | C44 | C45 | C46 | C47 | C48 |
| C49 | C50 | C51 | C52 | C53 | C54 | C55 | C56 | C57 | C58 | C59 | C60 |
| C61 | C62 | C63 | C64 | C65 | C66 | C67 | C68 | C69 | C70 | C71 | C72 |
| C73 | C74 | C75 | C76 | C77 | C78 | C79 | C80 | C81 | C82 | C83 | C84 |
| C85 | C86 | C87 | C88 | C89 | C90 | C91 | C92 | C93 | C94 | C95 | C96 |
| C97 | C98 | C99 | C100 | C101 | C102 | C103 | C104 | C105 | C106 | C107 | C108 |
| C109 | C110 | C111 | C112 | C113 | C114 | C115 | C116 | C117 | C118 | C119 | C120 |
| C121 | C122 | C123 | C124 | C125 | C126 | C127 | C128 | C129 | C130 | C131 | C132 |
| C133 | C134 | C135 | C136 | C137 | C138 | C139 | C140 | C141 | C142 | C143 | C144 |
| C145 | C146 | C147 | C148 | C149 | C150 | C151 | | | | | |

TABLE 19

Compounds of the formula Iq (p is 0 or 1):

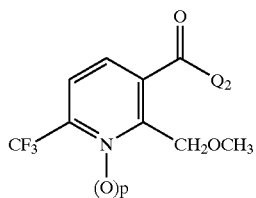

(Iq)

| Q₂ | Q₂ | Q₂ | Q₂ | Q₂ | Q₂ | Q₂ | Q₂ | Q₂ | Q₂ | Q₂ | Q₂ |
|---|---|---|---|---|---|---|---|---|---|---|---|
| C1 | C2 | C3 | C4 | C5 | C6 | C7 | C8 | C9 | C10 | C11 | C12 |
| C13 | C14 | C15 | C16 | C17 | C18 | C19 | C20 | C21 | C22 | C23 | C24 |
| C25 | C26 | C27 | C28 | C29 | C30 | C31 | C32 | C33 | C34 | C35 | C36 |
| C37 | C38 | C39 | C40 | C41 | C42 | C43 | C44 | C45 | C46 | C47 | C48 |
| C49 | C50 | C51 | C52 | C53 | C54 | C55 | C56 | C57 | C58 | C59 | C60 |
| C61 | C62 | C63 | C64 | C65 | C66 | C67 | C68 | C69 | C70 | C71 | C72 |
| C73 | C74 | C75 | C76 | C77 | C78 | C79 | C80 | C81 | C82 | C83 | C84 |
| C85 | C86 | C87 | C88 | C89 | C90 | C91 | C92 | C93 | C94 | C95 | C96 |
| C97 | C98 | C99 | C100 | C101 | C102 | C103 | C104 | C105 | C106 | C107 | C108 |
| C109 | C110 | C111 | C112 | C113 | C114 | C115 | C116 | C117 | C118 | C119 | C120 |
| C121 | C122 | C123 | C124 | C125 | C126 | C127 | C128 | C129 | C130 | C131 | C132 |
| C133 | C134 | C135 | C136 | C137 | C138 | C139 | C140 | C141 | C142 | C143 | C144 |
| C145 | C146 | C147 | C148 | C149 | C150 | C151 | | | | | |

TABLE 20

Compounds of the formula Ir (p is 0 or 1):

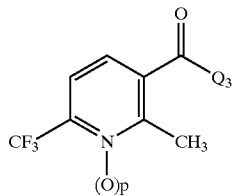

(Ir)

| Q₃ | Q₃ | Q₃ | Q₃ | Q₃ | Q₃ | Q₃ | Q₃ | Q₃ | Q₃ | Q₃ | Q₃ |
|---|---|---|---|---|---|---|---|---|---|---|---|
| D1 | D2 | D3 | D4 | D5 | D6 | D7 | D8 | D9 | D10 | D11 | D12 |
| D13 | D14 | D15 | D16 | D17 | D18 | D19 | D20 | D21 | D22 | D23 | D24 |
| D25 | D26 | D27 | D28 | D29 | D30 | D31 | D32 | D33 | D34 | D35 | D36 |
| D37 | D38 | D39 | D40 | D41 | D42 | D43 | D44 | D45 | D46 | D47 | D48 |
| D49 | D50 | D51 | D52 | D53 | D54 | D55 | D56 | D57 | D58 | D59 | D60 |
| D61 | D62 | D63 | D64 | D65 | D66 | D67 | D68 | D69 | D70 | D71 | D72 |
| D73 | D74 | D75 | D76 | D77 | D78 | D79 | D80 | D81 | D82 | D83 | D84 |
| D85 | D86 | D87 | D88 | D89 | D90 | D91 | D92 | D93 | D94 | D95 | D96 |
| D97 | D98 | D99 | D100 | D101 | D102 | D103 | D104 | D105 | D106 | D107 | D108 |
| D109 | D110 | D111 | D112 | D113 | D114 | D115 | D116 | D117 | D118 | D119 | D120 |
| D121 | D122 | D123 | D124 | D125 | D126 | D127 | D128 | D129 | D130 | D131 | D132 |
| D133 | D134 | D135 | D136 | D137 | D138 | D139 | D140 | | | | |

TABLE 21

Compounds of the formula Is (p is 0 or 1):

(Is)

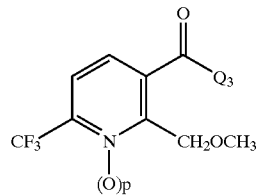

| Q₃ | Q₃ | Q₃ | Q₃ | Q₃ | Q₃ | Q₃ | Q₃ | Q₃ | Q₃ | Q₃ | Q₃ |
|---|---|---|---|---|---|---|---|---|---|---|---|
| D1 | D2 | D3 | D4 | D5 | D6 | D7 | D8 | D9 | D10 | D11 | D12 |
| D13 | D14 | D15 | D16 | D17 | D18 | D19 | D20 | D21 | D22 | D23 | D24 |
| D25 | D26 | D27 | D28 | D29 | D30 | D31 | D32 | D33 | D34 | D35 | D36 |
| D37 | D38 | D39 | D40 | D41 | D42 | D43 | D44 | D45 | D46 | D47 | D48 |
| D49 | D50 | D51 | D52 | D53 | D54 | D55 | D56 | D57 | D58 | D59 | D60 |
| D61 | D62 | D63 | D64 | D65 | D66 | D67 | D68 | D69 | D70 | D71 | D72 |
| D73 | D74 | D75 | D76 | D77 | D78 | D79 | D80 | D81 | D82 | D83 | D84 |
| D85 | D86 | D87 | D88 | D89 | D90 | D91 | D92 | D93 | D94 | D95 | D96 |
| D97 | D98 | D99 | D100 | D101 | D102 | D103 | D104 | D105 | D106 | D107 | D108 |
| D109 | D110 | D111 | D112 | D113 | D114 | D115 | D116 | D117 | D118 | D119 | D120 |
| D121 | D122 | D123 | D124 | D125 | D126 | D127 | D128 | D129 | D130 | D131 | D132 |
| D133 | D134 | D135 | D136 | D137 | D138 | D139 | D140 | | | | |

TABLE 22

Compounds of the formula It (p is 0 or 1):

(It)

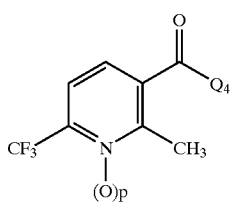

| Q₄ | Q₄ | Q₄ | Q₄ | Q₄ | Q₄ | Q₄ | Q₄ | Q₄ | Q₄ | Q₄ | Q₄ | Q₄ | Q₄ | Q₄ |
|---|---|---|---|---|---|---|---|---|---|---|---|---|---|---|
| E1 | E2 | E3 | E4 | E5 | E6 | E7 | E8 | E9 | E10 | E11 | E12 | E13 | E14 | E15 |
| E16 | E17 | E18 | E19 | E20 | E21 | E22 | E23 | E24 | E25 | E26 | E27 | E28 | E29 | E30 |

TABLE 23

Compounds of the formula Iu (p is 0 or 1);

(Iu)

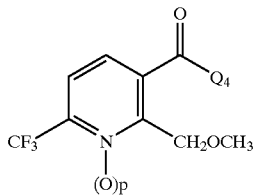

| Q₄ | Q₄ | Q₄ | Q₄ | Q₄ | Q₄ | Q₄ | Q₄ | Q₄ | Q₄ | Q₄ | Q₄ | Q₄ | Q₄ |
|---|---|---|---|---|---|---|---|---|---|---|---|---|---|
| E1 | E2 | E3 | E4 | E5 | E6 | E7 | E8 | E9 | E10 | E11 | E12 | E13 | E14 | E15 |
| E16 | E17 | E18 | E19 | E20 | E21 | E22 | E23 | E24 | E25 | E26 | E27 | E28 | E29 | E30 |

TABLE 24

Compounds of the formula Iv (p is 0 or 1):

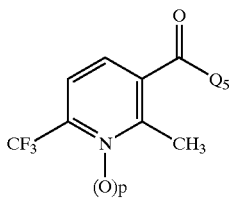

(Iv)

| $Q_5$ | $Q_5$ | $Q_5$ | $Q_5$ | $Q_5$ | $Q_5$ |
|---|---|---|---|---|---|
| F1 | F2 | F3 | F4 | F5 | F6 |

TABLE 25

Compounds of the formula Iw (P is 0 or 1):

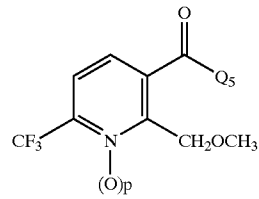

(Iw)

| $Q_5$ | $Q_5$ | $Q_5$ | $Q_5$ | $Q_5$ | $Q_5$ |
|---|---|---|---|---|---|
| F1 | F2 | F3 | F4 | F5 | F6 |

TABLE 26

Physical data of the intermediates:
Melting points are indicated in °C.

| Compound | Phys. dat. | Compound | Phys. dat. |
|---|---|---|---|
| A17 | 99–100 | A1025 | crystalline |
| A7 | 105–106 | A1206 | 94–95 |
| A9 | 73–74 | A1022 | oil |
| A6 | 148–150 | A1203 | crystalline |
| A26 | 143–144 | A21 | amorphous |
| A34 | 170–171 | A1023 | 110–111 |
| A1026 | crystalline | A1085 | 188–191 |
| A1304 | crystalline | A1088 | 157–158 |
| A1301 | crystalline | A1092 | crystalline |
| A1018 | 110–111 | A1095 | 136–138 |
| A1 | 195–197 | A1096 | 194–196 |
| A2 | 150–151 | A124 | 135–136 |
| A15 | 164–166 | A31 | 209–210 |
| A27 | 107–108 | H-B1057 | 166–167 |
| A29 | 173–174 | H-B1058 | crystalline |
| A32 | 145–146 | H-B1061 | crystalline |
| A30 | 178–181 | H-B1063 | crystalline |
| A4 | 143–144 | H-B1065 | oil |
| A3 | 148–149 | H-B1066 | 150–152 |
| A10 | 166–167 | H-B1067 | 122–123 |
| A8 | 123–124 | H-B1069 | 117–118 |
| A5 | 81–82 | H-B1070 | crystalline |
| A154 | 108–110 | H-C1 | 116–118 |
| A64 | 134–135 | H-C24 | 172–175 |
| A94 | 134–135 | A1205 | crystalline |
| A531 | crystalline | H-D113 | oil |
| A1045 | crystalline | H-F5 | oil |
| A1322 | crystalline | H-E16 | 145–148 |
| A184 | 146–147 | A1088 | 157–158 |
| A358 | 155–156 | A1103 | 152–153 |

TABLE 27

Physical data for the compounds of the formula I indicated in the above tables:
(The melting points are indicated in °C.)

| Comp. No. | m.p. | Phys. state | Comp. No. | m.p. | Phys. state |
|---|---|---|---|---|---|
| A2-B1 | 90–92 | crystalline | A34-B1 | 53–54 | crystalline |
| A2-B1082 | — | resin | A9-B1 | — | oil |
| A2-B1083 | — | resin | A184-B1 | 98–99 | crystalline |
| A2-B90 | — | resin | A184-B24 | 101–102 | crystalline |
| A2-B68 | 120–121 | crystalline | A7-B24 | — | oil |
| A2-B24 | 75–76 | crystalline | A3-B24 | — | oil |
| A7-B1 | — | oil | A34-B24 | 51–52 | crystalline |
| A2-B73 | — | resin | A2-B1091 | — | oil |
| A2-B75 | — | amorphous | A2-B1092 | — | oil |
| A2-B95 | 106–107 | crystalline | A8-B24 | 52–53 | crystalline |
| A2-B93 | 95–96 | crystalline | A18-B24 | — | oil |
| A8-B1 | 97–98 | crystalline | A2-B552 | — | resin |
| A2-B925 | — | oil | A2-C152 | — | oil |
| A3-B1 | 42-44 | crystalline | A2-B69 | — | resin |
| A94-B1 | 57–58 | crystalline | A2-D36 | — | resin |
| A2-B1057 | — | amorphous | A2-B618 | — | resin |
| A2-B1063 | — | oil | A2-B49 | — | resin |
| A2-B1061 | — | oil | A2-D71 | — | resin |
| A2-B133 | 58–60 | crystalline | A2-B1093 | — | resin |
| A2-B1058 | 89–91 | crystalline | A2-B26 | — | oil |
| A64-B24 | 80–82 | crystalline | A2-B33 | — | resin |
| A64-B1 | 49–51 | crystalline | A2-B34 | — | waxy |
| A2-B1089 | — | oil | A2-B35 | — | waxy |
| A2-B31 | 151–153 | crystalline | A2-B1087 | — | viscous |
| A2-B1090 | 139–140 | crystalline | A2-B1094 | — | viscous |
| A154-B1 | 94–95 | crystalline | A2-B1088 | 108–109 | crystalline |
| A2-B46(cis) | 61–62 | crystalline | A531-B24 | — | viscous |
| A2-B46(trans) | 83–84 | crystalline | A2-B1099 | 94–96 | crystalline |
| A2-B91 | — | resin | A2-B1095 | — | viscous |

TABLE 27-continued

Physical data for the compounds of the formula I indicated in the above tables:
(The melting points are indicated in ° C.)

| Comp. No. | m.p. | Phys. state | Comp. No. | m.p. | Phys. state |
| --- | --- | --- | --- | --- | --- |
| A2-B2 | — | resin | A2-B1097 | — | oil |
| A2-B29 | 87–88 | crystalline | A2-B1098 | 92–93 | crystalline |
| A2-B1066 | — | viscous | A2-C147 | — | resin |
| A2-B25 | — | oil | A2-B70 | — | resin |
| A2-B1067 | — | resin | A2-B49 | — | resin |
| A2-B1069 | — | oil | A2-C1 | — | oil |
| A2-B1068 | — | viscous | A2-B1096 | — | resin |
| A2-B1070 | — | viscous | A2-B1085 | 176–177 | crystalline |
| A2-B5 | — | resin | A1022-B24 | — | oil |
| A2-C149 | — | resin | A2-C47 | 107–110 | crystalline |
| A2-C146 | — | oil | A2-B1100 | 128–130 | crystalline |
| A2-B112 | — | resin | A8-B2 | 70–71 | crystalline |
| A2-D140 | — | oil | A8-B1064 | — | resin |
| A2-B354 | 139–140 | crystalline | A2-B45 | — | resin |
| A2-E16 | — | solid | A2-B10 | — | viscous |
| A6-B1 | 123–124 | crystalline | A8-B133 | 68–69 | crystalline |
| A6-B24 | — | oil | A8-B1101 | 113–114 | crystalline |
| A1322-B24 | — | oil | A8-B1106 | — | oil |
| A2-B1101 | 124–125 | crystalline | A2-D111(trans) | — | oil |
| A2-B156 | — | oil | A2-D111(cis) | — | resin |
| A2-B144 | — | resin | A8-D111(trans) | — | oil |
| A2-B145 | — | resin | A8-D109 | 62–62 | amorphous |
| A2-B134 | — | resin | A8-B35 | — | oil |
| A1210-B354 | 220 | crystalline | A1023-B2 | — | resin |
| A2-C2 | — | oil | A1023-B354 | 95–97 | crystalline |
| A358-B1 | — | oil | A15-B354 | — | resin |
| A2-D36 | — | resin | A8-B354 | — | oil |
| A1208-B354 | — | oil | A8-B1067 | — | oil |
| A2-D113(Isom. A) | — | oil | A8-C146 | — | oil |
| A2-D113(Isom. B) | — | oil | A8-C1 | — | oil |
| A2-D114(Isom. A) | 159–160 | crystalline | A94-B34 | 108-110 | crystalline |
| A2-D115 | — | amorphous | A94-B35 | 82–84 | crystalline |
| A1025-B354 | — | viscous | A1210-B354 | — | amorphous |
| A2-B1102 | 124–125 | crystalline | A2-B1105 | 119 | crystalline |
| A2-B1104 | 165–167 | crystalline | A1099-B1107 | — | amorphous |
| A1210-B1 | 117–119 | crystalline | A2-B1123 | — | resin |
| A8-B34 | — | oil | A8-B1123 | — | resin |
| A8-B1103 | — | oil | A2-B1138 | — | resin |
| A8-B1063 | 90–92 | crystalline | A124-B1 | 60–65 | crystalline |
| A8-B29 | — | oil | A1170-B1 | 106–107 | crystalline |
| A2-C24 | — | oil | A124-B34 | — | oil |
| A8-B552 | — | oil | A124-B35 | — | oil |
| A8-B156 | — | resin | A94-B2 | 53–57 | crystalline |
| A1210-B1105 | 145–146 | glassy-amorphous | A2-B1174 | — | crystalline |
| A1206-B354 | — | amorphous | A2-B1213 | 133–134 | crystalline |
| A8-B134 | — | oil | A3-B1213 | — | oil |
| A8-D36 | — | oil | A4-B1213 | — | oil |
| A8-B1213 | 71–72 | crystalline | A2-B1214 | — | resin |
| A8-F5 | — | resin | A2-F5 | — | resin |
| A1029-B1105 | 94.5–95 | crystalline | A2-D109 | — | oil |

BIOLOGICAL EXAMPLES

Example B1

Herbicidal Action Before Emergence of the Plants (Pre-emergence Action)

Monocotyledonous and dicotyledonous test plants are sown in standard soil in plastic pots. Immediately after sowing, the test substances as aqueous suspensions (prepared with a 25% wettable powder (Example F3, b) in accordance with WO 97/34485) or as emulsions (prepared with a 25% emulsion concentrate (Example F1, c)) are sprayed on at a rate of 2 kg of a.i./ha or 250 g of a.i./ha (500 l of water/ha). The test plants are then grown in the greenhouse under optimal conditions. After a test period of 3 weeks, the experiment is evaluated with reference to a nine-step scale (1=complete damage, 9=no effect). Score figures of 1 to 4 (in particular 1 to 3) mean a good to very good herbicidal action.

TABLE B1a pre-emergence action

| Compound | g/ha | Cyperus | Ipomoea | Setaria | Sinapis | Solanum | Stellaria |
|---|---|---|---|---|---|---|---|
| A2-B1 | 2000 | 2 | 2 | 1 | 2 | 2 | 1 |
| A2-B1082 | 2000 | 2 | 2 | 2 | 2 | 1 | 2 |
| A2-B1083 | 2000 | 2 | 3 | 3 | 4 | 2 | 3 |
| A2-B90 | 2000 | 1 | 1 | 1 | 1 | 1 | 1 |
| A2-B68 | 2000 | 1 | 2 | 1 | 2 | 1 | 2 |
| A2-B24 | 2000 | 1 | 1 | 1 | 2 | 1 | 1 |
| A2-B73 | 2000 | 3 | 4 | 2 | 2 | 2 | 2 |
| A2-B75 | 2000 | 2 | 3 | 2 | 2 | 1 | 2 |
| A2-B95 | 2000 | 2 | 4 | 2 | 2 | 1 | 2 |
| A2-B93 | 2000 | 2 | 4 | 2 | 2 | 1 | 2 |
| A3-B1 | 2000 | 2 | 2 | 4 | 2 | 3 | 2 |
| A94-B1 | 2000 | 1 | 2 | 2 | 1 | 1 | 2 |
| A2-B1063 | 2000 | 1 | 2 | 1 | 2 | 1 | 2 |
| A2-B1061 | 2000 | 3 | 3 | 2 | 2 | 1 | 2 |
| A2-B133 | 2000 | 1 | 2 | 2 | 2 | 1 | 2 |
| A64-B24 | 2000 | 4 | 4 | 2 | 2 | 1 | 2 |
| A2-B1089 | 2000 | 1 | 2 | 2 | 2 | 1 | 2 |
| A2-B31 | 2000 | 2 | 3 | 4 | 2 | 1 | 2 |
| A2-B46(cis) | 2000 | 1 | 2 | 1 | 2 | 1 | 2 |
| A2-B46(trans) | 2000 | 1 | 2 | 1 | 2 | 1 | 2 |
| A2-B91 | 2000 | 1 | 2 | 1 | 2 | 1 | 2 |
| A2-B2 | 2000 | 1 | 1 | 1 | 1 | 1 | 2 |
| A2-B25 | 2000 | 2 | 3 | 2 | 2 | 1 | 2 |
| A2-B1067 | 2000 | 2 | 3 | 2 | 2 | 3 | 3 |
| A2-B1068 | 2000 | 2 | 2 | 2 | 2 | 1 | 2 |
| A2-B1070 | 2000 | 2 | 3 | 3 | 2 | 2 | 2 |
| A2-C146 | 2000 | 1 | 2 | 2 | 2 | 1 | 2 |
| A2-B354 | 2000 | 1 | 1 | 1 | 1 | 1 | 2 |
| A34-B1 | 2000 | 1 | 2 | 2 | 2 | 2 | 3 |
| A9-B1 | 2000 | 2 | 1 | 2 | 1 | 1 | 2 |
| A184-B1 | 2000 | 2 | 4 | 2 | 2 | 1 | 2 |
| A184-B24 | 2000 | 1 | 3 | 2 | 2 | 1 | 2 |
| A3-B24 | 2000 | 1 | 3 | 2 | 2 | 1 | 2 |
| A8-B24 | 2000 | 1 | 2 | 2 | 2 | 1 | 3 |
| A18-B24 | 2000 | 1 | 1 | 1 | 1 | 1 | 2 |
| A2-B552 | 2000 | 1 | 2 | 2 | 2 | 1 | 2 |
| A2-C152 | 2000 | 1 | 1 | 2 | 2 | 1 | 2 |
| A2-B69 | 2000 | 1 | 4 | 2 | 2 | 1 | 1 |
| A2-D36 | 2000 | 1 | 2 | 2 | 2 | 1 | 1 |
| A2-B618 | 2000 | 1 | 1 | 1 | 2 | 1 | 1 |
| A2-B33 | 2000 | 1 | 3 | 2 | 2 | 1 | 3 |
| A2-B34 | 2000 | 1 | 3 | 2 | 2 | 1 | 2 |
| A2-B35 | 2000 | 2 | 4 | 2 | 2 | 2 | 2 |
| A2-B1095 | 2000 | 3 | 4 | 2 | 2 | 1 | 2 |
| A2-C147 | 2000 | 2 | 4 | 2 | 2 | 2 | 2 |
| A2-B49 | 2000 | 2 | 4 | 2 | 2 | 1 | 2 |
| A2-C1 | 2000 | 2 | 3 | 1 | 2 | 1 | 2 |
| A2-B1100 | 2000 | 1 | 3 | 1 | 2 | 1 | 2 |
| A8-B2 | 2000 | 1 | 3 | 2 | 2 | 1 | 2 |
| A8-B1064 | 2000 | 2 | 4 | 3 | 2 | 1 | 3 |
| A8-B1101 | 2000 | 2 | 4 | 2 | 2 | 1 | 1 |
| A2-B156 | 2000 | 1 | 2 | 1 | 2 | 1 | 2 |
| A2-B144 | 2000 | 3 | 4 | 2 | 2 | 2 | 4 |
| A2-B134 | 2000 | 1 | 2 | 1 | 2 | 1 | 1 |
| A1210-B354 | 2000 | 2 | 3 | 2 | 1 | 1 | 2 |
| A2-C2 | 2000 | 2 | 3 | 1 | 1 | 1 | 1 |
| A2-D36 | 2000 | 1 | 2 | 1 | 2 | 3 | 1 |
| A2-D113(Isom. A) | 2000 | 4 | 4 | 2 | 1 | 3 | 3 |
| A2-D115 | 2000 | 3 | 3 | 2 | 2 | 2 | 3 |
| AB-B34 | 2000 | 2 | 3 | 2 | 2 | 2 | 2 |
| AB-B1103 | 2000 | 1 | 3 | 2 | 1 | 1 | 2 |
| A2-C24 | 2000 | 1 | 2 | 1 | 1 | 1 | 2 |

TABLE B1b

Pre-emergence action:

| Compound | g/ha | Panicum | Digitaria | Echino. | Abutilon | Amaranthus | Chenop. |
|---|---|---|---|---|---|---|---|
| A8-B1 | 250 | 2 | 2 | 2 | 1 | 1 | 1 |
| A1022-B24 | 250 | 2 | 4 | 4 | 3 | 4 | 1 |
| A2-B145 | 250 | 2 | 2 | 4 | 2 | 3 | 1 |

TABLE B1b-continued

Pre-emergence action:

| Compound | g/ha | Panicum | Digitaria | Echino. | Abutilon | Amaranthus | Chenop. |
|---|---|---|---|---|---|---|---|
| A1208-B364 | 250 | 1 | 1 | 1 | 1 | 1 | 1 |
| A8-B1063 | 250 | 2 | 3 | 3 | 2 | 4 | 1 |
| A8-B552 | 250 | 2 | 3 | 4 | 1 | 4 | 1 |
| A8-B156 | 250 | 3 | 3 | 3 | 3 | 4 | 2 |
| A1210-B1105 | 250 | 2 | 3 | 2 | 1 | 4 | 1 |

The same results are obtained when the compounds of the formula I are formulated in accordance with Examples F2 and F4 to F8 in accordance with WO 97/34485.

Example B2

Post-emergence Herbicidal Action

Monocotyledonous and dicotyledonous test plants are grown in the greenhouse in plastic pots containing standard soil, and, in the 4- to 6-leaf stage, sprayed with an aqueous suspension of the test substances of the formula I prepared with a 25% wettable powder (Example F3, b) in accordance with WO 97/34485) or with an emulsion of the test substances of the formula I prepared with a 25% emulsion concentrate (Example F1, c) in accordance with WO 97/34485), corresponding to a rate of 2 kg of a.i./ha or 250 g of a.i./ha (500 l of water/ha). The test plants are subsequently grown on in the greenhouse under optimal conditions. After a test period of approximately 18 days, the test is evaluated; with reference to a nine-step scale (1=complete damage, 9=no effect). Score figures of 1 to 4 (in particular 1 to 3) mean a good to very good herbicidal action. In this test, the compounds of the formula I show a potent herbicidal action.

TABLE B2a

Post-emergence action:

| Compound | g/ha | Ipomoea | Lolium | Setaria | Sinapis | Solanum | Stellaria |
|---|---|---|---|---|---|---|---|
| A2-B1 | 2000 | 1 | 2 | 1 | 1 | 1 | 2 |
| A2-B1082 | 2000 | 1 | 2 | 2 | 1 | 1 | 2 |
| A2-B1083 | 2000 | 1 | 4 | 2 | 1 | 1 | 2 |
| A2-B90 | 2000 | 1 | 2 | 2 | 1 | 2 | 2 |
| A2-B68 | 2000 | 1 | 2 | 2 | 1 | 1 | 2 |
| A2-B24 | 2000 | 1 | 2 | 2 | 1 | 2 | 2 |
| A2-B73 | 2000 | 1 | 3 | 2 | 1 | 1 | 2 |
| A2-B75 | 2000 | 2 | 2 | 3 | 1 | 2 | 2 |
| A2-B95 | 2000 | 1 | 2 | 2 | 1 | 2 | 2 |
| A2-B93 | 2000 | 1 | 2 | 2 | 1 | 2 | 2 |
| A3-B1 | 2000 | 1 | 3 | 2 | 1 | 1 | 2 |
| A94-B1 | 2000 | 1 | 2 | 2 | 1 | 1 | 1 |
| A2-B1063 | 2000 | 2 | 2 | 4 | 1 | 2 | 2 |
| A2-B1061 | 2000 | 2 | 2 | 2 | 1 | 2 | 2 |
| A2-B133 | 2000 | 1 | 2 | 2 | 1 | 2 | 2 |
| A2-B1058 | 2000 | 1 | 2 | 4 | 1 | 2 | 2 |
| A64-B24 | 2000 | 2 | 2 | 4 | 1 | 2 | 2 |
| A64-B1 | 2000 | 2 | 3 | 4 | 1 | 1 | 2 |
| A2-B1089 | 2000 | 1 | 2 | 2 | 1 | 1 | 2 |
| A2-B31 | 2000 | 2 | 2 | 2 | 1 | 2 | 2 |
| A2-B1090 | 2000 | 2 | 4 | 4 | 2 | 2 | 2 |
| A2-B46(cis) | 2000 | 1 | 2 | 3 | 1 | 2 | 2 |
| A2-B46(trans) | 2000 | 1 | 2 | 2 | 1 | 1 | 2 |
| A2-B91 | 2000 | 1 | 2 | 2 | 1 | 2 | 2 |
| A2-B2 | 2000 | 1 | 2 | 2 | 1 | 2 | 2 |
| A2-B29 | 2000 | 2 | 3 | 2 | 1 | 2 | 2 |
| A2-B1066 | 2000 | 1 | 3 | 2 | 1 | 2 | 2 |
| A2-B25 | 2000 | 1 | 2 | 2 | 2 | 1 | 2 |
| A2-B1068 | 2000 | 1 | 2 | 4 | 1 | 1 | 2 |
| A2-B1070 | 2000 | 2 | 4 | 2 | 2 | 2 | 2 |
| A2-B5 | 2000 | 1 | 2 | 2 | 1 | 2 | 2 |
| A2-C149 | 2000 | 1 | 3 | 2 | 1 | 2 | 2 |
| A2-C146 | 2000 | 1 | 2 | 2 | 1 | 2 | 2 |
| A2-B112 | 2000 | 2 | 3 | 2 | 1 | 2 | 2 |
| A2-B354 | 2000 | 2 | 2 | 2 | 2 | 2 | 2 |
| A2-E16 | 2000 | 2 | 3 | 2 | 2 | 2 | 2 |
| A6-B24 | 2000 | 1 | 3 | 2 | 1 | 1 | 2 |
| A34-B1 | 2000 | 1 | 2 | 2 | 1 | 1 | 2 |
| A9-B1 | 2000 | 2 | 4 | 2 | 2 | 2 | 2 |
| A184-B1 | 2000 | 1 | 3 | 2 | 1 | 2 | 2 |
| A184-B24 | 2000 | 1 | 2 | 2 | 1 | 2 | 2 |
| A7-B24 | 2000 | 1 | 2 | 2 | 1 | 2 | 2 |
| A3-B24 | 2000 | 2 | 2 | 2 | 1 | 2 | 2 |

TABLE B2a-continued

Post-emergence action:

| Compound | g/ha | Ipomoea | Lolium | Setaria | Sinapis | Solanum | Stellaria |
|---|---|---|---|---|---|---|---|
| A34-B24 | 2000 | 1 | 2 | 2 | 1 | 2 | 2 |
| A8-B24 | 2000 | 2 | 2 | 2 | 1 | 2 | 2 |
| A18-B24 | 2000 | 1 | 2 | 2 | 1 | 2 | 2 |
| A2-C152 | 2000 | 2 | 2 | 3 | 1 | 2 | 2 |
| A2-B69 | 2000 | 1 | 2 | 2 | 1 | 2 | 2 |
| A2-D36 | 2000 | 2 | 2 | 2 | 1 | 2 | 2 |
| A2-B618 | 2000 | 2 | 2 | 2 | 1 | 2 | 2 |
| A2-B49 | 2000 | 2 | 2 | 2 | 1 | 2 | 2 |
| A2-B1093 | 2000 | 2 | 2 | 2 | 1 | 2 | 2 |
| A2-B33 | 2000 | 2 | 4 | 2 | 1 | 2 | 2 |
| A2-B34 | 2000 | 1 | 3 | 2 | 1 | 1 | 2 |
| A2-B35 | 2000 | 1 | 3 | 2 | 1 | 1 | 2 |
| A2-B1087 | 2000 | 1 | 4 | 3 | 1 | 2 | 2 |
| A531-B24 | 2000 | 2 | 2 | 2 | 1 | 2 | 2 |
| A2-B1095 | 2000 | 1 | 2 | 4 | 1 | 2 | 2 |
| A2-C147 | 2000 | 1 | 2 | 2 | 1 | 2 | 2 |
| A2-B70 | 2000 | 3 | 4 | 3 | 1 | 2 | 2 |
| A2-B49 | 2000 | 2 | 2 | 2 | 1 | 2 | 2 |
| A2-C1 | 2000 | 3 | 2 | 2 | 1 | 2 | 2 |
| A2-B1100 | 2000 | 2 | 2 | 3 | 1 | 1 | 2 |
| A8-B2 | 2000 | 2 | 2 | 2 | 2 | 2 | 3 |
| A8-B1064 | 2000 | 2 | 4 | 2 | 1 | 1 | 2 |
| A8-B133 | 2000 | 2 | 4 | 2 | 1 | 2 | 2 |
| A8-B1101 | 2000 | 2 | 3 | 2 | 1 | 2 | 2 |
| A2-B1101 | 2000 | 2 | 2 | 2 | 1 | 1 | 3 |
| A2-B156 | 2000 | 1 | 2 | 2 | 1 | 2 | 2 |
| A2-B134 | 2000 | 2 | 2 | 1 | 1 | 1 | 2 |
| A1210-B354 | 2000 | 2 | 2 | 2 | 1 | 1 | 2 |
| A2-C2 | 2000 | 2 | 1 | 1 | 1 | 1 | 1 |
| A2-D36 | 2000 | 2 | 1 | 1 | 1 | 1 | 1 |
| A2-D113(Isom. A) | 2000 | 2 | 1 | 1 | 1 | 1 | 2 |
| A2-D113(Isom. B) | 2000 | 2 | 2 | 2 | 2 | 1 | 2 |
| A2-D114 | 2000 | 2 | 1 | 1 | 1 | 1 | 1 |
| A2-D115 | 2000 | 1 | 2 | 1 | 1 | 1 | 1 |
| A8-B34 | 2000 | 2 | 2 | 2 | 2 | 2 | 2 |
| A8-B1103 | 2000 | 1 | 4 | 1 | 1 | 1 | 1 |
| A2-C24 | 2000 | 1 | 1 | 1 | 1 | 1 | 1 |

TABLE B2b

Post-emergence action:

| Compound | g/ha | Panicum | Digitaria | Echino. | Abutilon | Xanth. | Ipopur. | Chenop. |
|---|---|---|---|---|---|---|---|---|
| A8-Bl | 250 | 4 | 3 | 3 | 3 | 3 | 3 | 2 |
| A2-B1091 | 250 | 4 | 4 | 2 | 3 | 4 | 3 | 3 |
| A2-B1094 | 250 | 2 | 3 | 2 | 3 | 3 | 3 | 2 |
| A2-B145 | 250 | 2 | 2 | 2 | 3 | 3 | 3 | 1 |
| A1208-B354 | 250 | 3 | 4 | 2 | 1 | 2 | 2 | 2 |
| A1210-B1 | 250 | 2 | 2 | 2 | 2 | 2 | 2 | 1 |
| A8-B552 | 250 | 2 | 3 | 3 | 2 | 2 | 2 | 2 |
| A8-B156 | 250 | 2 | 3 | 3 | 1 | 2 | 2 | 1 |
| A1210-B1105 | 250 | 1 | 2 | 3 | 2 | 2 | 2 | 1 |
| A8-B134 | 250 | 3 | 3 | 3 | 2 | 3 | 3 | 2 |
| A8-D36 | 250 | 3 | 3 | 2 | 2 | 3 | 3 | 2 |
| A2-D111(cis) | 250 | 2 | 2 | 4 | 2 | 1 | 2 | 2 |
| A2-D111(trans) | 250 | 3 | 3 | 3 | 3 | 1 | 3 | 2 |
| A8-D111 | 250 | 3 | 3 | 3 | 3 | 1 | 2 | 3 |
| A8-D109 | 250 | 3 | 3 | 3 | 3 | 1 | 2 | 3 |
| A8-F5 | 250 | 4 | 3 | 4 | 3 | 3 | 3 | 3 |
| A2-F5 | 250 | 3 | 3 | 3 | 3 | 3 | 4 | 3 |

The same results are obtained when the compounds of the formula I are formulated in accordance with Examples F2 and F4 to F8 in accordance with WO 97/34485.

What is claimed is:

1. A compound of the formula I

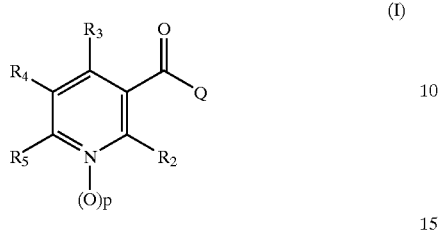

in which p is 0 or 1;

$R_5$ is $C_1$–$C_6$haloalkyl;

$R_2$ is hydrogen, $C_1$–$C_6$alkyl, $C_1$–$C_6$haloalkyl, $C_2$–$C_6$alkenyl, $C_2$–$C_6$haloalkenyl, vinyl substituted by $C_1$–$C_2$alkoxycarbonyl or phenyl, or is $C_2$–$C_6$alkynyl, $C_2$–$C_6$haloalkynyl, ethynyl which is substituted by trimethylsilyl, hydroxyl, $C_1$–$C_2$alkoxy, $C_1$–$C_2$alkoxycarbonyl or phenyl, or is $C_3$–$C_6$allenyl, $C_3$–$C_6$cycloalkyl, $C_3$–$C_6$cycloalkyl which is substituted by halogen, or is $C_1$–$C_6$alkoxy, $C_3$–$C_6$alkenyloxy, $C_3$–$C_6$-alkynyloxy, $C_1$–$C_6$haloalkoxy, $C_3$–$C_6$haloalkenyloxy, cyano-$C_1$–$C_4$alkoxy, $C_1$–$C_4$alkoxy-$C_1$–$C_4$alkoxy, $C_1$–$C_4$alkylthio-$C_1$–$C_4$alkoxy, $C_1$–$C_4$alkylsulfinyl-$C_1$–$C_4$alkoxy, $C_1$–$C_4$alkylsulfonyl-$C_1$–$C_4$alkoxy, $C_1$–$C_4$alkoxycarbonyl-$C_1$–$C_4$alkoxy, $C_1$–$C_6$alkylthio, $C_1$–$C_6$alkylsulfinyl, $C_1$–$C_6$alkylsulfonyl, $C_1$–$C_6$haloalkylthio, $C_1$–$C_6$haloalkylsulfinyl, $C_1$–$C_6$haloalkylsulfonyl, $C_1$–$C_4$alkoxycarbonyl-$C_1$–$C_4$alkylthio, $C_1$–$C_4$-alkoxycarbonyl-7$_1$–$C_4$alkylsulfinyl, $C_1$–$C_4$alkoxycarbonyl-$C_1$–$C_4$alkylsulfonyl, benzyl-$S(O)_{n1}$—, $C_1$–$C_6$alkylamino, $C_2$–$C_6$dialkylamino, $C_1$–$C_6$alkylaminosulfonyl, di-($C_1$–$C_6$alkylamino)sulfonyl, benzyloxy, benzyl, phenyl, phenoxy, phenylthio, phenylsulfinyl or phenylsulfonyl, it being possible for the phenyl-containing groups, in turn, to be substituted by $C_1$–$C_3$alkyl, $C_1$–$C_3$haloalkyl, $C_1$–$C_3$alkoxy, $C_1$–$C_3$haloalkoxy, halogen, cyano or nitro or $R_2$ is $OS(O)_{n2}$—$R_{21}$, $N(R_{23})$—$S(O)_{n3}$—$R_{22}$, cyano, carbamoyl, $C_1$–$C_4$alkoxycarbonyl, formyl, halogen, thiocyanato, amino, hydroxy-$C_1$–$C_4$alkyl, $C_1$–$C_4$alkoxy-$C_1$–$C_4$alkyl, $C_1$–$C_4$alkyl-$S(O)_{n4}$—$C_1$–$C_4$alkyl, cyano-$C_1$–$C_4$alkyl, $C_1$–$C_6$alkylcarbonyloxy-$C_1$–$C_4$alkyl, $C_1$–$C_4$alkoxycarbonyl-$C_1$–$C_4$alkyl, $C_1$–$C_4$alkoxycarbonyloxy-$C_1$–$C_4$alkyl, $C_1$–$C_4$thiocyanato-$C_1$–$C_4$alkyl, benzoyloxy-$C_1$–$C_4$alkyl, $C_2$–$C_6$oxiranyl, $C_1$–$C_4$alkylamino-$C_1$–$C_4$alkyl, di-($C_1$–$C_4$-alkyl)amino-$C_1$–$C_4$alkyl, $C_1$–$C_{12}$alkylthiocarbonyl-$C_1$–$C_4$alkyl or formyl-$C_1$–$C_4$alkyl, or $R_2$ is a five- to ten-membered monocyclic or fused bicyclic ring system which can be aromatic or partially saturated and can contain 1 to 4 hetero atoms selected from the group consisting of nitrogen, oxygen and sulfur, the ring system being bonded to the pyridine ring via a $C_1$–$C_4$alkylene, —CH=CH—, —C≡C—, —CH$_2$O—, —CH$_2$N($C_1$–$C_4$alkyl)—, —CH$_2$SO—, or —CH$_2$SO$_2$ group and it not being possible for each ring system to contain more than 2 oxygen atoms and more than 2 sulfur atoms, and it being possible for the ring system itself to be mono-, di- or trisubstituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_2$–$C_5$alkoxyalkylthio, $C_3$–$C_5$acetylalkylthio, $C_3$–$C_6$alkoxycarbonylalkylthio, $C_2$–$C_4$cyanoalkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylaminosulfonyl, di-($C_1$–$C_2$alkyl)aminosulfonyl, di-($C_1$–$C_4$alkyl)amino, halogen, cyano, nitro, phenyl and benzylthio, it being possible for phenyl and benzylthio, in turn, to be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or nitro, and where substituents on the nitrogen in the heterocyclic ring are other than halogen;

$R_3$ is hydrogen, $C_1$–$C_6$alkyl, $C_1$–$C_6$haloalkyl, $C_2$–$C_6$alkenyl, $C_2$–$C_6$haloalkenyl, $C_2$–$C_6$alkynyl, $C_2$–$C_6$haloalkynyl, $C_3$–$C_6$cycloalkyl, $C_1$–$C_6$alkoxy, $C_1$–$C_6$haloalkoxy, $C_1$–$C_6$alkylthio, $C_1$–$C_6$alkylsulfinyl, $C_1$–$C_6$alkylsulfonyl, $C_1$–$C_6$haloalkylthio, $C_1$–$C_6$haloalkylsulfinyl, $C_1$–$C_6$haloalkylsulfonyl, $C_1$–$C_6$alkylamino, $C_2$–$C_6$dialkylamino, $C_1$–$C_6$alkylaminosulfonyl, $C_2$–$C_6$dialkylaminosulfonyl, phenyl, phenylthio, phenylsulfinyl, phenylsulfonyl or phenoxy, it being possible for phenyl, in turn, to be substituted by $C_1$–$C_3$alkyl, $C_1$–$C_3$haloalkyl, $C_1$–$C_3$alkoxy, $C_1$–$C_3$haloalkoxy, halogen, cyano or nitro, or $R_3$ is —N($R_{23}$)—$S(O)_n$—$R_{22}$, cyano, halogen, amino, $C_1$–$C_4$alkoxy-$C_1$–$C_4$alkyl or $C_1$–$C_4$alkyl-$S(O)_n$—$C_1$–$C_4$alkyl;

$R_4$ is hydrogen, $C_1$–$C_6$alkyl, hydroxyl, $C_1$–$C_6$alkoxy, $C_1$–$C_6$haloalkoxy, $C_3$–$C_6$alkenyloxy, $C_3$–$C_6$haloalkenyloxy, $C_3$–$C_6$alkynyloxy, $C_1$–$C_4$alkylcarbonyloxy, $C_1$–$C_4$alkylsulfonyloxy, tosyloxy, $C_1$–$C_4$alkylthio, $C_1$–$C_4$alkylsulfinyl, $C_1$–$C_4$alkylsulfonyl, $C_1$–$C_4$alkylamino, $C_1$–$C_4$dialkylamino, $C_1$–$C_4$alkoxycarbonyl, $C_1$–$C_4$haloalkyl, formyl, cyano, halogen, phenyl or phenoxy, it being possible for phenyl, in turn, to be substituted by $C_1$–$C_3$alkyl, $C_1$–$C_3$haloalkyl, $C_1$–$C_3$alkoxy, $C_1$–$C_3$haloalkoxy, halogen, cyano or nitro;

or $R_4$ is a five to ten-membered monocyclic or $R_3$-fused bicyclic ring system which can contain 1 to 4 hetero atoms selected from the group consisting of nitrogen, oxygen and sulfur, the ring system, unless fused, being bonded to the pyridine ring directly or via a $C_1$–$C_4$alkylene, —CH=CH—, —C≡C—, —CH$_2$O—, —CH$_2$N($C_1$–$C_4$alkyl)—, —CH$_2$S—, —CH$_2$SO—, or —CH$_2$SO$_2$— group and it not being possible for the ring system to contain more than 2 oxygen atoms and more than two sulfur atoms, and it being possible for the ring system itself to be mono-, di- or trisubstituted by $C_1$–$C_6$alkyl, $C_1$–$C_6$haloalkyl, $C_2$–$C_6$alkenyl, $C_2$–$C_6$haloalkenyl, $C_2$–$C_6$alkynyl, $C_2$–$C_6$haloalkynyl, $C_1$–$C_6$alkoxy, $C_1$–$C_6$haloalkoxy, $C_3$–$C_6$alkenyloxy, $C_3$–$C_6$alkynyloxy, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_1$–$C_4$alkoxy-$C_1$–$C_2$alkylthio, $C_1$–$C_4$alkylcarbonyl- $C_1$–$C_2$alkylthio, $C_1$–$C_4$alkoxycarbonyl-$C_1$–$C_2$alkylthio, cyano-$C_1$–$C_4$alkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylaminosulfonyl, di-($C_1$–$C_2$alkyl)aminosulfonyl, di-($C_1$–$C_4$alkyl)amino, halogen, cyano, nitro, phenyl and benzylthio, it being possible for phenyl and benzylthio, in turn, to be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or nitro, and where substituents on the nitrogen in the heterocyclic ring are other than halogen;

$R_{21}$ is $C_1$–$C_4$alkyl or $C_1$–$C_4$haloalkyl;

$R_{22}$ is $C_1$–$C_4$alkyl, $C_1$–$C_4$haloalkyl or di-($C_1$–$C_4$alkyl)amino;

$R_{23}$, $R_{24}$, $R_{25}$ independently of one another are hydrogen or $C_1$–$C_4$alkyl;

n, $n_1$, $n_2$, $n_3$ and $n_4$ independently of one another are 0, 1 or 2;

Q is $Q_1$

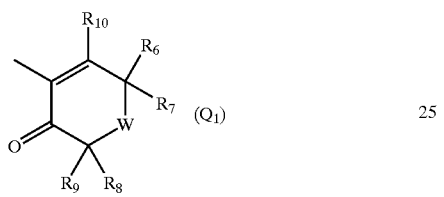

in which $R_6$, $R_7$, $R_8$ and $R_9$ independently of one another are hydrogen, $C_1$–$C_6$alkyl, $C_1$–$C_6$haloalkyl, $C_2$–$C_6$alkenyl, $C_2$–$C_6$alkynyl, $C_1$–$C_6$alkoxycarbonyl, $C_1$–$C_6$alkylcarbonyl, $C_1$–$C_6$alkyl-S(O)$_{n17}$, $C_1$–$C_6$alkyl-NHS(O)$_2$, $C_1$–$C_6$alkylamino, di-($C_1$–$C_6$alkyl)amino, hydroxyl, $C_1$–$C_6$alkoxy, $C_3$–$C_6$alkenyloxy, $C_3$–$C_6$alkynyloxy, hydroxy-$C_1$–$C_6$alkyl, $C_1$–$C_4$alkylsulfonyloxy-$C_1$–$C_6$alkyl, tosyloxy-$C_1$–$C_6$alkyl, $C_1$–$C_6$alkoxy-$C_1$–$C_6$alkyl, $C_1$–$C_6$alkyl-S(O)$_{n4}$—$C_1$–$C_6$alkyl, cyano-$C_1$–$C_6$alkyl, $C_1$–$C_6$alkoxy-$C_1$–$C_6$alkoxy, benzyloxy-$C_1$–$C_6$alkyl, $C_1$–$C_6$alkoxycarbonyl-$C_1$–$C_6$alkyl, $C_1$–$C_6$alkoxycarbonyloxy-$C_1$–$C_6$alkyl, thiocyanato-$C_1$–$C_6$alkyl, oxiranyl, $C_1$–$C_6$alkylamino-$C_1$–$C_6$alkyl, di($C_1$–$C_6$alkyl)amino-$C_1$–$C_6$alkyl, formyl-$C_1$–$C_6$alkyl, $C_1$–$C_6$alkyloximo, halogen, cyano, nitro, phenyl or phenyl which is substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, amino, $C_1$–$C_4$alkylamino, di-$C_1$–$C_4$alkylamino, $C_1$–$C_4$alkyl-S(O)$_{n18}$, $C_1$–$C_4$alkyl-S(O)$_2$O, $C_1$–$C_4$haloalkyl-S(O)$_{n5}$, $C_1$–$C_4$haloalkyl-S(O)$_2$O, $C_1$–$C_4$alkyl-S(O)$_2$NH, $C_1$–$C_4$alkyl-S(O)$_{n19}$N($C_1$–$C_4$alkyl)$_2$, halogen, nitro, COOH or cyano;

or adjacent $R_6$ and $R_7$ or $R_8$ and $R_9$ together are —(CH$_2$)$_m$—, C(O)O(CH$_2$)$_{n20}$— or —S(O)$_{n21}$(CH$_2$)$_{n22}$—;

$n_5$, $n_{17}$, $n_{18}$, $n_{19}$ and $n_{21}$ independently of one another are 0, 1 or 2;

$n_{20}$ is 2 or 3;

$n_{22}$ is 2,3 or 4;

m is 2,3,4,5, or 6;

W is oxygen, S(O)$_{n6}$—CR$_{11}$R$_{12}$, —CR$_{63}$R$_{64}$CR$_{65}$R$_{66}$, —C(O)— or —NR$_{13}$;

$R_{63}$, $R_{64}$, $R_{65}$ and $R_{66}$ independently of one another are hydrogen or $C_1$–$C_6$alkyl, or $R_{65}$ together with $R_7$ or $R_9$ forms a direct bond;

$n_6$ is 0, 1 or 2;

$R_{11}$ is hydrogen, $C_1$–$C_4$alkyl, $C_1$–$C_4$haloalkyl, $C_1$–$C_4$alkoxy-$C_1$–$C_4$alkyl, $C_1$–$C_4$alkylthio-$C_1$–$C_4$alkyl, $C_1$–$C_4$alkylthio-$C_3$–$C_6$cycloalkyl, $C_1$–$C_4$alkycarbonyloxy-$C_1$–$C_4$alkyl, $C_1$–$C_4$alkysulfonyloxy-$C_1$–$C_4$alkyl, tosyloxy-$C_1$–$C_4$alkyl, di-($C_1$–$C_3$alkoxyalkyl)methyl, di-($C_1$–$C_3$alkthioalkyl)methyl, ($C_1$–$C_3$alkoxyalkyl)-($C_1$–$C_3$alkthioalkyl)methyl, $C_3$–$C_5$oxacycloalkyl, $C_3$–$C_5$thiacycloalkyl, $C_3$–$C_4$dioxacycloalkyl, $C_3$–$C_4$dithiacycloalkyl, $C_3$–$C_4$oxathiacycloalkyl, formyl, $C_1$–$C_4$alkoxycarbonyl, carbamoyl, $C_1$–$C_4$alkylaminocarbonyl, di-($C_1$–$C_4$alkyl)aminocarbonyl, phenylaminocarbonyl, benzylaminocarbonyl or phenyl which, in turn, can be substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, amino, $C_1$–$C_4$alkylamino, di-$C_1$–$C_4$alkylamino, $C_1$–$C_4$alkyl-S(O)$_{n21}$, $C_1$–$C_4$alkyl-S(O)$_2$O, $C_1$–$C_4$haloalkyl-S(O)$_{n7}$, $C_1$–$C_4$haloalkyl-S(O)$_2$O, $C_1$–$C_4$alkyl-S(O)$_2$NH, $C_1$–$C_4$alkyl-S(O)$_{n20}$N($C_1$–$C_4$alkyl), halogen, nitro, COOH or cyano;

$n_7$, $n_{20}$ and $n_{21}$ independently of one another are 0, 1 or 2;

or $R_{12}$ together with $R_6$ or $R_9$ is a group —(CH$_{2o}$—;

o is 1, 2, 3, 4 or 5;

$R_{12}$ is hydrogen, $C_1$–$C_4$alkyl or $C_1$–$C_4$haloalkyl;

or $R_{12}$ together with $R_{11}$ is a group —(CH$_2$)$_{m1}$;

$m_1$ is 2, 3, 4, 5, or 6;

$R_{10}$ is hydroxyl, O$^-$M$^+$, halogen, cyano, SCN, OCN, $C_1$–$C_{12}$alkoxy, $C_1$–$C_4$alkoxycarbonyl-$C_1$–$C_4$alkoxy, $C_1$–$C_{12}$alkylthio, $C_1$–$C_{12}$alkylsulfinyl, $C_1$–$C_{12}$alkylsulfonyl, $C_1$–$C_{12}$haloalkylthio, $C_1$–$C_{12}$haloalkylsulfinyl, $C_1$–$C_{12}$haloalkylsulfonyl, $C_1$–$C_6$alkoxy-$C_1$–$C_6$alkylthio, $C_1$–$C_6$alkoxy-$C_1$–$C_6$alkylsulfinyl, $C_1$–$C_6$alkoxy-$C_1$–$C_6$alkylsulfonyl, $C_1$–$C_{12}$alkenylthio, $C_2$–$C_{12}$alkenylsulfinyl, $C_2$–$C_{12}$alkenylsulfonyl, $C_2$–$C_{12}$alkynylthio, $C_2$–$C_{12}$alkynylsulfinyl, $C_2$–$C_{12}$alkynylsulfonyl, $C_2$–$C_{12}$haloalkenylthio, $C_2$–$C_{12}$haloalkenylsulfinyl, $C_2$–$C_{12}$haloalkenylsulfonyl, $C_1$–$C_4$-alkoxycarbonyl-$C_1$–$C_4$alkylthio, $C_1$–$C_4$alkoxycarbonyl-$C_1$–$C_4$alkylsulfinyl, $C_1$–$C_4$alkoxycarbonyl-$C_1$–$C_4$alkylsulfonyl, ($C_1$–$C_4$alkoxy)$_2$P(O)O, $C_1$–$C_4$alkyl-($C_1$–$C_4$alkoxy)P(O)O, H($C_1$–$C_4$alkoxy)P(O)O, $R_{14}R_{15}$N, $R_{14}R_{15}$NNH, $R_{16}R_{17}$NC(O)O—, $R_{16}R_{17}$NC(O)NH—, $C_1$–$C_{12}$alkyl-S(O)$_2$NR$_{18}$, $C_1$–$C_4$haloalkyl-S(O)$_2$NR$_{19}$, $C_1$–$C_1$ alkyl-S(O)$_2$O, $C_1$–$C_4$haloalkyl-S(O)$_2$O, $C_1$–$C_{18}$alkylcarbonyloxy, it being possible for the alkyl group to be substituted by halogen, $C_1$–$C_6$alkoxy, $C_1$–$C_6$alkylthio or cyano, or is $C_2$–$C_{18}$alkenylcarbonyloxy, $C_2$–$C_{18}$alkynylcarbonyloxy, $C_3$–$C_6$cycloalkylcarbonyloxy, $C_1$–$C_{12}$alkoxycarbonyloxy, $C_1$–$C_{12}$alkylthiocarbonyloxy, $C_1$–$C_{12}$alkylthiocarbamoyl, $C_1$–$C_6$alkyl-NH(CS)N($C_1$–$C_6$alkyl)—NH—, di-$C_1$–$C_6$alkyl-N(CS)N($C_1$–$C_6$alkyl)—NH—, benzyloxy, benzylthio, benzylsulfinyl, benzylsulfonyl, phenoxy, phenylthio, phenylsulfinyl, phenylsulfonyl, phenylsulfonylamino, phenylsulfonyloxy or benzoyloxy, it being possible for the phenyl groups, in turn, to be substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, $C_1$–$C_4$alkylamino, di-$C_1$-$C_4$alkylamino, $C_1$-$C_4$alkylthio, $C_1$-$C_4$alkylsulfinyl, $C_1$-$C_4$alkylsulfonyl, $C_1$-$C_4$alkyl-S(O)$_2$O, $C_1$-$C_4$haloalkylthio, $C_1$-$C_4$haloalkylsulfinyl, $C_1$-$C_4$haloalkylsulfonyl, $C_1$-$C_4$haloalkyl-S(O)$_2$O, $C_1$-$C_4$alkyl-S(O)$_2$NH, $C_1$-$C_4$alkyl-S(O)$_2$N($C_1$-$C_4$alkyl), halogen, nitro or cyano;

or $R_{10}$ is a group $Ar_1$-thio, $Ar_2$-sulfinyl, $Ar_3$-sulfonyl, —OCO—$Ar_4$ or NH-$Ar_5$ in which $Ar_1$, $Ar_2$, $Ar_3$, $Ar4$ and $Ar_5$ independently of one another are a five to ten-membered monocyclic or fused bicyclic ring system which can be aromatic or partially saturated and can contain 1 to 4 hetero atoms selected from the group consisting of nitrogen, oxygen and sulfur, and it not being possible for each ring system to contain more than 2 oxygen atoms and more than two sulfur atoms, and it being possible for the ring system itself to be mono-, di- or trisubstituted by $C_1$-$C_6$alkyl, $C_1$-$C_6$haloalkyl, $C_3$-$C_6$alkenyl, $C_3$-$C_6$haloalkenyl, $C_3$-$C_6$alkynyl, $C_3$-$C_6$haloalkynyl, $C_1$-$C_6$alkoxy, $C_1$-$C_6$haloalkoxy, $C_3$-$C_6$alkenyloxy, $C_3$-$C_6$alkynyloxy, mercapto, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_2$-$C_5$alkoxyalkylthio, $C_3$-$C_5$acetylalkylthio, $C_3$-$C_6$alkoxycarbonylalkylthio, $C_2$-$C_4$-cyanoalkylthio, $C_1$-$C_6$alkylsulfinyl, $C_1$-$C_6$haloalkylsulfinyl, $C_1$-$C_6$alkylsulfonyl, $C_1$-$C_6$-haloalkylsulfonyl, aminosulfonyl, $C_1$-$C_2$alkylaminosulfonyl, di-($C_1$-$C_2$alkyl)aminosulfonyl, di-($C_1$-$C_4$alkyl)amino, halogen, cyano, nitro, phenyl and benzylthio, it being possible for phenyl and benzylthio, in turn, to be substituted on the phenyl ring by $C_1$-$C_3$alkyl, $C_1$-$C_3$haloalkyl, $C_1$-$C_3$alkoxy, $C_1$-$C_3$haloalkoxy, halogen, cyano or nitro, and where substituents on the nitrogen in the heterocyclic rings are other than halogen;

$R_{14}$, $R_{15}$, $R_{16}$, $R_{17}$ and $R_{18}$ independently of one another are hydrogen or $C_1$-$C_6$alkyl;

$n_8$, $n_9$, $n_{10}$, $n_{11}$, $n_{12}$, $n_{13}$ and $n_{14}$ independently of one another are 0, 1 or 2;

$R_{13}$ is hydrogen, $C_1$-$C_4$alkyl, $C_1$-$C_4$alkythio-$C_1$-$C_4$carbonyl, $C_1$-$C_4$alkylsulfinyl-$C_1$-$C_4$carbonyl, $C_1$-$C_4$alkylsulfonyl-$C_1$-$C_4$carbonyl, $C_1$-$C_4$-alkoxycarbonyl, $C_1$-$C_4$alkylcarbonyl, phenylcarbonyl, or is phenyl which, in turn, can be substituted by $C_1$-$C_4$alkyl, $C_1$-$C_4$haloalkyl, $C_1$-$C_4$alkoxy, $C_1$-$C_4$haloalkoxy, $C_1$-$C_4$alkylcarbonyl, $C_1$-$C_4$alkoxycarbonyl, $C_1$-$C_4$alkylamino, di-$C_1$-$C_4$-alkylamino, $C_1$-$C_4$alkyl-S(O)$_{n15}$, $C_1$-$C_4$alkyl-S(O)$_2$O, $C_1$-$C_4$haloalkyl-S(O)$_{n16}$, $C_1$-$C_4$haloalkyl-S(O)$_2$O, $C_1$-$C_4$alkyl-S(O)$_2$NH, $C_1$-$C_4$alkyl-S(O)$_2$N($C_1$-$C_4$alkyl), halogen, nitro, or cyano; and $n_{15}$ and $n_{16}$ independently of one another are 0, 1 or 2;

or an agrochemically tolerated salt M$^+$ or a stereoisomer or tautomer of a compound of the formula I.

2. A compound according to claim 1, wherein p is 0;

$R_5$ is $C_1$-$C_6$haloalkyl;

$R_2$ is hydrogen, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$-haloalkylsulfonyl, benzyl-S(O)$_{n1}$, $C_1$-$C_6$alkylamino, $C_2$-$C_6$dialkylamino, $C_1$-$C_6$-alkylaminosulfonyl, $C_2$-$C_6$-dialkylaminosulfonyl, phenyl, phenoxy, phenylthio, phenylsulfinyl or phenylsulfonyl, it being possible for the phenyl group, in turn, to be substituted by $C_1$-$C_3$-alkyl, $C_1$-$C_3$haloalkyl, $C_1$-$C_3$alkoxy, $C_1$-$C_3$haloalkoxy, halogen, cyano or nitro, or is OS(O)$_{n2}$—$R_{21}$, N($R_{23}$)—S(O)$_{n3}$—$R_{22}$, cyano, halogen, amino, $C_1$-$C_4$alkoxy-$C_1$-$C_4$alkyl, $C_1$-$C_4$alkyl-S(O)$_{n4}$—$C_1$-$C_4$alkyl, cyano-$C_1$-$C_4$alkyl or $C_1$-$C_4$alkoxy-$C_1$-$C_4$alkoxy;

$R_3$ is hydrogen, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_1$-$C_6$alkoxy, $C_1$-$C_6$haloalkoxy, $C_1$-$C_6$alkylthio, $C_1$-$C_6$-alkylsulfinyl, $C_1$-$C_6$alkylsulfonyl, $C_1$-$C_6$haloalkylthio, $C_1$-$C_6$haloalkylsulfinyl, $C_1$-$C_6$-haloalkylsulfonyl, $C_1$-$C_6$alkylamino, $C_2$-$C_6$dialkylamino, $C_1$-$C_6$-alkylaminosulfonyl, $C_2$-$C_6$-dialkylaminosulfonyl, phenyl, phenylthio, phenylsulfinyl, phenylsulfonyl or phenoxy, it being possible for phenyl, in turn, to be substituted by $C_1$-$C_3$alkyl, $C_1$-$C_3$haloalkyl, $C_1$-$C_3$alkoxy, $C_1$-$C_3$haloalkoxy, halogen, cyano or nitro, or is —N($R_{23}$)—S(O)$_n$—$R_{22}$, cyano, halogen, amino, $C_1$-$C_4$alkoxy-$C_1$-$C_4$alkyl or $C_1$-$C_4$alkyl-S(O)$_n$—$C_1$-$C_4$alkyl;

$R_4$ is hydrogen, $C_1$-$C_6$alkyl, $C_1$-$C_4$alkoxy, $C_1$-$C_4$haloalkoxy, $C_1$-$C_4$alkylcarbonyloxy, $C_1$-$C_4$-Alkylthio, $C_1$-$C_4$alkylsulfinyl, $C_1$-$C_4$alkylsulfonyl, $C_1$-$C_4$haloalkyl, formyl, cyano, halogen, phenyl or phenoxy, it being possible for phenyl, in turn, to be substituted by $C_1$-$C_3$alkyl, $C_1$-$C_3$haloalkyl, $C_1$-$C_3$alkoxy, $C_1$-$C_3$haloalkoxy, halogen, cyano or nitro;

or $R_4$ is a five- to ten-membered monocyclic or $R_3$-fused bicyclic ring system which can contain 1 to 4 hetero atoms selected from the group consisting of nitrogen, oxygen and sulfur, the ring system being bonded to the pyridine ring via a $C_1$-$C_4$alkylene group and it not being possible for the ring system to contain more than 2 oxygen atoms and more than two sulfur atoms, and it being possible for the ring system itself to be mono-, di- or trisubstituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$alkynyloxy, $C_1$-$C_6$-Alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_4$-alkoxy-$C_1$-$C_2$alkylthio, $C_1$-$C_4$alkylcarbonyl-$C_1$-$C_2$alkylthio, $C_1$-$C_4$alkoxycarbonyl-$C_1$-$C_2$alkylthio, cyano-$C_1$-$C_4$alkylthio, $C_1$-$C_6$alkylsulfinyl, $C_1$-$C_6$haloalkylsulfinyl, $C_1$-$C_6$alkylsulfonyl, $C_1$-$C_6$-haloalkylsulfonyl, aminosulfonyl, $C_1$-$C_2$alkylaminosulfonyl, $C_2$-$C_4$dialkylaminosulfonyl, halogen, cyano, nitro, phenyl and benzylthio, it being possible for phenyl and benzylthio, in turn, to be substituted on the phenyl ring by $C_1$-$C_3$alkyl, $C_1$-$C_3$haloalkyl, $C_1$-$C_3$alkoxy, $C_1$-$C_3$-haloalkoxy, halogen, cyano or nitro, and where substituents on the nitrogen in the heterocyclic ring are other than halogen;

$R_{21}$ and $R_{22}$ independently of one another are $C_1$-$C_4$alkyl or $C_1$-$C_4$haloalkyl;

$R_{23}$ $R_{24}$ and $R_{25}$ independently of one another are hydrogen or $C_1$-$C_4$alkyl;

n, $n_1$, $n_2$, $n_3$ and $n_4$ independently of one another are 0, 1 or 2;

Q is Q$_1$

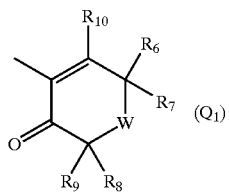

(Q$_1$)

in which

R$_6$, R$_7$, R$_8$ and R$_9$ independently of one another are hydrogen, C$_1$–C$_6$alkyl, C$_1$–C$_6$-haloalkyl, C$_2$–C$_6$alkenyl, C$_2$–C$_6$alkynyl, C$_1$–C$_6$alkoxycarbonyl, C$_1$–C$_6$alkyl-S(O)$_{n17}$, C$_1$–C$_6$alkyl-NHS(O)$_2$, C$_1$–C$_6$alkylamino, di-(C$_1$–C$_6$alkyl)amino, hydroxyl, C$_1$–C$_6$alkoxy, C$_3$–C$_6$alkenyloxy, C$_3$–C$_6$-alkynyloxy, hydroxy-C$_1$–C$_6$alkyl, C$_1$–C$_4$alkylsulfonyloxy-C$_1$–C$_6$alkyl, tosyloxy-C$_1$–C$_6$alkyl, halogen, cyano, nitro, phenyl or phenyl which is substituted by C$_1$–C$_4$alkyl, C$_1$–C$_4$haloalkyl, C$_1$–C$_4$alkoxy, C$_1$–C$_4$haloalkoxy, C$_1$–C$_4$alkylcarbonyl, C$_1$–C$_4$alkoxycarbonyl, amino, C$_1$–C$_4$-alkylamino, di-C$_1$–C$_4$alkylamino, C$_1$–C$_4$alkyl-S(O)$_{n18}$, C$_1$–C$_4$alkyl-S(O)$_2$O, C$_1$–C$_4$haloalkyl-S(O)$_{n5}$, C$_1$–C$_4$haloalkyl-S(O)$_2$O, C$_1$–C$_4$alkyl-S(O)$_2$NH, C$_1$–C$_4$alkyl-S(O)$_{n19}$N(C$_1$–C$_4$alkyl), halogen, nitro, COOH or cyano;

or adjacent R$_6$ and R$_7$ or R$_8$ and R$_9$ together are —(CH$_2$)$_m$—;

n$_5$ n$_{17}$, n$_{18}$ and n$_{19}$ independently of one another are 0, 1 or 2;

m is 2, 3, 4, 5, or 6;

W is oxygen, S(O)$_{n6}$, —CR$_{11}$R$_{12}$—, —C(O)— or —NR$_{13}$—;

n$_6$ is 0, 1 or 2;

R$_{11}$ is hydrogen, C$_1$–C$_4$alkyl, C$_1$–C$_4$haloalkyl, C$_1$–C$_4$alkoxy-C$_1$–C$_4$alkyl, C$_1$–C$_4$alkylthio-C$_1$–C$_4$alkyl, C$_1$–C$_4$alkylcarbonyloxy-C$_1$–C$_4$alkyl, C$_1$–C$_4$alkylsulfonyloxy-C$_1$–C$_4$alkyl, tosyloxy-C$_1$–C$_4$alkyl, di-(C$_1$–C$_3$alkoxyalkyl)methyl, di-(C$_1$–C$_3$alkylthioalkyl)methyl, (C$_1$–C$_3$alkoxyalkyl)-(C$_1$–C$_3$alkylthioalkyl)methyl, C$_3$–C$_5$oxacycloalkyl, C$_3$–C$_5$thiacycloalkyl, C$_3$–C$_4$dioxacycloalkyl, C$_3$–C$_4$dithiacycloalkyl, C$_3$–C$_4$oxathiacycloalkyl, formyl, C$_1$–C$_4$alkoxycarbonyl or phenyl which, in turn, can be substituted by C$_1$–C$_4$alkyl, C$_1$–C$_4$haloalkyl, C$_1$–C$_4$alkoxy, C$_1$–C$_4$haloalkoxy, C$_1$–C$_4$-alkylcarbonyl, C$_1$–C$_4$alkoxycarbonyl, amino, C$_1$–C$_4$alkylamino, di-C$_1$–C$_4$alkylamino, C$_1$–C$_4$alkyl-S(O)$_{n21}$, C$_1$–C$_4$alkyl-S(O)$_2$O, C$_1$–C$_4$haloalkyl-S(O)$_{n7}$, C$_1$–C$_4$haloalkyl-S(O)$_2$O, C$_1$–C$_4$alkyl-S(O)$_2$NH, C$_1$–C$_4$alkyl-S(O)$_{n20}$N(C$_1$–C$_4$alkyl), halogen, nitro, COOH or cyano;

n$_7$, n$_{20}$ and n$_{21}$ independently of one another are 0, 1 or 2;

or R$_{12}$ together with R$_9$ is a group —(CH$_{2o}$—; o is 1, 2, 3, 4 or 5;

R$_{12}$ is hydrogen, C$_1$–C$_4$alkyl or C$_1$–C$_4$haloalkyl;

or R$_{12}$ together with R$_{11}$ is a group —(CH$_2$)$_{m1}$;

m$_1$, is 2, 3, 4, 5, or 6;

R$_{10}$ is hydroxyl, O$^-$M$^+$, halogen, C$_1$–C$_{12}$alkoxy, C$_1$–C$_{12}$alkylcarbonyloxy, C$_2$–C$_4$-alkenylcarbonyloxy, C$_3$–C$_6$cycloalkylcarbonyloxy, C$_1$–C$_{12}$alkoxycarbonyloxy, C$_1$–C$_{12}$-alkylcarbonyloxy, R$_{23}$R$_{24}$N-C(O)O, C$_1$–C$_{12}$alkylS(O)$_{n8}$—, C$_1$–C$_4$haloalkyl-S(O)$_{n9}$—, C$_2$–C$_{12}$-alkenylS(O)$_{n10}$—, C$_2$–C$_{12}$haloalkenylS(O)$_{n11}$—, C$_2$–C$_{12}$alkynylS(O)$_{n12}$—; benzyloxy, phenoxy, phenylthio, phenylsulfinyl or phenylsulfonyl, where the phenyl group, in turn, can be substituted by C$_1$–C$_4$alkyl, C$_1$–C$_4$haloalkyl, C$_1$–C$_4$alkoxy, C$_1$–C$_4$haloalkoxy, C$_1$–C$_4$alkylcarbonyl, C$_1$–C$_4$alkoxycarbonyl, C$_1$–C$_4$alkylamino, di-C$_1$–C$_4$alkylamino, C$_1$–C$_4$alkyl-S(O)$_{n13}$, C$_1$–C$_4$alkyl-S(O)$_2$O, C$_1$–C$_4$haloalkyl-S(O)$_{n14}$, C$_1$–C$_4$haloalkyl-S(O)$_2$O, C$_1$–C$_4$alkyl-S(O)$_2$NH, C$_1$–C$_4$alkyl-S(O)$_2$N(C$_1$–C$_4$alkyl), halogen, nitro or cyano, or is C$_1$–C$_4$alkyl-S(O)$_2$O, phenyl-S(O)$_2$O, (C$_1$–C$_4$-alkoxy)$_2$P(O)O, C$_1$–C$_4$alkyl(C$_1$–C$_4$alkoxy)P(O)O, or H(C$_1$–C$_4$alkoxy)P(O)O;

n$_8$, n$_9$, n$_{10}$, n$_{11}$, n$_{12}$, n$_{13}$ and n$_{14}$ independently of one another are 0, 1 or 2;

R13 is hydrogen, C$_1$–C$_4$alkyl, C$_1$–C$_4$alkoxycarbonyl or phenyl which, in turn, can be substituted by C$_1$–C$_4$alkyl, C$_1$–C$_4$haloalkyl, C$_1$–C$_4$alkoxy, C$_1$–C$_4$haloalkoxy, C$_1$–C$_4$alkylcarbonyl, C$_1$–C$_4$alkoxycarbonyl, C$_1$–C$_4$alkylamino, di-C$_1$–C$_4$alkylamino, C$_1$–C$_4$alkyl-S(O)$_{n15}$, C$_1$–C$_4$alkyl-S(O)$_2$O, C$_1$–C$_4$haloalkyl-S(O)$_{n16}$, C$_1$–C$_4$haloalkyl-S(O)$_2$O, C$_1$–C$_4$alkyl-S(O)$_2$N(C$_1$–C$_4$alkyl), halogen, nitro or cyano;

n$_{15}$ and n$_{16}$ independently of one another are 0, 1 or 2;

or an agrochemically tolerated salt M$^+$ or a stereoisomer or tautomer of a compound of the formula I.

3. A compound according to claim 1, in which R$_{10}$ is hydroxyl or O$^-$M$^+$.

4. A compound according to claim 1, in which W is oxygen, —CR$_{11}$R$_{12}$— or —C(O)—.

5. A compound according to claim 1, in which W is oxygen and R$_6$, R$_7$, R$_8$ and R$_9$ independently of one another are hydrogen or C$_1$–C$_3$alkyl.

6. A compound according to claim 1, in which W is —C(O)— and R$_6$, R$_7$, R$_8$ and R$_9$ independently of one another are C$_1$–C$_3$alkyl.

7. A compound according to claim 1, in which R$_2$ is hydrogen and R$_3$ is methyl.

8. A compound according to claim 1, in which R$_2$ is methyl, ethyl, n-propyl, i-propyl, vinyl, methoxymethyl, methoxycarbonyloxymethyl, ethoxycarbonyloxymethyl, acetoxymethyl, propionyloxymethyl, chloromethyl, bromomethyl, fluoromethyl, difluoromethyl, trifluoromethyl or cyanomethyl.

9. A compound according to claim 1, in which R$_4$ is hydrogen or methyl.

10. A compound according to claim 1, in which R$_5$ is trifluoromethyl, difluorochloromethyl, pentafluoroethyl, heptafluoropropyl or difluoromethyl.

11. A compound according to claim 1, in which R$_3$ is hydrogen and R$_2$ is C$_1$–C$_4$alkyl, C$_1$–C$_3$haloalkyl, cyclopropyl, C$_2$–C$_3$alkenyl, C$_2$–C$_3$haloalkenyl, C$_2$–C$_3$alkynyl, allenyl, C$_1$–C$_2$-alkoxy-C$_1$–C$_2$alkyl, C$_1$–C$_2$alkylthio-C$_1$–C$_2$alkyl, cyano-C$_1$–C$_2$alkyl, C$_1$–C$_2$alkoxycarbonyl-C$_1$–C$_2$-alkyl, C$_1$–C$_4$alkylcarbonyloxy-C$_1$–C$_2$alkyl, C$_1$–C$_3$alkoxy, C$_1$–C$_3$haloalkoxy, allyloxy, propargyloxy, C$_1$–C$_3$alkylthio, C$_1$–C$_3$alkylsulfinyl or cyano.

12. A herbicidal and plant-growth-inhibitory composition, which has a herbicidally active content of a compound of the formula I according to claim 1 and an inert carrier.

13. A method of controlling undesired vegetation, in which a herbicidally active amount of an active ingredient of the formula I according to claim 1 or of a composition comprising said active ingredient is applied to the plants or to their environment.

14. A method of inhibiting plant growth, in which a herbicidally active amount of an active ingredient of the formula I according to claim 1 or of a composition comprising said active ingredient is applied to the plants or to their environment.

* * * * *